US009085570B2

(12) United States Patent
Giaccia et al.

(10) Patent No.: US 9,085,570 B2
(45) Date of Patent: Jul. 21, 2015

(54) SUBSTITUTED BENZAMIDES AND THEIR USES

(75) Inventors: Amato Giaccia, Palo Alto, CA (US); Edwin Lai, Menlo Park, CA (US); Olga Razorenova, Menlo Park, CA (US); Denise Chan, San Francisco, CA (US); Michael Patrick Hay, Auckland (NZ); Muriel Bonnet, Auckland (NZ); Connie Sun, Palo Alto, CA (US); Ray Tabibiazar, Portola Valley, CA (US); Po-wai Yuen, Ann Arbor, MI (US)

(73) Assignees: The Board of Trustees of the Leland Stanford Junior University, Stanford, CA (US); Auckland UniServices Limited, Auckland (NZ); Ruga Corporation, San Francisco, CA (US)

( * ) Notice: Subject to any disclaimer, the term of this patent is extended or adjusted under 35 U.S.C. 154(b) by 0 days.

(21) Appl. No.: 13/878,682

(22) PCT Filed: Oct. 10, 2011

(86) PCT No.: PCT/US2011/055624
§ 371 (c)(1),
(2), (4) Date: Sep. 30, 2013

(87) PCT Pub. No.: WO2012/051117
PCT Pub. Date: Apr. 19, 2012

(65) Prior Publication Data
US 2014/0024649 A1    Jan. 23, 2014

Related U.S. Application Data

(60) Provisional application No. 61/475,549, filed on Apr. 14, 2011, provisional application No. 61/434,976, filed on Jan. 21, 2011, provisional application No. 61/391,958, filed on Oct. 11, 2010.

(51) Int. Cl.
| C07D 413/12 | (2006.01) |
| C07D 417/12 | (2006.01) |
| C07D 413/14 | (2006.01) |
| C07D 405/12 | (2006.01) |
| C07D 401/12 | (2006.01) |
| C07D 409/12 | (2006.01) |
| C07D 213/75 | (2006.01) |
| C07D 263/32 | (2006.01) |

(52) U.S. Cl.
CPC .......... C07D 413/12 (2013.01); C07D 213/75 (2013.01); C07D 263/32 (2013.01); C07D 401/12 (2013.01); C07D 405/12 (2013.01); C07D 409/12 (2013.01); C07D 413/14 (2013.01); C07D 417/12 (2013.01)

(58) Field of Classification Search
CPC ............................ C07D 413/12; A61K 31/421
USPC ........................ 546/271.4; 514/340
See application file for complete search history.

(56) References Cited

U.S. PATENT DOCUMENTS

| 4,172,896 | A | 10/1979 | Uno et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,731,000 | A | 3/1998 | Ruff et al. |
| 5,763,493 | A | 6/1998 | Ruff et al. |
| 5,846,514 | A | 12/1998 | Foster et al. |
| 6,110,973 | A | 8/2000 | Young |
| 6,334,997 | B1 | 1/2002 | Foster et al. |
| 7,312,234 | B2 | 12/2007 | Bridger et al. |
| 2007/0173489 | A1* | 7/2007 | Klingler et al. .......... 514/210.21 |
| 2008/0293711 | A1 | 11/2008 | Clark et al. |
| 2009/0227624 | A1 | 9/2009 | Dasgupta et al. |
| 2011/0301149 | A1 | 12/2011 | Wu |

FOREIGN PATENT DOCUMENTS

| WO | 2004065374 A1 | 8/2004 |
| WO | 2009114552 A1 | 9/2009 |
| WO | 2011011514 A1 | 1/2011 |
| WO | 2012100223 A1 | 7/2012 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
STN Record for RN 894194-14-0, Jul. 18, 2006.*
McDonough et al., "Cellular oxygen sensing: crystal structure of hypoxia-inducible factor proly hydroxylase (PHD2)", PNAS USA 2006, 103(26):9814-9819.
Minchenko et al., "Hypoxia-inducible factor-1-mediated expression of the 6-phosphofructo-2-kinase/fructose-2, 6-bisphosphatase-3 (PFKFB3) Gene", The Journal of Biological Chemistry 2002, 277(8):6183-6187.
Papandreou et al., "HIF-1 mediates adaptation to hypoxia by actively downregulating mitochondrial oxygen consumption", Cell Metabolism 2006, 3(3):187-197.
International Search Report and Written Opinion, PCT/US11/55624, Dated Apr. 25, 2012.
International Search Report and Written Opinion, PCT/US13/36229, Dated Nov. 1, 2013.
Supplemental European Search Report, Application No. 11833208. 9, Dated Apr. 8, 2014.
Wu, B. et al., "Structures of the CXCR4 chemokine receptor in complex with small molecule and cyclic peptide antagonists", Science, 330(6007):1066-1071 (2010).

(Continued)

Primary Examiner — John Mabry
Assistant Examiner — Daniel Carcanague
(74) Attorney, Agent, or Firm — David J. Aston; Bozicevic, Field & Francis LLP

(57) ABSTRACT

Provided herein are Substituted Benzamides, compositions, and method of their manufacture and use.

9 Claims, No Drawings

(56) References Cited

OTHER PUBLICATIONS

CAS RN 950326-00-8, Entered STN: Oct. 11, 2007, 1 p.
CAS RN 931754-06-2; Entered STN: Apr. 22, 2007, 1 p.
CAS RN 894189-61-8; Entered STN: Jul. 18, 2006, 1 p.
CAS RN 894188-70-6; Entered STN: Jul. 18, 2006, 1 p.
Patent Examination Report No. 1, AU Patent Application No. 2011313853, Feb. 10, 2015, 7 pp.
Examination Report, EP Patent Application No. 11833208.9, Mar. 30, 2015, 5 pp.
CN Patent Application No. 201180059510.0, Second Office Action, Apr. 20, 2015, 10 pp.

\* cited by examiner

SUBSTITUTED BENZAMIDES AND THEIR USES

PRIORITY

The present application claims the benefit of U.S. Provisional Application No. 61/391,958 filed Oct. 11, 2010, U.S. Provisional Application No. 61/434,976 filed Jan. 21, 2011, U.S. Provisional Application No. 61/475,549 filed Apr. 14, 2011, and this application further is a national stage application of PCT/US2011/055624, having an international filing date of 10 Oct. 2011. The entire disclosures of those applications are relied on for all purposes and are incorporated into this application by reference.

This invention was made with Government support under contract CA082566 awarded by the National Institutes of Health. The Government has certain rights in the invention.

FIELD OF THE INVENTION

The present invention relates to novel GLUT1 inhibitors and modulator compounds useful for the treatment of various diseases. More particularly, the invention is concerned with such compounds, methods or treating diseases and methods of synthesis of the compounds.

BACKGROUND OF THE INVENTION

The concept of synthetic lethality, or conditional genetics, describes the genetic interaction of two genes, both involved in a cellular process. When either gene is mutated alone, the cell remains viable. However, the combination of mutations in these two genes results in cell death (Hartwell, et al., Science, 278:1064-1068 (1997)). In the case of chemical synthetic lethality, the first mutation is essential to the development of cancer, while a second gene is inhibited by a small molecule, resulting in cytotoxic cell death (Kaelin, W. G., Jr., Nat Rev Cancer, 5:689-698 (2005); Sutphin, et al., Cancer Res., 67:5896-5905 (2007)). This approach is particularly attractive because it should not affect normal, non-cancerous tissue. Furthermore, synthetic lethality is a therapeutically advantageous approach to drug discovery and is particularly suited to developing therapeutics to treat cancers. It describes a genetic interaction whereby the combination of mutation and/or inhibition of two genes leads to tumor cell death. If only one of these two genes is altered, there are no deleterious effects. For example, in the vast majority of renal carcinomas, the VHL tumor suppressor gene is inactivated, driving growth and expansion.

Conventional chemotherapeutic agents have been identified only by their ability to kill rapidly proliferating cells and therefore such agents cannot distinguish between normal, healthy dividing cells and tumor cells. For this reason, standard agents have low therapeutic indices and are often limited by their severe toxicity to normal tissue. While many solid tumors respond to different combinations of cytotoxic chemotherapies, kidney cancer is a particularly intractable disease. Renal cell carcinoma (RCC), the most common type of kidney cancer, has proven to be particularly challenging, resistant to both radiation therapy and standard systemic chemotherapies (Atkins, et al., Clin Cancer Res., 10:6277 S-6281 S. (2004); Motzer, R. J., and Russo, P., J. Urol., 163:408-417 (2000)). To date, immunotherapy using interferon or interleukin-2 has had mild success with responses in less than 10% of patients with metastatic RCC (Rosenberg, et al., Ann Surg., 228:307-319 (1998)). The recent development of anti-angiogenic therapies sunitinib (Sutent) and sorafenib (Nexavar) is encouraging although these agents are not curative (Ahmad, T., and Eisen, T., Clin Cancer Res., 10:6388 S-6392S (2004); Motzer, et al., J Clin Oncol., 24:16-24 (2006)). The targeting of receptor tyrosine kinases, which is not specific to the development of RCC, has become the standard of care for advanced RCC (Rathmell, et al., Curr Opin Oncol., 19:234-240 (2007)). One key distinguishing feature in RCC is the loss of function of the VHL tumor suppressor gene, an essential and frequent mutation in the development of RCC. In order to specifically target RCC cells without toxicity to normal cells, we have employed a synthetic lethal approach, seeking to identify compounds that exhibit selective cytotoxicity to cells that have lost functional VHL.

Tumor hypoxia has a well defined role in driving tumor progression and metastasis, as well as resistance to therapy. A key mediator of hypoxic stress is HIFα. HIF is a bHLH heterodimeric transcription factor, made up of an oxygen-labile subunit (HIF-α) and a constitutive subunit (HIF-β). In the presence of oxygen, hydroxylation on proline residues 564 and 402 by prolyl hydroxylases (PHDs) marks HIF-α for recognition and binding with Von Hippel-Lindau protein (pVHL), leading to degradation of HIF-α. Under hypoxic conditions, activity of the PHDs decrease, which prevents the recognition of HIF-α by pVHL. In cells that lack VHL, stabilized HIF-α binds HIF-β to activate the transcription of genes involved in several processes. HIF transcribes genes that mediate glycolysis, angiogenesis, tissue remodelling, epithelial permeability and vascular tone. These genes, and processes driven by these genes, act to promote tumor growth and survival in hypoxic conditions.

Functional studies indicate that pVHL, the protein product of VHL, is an E3 ubiquitin ligase that targets the α-subunit of the hypoxia-inducible factor (HIF) for proteasomal degradation under normoxia. In addition to its role in HIF regulation, pVHL has been implicated in a variety of processes including extracellular matrix assembly, regulation of microtubule stability, polyubiquitination of atypical PKC family members, regulation of fibronectin, and RNA polymerase II subunits. Glucose transporter 1 (GLUT1), also known as solute carrier family 2 (SLCA2) or facilitated glucose transporter member 1 (SLC2A1) is a 492 amino acid protein (NCBI accession numbers NP_006507.2 or P11166.2). GLUT1 is a member of a small family 45-55 kDa hexose transport proteins and is invovled in facilitating the transport of glucose across the plasma membranes of mammalian cells. (See, e.g., Doege et al., Biochem J., 15:(359):443-449 (2001); Mueckler, et al., Science 229(4717):941-945 (1985); and Olsen et al., Annual Review of Nutrition, 16:235-256 (1996)).

There is considerable interest in the identification of inhibitors of HIF and its downstream genes such as GLUT1. A variety of pharmacological HIF inhibitors have been identified, although the interaction of these agents is not directly with HIF, but via modulation of cellular processes in which HIF is integral.

An extension of this therapy would be in the treatment of cells defective in the von Hippel-Lindau gene and diseases associated with such defects or inhibition of downstream pathways such as inhibition of GLUT1 activity.

Identifying new molecular targeted therapies that specifically kill tumor cells while sparing normal tissue is the next major challenge of cancer research. A characteristic of VHL-deficient cells, namely reliance on GLUT1 and aerobic glycolysis can now be exploited in treatment of diseases related to rapidly dividing cells. High-throughput chemical synthetic lethal screens have been used to identify small molecules that exploit the loss of the von Hippel-Lindau (VHL) tumor suppressor gene, which occurs in approximately 80% of renal carcinomas. These small molecules selectively kill cells with mutant VHL but not cells with wild-type VHL by specifically targeting glucose uptake via GLUT1 in VHL-deficient tumors, which are dependent on glycolysis for ATP production. The present application describes small molecules that impair glucose transport in VHL-deficient cells, but not in cells with wild-type VHL, resulting in specific killing of renal carcinoma cells. The potential to target glucose uptake in VHL-deficient tumors therapeutically with the use of small molecules provides a new way to treat metastatic renal carcinoma, among others types of diseases mediated by elevated expression of GLUT1. Treatment with these small molecules inhibits the growth of VHL-deficient tumors by binding GLUT1 directly and impeding glucose uptake in vivo without toxicity to normal tissue.

SUMMARY OF THE INVENTION

Provided herein are compounds of Formula I:

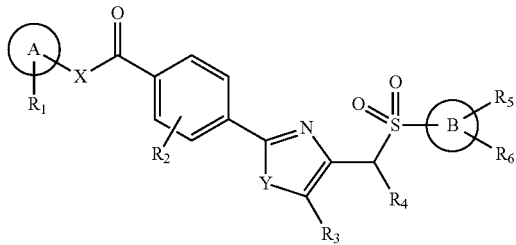

Formula I and pharmaceutically acceptable salts, hydrates, solvates, prodrugs, enantiomers and stereoisomers thereof;
wherein
  A is a nitrogen-containing heteroaryl ring chosen from pyridinyl, pyrazinyl, and imidazolyl, each of which is optionally substituted;
  X is $CH_2CH_2NR$, $CH_2NR$, or NR wherein each R is independently chosen from hydrogen, alkyl, alkenyl, alkynyl, cycloalkyl, aryl, heterocycloalkyl, and heteroaryl, each of which, except for hydrogen, is optionally substituted;
  $R_1$, $R_2$, $R_3$, $R_4$, $R_5$, and $R_6$ are each independently chosen from hydrogen, alkyl, alkenyl, alkynyl, cycloalkyl, aryl, heterocycloalkyl, and heteroaryl, each of which, except for hydrogen, is optionally substituted;
  Y is chosen from O, S, NR; wherein each R is independently chosen from hydrogen, alkyl, alkenyl, alkynyl, cycloalkyl, aryl, heterocycloalkyl, and heteroaryl, each of which, except for hydrogen, is optionally substituted;
  B is an optionally substituted aryl ring;
  provided that if A is 3-pyridinyl, X is $CH_2NH$, $R_1$, $R_2$, and $R_4$ are each hydrogen, $R_3$ is Me, and Y is O, then B is not phenyl or 4-methylphenyl.
In one aspect, compounds of Formula II are provided:

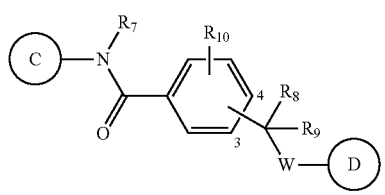

II and pharmaceutically acceptable salts, hydrates, solvates, prodrugs, enantiomers, and stereoisomers thereof;

wherein:
  C is a nitrogen-containing heteroaryl ring chosen from pyridinyl, pyrimidinyl, pyrazinyl, quinolinyl, pyrazolyl, imidazolyl, and thiazolyl, each of which is optionally substituted;

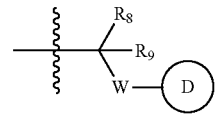

is attached to the phenyl ring at either the 3 or 4 position;
  $R_7$, $R_8$, and $R_9$ are each independently chosen from hydrogen, optionally substituted alkyl, and optionally substituted alkenyl;
  $R_{10}$ is chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;
  W is chosen from $-NRSO_2-$, $-SO_2NR-$, and $-NRCO-$, wherein each R is independently chosen from hydrogen, alkyl, alkenyl, alkynyl, cycloalkyl, aryl, heterocycloalkyl, and heteroaryl, each of which, except for hydrogen, is optionally substituted; and
  D is heteroaryl.
In one embodiment, the compounds of Formula II are of the Formula IIA:

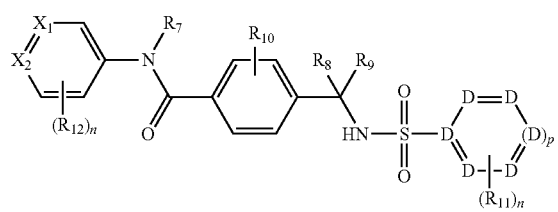

IIA wherein
  $X_1$ and $X_2$ are each independently chosen from N, NO, and CH, provided that at least one of $X_1$ and $X_2$ is not CH;
  each D is individually taken from the group consisting of C, CH, NH, N, S and O, such that the resultant ring is selected from pyridyl, furanyl, imidazolyl, triazolyl, and thienyl;
  $R_7$, $R_8$, and $R_9$ are each independently chosen from hydrogen, optionally substituted alkyl, and optionally substituted alkenyl;
  $R_{10}$ and $R_{11}$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and
  for each occurrence, $R_{12}$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy;
  each n is 0, 1 or 2; and
  p is 0 or 1.

In another aspect, compounds of Formula III are provided:

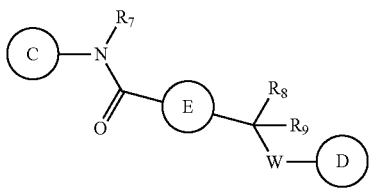

III and pharmaceutically acceptable salts, hydrates, solvates, prodrugs, enantiomers, and stereoisomers thereof;
wherein:
C is a nitrogen-containing heteroaryl ring chosen from pyridinyl, pyrimidinyl, pyrazinyl, quinolinyl, pyrazolyl, imidazolyl, and thiazolyl, each of which is optionally substituted;
$R_7$, $R_8$, and $R_9$ are each independently chosen from hydrogen, optionally substituted alkyl, and optionally substituted alkenyl;
W is chosen from —N(R)SO$_2$R$_X$—, —SO$_2$N(R)R$_X$—, and —N(R)COR$_X$—, wherein each R is independently chosen from hydrogen, alkyl, alkenyl, alkynyl, cycloalkyl, aryl, heterocycloalkyl, and heteroaryl, each of which, except for hydrogen, is optionally substituted; and $R_X$ is an bivalent $C_0$-$C_6$alkylene, bivalent $C_3$-$C_6$cycloalkyl, or phenyl, each of which is optionally substituted;
E is selected from $C_5$-$C_6$cycloalkyl, $C_5$-$C_6$heterocycle, phenyl, wherein C is optionally substituted hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino; and
D is an optionally substituted heterocycle.

In one embodiment, the compounds of Formula III are of the Formula IIIA:

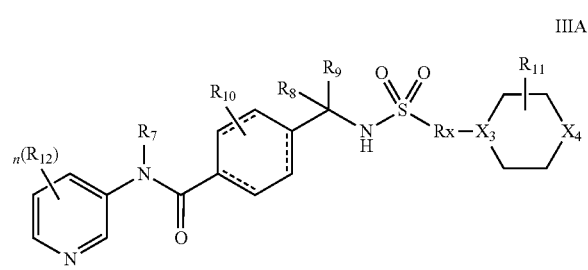

IIIA wherein:
$X_3$ is selected from CH or N;
$X_4$ is selected from O, NH, or NR$_7$;
----- represents a single or double bond;
each $R_7$, $R_8$, and $R_9$ is independently chosen from hydrogen, optionally substituted alkyl, and optionally substituted alkenyl;
$R_{10}$ and $R_{11}$ are independently chosen from hydrogen, hydroxy, optionally substituted alkyl, optionally substituted alkenyl, optionally substituted alkoxy, optionally substituted cycloalkyl, optionally substituted aryl, optionally substituted heterocycloalkyl, optionally substituted heteroaryl, halo, carboxy, nitro, sulfonyl, sulfinyl, and optionally substituted amino;

for each occurrence, $R_{12}$ is independently chosen from alkyl optionally substituted with one or more halo, alkoxy, halo, nitro, heterocycloalkyl, and amino optionally substituted with C(O)R$_a$, wherein R$_a$ is chosen from alkyl and optionally substituted alkoxy;
$R_X$ is an bivalent $C_4$alkylene, bivalent $C_6$cycloalkyl, or phenyl, each of which is optionally substituted; and
n is 0, 1, or 2.

In one aspect, compounds of Formula IV are provided:

Formula IV

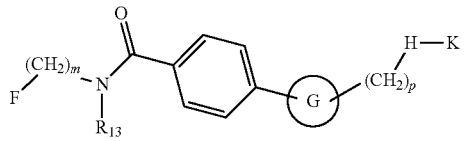

and pharmaceutically acceptable salts, hydrates, solvates, prodrugs, enantiomers, and stereoisomers thereof;
wherein:
F is a heteroaryl selected from pyridine, pyrazine, pyridazine, pyrimidine, 1,2,4-triazine or 1,3,5-triazine, optionally substituted with halogen, hydroxyl group, —CF3 group, C1-C6 alkoxy group, C1-C6 straight chain alkyl, C3-C6 branched chain alkyl or C3-C6 cycloalkyl group, wherein the number of substituents does not exceed the number of available C—H bonds of the heteroaryl; with multiple substitutions, each substituent on the heteroaryl is chosen independent of the other substituents;
G is a 5 membered heteroaryl selected from thiophene, imidazole, pyrazole, thiazole, oxazole, isoxazole, isothiazole, triazole, oxadiazole, and thiadiazole;
m is an integer ranging from 0 to 3;
p is an integer ranging from 1 to 5;
H is —S(O)n-(CH2)q—, —O—(CH2)q-, or —C(O)—(CH2)q-;
n is an integer ranging from 0 to 2;
q is an integer ranging from 0 to 5;
K is selected from

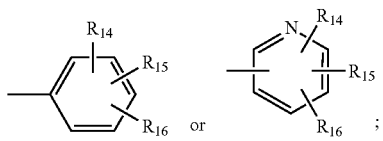

R13 is H, C1-C6 straight chain alkyl, C3-C6 branched chain alkyl or C3-C6 cycloalkyl;
R14, R15 and R16 are each independently H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles selected from pyrrolidine, piperidine, piperazine, morpholine, thiomorpholine, azepane, 1,4-diazepane, 1,4-oxazepane and 1,4-thiazepane; or

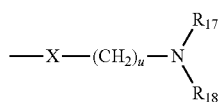

wherein X can be a bond, O, S or NR19,

R17, R18 and R19 are each independently H, C1-C6 straight chain alkyl, C3-C6 branched chain alkyl, C1-C6 hydroxyalkyl, alkoxyalkyl in which the alkoxy and alkyl portions each independently contain from 1 to 6 carbon atoms, —CF3; or R17 and R18 can be taken together to form a 4 to 7 membered optionally substituted ring containing 0-4 heteroatoms selected from N, O or S;

r is an integer ranging from 0 to 3;

t is an integer ranging from 1 to 2; and u is an integer ranging from 1 to 6.

In another aspect, the compounds of Formula V are described:

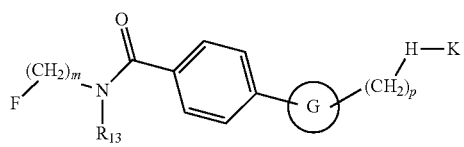

Formula V and pharmaceutically acceptable salts, hydrates, solvates, prodrugs, enantiomers, and stereoisomers thereof;

wherein:

F is a heteroaryl selected from pyridine, pyrazine, pyridazine, pyrimidine, 1,2,4-triazine or 1,3,5-triazine, optionally substituted with halogen, hydroxyl group, —CF3 group, C1-C6 alkoxy group, C1-C6 straight chain alkyl, C3-C6 branched chain alkyl or C3-C6 cycloalkyl group, wherein the number of substituents does not exceed the number of available C—H bonds of the heteroaryl; with multiple substitutions, each substituent on the heteroaryl is chosen independent of the other substituents;

G is a 5 membered heteroaryl selected from thiophene, imidazole, pyrazole, thiazole, oxazole, isoxazole, isothiazole, triazole, oxadiazole, and thiadiazole;

m is an integer ranging from 0 to 3;

p is an integer ranging from 1 to 5;

H is selected from —S(O)n-(CH2)q-, —O—(CH2)q-, or —C(O)—(CH2)q-;

n is an integer ranging from 0 to 2;

q is an integer ranging from 0 to 5;

K is selected from C3-C7 cycloalkyl optionally substituted with two or more of R14, R15, and R16, C1-C6 straight or branched optionally substituted alkyl,

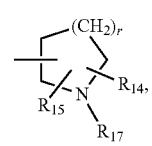 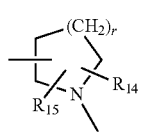 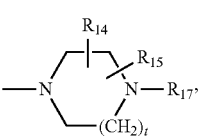

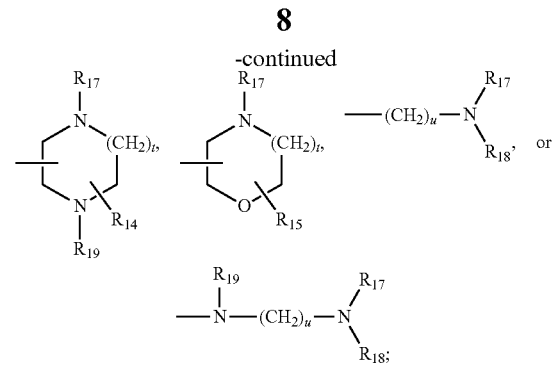

R13 is selected from H, C1-C6 straight chain alkyl, C3-C6 branched chain alkyl or C3-C6 cycloalkyl;

R14, R15 and R16 can independently be H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles such as pyrrolidine, piperidine, piperazine, morpholine, thiomorpholine, azepane, 1,4-diazepane, 1,4-oxazepane and 1,4-thiazepane; or

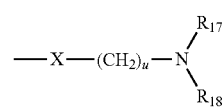

wherein X can be a bond, O, S or NR19;

R17, R18 and R19 are independently selected from H, C1-C6 straight chain alkyl, C3-C6 branched chain alkyl, C3-C6 cycloalkyl, C1-C6 hydroxyalkyl, alkoxyalkyl in which the alkoxy and alkyl portions each independently contain from 1 to 6 carbon atoms, —CF3, or —C(O)O—, or R17 and R18 can be taken together to form a 4 to 7 membered optionally substituted monocycloalkyl ring or 8-14 bicycloalkyl ring, each optionally containing between 1-3 heteroatoms selected from N, O or S, or;

r is an integer ranging from 0 to 3;

t is an integer ranging from 1 to 2; and u is an integer ranging from 1 to 6.

In one aspect, compounds of Formula VI are provided:

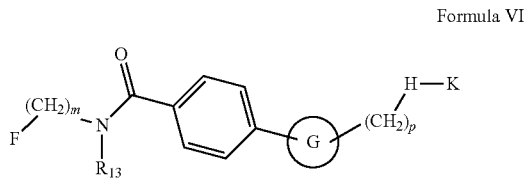

Formula VI and pharmaceutically acceptable salts, hydrates, solvates, prodrugs, enantiomers, and stereoisomers thereof;

wherein:

F is selected from the group consisting of C3-C7 cycloalkyl optionally substituted with two or more of R14, R15, and R16, or C1-C6 straight or branched optionally substituted alkyl,

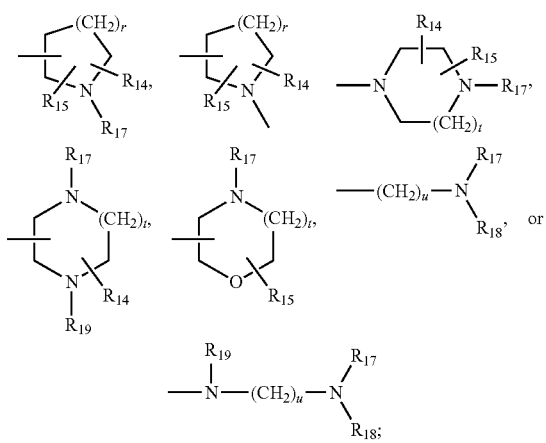

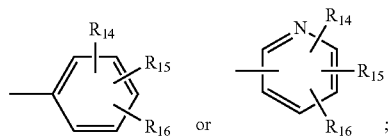

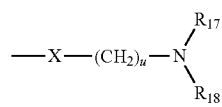

G is a 5 membered heteroaryl selected from thiophene, imidazole, pyrazole, thiazole, oxazole, isoxazole, isothiazole, triazole, oxadiazole, and thiadiazole;

m is an integer ranging from 0 to 3;

p is an integer ranging from 1 to 5;

H is —S(O)n-(CH2)q-, —O—(CH2)q-, or —C(O)—(CH2)q-;

n is an integer ranging from 0 to 2;

q is an integer ranging from 0 to 5;

K is selected from

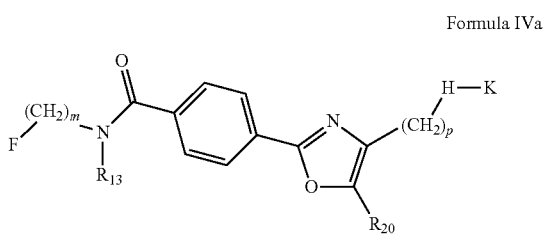

R13 is H, C1-C6 straight chain alkyl, C3-C6 branched chain alkyl or C3-C6 cycloalkyl;

R14, R15 and R16 can independently be H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles such as pyrrolidine, piperidine, piperazine, morpholine, thiomorpholine, azepane, 1,4-diazepane, 1,4-oxazepane and 1,4-thiazepane; or

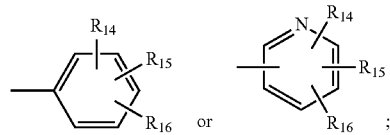

wherein X can be a bond, O, S or NR19;

R17, R18 and R19 are each independently be H, C1-C6 straight chain alkyl, C3-C6 branched chain alkyl, C1-C6 hydroxyalkyl, alkoxyalkyl in which the alkoxy and alkyl portions each independently contain from 1 to 6 carbon atoms, —CF3; or R17 and R18 can be taken together to form a 4 to 7 membered optionally substituted ring that can contain additional heteroatoms such as N, O or S;

r is an integer ranging from 0 to 3;

t is an integer ranging from 1 to 2; and u is an integer ranging from 1 to 6.

In some embodiments, the compounds of Formula IV are of the Formula IVa:

Formula IVa and pharmaceutically acceptable salts, hydrates, solvates, prodrugs, enantiomers, and stereoisomers thereof;

wherein:

F is a heteroaryl selected from pyridine, pyrazine, pyridazine, pyrimidine, 1,2,4-triazine or 1,3,5-triazine, optionally substituted with halogen, hydroxyl group, —CF3 group, C1-C6 alkoxy group, C1-C6 straight chain alkyl, C3-C6 branched chain alkyl or C3-C6 cycloalkyl group, wherein the number of substituents does not exceed the number of available C—H bonds of the heteroaryl; with multiple substitutions, each substituent on the heteroaryl is chosen independent of the other substituents;

m is an integer ranging from 0 to 3;

p is an integer ranging from 1 to 5;

H is —S(O)n-(CH2)q-, —O—(CH2)q-, or —C(O)—(CH2)q-;

n is an integer ranging from 0 to 2;

q is an integer ranging from 0 to 5;

K is selected from

R13 is H, C1-C6 straight chain alkyl, C3-C6 branched chain alkyl or C3-C6 cycloalkyl;

R20 is H, —CF3, C1-C6 straight chain alkyl, C3-C6 branched chain alkyl or C3-C6 cycloalkyl;

R14, R15 and R16 are each independently H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles selected from pyrrolidine, piperidine, piperazine, morpholine, thiomorpholine, azepane, 1,4-diazepane, 1,4-oxazepane and 1,4-thiazepane; or

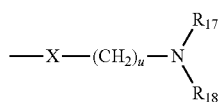

wherein X can be a bond, O, S or NR19;

R17, R18 and R19 are each independently H, C1-C6 straight chain alkyl, C3-C6 branched chain alkyl, C1-C6 hydroxyalkyl, alkoxyalkyl in which the alkoxy and alkyl portions each independently contain from 1 to 6 carbon atoms, —CF3; or R17 and R18 can be taken together to form a 4 to 7 membered optionally substituted ring containing 0-4 heteroatoms selected from N, O or S;

r is an integer ranging from 0 to 3;

t is an integer ranging from 1 to 2; and u is an integer ranging from 1 to 6.

In some embodiments, the compounds of Formula V are of the Formula Va:

Formula Va

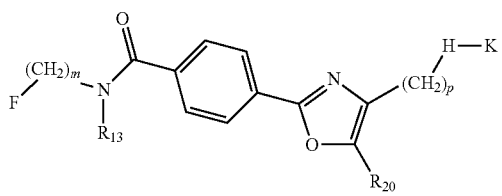

and pharmaceutically acceptable salts, hydrates, solvates, prodrugs, enantiomers, and stereoisomers thereof;

wherein:

F is a heteroaryl selected from pyridine, pyrazine, pyridazine, pyrimidine, 1,2,4-triazine or 1,3,5-triazine, optionally substituted with halogen, hydroxyl group, —CF3 group, C1-C6 alkoxy group, C1-C6 straight chain alkyl, C3-C6 branched chain alkyl or C3-C6 cycloalkyl group, wherein the number of substituents does not exceed the number of available C—H bonds of the heteroaryl; with multiple substitutions, each substituent on the heteroaryl is chosen independent of the other substituents;

m is an integer ranging from 0 to 3;

p is an integer ranging from 1 to 5;

H is selected from —S(O)n-(CH2)q-, —O—(CH2)q-, or —C(O)—(CH2)q-;

n is an integer ranging from 0 to 2;

q is an integer ranging from 0 to 5;

K is selected from C3-C7 cycloalkyl optionally substituted with two or more of R14, R15, and R16, C1-C6 straight or branched optionally substituted alkyl,

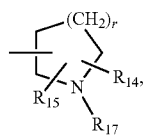 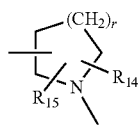 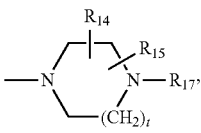

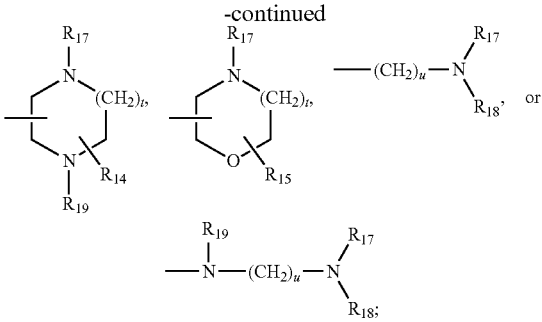

R13 is selected from H, C1-C6 straight chain alkyl, C3-C6 branched chain alkyl or C3-C6 cycloalkyl;

R20 is selected from H, —CF3, C1-C6 straight chain alkyl, C3-C6 branched chain alkyl or C3-C6 cycloalkyl;

R14, R15 and R16 can independently be H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles such as pyrrolidine, piperidine, piperazine, morpholine, thiomorpholine, azepane, 1,4-diazepane, 1,4-oxazepane and 1,4-thiazepane; or

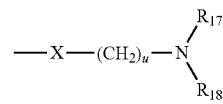

wherein X can be a bond, O, S or NR19;

R17, R18 and R19 are independently selected from H, C1-C6 straight chain alkyl, C3-C6 branched chain alkyl, C3-C6 cycloalkyl, C1-C6 hydroxyalkyl, alkoxyalkyl in which the alkoxy and alkyl portions each independently contain from 1 to 6 carbon atoms, —CF3, or —C(O)O—, or R17 and R18 can be taken together to form a 4 to 7 membered optionally substituted monocycloalkyl ring or 8-14 bicycloalkyl ring, each optionally containing between 1-3 heteroatoms selected from N, O or S, or;

r is an integer ranging from 0 to 3;

t is an integer ranging from 1 to 2; and u is an integer ranging from 1 to 6.

In some embodiments, the compounds of Formula VI are of the Formula VIa:

Formula VIa

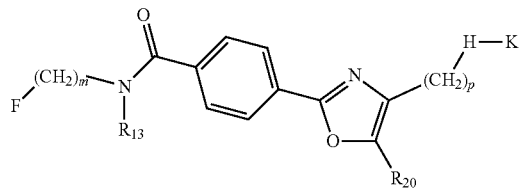

and pharmaceutically acceptable salts, hydrates, solvates, prodrugs, enantiomers, and stereoisomers thereof;

wherein:

F is selected from the group consisting of C3-C7 cycloalkyl optionally substituted with two or more of R14, R15, and R16, or C1-C6 straight or branched optionally substituted alkyl,

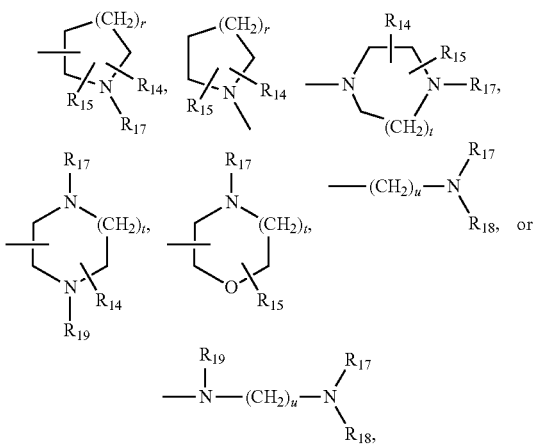

m is an integer ranging from 0 to 3;
p is an integer ranging from 1 to 5;
H is —S(O)n-(CH2)q-, —O—(CH2)q-, or —C(O)—(CH2)q-;
n is an integer ranging from 0 to 2;
q is an integer ranging from 0 to 5;
K is selected from

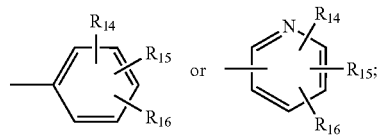

R13 is H, C1-C6 straight chain alkyl, C3-C6 branched chain alkyl or C3-C6 cycloalkyl;
R20 is H, —CF3, C1-C6 straight chain alkyl, C3-C6 branched chain alkyl or C3-C6 cycloalkyl
R14, R15 and R16 can independently be H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, optionally substituted nitrogen containing heterocycles such as pyrrolidine, piperidine, piperazine, morpholine, thiomorpholine, azepane, 1,4-diazepane, 1,4-oxazepane and 1,4-thiazepane; or

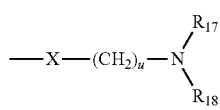

wherein X can be a bond, O, S or NR19;
R17, R18 and R19 are each independently be H, C1-C6 straight chain alkyl, C3-C6 branched chain alkyl, C1-C6 hydroxyalkyl, alkoxyalkyl in which the alkoxy and alkyl portions each independently contain from 1 to 6 carbon atoms, —CF3; or R17 and R18 can be taken together to form a 4 to 7 membered optionally substituted ring that can contain additional heteroatoms such as N, O or S;
r is an integer ranging from 0 to 3;
t is an integer ranging from 1 to 2; and
u is an integer ranging from 1 to 6.

Also provided are pharmaceutical compositions comprising at least one compound of Formulae I, II, III, IV, V, or VI and a pharmaceutically acceptable carrier.

Also provided are methods for treating diseases mediated by HIF-1α and/or HIF-2α.

Also provided are methods of targeting cells which express HIF-1α and/or HIF-2α.

Also provided are methods for treating diseases mediated by defective pVHL protein.

Also provided are methods of targeting cells which have defective pVHL protein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Definitions

As used in the present specification, the following words, phrases, and symbols are generally intended to have the meanings set forth below, except to the extent that the context in which they are used indicated otherwise. The following abbreviations and terms have the indicated meanings throughout:

"Subject" refers to an animal, such as a mammal, that has been or will be the object of treatment, observation, or experiment. The compounds and methods described herein may be useful for both human therapy and veterinary applications. In some embodiments, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

As used herein, "prevention" or "preventing" refers to a reduction of the risk of acquiring a given disease or disorder.

As used herein, "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

As used herein, "parenteral administration" and "administered parenterally" refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

A dash ("-") that is not between two letters or symbols is used to indicate a point of attachment for a substituent. For example, —CONH$_2$ is attached through the carbon atom.

The term "alkyl" refers to refers to a saturated straight or branched hydrocarbon, such as a straight or branched group of 1-20, 1-8, or 1-6 carbon atoms, referred to herein as $C_1$-$C_{20}$ alkyl, $C_1$-$C_8$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, and the like.

The term "alkenyl" refers to an unsaturated straight or branched hydrocarbon having at least one carbon-carbon double bond, such as a straight or branched group of 2-20, 2-8, or 2-6 carbon atoms, referred to herein as ($C_2$-$C_{20}$) alkenyl, ($C_2$-$C_8$) alkenyl, and ($C_2$-$C_6$) alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" refers to an unsaturated straight or branched hydrocarbon having at least one carbon-carbon triple bond, such as a straight or branched group of 2-20, 2-8, or 2-6 carbon atoms, referred to herein as $C_2$-$C_{20}$ alkynyl, $C_2$-$C_8$ alkynyl, and $C_2$-$C_6$ alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

"Cycloalkyl" refers to a saturated hydrocarbon ring group, having the specified number of carbon atoms, such as, for example from 3 to 7 ring carbon atoms. Examples of cycloalkyl groups include cyclopropyl, cyclobutyl, cyclopentyl, and cyclohexyl as well as bridged and caged saturated ring groups such as, for example, adamantane.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-20, 1-8, or 1-6 carbon atoms, referred to herein as ($C_1$-$C_{20}$) alkoxy, ($C_1$-$C_8$) alkoxy, and ($C_1$-$C_6$) alkoxy, respectively. Exemplary alkoxy groups include, but are not limited to methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like.

"Acyl" refers to the groups (alkyl)-C(O)—, (cycloalkyl)-C(O)—, (aryl)-C(O)—, (heteroaryl)-C(O)—, and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

"Alkoxycarbonyl" refers to an ester group of the formula (alkoxy)(C=O)— attached through the carbonyl carbon wherein the alkoxy group has the indicated number of carbon atoms. Thus, a $C_1$-$C_6$ alkoxycarbonyl group is an alkoxy group having from 1 to 6 carbon atoms attached through its oxygen to a carbonyl linker.

By "amino" is meant the group —NH$_2$.

"Aryl" encompasses: 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Heteroaryl" encompasses: 5- to 7-membered aromatic, monocyclic rings containing one or more, for example, from 1 to 4, or In some embodiments, from 1 to 3, heteroatoms chosen from N, O, and S, with the remaining ring atoms being carbon; and bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2-pyrazinyl, 2-pyrimidinyl, 3-pyrazolinyl, 2-thiazolyl, imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, and pyrazolyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined herein. Substituted heteroaryl also includes ring systems substituted with one or more oxide (—O⁻) substituents, such as pyridinyl N-oxides.

"Heterocycle" refers to a single aliphatic ring, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "cyano" as used herein refers to —CN.

The term "carboxy" as used herein refers to —COOH or its corresponding carboxylate salts (e.g., —COONa). The term carboxy also includes "carboxycarbonyl," for example, a carboxy group attached to a carbonyl group, for example, —C(O)—COOH or salts, such as —C(O)—COONa.

The term "nitro" refers to —NO$_2$.

The term "hydroxy" and "hydroxyl" refer to —OH.

The term "sulfinyl" includes the groups: —S(O)—H, —S(O)-(optionally substituted (C$_1$-C$_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)—H, —S(O$_2$)-(optionally substituted (C$_1$-C$_6$)alkyl), —S(O$_2$)-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocycyloxy); and —S(O$_2$)-(optionally substituted amino).

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, alkenyl, cycloalkyl, aryl, heterocycloalkyl, and heteroaryl (including "substituted" pyridinyl, pyrimidinyl, pyrazinyl, quinolinyl, pyrazolyl, and thiazolyl"), unless otherwise expressly defined, refer respectively to alkyl, alkenyl, cycloalkyl, aryl, heterocycloalkyl, and heteroaryl wherein one or more (such as up to 5, for example, up to 3) hydrogen atoms are replaced by a substituent independently chosen from:
—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, oxo (as a substituent for heterocycloalkyl), nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted C$_2$-C$_6$ alkenyl, optionally substituted cycloalkyl, optionally substituted aryl, optionally substituted heterocycloalkyl, and optionally substituted heteroaryl;

R$^b$ is chosen from hydrogen, optionally substituted C$_1$-C$_6$ alkyl, optionally substituted cycloalkyl, optionally substituted aryl, optionally substituted heterocycloalkyl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

In some embodiments, the terms "substituted" alkyl, alkenyl, cycloalkyl, aryl, heterocycloalkyl, and heteroaryl (including "substituted" pyridinyl, pyrimidinyl, pyrazinyl, quinolinyl, pyrazolyl, and thiazolyl"), unless otherwise expressly defined, refer respectively to alkyl, alkenyl, cycloalkyl, aryl, heterocycloalkyl, and heteroaryl wherein one or more (such as up to 5, for example, up to 3) hydrogen atoms are replaced by a substituent independently chosen from: —R$^a$, —OR$^b$, —COR$^b$, —CO$_2$R$^b$, NO$_2$, —NR$^b$R$^c$, —NR$^c$COR$^b$, —NR$^c$CO$_2$R$^a$, —NR$^c$CONR$^b$R$^c$, —NR$^c$SO$_2$R$^a$ and CN, where R$^a$, R$^b$, and R$^c$ are as described herein.

The term "substituted acyl" refers to the groups (substituted alkyl)-C(O)—, (substituted cycloalkyl)-C(O)—, (substituted aryl)-C(O)—, (substituted heteroaryl)-C(O)—, and (substituted heterocycloalkyl)-C(O)—, wherein substituted alkyl, substituted cycloalkyl, substituted aryl, substituted heteroaryl, and substituted heterocycloalkyl are as described herein. In some embodiments, the term "substituted acyl" refers to the groups (substituted alkyl)-C(O)—, (substituted aryl)-C(O)—, and (substituted heteroaryl)-C(O)—, wherein substituted alkyl, substituted aryl, and substituted heteroaryl are as described herein.

The term "substituted alkoxycarbonyl" refers to the group (substituted alkyl)-O—C(O)— wherein the group is attached to the parent structure through the carbonyl functionality and wherein "substituted alkyl" is as described herein.

The term "substituted cycloalkyloxy" refers to cycloalkyloxy wherein the cycloalkyl constituent is substituted (i.e., —O-(substituted cycloalkyl)) wherein "substituted cycloalkyl" is as described herein.

The term "substituted amino" refers to the group —NR$^b$R$^c$, —NR$^c$COR$^b$, —NR$^c$CO$_2$R$^a$, —NR$^c$CONR$^b$R$^c$, and —NR$^c$SO$_2$R$^a$, wherein R$^b$ and R$^c$ are as described herein. The term "substituted amino" also refers to N-oxides of the groups —NHR$^d$, and NR$^d$R$^d$ each as described herein. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "substituted aryloxy" refers to aryloxy wherein the aryl constituent is substituted (i.e., —O-(substituted aryl)) wherein "substituted aryl" is as described herein.

Compounds described herein include, but are not limited to, any stereoisomer, tautomer, rotomer, deuterated analogues, and/or pharmaceutically acceptable salt as defined herein.

The compounds described herein can be asymmetric (e.g., having one or more stereocenters). All stereoisomers, such as enantiomers and diastereomers, are intended unless otherwise indicated.

Compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional crystallization using a "chiral resolving acid" which is an optically active, salt-forming organic acid. Suitable resolving agents for fractional recrystallization methods are, for example, optically active acids, such as the D and L forms of tartaric acid, diacetyltartaric-acid, dibenzoyltartaric acid, mandelic acid, malic acid, lactic acid or the various optically active camphorsulfonic acids such as β-camphorsulfonic acid. Resolution of racemic mixtures can also be carried out by elution on a column packed with an optically active resolving agent (e.g., dinitrobenzoylphenylglycine). Suitable elution solvent composition can be determined by one skilled in the art.

Compounds as described herein can also include all isotopes of atoms occurring in the intermediates or final compounds. Isotopes include those atoms having the same atomic number but different mass numbers. For example, isotopes of hydrogen include tritium and deuterium.

The compounds disclosed herein can be used in different enriched isotopic forms, e.g., enriched in the content of $^2$H, $^3$H, $^{11}$C, $^{13}$C, $^{14}$C, and or $^{18}$F. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 12000, 110 pp.; Kabalka, George W. and Varma, Rajender S. The Synthesis of Radiolabeled Compounds via Organometallic Intermediates, Tetrahedron, 1989, 45(21), 6601-21, Evans, E. Anthony. Synthesis of radiolabeled compounds, J. Radioanal. Chem., 1981, 64(1-2), 9-32.

Compounds as described herein can also include tautomeric forms, such as keto-enol tautomers. Tautomeric forms can be in equilibrium or sterically locked into one form by appropriate substitution.

Compounds as described herein also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds as described herein also include pharmaceutically acceptable forms of the recited compounds, including chelates, non-covalent complexes, pharmaceutically acceptable prodrugs, and mixtures thereof.

A "solvate" is formed by the interaction of a solvent and a compound. The term "compound" is intended to include solvates of compounds. Similarly, "salts" includes solvates of salts. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

Provided herein are compounds of Formula I:

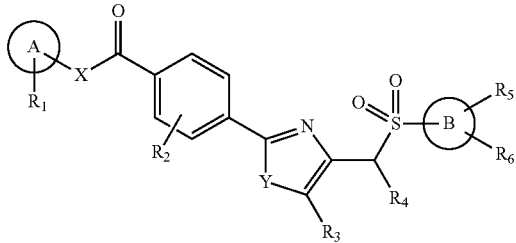

Formula I and pharmaceutically acceptable salts, hydrates, solvates, prodrugs, enantiomers and stereoisomers thereof;
wherein:
A, B, X, B, R₁, R₂, R₃, R₄, R₅, and R₆, are as defined above for Formula I;
provided that if A is 3-pyridinyl, X is CH₂NH, R₁, R₂, and R₄ are each hydrogen, R₃ is Me, and Y is O, then B is not phenyl or 4-methylphenyl.

In some embodiments, A is chosen from 2-pyrazinyl, 2-pyridinyl, 3-pyridinyl, 4-pyridinyl, 2-imidazolyl, and 5-imidazolyl, each of which is optionally substituted.

In some embodiments, A is chosen from 2-pyrazinyl, 2-pyridinyl, 3-pyridinyl, 4-pyridinyl, (1-methyl)-2-imidazolyl, and (1-methyl)-5-imidazolyl.

In some embodiments, A is chosen from 2-pyridinyl, 3-pyridinyl, and 4-pyridinyl.

In some embodiments, A is 3-pyridinyl.

In some embodiments, R₁ is chosen from hydrogen and optionally substituted alkyl.

In some embodiments, R₁ is chosen from hydrogen and lower alkyl.

In some embodiments, R₁ is hydrogen or methyl.

In some embodiments, R₁ is hydrogen.

In some embodiments, R₂, R₃ and R₄ are each independently chosen from hydrogen and optionally substituted alkyl.

In some embodiments, R₂ is hydrogen.

In some embodiments, R₃ is chosen from hydrogen and lower alkyl.

In some embodiments, R₃ is hydrogen or methyl.

In some embodiments, R₄ is chosen from hydrogen and lower alkyl.

In some embodiments, R₄ is hydrogen.

In some embodiments, X is chosen from CH₂CH₂NR, CH₂NR, or NR.

In some embodiments, R is chosen from hydrogen and lower alkyl.

In some embodiments, R is hydrogen.

In some embodiments, Y is chosen from O, S, or NR.

In some embodiments, R is chosen from hydrogen and lower alkyl.

In some embodiments, R is hydrogen.

In some embodiments, R is O.

In some embodiments, R is S.

In some embodiments, B is phenyl optionally substituted with one or more groups chosen from halo, alkyl, alkenyl, alkynyl, cycloalkyl, aryl, heteroaryl, heterocycloalkyl, hydroxyl, alkoxy, aryloxy, acyl, carboxy, alkoxycarbonyl, NO₂, optionally substituted amino, and CN, wherein each of said alkyl, alkenyl, alkynyl, alkoxy, cycloalkyl, aryl, heteroaryl, heterocycloalkyl, alkoxy, and aryloxy groups may be optionally independently substituted with one or more groups chosen from halo, alkyl, hydroxyl, alkoxy, carboxy, alkoxycarbonyl, heterocycloalkyl, and optionally substituted amino.

In some embodiments, B is phenyl optionally substituted with one or more groups chosen from optionally substituted amino, halo, and lower alkyl optionally substituted with optionally substituted amino, heterocycloalkyl, alkoxy, or hydroxyl.

In some embodiments, B is phenyl optionally substituted with one or more groups chosen from halo, optionally substituted amino and lower alkyl optionally substituted with optionally substituted amino or heterocycloalkyl.

In some embodiments, B is chosen from phenyl, 3-methylphenyl, 3-methoxyphenyl, 4-chlorophenyl, 4-tert-butylphenyl, 4-bromophenyl, 4-fluorophenyl, 4-methoxyphenyl, 4-(4-methylpiperazinyl)phenyl, 4-morpholinylphenyl, 3,5-dimethylphenyl, 2,4-dimethylphenyl, 3,4-dimethoxyphenyl.

In other illustrative embodiments, compounds of Formula I are as set forth below:

4-(5-Methyl-4-{[(4-methylphenyl)sulfonyl]methyl}-1,3-oxazol-2-yl)-N-(3-pyridinyl)benzamide;

4-(5-Methyl-4-{[(4-methylphenyl)sulfonyl]methyl}-1,3-oxazol-2-yl)-N-(4-pyridinyl)benzamide;

N-Methyl-4-(5-methyl-4-{[(4-methylphenyl)sulfonyl]methyl}-1,3-oxazol-2-yl)-N-(3-pyridinyl)benzamide;

4-(5-Methyl-4-{[(4-methylphenyl)sulfonyl]methyl}-1,3-oxazol-2-yl)-N-(2-pyridinylmethyl)benzamide;

4-(5-Methyl-4-{[(4-methylphenyl)sulfonyl]methyl}-1,3-oxazol-2-yl)-N-(3-pyridinylmethyl)benzamide;

4-(5-Methyl-4-{[(4-methylphenyl)sulfonyl]methyl}-1,3-oxazol-2-yl)-N-(4-pyridinylmethyl)benzamide;

N-Methyl-4-(5-methyl-4-{[(4-methylphenyl)sulfonyl]methyl}-1,3-oxazol-2-yl)-N-(3-pyridinylmethyl)benzamide;

4-(5-Methyl-4-{[(4-methylphenyl)sulfonyl]methyl}-1,3-oxazol-2-yl)-N-[2-(3-pyridinyl)ethyl]benzamide;

4-(5-Methyl-4-{[(4-methylphenyl)sulfonyl]methyl}-1,3-oxazol-2-yl)-N-(2-pyrazinylmethyl)benzamide;

N-[(1-Methyl-1H-imidazol-2-yl)methyl]-4-(5-methyl-4-{[(4-methylphenyl)sulfonyl]methyl}-1,3-oxazol-2-yl)benzamide;

N-[(1-Methyl-1H-imidazol-5-yl)methyl]-4-(5-methyl-4-{[(4-methylphenyl)sulfonyl]methyl}-1,3-oxazol-2-yl)benzamide;

4-{5-Methyl-4-[(phenylsulfonyl)methyl]-1,3-oxazol-2-yl}-N-(3-pyridinylmethyl)benzamide;

4-(4-{[(4-Chlorophenyl)sulfonyl]methyl}-5-methyl-1,3-oxazol-2-yl)-N-(3-pyridinylmethyl)benzamide;

4-(4-{[(4-tert-Butylphenyl)sulfonyl]methyl}-5-methyl-1,3-oxazol-2-yl)-N-(3-pyridinylmethyl)benzamide;

4-(4-{[(3,5-Dimethylphenyl)sulfonyl]methyl}-5-methyl-1,3-oxazol-2-yl)-N-(3-pyridinylmethyl)benzamide;

4-(4-{[(4-Bromophenyl)sulfonyl]methyl}-5-methyl-1,3-oxazol-2-yl)-N-(3-pyridinylmethyl)benzamide;

4-(5-Methyl-4-{[(3-methylphenyl)sulfonyl]methyl}-1,3-oxazol-2-yl)-N-(3-pyridinylmethyl)benzamide;

4-(4-{[(4-Methoxyphenyl)sulfonyl]methyl}-5-methyl-1,3-oxazol-2-yl)-N-(3-pyridinylmethyl)benzamide;

4-(5-Methyl-4-{[(3-methoxyphenyl)sulfonyl]methyl}-1,3-oxazol-2-yl)-N-(3-pyridinylmethyl)benzamide;

4-(4-{[(3,4-Dimethoxyphenyl)sulfonyl]methyl}-5-methyl-1,3-oxazol-2-yl)-N-(3-pyridinylmethyl)benzamide;

4-(5-Methyl-4-{[(2,4-dimethylphenyl)sulfonyl]methyl}-1,3-oxazol-2-yl)-N-(3-pyridinylmethyl)benzamide;

4-(4-{[(4-Fluorophenyl)sulfonyl]methyl}-5-methyl-1,3-oxazol-2-yl)-N-(3-pyridinylmethyl)benzamide;

4-[5-Methyl-4-({[4-(4-methyl-1-piperazinyl)phenyl]
sulfonyl}methyl)-1,3-oxazol-2-yl]-N-(3-pyridinylm-
ethyl)benzamide;
4-[5-Methyl-4-({[4-(4-morpholinyl)phenyl]
sulfonyl}methyl)-1,3-oxazol-2-yl]-N-(3-pyridinylm-
ethyl)benzamide;
4-(4-{[(4-Methylphenyl)sulfonyl]methyl}-1,3-thiazol-2-yl)-
N-(3-pyridinylmethyl)benzamide;
or a pharmaceutically acceptable salt thereof.

Described herein are compounds of Formula II:

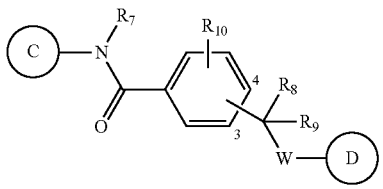

and pharmaceutically acceptable salts, hydrates, solvates, prodrugs, enantiomers, and stereoisomers thereof;
wherein C, $R_7$, $R_8$, $R_9$, $R_{10}$, W, and D are as defined above for Formula II.

In some embodiments, C is chosen from 2-pyridyl, 3-pyridyl, 4-pyridyl, 2-pyrazinyl, 2-pyrimidinyl, 3-pyrazolinyl, imidazolinyl, isoxazolinyl, oxazolinyl, thiadiazolinyl, thiazole, tetrazolyl, benzoimidazolinyl, indolinyl, pyridizinyl, triazolyl, quinolinyl, and pyrazolyl, each of which is optionally substituted. In some embodiments, A is chosen from 3-pyrazolyl, 3-quinolinyl, 5-quinolinyl, 2-pyrazinyl, 2-pyrimidinyl, 2-pyridinyl, 3-pyridinyl, and 4-pyridinyl. In some embodiments, A is chosen from 2-pyridinyl, 3-pyridinyl, and 4-pyridinyl. In some embodiments, A is 3-pyridinyl.

In some embodiments, C is

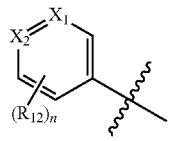

wherein
n is 0, 1 or 2;
for each occurrence, $R_{12}$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy; and
$X_1$ and $X_2$ are each independently chosen from N, NO, and CH, provided that at least one of $X_1$ and $X_2$ is not CH.
In some embodiments, $X_1$ is N and $X_2$ is CH.
In some embodiments, for each occurrence, $R_{12}$ is independently chosen from methyl, methoxy, halo, nitro, morpholino, trifluoromethyl, and NHC(O)Me.
In some embodiments, n is 0.
In some embodiments, $R_7$ is chosen from hydrogen and optionally substituted alkyl. In some embodiments, $R_7$ is chosen from hydrogen and lower alkyl. In some embodiments, $R_7$ is hydrogen or methyl. In some embodiments, $R_7$ is hydrogen.
In some embodiments, $R_8$ and $R_9$ are each independently chosen from hydrogen and optionally substituted alkyl. In some embodiments, $R_8$ is hydrogen.

In some embodiments, $R_9$ is chosen from hydrogen and lower alkyl. In some embodiments, $R_9$ is hydrogen.
In some embodiments, $R_{10}$ is chosen from hydrogen, hydroxy, lower alkyl, lower alkoxy, halo, carboxy, and nitro. In some embodiments, $R_{10}$ is chosen from hydrogen, methyl, halo, and nitro. In some embodiments, $R_{10}$ is chosen from hydrogen and lower alkyl. In some embodiments, $R_{10}$ is hydrogen.
In some embodiments, W is —NRSO$_2$. In some embodiments, W is —NRCO—. In some embodiments, W is SO$_2$NR—.
In some embodiments, R is chosen from hydrogen and lower alkyl. In some embodiments, R is hydrogen.
In some embodiments, D is pyridyl, pyrazinyl, pyrimidinyl, pyrazolinyl, thiazolyl, imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, and pyrazolyl.
In some embodiments, D is an optionally substituted pyridyl ring.
In some embodiments, D is pyridyl optionally substituted with one or more groups chosen from halo, alkyl, alkenyl, alkynyl, cycloalkyl, aryl, heteroaryl, heterocycloalkyl, hydroxyl, alkoxy, aryloxy, acyl, carboxy, alkoxycarbonyl, NO$_2$, optionally substituted amino, and CN, wherein each of said alkyl, alkenyl, alkynyl, alkoxy, cycloalkyl, aryl, heteroaryl, heterocycloalkyl, alkoxy, and aryloxy groups may be optionally independently substituted with one or more groups chosen from halo, alkyl, hydroxyl, alkoxy, carboxy, alkoxycarbonyl, heterocycloalkyl, and optionally substituted amino.
In some embodiments, D is pyridyl optionally substituted with one or more groups chosen from optionally substituted amino, halo, and lower alkyl optionally substituted with optionally substituted amino, heterocycloalkyl, alkoxy, or hydroxyl.
In some embodiments, D is pyridyl optionally substituted with one or more groups chosen from halo, optionally substituted amino and lower alkyl optionally substituted with optionally substituted amino or heterocycloalkyl.
In some embodiments, D is chosen from pyridyl, 2-methylpyridyl, 2-fluoropyridyl, 2-chloropyridyl, 2-bromopyridyl, 2-methoxycarbonylpyridyl, 2-trifluoromethylpyridyl, 2-cyanopyridyl, 3-aminopyridyl, 3-methoxypyridyl, 3-methylpyridyl, 3-fluoropyridyl, 3-chloropyridyl, 3-bromopyridyl, 3-trifluoromethylpyridyl, 4-ethynylpyridyl, 3-cyanopyridyl, 3-nitropyridyl, 3-pyridylpyridyl, 3-(2-pyrimidinyl)pyridyl, 3-(1-methyl-1H-pyrazol-3-yl)pyridyl, 3-(5-methyl-1,3,4-oxadiazol-2-yl)pyridyl, 3-(5-methyl-1,2,4-oxadiazol-2-yl)pyridyl, 3-(2-methyl-1,3-thiazol-4-yl)pyridyl, 4-aminopyridyl, 4-methoxypyridyl, 4-butoxypyridyl, 4-phenoxypyridyl, 4-methylpyridyl, 4-propylpyridyl, 4-tert-butylpyridyl, 4-(1-adamantyl)pyridyl, 4-(3-chloro-1-adamantyl)pyridyl, 4-methoxycarbonylethylpyridyl, 4-acetamidopyridyl, 4-fluoropyridyl, 4-chloropyridyl, 4-bromopyridyl, 4-iodopyridyl, 4-trifluoromethoxypyridyl, 4-methoxycarbonylpyridyl, 4-acetylpyridyl, 4-trifluoromethylpyridyl, 4-cyanopyridyl, 4-nitropyridyl, 4'-methoxy[1,1'-bipyridyl]-4-yl, 4'-methyl[1,1'-bipyridyl]-4-yl, 4-pyridylpyridyl, 4'-fluoro[1,1'-bipyridyl]-4-yl, 4'-chloro[1,1'-bipyridyl]-4-yl, 4-(2-pyrimidinyl)pyridyl, 4-(1H-pyrazol-1-yl)pyridyl, 4-(2-methyl-1,3-thiazol-4-yl)pyridyl, 4-(1,3-oxazol-5-yl)pyridyl, 3,4-dimethoxypyridyl, 3-tert-butyl-4-methoxypyridyl, 2,3,4,5,6-pentamethylpyridyl, 2,4-dimethylpyridyl, 3,4-dimethylpyridyl, 3,5-dimethylpyridyl, 3-fluoro-4-methylpyridyl, 3-chloro-2-methylpyridyl, 3-chloro-4-methylpyridyl, 3,4-dichloropyridyl, 3-cyano-4-fluoropyridyl, 2-naphthalenyl, 5-(dimethylamino)-2-naphthalenyl, 2,3-dihydro-5-indeneyl, 2-(dimethylamino)-2,3-dihydro-5-indeneyl, 4-(4-methylpiperazin-1-yl)pyridyl, 4-(dimethylamino)methylphenyl, 4-(diethylamino)methylphenyl, 4-(dipropylamino)methylphenyl, 4-(1-pyrrolidinylmethyl)phenyl, 4-(1-piperidinylmethyl)phenyl, 4-(1-azepanylmethyl)phenyl, 4-(4-morpholinylmethyl)phenyl, 4-(4-methoxy-1-piperidinyl)methylphenyl, 4-(4-methyl-1-piperazinyl)methylphenyl, 4-(3-hydroxypropyl)phenyl, 3-morpholinophenyl, 4-morpholinophenyl, 4-(1-piperidinyl)pyridyl, (4-methoxy-1-piperidinyl)pyridyl, (21-amino-4,7,10,13,16,19-hexaoxahenicos-1-yl)pyridyl, {[3-(4-morpholinyl)propyl]amino}pyridyl, 3-(4-methyl-1-piperazinyl)pyridyl, 4-{[2-(dimethylamino)ethyl]amino}pyridyl, 3'-(trifluoromethyl)[1,1'-bipyridyl], 4-benzylpyridyl, 4-[3-(4-morpholinyl)-1-propynyl]pyridyl, 4-[3-(dimethylamino)-1-propynyl]pyridyl, 4-[3-(4-morpholinyl)propyl]pyridyl, 4-[3-(dimethylamino)propyl]pyridyl, 3-(propionylamino)pyridyl, and 3-(acryloylamino)pyridyl.

In some embodiments, D is chosen from 3-fluoropyridyl, 3-chloropyridyl, 3-bromopyridyl, 3-(2-pyrimidinyl)pyridyl, 3-(1-methyl-1H-pyrazol-3-yl)pyridyl, 3-(5-methyl-1,3,4-oxadiazol-2-yl)pyridyl, 3-(5-methyl-1,2,4-oxadiazol-2-yl)pyridyl, 4-butoxypyridyl4-tert-butylpyridyl, 4-(2-pyrimidinyl)pyridyl, 3,4-dimethoxypyridyl, 3-tert-butyl-4-methoxypyridyl, 3,4-dimethylpyridyl, 3,5-dimethylpyridyl, 3-fluoro-4-methylpyridyl, 3-chloro-4-methylpyridyl, 2-(dimethylamino)-2,3-dihydro-5-indeneyl, 4-(4-methylpiperazin-1-yl)pyridyl, 4-(dimethylamino)methylpyridyl, 4-(diethylamino)methylpyridyl, 4-(dipropylamino)methylpyridyl, 4-(1-pyrrolidinylmethyl)pyridyl, 4-(1-piperidinylmethyl)pyridyl, 4-(1-azepanylmethyl)pyridyl, 4-(4-morpholinylmethyl)pyridyl, 4-(4-methoxy-1-piperidinyl)methylpyridyl, 4-(4-methyl-1-piperazinyl)methylpyridyl, and 4-(3-hydroxypropyl)pyridyl.

In some embodiments, the radical

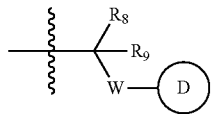

is attached to the phenyl ring at the 3 position. In some embodiments, the radical

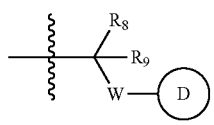

is attached to the phenyl ring at the 4 position.

In other illustrative embodiments, compounds of Formula II and IIA are as set forth below:

N-(3-Pyridinyl)-4-{[(3-pyridylsulfonyl)amino]methyl}benzamide II-1;
4-({[(6-Chloro-3-pyridinyl)sulfonyl[amino}methyl)-N-(3-pyridinyl)benzamide II-2;
4-({[(6-Phenoxy-3-pyridinyl)sulfonyl]amino}methyl)-N-(3-pyridinyl)benzamide II-3;
N-(3-Pyridinyl)-4-{[(2-thienylsulfonyl)amino]methyl}benzamide II-4;
N-(3-Pyridinyl)-4-{[(3-thienylsulfonyl)amino]methyl}benzamide II-5;
4-({[(1,2-Dimethyl-1H-imidazol-5-yl)sulfonyl]amino}methyl)-N-(3-pyridinyl)benzamide II-6;
N-(3-pyridinyl)-4-{[(4H-1,2,4-triazol-3-ylsulfonyl)amino]methyl}benzamide II-7; and
N-(3-Pyridinyl)-4-{[(2-furanylsulfonyl)amino]methyl}benzamide II-8.

Also described herein are compounds of Formula III:

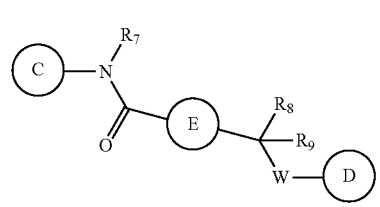

and pharmaceutically acceptable salts, hydrates, solvates, prodrugs, enantiomers, and stereoisomers thereof;
wherein C, E, D, $R_7$, $R_8$, $R_9$, and W are as described above for Formula III.

In some embodiments, A is chosen from 2-thiazolyl, 3-pyrazolyl, 3-quinolinyl, 5-quinolinyl, 2-pyrazinyl, 2-pyrimidinyl, 2-pyridinyl, 3-pyridinyl, and 4-pyridinyl, each of which is optionally substituted. In some embodiments, A is chosen from 2-thiazolyl, 3-pyrazolyl, 3-quinolinyl, 5-quinolinyl, 2-pyrazinyl, 2-pyrimidinyl, 2-pyridinyl, 3-pyridinyl, and 4-pyridinyl. In some embodiments, A is chosen from 2-pyridinyl, 3-pyridinyl, and 4-pyridinyl. In some embodiments, A is 3-pyridinyl.

In some embodiments, C is

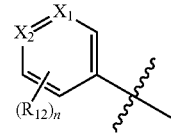

wherein
n is 0, 1 or 2;
for each occurrence, $R_{12}$ is independently chosen from alkyl optionally substituted with one or more halo, alkoxy, halo, nitro, heterocycloalkyl, and amino optionally substituted with $C(O)R_a$, wherein $R_a$ is chosen from alkyl and optionally substituted alkoxy; and
$X_1$ and $X_2$ are each independently chosen from N, NO, and CH, provided that at least one of $X_1$ and $X_2$ is not CH.

In some embodiments, $X_1$ is N and $X_2$ is CH.

In some embodiments, for each occurrence, $R_5$ is independently chosen from methyl, methoxy, halo, nitro, morpholino, trifluoromethyl, and NHC(O)Me.

In some embodiments, n is 0.

In some embodiments, $R_7$ is chosen from hydrogen and optionally substituted alkyl. In some embodiments, $R_7$ is chosen from hydrogen and lower alkyl. In some embodiments, $R_7$ is hydrogen or methyl. In some embodiments, $R_7$ is hydrogen.

In some embodiments, $R_8$ and $R_9$ are each independently chosen from hydrogen and optionally substituted alkyl. In some embodiments, $R_8$ is hydrogen.

In some embodiments, $R_9$ is chosen from hydrogen and lower alkyl. In some embodiments, $R_9$ is hydrogen.

In some embodiments, W is —N(R)SO$_2$R$_x$—. In some embodiments, W is —SO$_2$N(R)R$_x$—. In some embodiments, W is —N(R)COR$_x$—.

In some embodiments, R is chosen from hydrogen and lower alkyl. In some embodiments, R is hydrogen.

In some embodiments, $R_x$ is an optionally substituted bivalent $C_0$-$C_6$alkylene. In certain embodiments, the bivalent $C_0$-$C_6$alkylene is $C_4$ alkylene. In other embodiments, $R_X$ is optionally substituted bivalent $C_3$-$C_6$cycloalkyl. In certain embodiments, the bivalent $C_3$-$C_6$cycloalkyl is $C_6$cycloalkyl. In other embodiments, $R_X$ is optionally substituted phenyl.

In some embodiments, E is a $C_5$-$C_6$cycloalkyl. In some embodiments, the $C_5$-$C_6$cycloalkyl is $C_6$cycloalkyl. In some embodiments, E is a $C_5$-$C_6$heterocyle.

In some embodiments, E is phenyl.

In another aspect, compounds of Formula IIIA are provided:

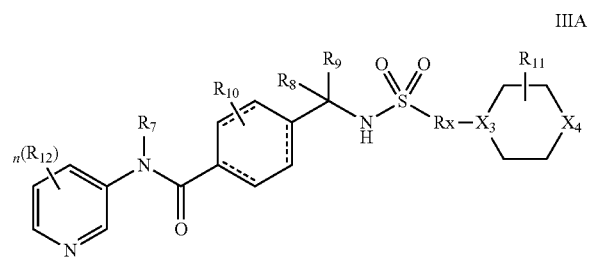

IIIA wherein: $X_3$ $X_4$, -----, $R_7$, $R_8$, $R_9$, $R_{10}$, $R_{11}$, $R_{12}$, and Rx are as defined above for Formula IIIA.

In some embodiments, X3 is CH. In some embodiments, X3 is N.

In some embodiments, $X_4$ is NH. In some embodiments, $X_4$ is $NR_7$ and $R_7$ is $C_1$alkyl.

In some embodiments, $R_X$ is a bivalent $C_4$alkylene. In some embodiments, $R_X$ is a bivalent $C_6$cycloalkyl. In some embodiments, $R_X$ is phenyl.

In some embodiments, all three ----- represent single bonds. In some embodiments, all three ----- represent double bonds.

In another illustrative embodiment, a compound of Formula III and Formula IIIA is as set forth below:
4-((4-(4-methylpiperazin-1-yl)cyclohexanesulfonamido)methyl)-N-(pyridin-3-yl)benzamide III-1.

Described herein are compounds of Formula IV:

Formula IV

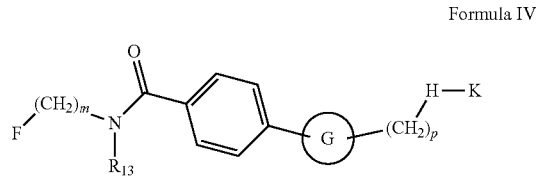

and pharmaceutically acceptable salts, hydrates, solvates, prodrugs, enantiomers, and stereoisomers thereof;
wherein F, G, H, K, $R_{13}$, m and p are as defined above for Formula IV.

In some embodiments, F is chosen from 2-pyridyl, 3-pyridyl, 4-pyridyl, 2-pyrazinyl, 2-pyrimidinyl, 3-pyrazolinyl, imidazolinyl, triazolyl, and pyrazolyl, each of which is optionally substituted. In some embodiments, A is chosen from 3-pyrazolyl, 2-pyrazinyl, 2-pyrimidinyl, 2-pyridinyl, 3-pyridinyl, and 4-pyridinyl. In some embodiments, A is chosen from 2-pyridinyl, 3-pyridinyl, and 4-pyridinyl. In some embodiments, A is 3-pyridinyl.

In some embodiments, G is selected from imidazole, pyrazole, and triazole.

In some embodiments, G is selected from oxazole, isoxazole, and oxadiazole.

In some embodiments, G is selected from thiophene, thiazole, isothiazole, and thiadiazole.

In some embodiments, H is —S(O)n-(CH2)q-.

In some embodiments, H is —S(O)$_2$.

In some embodiments, K is

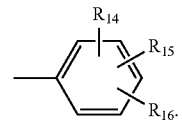

In some embodiments, K is

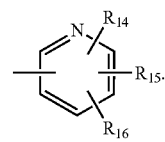

In another aspect, the compounds of Formula V are described:

Formula V

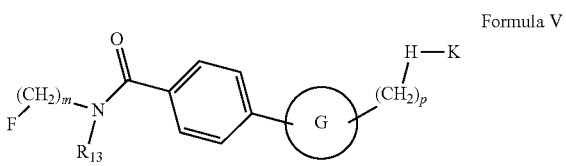

and pharmaceutically acceptable salts, hydrates, solvates, prodrugs, enantiomers, and stereoisomers thereof;
wherein F, G, H, K, $R_{13}$, m and p are as defined above for Formula V.

In some embodiments, F is chosen from 2-pyridyl, 3-pyridyl, 4-pyridyl, 2-pyrazinyl, 2-pyrimidinyl, 3-pyrazolinyl, imidazolinyl, triazolyl, and pyrazolyl, each of which is optionally substituted. In some embodiments, F is chosen from 3-pyrazolyl, 2-pyrazinyl, 2-pyrimidinyl, 2-pyridinyl, 3-pyridinyl, and 4-pyridinyl.

In some embodiments, F is chosen from 2-pyridinyl, 3-pyridinyl, and 4-pyridinyl.

In some embodiments, F is 3-pyridinyl.

In some embodiments, G is selected from imidazole, pyrazole, and triazole.

In some embodiments, G is selected from oxazole, isoxazole, and oxadiazole.

In some embodiments, G is selected from thiophene, thiazole, isothiazole, and thiadiazole.

In some embodiments, H is —S(O)n-(CH2)q-.

In some embodiments, H is —S(O)$_2$.

In some embodiments, K is C3-C7 cycloalkyl optionally substituted with two or more of R14, R15, and R16.

In some embodiments, K is C 1-C6 straight or branched optionally substituted alkyl.

In some embodiments, K is,

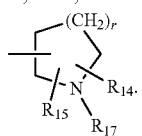

In some embodiments, K is,

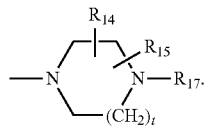

In some embodiments, K is,

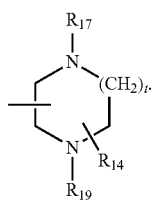

In some embodiments, K is,

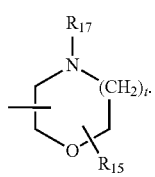

In some embodiments, K is,

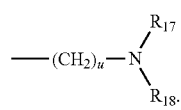

In some embodiments, K is,

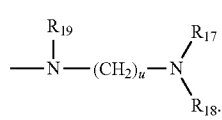

In one aspect, compounds of Formula VI are provided:

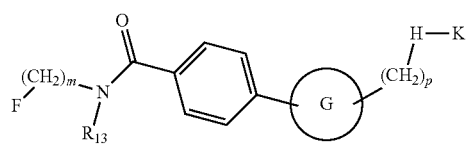

Formula VI and pharmaceutically acceptable salts, hydrates, solvates, prodrugs, enantiomers, and stereoisomers thereof;

wherein F, G, H, K, $R_{13}$, m and p are as defined above for Formula VI.

In some embodiments, F is C3-C7 cycloalkyl optionally substituted with two or more of R14, R15, and R16.

In some embodiments, F is C1-C6 straight or branched optionally substituted alkyl.

In some embodiments, F is

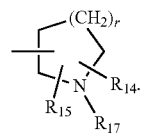

In some embodiments, F is

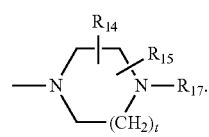

In some embodiments, F is

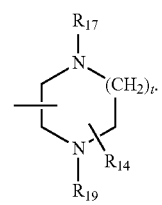

In some embodiments, F is

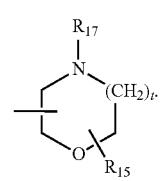

In some embodiments, F is

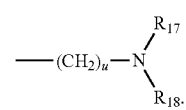

In some embodiments, F is

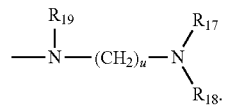

In some embodiments, G is selected from imidazole, pyrazole, and triazole.

In some embodiments, G is selected from oxazole, isoxazole, and oxadiazole.

In some embodiments, G is selected from thiophene, thiazole, isothiazole, and thiadiazole.

In some embodiments, H is —S(O)n-(CH2)q-.

In some embodiments, H is —S(O)2.

In some embodiments, K is

[structure with $R_{14}$, $R_{15}$, $R_{16}$ on a six-membered carbocyclic ring]

In some embodiments, K is

[structure with N in ring, and $R_{14}$, $R_{15}$, $R_{16}$]

In other illustrative embodiments, compounds of Formula IV, V, and VI are as set forth below:

5-methyl-4-((piperidin-4-ylsulfonyl)methyl)oxazol-2-yl)-N-(pyridine-3-ylmethyl)benzamide;

(4-(5-methyl-4-((1-methylpiperidin-4-ylsulfonyl)methyl)oxazol-2-yl)-N-(pyridin-3-ylmethyl)benzamide);

4-(4-((1-isobutylpiperidin-4-ylsulfonyl)methyl)-5-methyloxazol-2-yl)-N-(pyridin-3-ylmethyl)benzamide;

4-[5-methyl-4-([[4-(pyrrolidin-1-yl)cyclohexane]sulfonyl]methyl)-1,3-oxazol-2-yl]-N-(pyridin-3-ylmethyl)benzamide;

4-[5-methyl-4-([[4-(piperidin-1-yl)cyclohexane]sulfonyl]methyl)-1,3-oxazol-2-yl]-N-(pyridin-3-ylmethyl)benzamide;

4-(4-[[(4-aminocyclohexane)sulfonyl]methyl]-5-methyl-1,3-oxazol-2-yl)-N-(pyridin-3-ylmethyl)benzamide;

4-[5-methyl-4-([[4-(pyrrolidin-1-yl)cyclohexane]sulfonyl]methyl)-1,3-oxazol-2-yl]-N-(pyridin-3-ylmethyl)benzamide;

4-[5-methyl-4-([[4-(piperidin-1-yl)cyclohexane]sulfonyl]methyl)-1,3-oxazol-2-yl]-N-(pyridin-3-ylmethyl)benzamide;

4-[4-([[(1S,3S)-3-aminocyclopentane]sulfonyl]methyl)-5-methyl-1,3-oxazol-2-yl]-N-(pyridin-3-ylmethyl)benzamide;

4-[5-methyl-4-([[(1S,3S)-3-(pyrrolidin-1-yl)cyclopentane]sulfonyl]methyl)-1,3-oxazol-2-yl]-N-(pyridin-3-ylmethyl)benzamide;

4-[5-methyl-4-([[(1S,3S)-3-(piperidin-1-yl)cyclopentane]sulfonyl]methyl)-1,3-oxazol-2-yl]-N-(pyridin-3-ylmethyl)benzamide;

4-[4-([[(1R,3S)-3-aminocyclopentane]sulfonyl]methyl)-5-methyl-1,3-oxazol-2-yl]-N-(pyridin-3-ylmethyl)benzamide;

4-[5-methyl-4-([[(1R,3S)-3-(pyrrolidin-1-yl)cyclopentane]sulfonyl]methyl)-1,3-oxazol-2-yl]-N-(pyridin-3-ylmethyl)benzamide;

4-[5-methyl-4-([[(1R,3S)-3-(piperidin-1-yl)cyclopentane]sulfonyl]methyl)-1,3-oxazol-2-yl]-N-(pyridin-3-ylmethyl)benzamide;

4-(4-((1-tert-butylpiperidin-4-ylsulfonyl)methyl)-5-methyloxazol-2-yl)-N-(pyridin-3-ylmethyl)benzamide;

4-(5-methyl-4-((1-neopentylpiperidin-4-ylsulfonyl)methyl)oxazol-2-yl)-N-(pyridin-3-ylmethyl)benzamide;

4-(4-((1-isobutylpiperidin-4-ylsulfonyl)methyl)-5-methyloxazol-2-yl)-N-(pyridin-3-ylmethyl)benzamide;

4-(4-(((2S,6R)-1-isobutyl-2,6-dimethylpiperidin-4-ylsulfonyl)methyl)-5-methyloxazol-2-yl)-N-(pyridin-3-ylmethyl)benzamide;

4-(4-(((2S,6R)-2,6-dimethylpiperidin-4-ylsulfonyl)methyl)-5-methyloxazol-2-yl)-N-(pyridin-3-ylmethyl)benzamide;

4-(5-methyl-4-((1-(2,2,2-trifluoroethyl)piperidin-4-ylsulfonyl)methyl)oxazol-2-yl)-N-(pyridin-3-ylmethyl)benzamide;

4-(4-((1-isobutyl-2-oxopiperidin-4-ylsulfonyl)methyl)-5-methyloxazol-2-yl)-N-(pyridin-3-ylmethyl)benzamide;

4-(4-((1-isobutyl-2,6-dioxopiperidin-4-ylsulfonyl)methyl)-5-methyloxazol-2-yl)-N-(pyridin-3-ylmethyl)benzamide; and 4-(4-((4-isobutylpiperidin-1-ylsulfonyl)methyl)-5-methyloxazol-2-yl)-N-(pyridin-3-ylmethyl)benzamide.

Methods for obtaining the compounds and pharmaceutically acceptable salts described herein will be apparent to those of ordinary skill in the art, suitable procedures being described, for example, in the reaction schemes and examples below, and the references cited herein.

Reaction Scheme 1

[Reaction scheme showing compound 100 (4-formyl methyl benzoate) + compound 101 (oxime with $R_3$, $R_4$) → Step 1 → compound 102 (N-oxide oxazole with $R_2$, $R_3$, $R_4$, CO2Me) → Step 2 → compound 103 (chloromethyl oxazole with $R_2$, $R_3$, $R_4$) + B—SO2Na → Step 3]

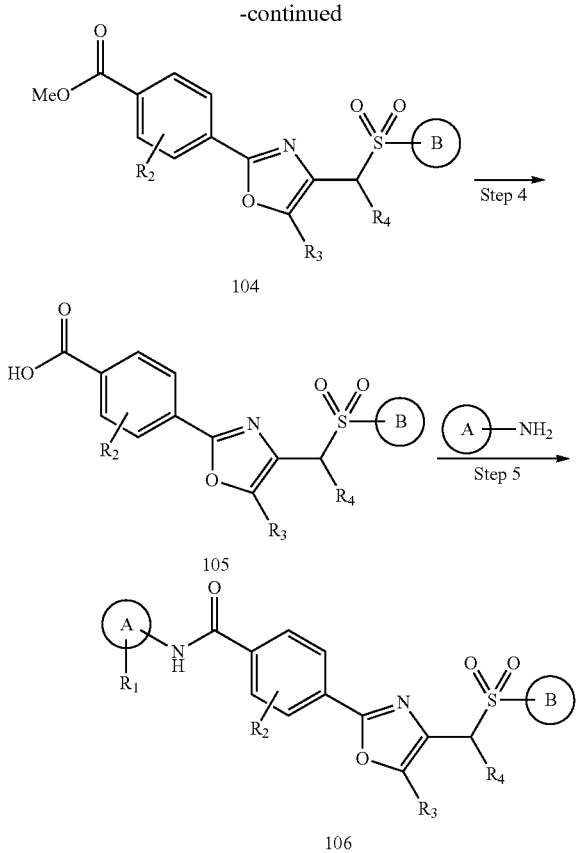

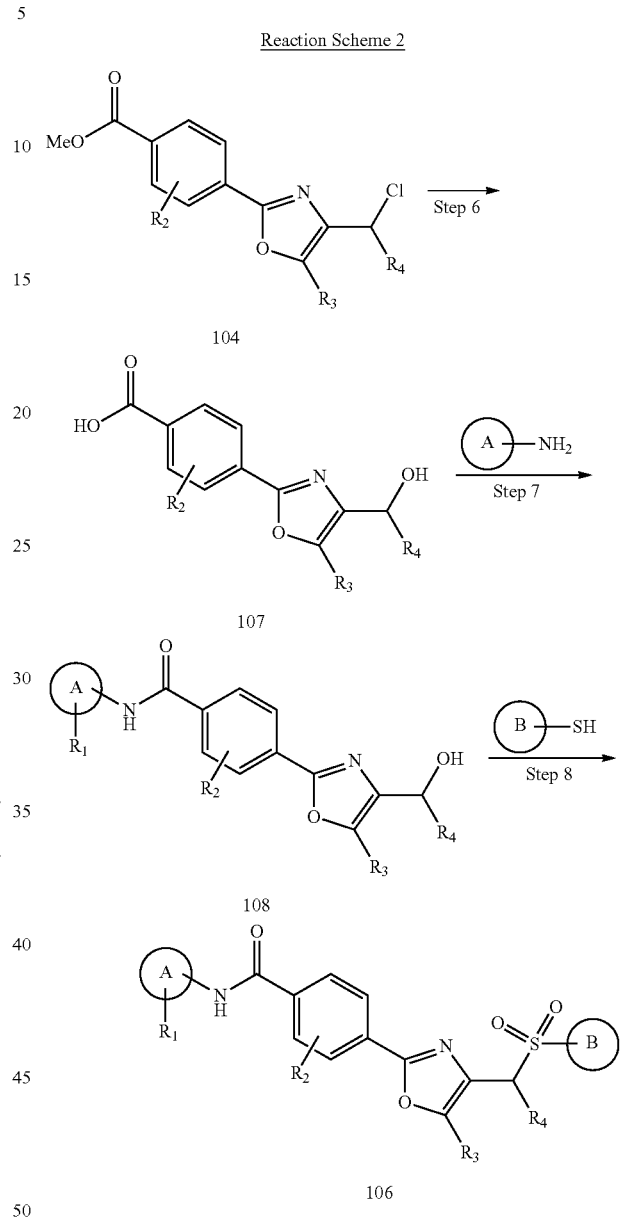

Referring to Reaction Scheme 1, Step 1, a compound of Formula 101, is combined with compound 100 in the presence of an acid (such as gaseous HCl) to give a compound of Formula 102, which is isolated and optionally purified.

Referring to Reaction Scheme 1, Step 2, a mixture of a compound of Formula 102 is combined with a chlorinating agent (such as $POCl_3$) in an organic solvent to give the product, a compound of Formula 103, which is isolated and optionally purified.

Referring to Reaction Scheme 1, Step 3, a mixture of a compound of Formula 103 is combined with a arylsulfinic acid and a base, or with the salt of the arylsulfinic acid, in a polar organic solvent (such as DMF and/or THF) to give the product, a compound of Formula 104, which is isolated and optionally purified.

Referring to Reaction Scheme 1, Step 3, an alternative preparation may be achieved by treating a mixture of compound 103 with an arylthiol and an inorganic base (such as $K_2CO_3$) in a polar organic solvent (such as DMF). This mixture is subsequently treated with an oxidizing agent (such as meta-chloroperbenzoic acid) to give the product, a compound of Formula 104, which is isolated and optionally purified.

Referring to Reaction Scheme 1, Step 4, a compound of Formula 104 is treated with an acidic solution (such as hydrochloric acid), or alternatively is treated with a basic solution (such as sodium hydroxide solution) to provide a compound of Formula 105, which is isolated and optionally purified.

Referring to Reaction Scheme 1, Step 5, a mixture of a compound of Formula 105 is combined with a halogenating agent (such as oxalyl chloride), to give an acid chloride, or reacted with other reagents to add other suitable leaving groups. This intermediate is combined with an organic base (such as pyridine), in a polar organic solvent (such as DMF and/or THF). An amine is then added to give the product, a compound of Formula 106, which is isolated and optionally purified.

Referring to Reaction Scheme 2, Step 6, a mixture of a compound of Formula 104 is treated with an acidic solution (such as hydrochloric acid), or alternatively is treated with a basic solution (such as sodium hydroxide solution) to provide a compound of Formula 107, which is isolated and optionally purified.

Referring to Reaction Scheme 2, Step 7, a mixture of a compound of Formula 107 is combined with a coupling reagent such as HBTU and treated with the appropriate amine in a polar organic solvent (such as DMF and/or THF) and in the presence of a base such as DIEA The product, a compound of Formula 108, is isolated and optionally purified. Product 108 is then reacted first with MsCl in the presence of a base such as $NEt_3$ in a polar organic solvent (such as DMF and/or THF) and subsequently treated with an arylthiol, in the presence of a base such as $K_2CO_3$. The intermediate sulfide is isolated and the crude product is treated with xone in MeOH, to give the product, a compound of formula 106 which is isolated and optionally purified.

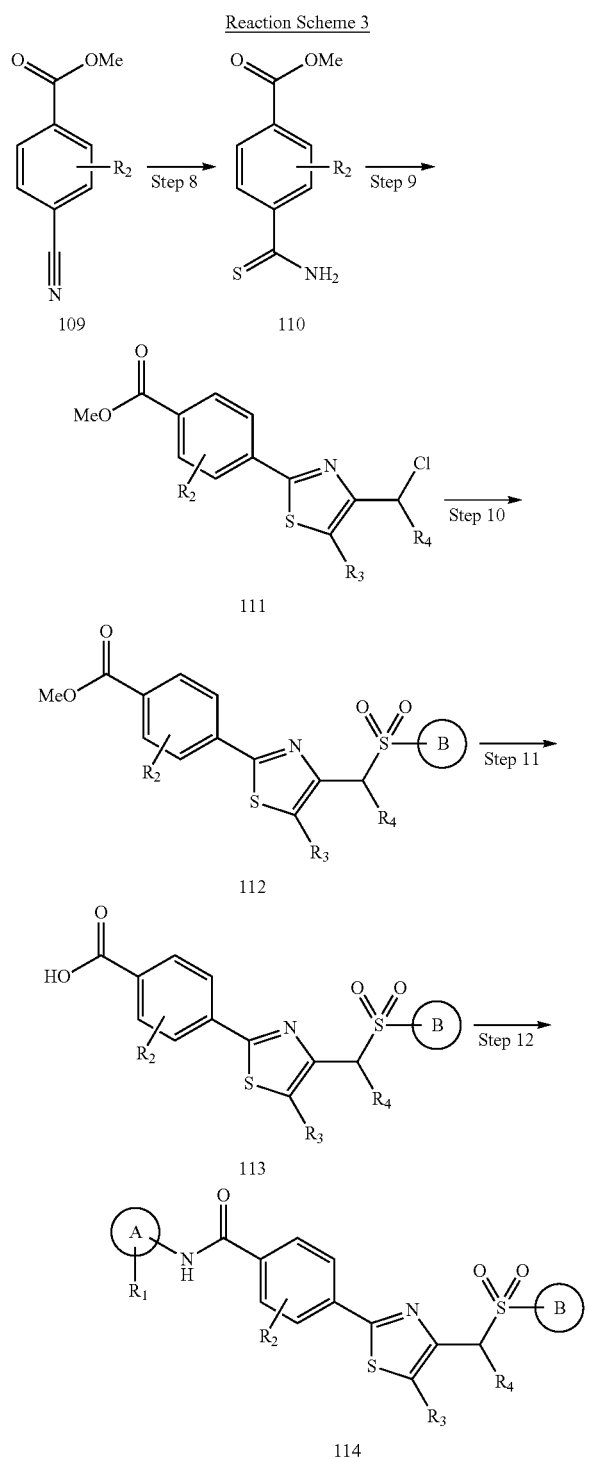

Referring to Reaction Scheme 3, Step 8, a mixture of a compound of Formula 109 is treated with a thiating agent (such as O,O-diethyl hydrogen dithiophosphate) to give a compound of Formula 110, which is isolated and optionally purified.

Referring to Reaction Scheme 3, Step 9, a mixture of a compound of Formula 110 is treated with a dichloroketone (such as dichloroacetone) in a polar organic solvent (such as DMF) to give to provide a compound of Formula 111, which is isolated and optionally purified.

Referring to Reaction Scheme 3, Step 10, a mixture of a compound of Formula 111 is combined with an arylsulfinic acid and a base, or with the salt of the arylsulfinic acid, in a polar organic solvent (such as DMF and/or THF) to give the product, a compound of Formula 112, which is isolated and optionally purified.

Referring to Reaction Scheme 3, Step 10, an alternative preparation may be achieved by treating a mixture of compound 111 with an arylthiol and an inorganic base (such as $K_2CO_3$) in a polar organic solvent (such as DMF). This mixture is subsequently treated with an oxidizing agent (such as meta-chloroperbenzoic acid) to give the product, a compound of Formula 112, which is isolated and optionally purified.

Referring to Reaction Scheme 3, Step 11, a mixture of a compound of Formula 112 is treated with an acidic solution (such as hydrochloric acid), or alternatively is treated with a basic solution (such as sodium hydroxide solution) to provide a compound of Formula 113, which is isolated and optionally purified.

Referring to Reaction Scheme 3, Step 12, a mixture of a compound of Formula 113 is combined with a halogenating agent (such as oxalyl chloride), to give an acid chloride, or other reagents to add other suitable leaving groups (such as HBTU). This intermediate is combined with an organic base (such as pyridine), in a polar organic solvent (such as DMF and/or THF). An amine is then added to give the product, a compound of Formula 114, which is isolated and optionally purified.

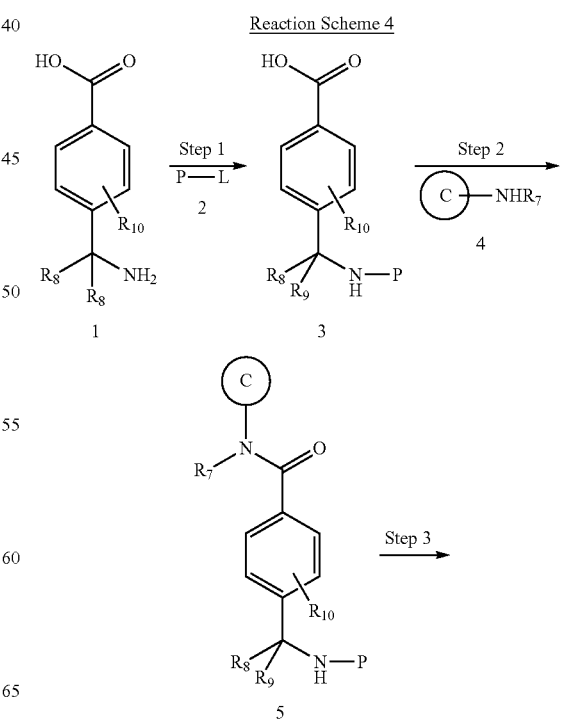

-continued

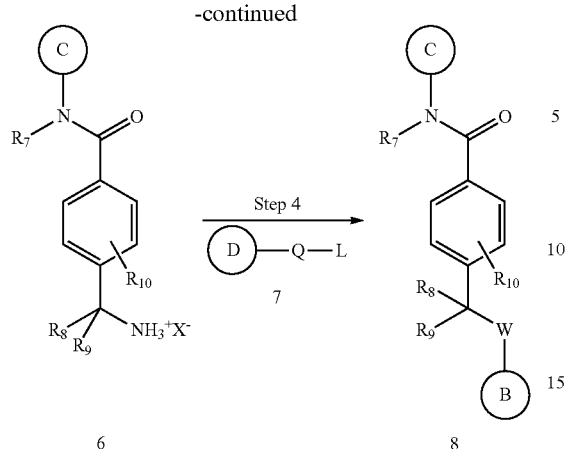

wherein C, D, R, $R_7$, $R_8$, $R_9$, $R_{10}$, and W are as defined above for Formula III.

wherein C, D, R, $R_7$, $R_8$, $R_9$, $R_{10}$, and W are as defined above for Formula III.

Referring to Reaction Scheme 1, Step 1, a compound of Formula 1, is combined with an aqueous solution of base (such as NaOH in water), and treated with a compound of Formula 2, where P is a nitrogen protecting group (such as benzenesulfonyl), and L is a leaving group (such as bromide), to give a compound of Formula 3, which is isolated and optionally purified. A mixture of a compound of Formula 3 is combined with a halogenating agent (such as oxalyl chloride), an organic base (such as pyridine), in a polar organic solvent (such as DMF and/or THF). A compound of Formula 4 is then added to give the product, a compound of Formula 5, which is isolated and optionally purified. A compound of Formula 5 is treated with an acidic mixture (such as hydrobromic acid and acetic acid), to provide a compound of Formula 6, where X is a halogen (such as bromide), where the product, a compound of Formula 7, is isolated and optionally purified. A mixture of a compound of Formula 6 is combined with a compound of Formula 7, where L is a leaving group (such as chloride) and Q is a substitutent group (such as carbonyl or $SO_2$), and an organic base (such a pyridine) to give the product, a compound of Formula 8, which is isolated and optionally purified.

Reaction Scheme 5

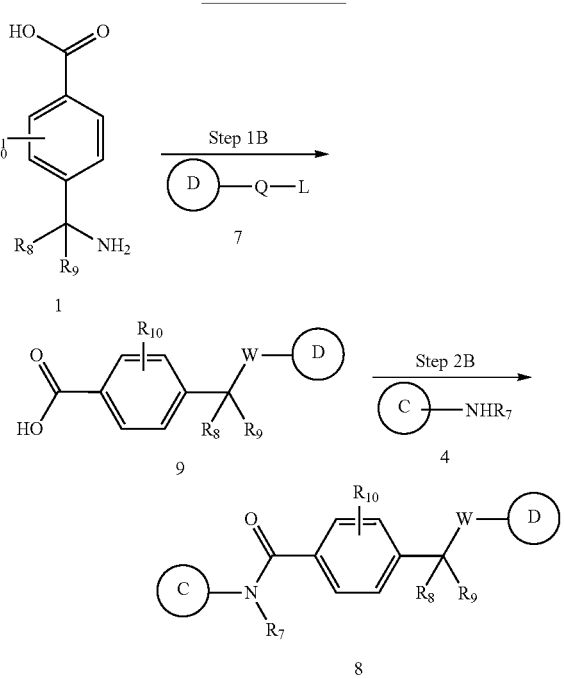

wherein C, D, $R_7$, $R_8$, $R_9$, $R_{10}$ and W are as defined above for Formula III.

Referring to Reaction Scheme 2, Step 1B, a mixture of a compound of Formula 1 is combined with a compound of Formula 7, where L is a leaving group (such as chloride) and Q is a substitutent group (such as carbonyl or $SO_2$), and an organic base (such a pyridine) to give the product, a compound of Formula 9, which is isolated and optionally purified. A mixture of a compound of Formula 9 is combined with a halogenating agent (such as oxalyl chloride), an organic base (such as pyridine), in a polar organic solvent (such as DMF and/or THF). A compound of Formula 4 is then added to give the product, a compound of Formula 8, which is isolated and optionally purified.

Reaction Scheme 6

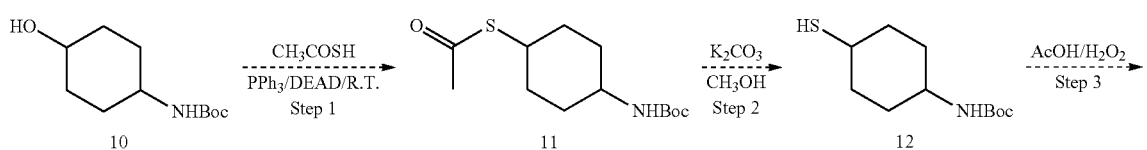

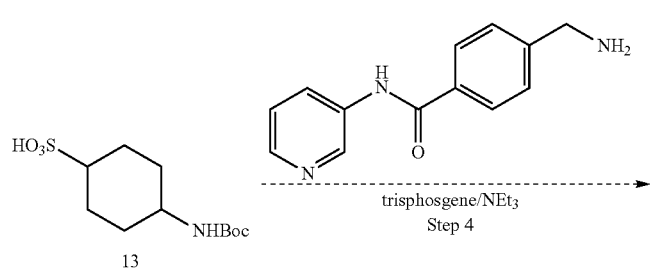

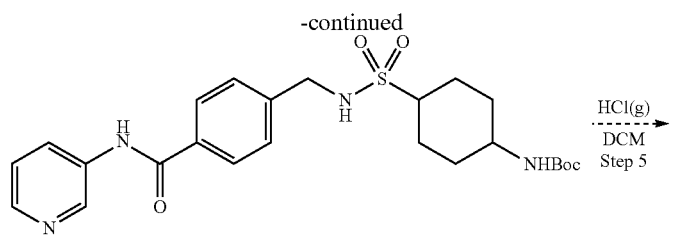

14

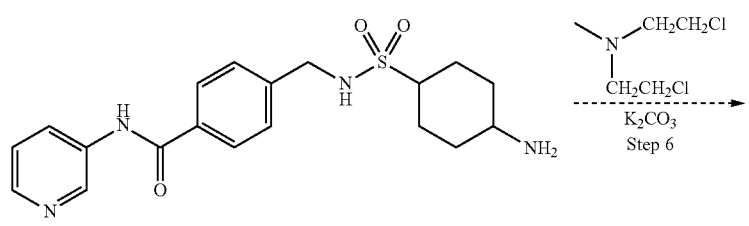

15

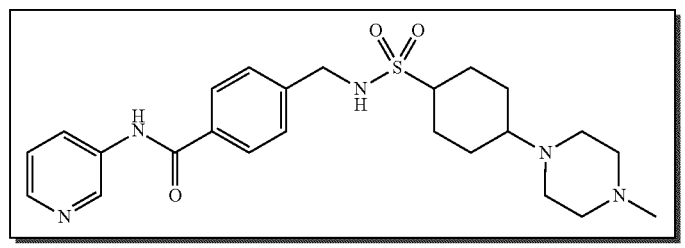

III-1

Referring to Reaction Scheme 4, Step 1, the alcohol of alcohol 10, is reacted with thioacetic acid under Mitsunobu conditions to give the thioacetate 11. A mixture of the thioacetate 11 and potassium carbonate is stirred in aqueous methanol to give the thiol compound 12. Thiol 12 is oxidized by hydrogen peroxide in acetic acid to give the sulfonic acid 13. The sulfonic acid 13 is treated with triphosgene and then reacted with the amine of Compound 5 to give the sulfonamide 14. The Boc protecting group of the carbamate 14 is removed by reacting with hydrogen chloride to form the amine 15 after aqueous base (such as sodium carbonate solution) treatment. The amine 15 is reacted with 2-chloro-N-(2-chloroethyl)-N-methylethanamine in the presence of a base (such as potassium carbonate) to give the product, compound III-1, which is isolated and optionally purified.

Reaction Scheme 7

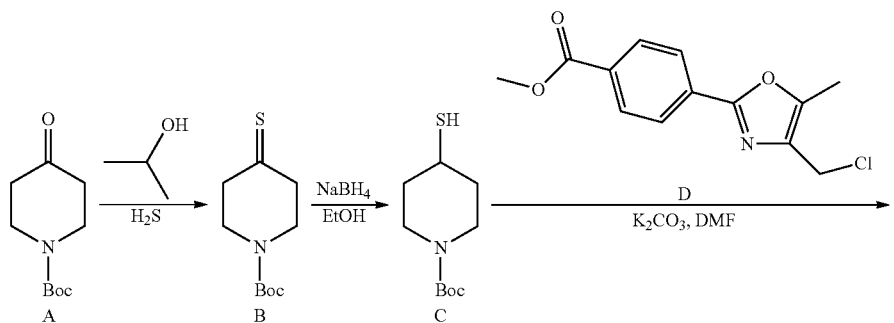

-continued

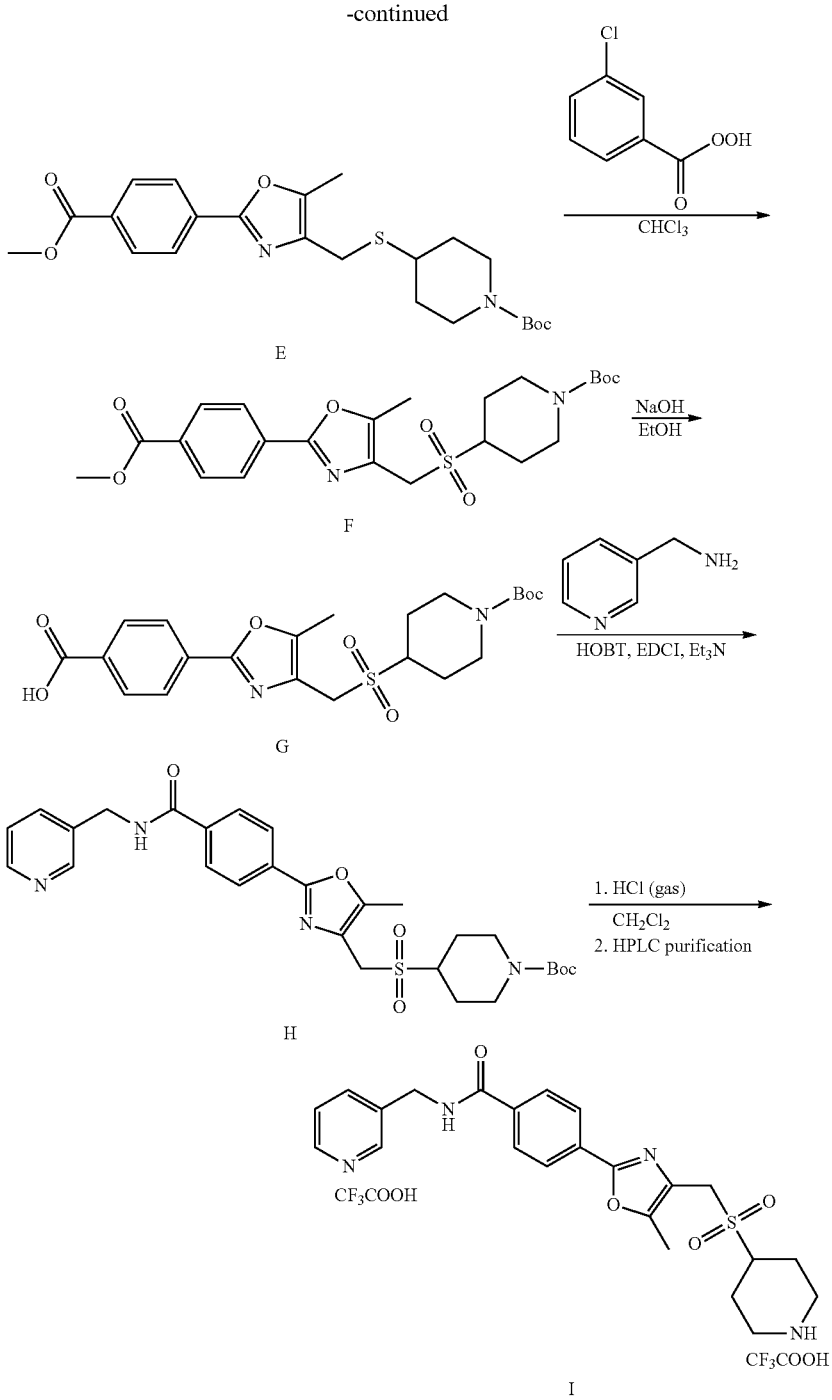

Ketone A is converted to thioketone B using hydrogen sulfide gas followed by sodium borohydride reduction to the thiol C. Thiol C is coupled with compound D in N,N-dimethylformamide. The thioether E is oxidized using m-chloroperbenzoic acid at 0° C. with stirring at 0° C. in an ice/water bath for 1 h to give compound F. Afterwards ester F is hydrolyzed with sodium hydroxide in ethanol at 50° C. overnight to give the acid G. Pyridin-3-ylmethanamine is coupled to the free acid G using EDCI and HOBT in N,N-dimethylformamide. Finally, Compound H is deprotected using hydrogen chloride gas in dichloromethane at 0° C. to give Compound I after standard workup.

Also provided is a pharmaceutical composition comprising at least one compound and/or pharmaceutically acceptable salt described herein and at least one pharmaceutically acceptable carrier.

The term "pharmaceutically acceptable carrier" refers to any and all solvents, dispersion media, coatings, isotonic and absorption delaying agents, and the like, that are compatible with pharmaceutical administration. The use of such media and agents for pharmaceutically active substances is well known in the art, such as, for example, aqueous solutions such as water or physiologically buffered saline or other solvents or vehicles such as glycols, glycerol, oils such as olive oil or injectable organic esters. The compositions may also contain other active compounds providing supplemental, additional, or enhanced therapeutic functions.

A pharmaceutically acceptable carrier may contain physiologically acceptable agents that act, for example, to stabilize or to increase the absorption of a compound or pharmaceutically acceptable salt thereof. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, may depend, for example, on the route of administration of the composition. The pharmaceutical composition also may comprise a liposome or other polymer matrix, which may have incorporated therein, for example, a compound as described herein. Liposomes, for example, which consist of phospholipids or other lipids, are nontoxic, physiologically acceptable and metabolizable carriers that are relatively simple to make and administer.

In some embodiments, a "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier is typically "acceptable" in the sense of being compatible with the other ingredients of the formulation and not injurious to the patient. Some examples of materials that may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See Remington: The Science and Practice of Pharmacy, 20th ed. (Alfonso R. Gennaro ed.), 2000.

In some embodiments, a pharmaceutical composition comprising at least one compound and/or salt as described herein may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramusclularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). At least one compound and/or salt as described herein may also be formulated for inhalation.

In some embodiments, at least one compound of Formulae I, II, III, IV. V, or VI, or a pharmaceutically acceptable salt thereof, may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The pharmaceutical compositions described herein may conveniently be presented in unit dosage form and may be prepared by any methods well known in the art of pharmacy. The amount of active ingredient that can be combined with a carrier material to produce a single dosage form will vary depending upon the subject being treated and the particular mode of administration. The amount of active ingredient that can be combined with a carrier material to produce a single dosage form will generally be that amount of the compound that produces a therapeutic effect.

In some embodiments, this amount ranges from about 1 percent to about 99 percent of active ingredient.

In another embodiment, this amount ranges from about 5 percent to about 70 percent, and in a further embodiment from about 10 percent to about 30 percent.

Methods of preparing these compositions include the step of combining at least one compound and/or pharmaceutically acceptable salt as described herein with at least one carrier and, optionally, one or more excipients.

In some embodiments, the pharmaceutical compositions are prepared by uniformly and combining at least one compound and/or pharmaceutically acceptable salt as described herein with liquid carriers, or finely divided solid carriers, or both, and then, if necessary, shaping the product.

Pharmaceutical compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of at least one compound and/or salt as described herein as an active ingredient. The pharmaceutical compositions described herein may also be administered as a bolus, electuary, or paste.

In some embodiments, compounds and/or pharmaceutically acceptable salts described herein are mixed with one or more pharmaceutically acceptable excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In some embodiments, the tablets, and other solid dosage forms pharmaceutical compositions, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition in that they release the active ingredient(s) only, preferentially, in a certain portion of the gastrointestinal tract, optionally, or in a delayed manner. Examples of embedding compositions that may be used include polymeric substances and waxes. The active ingredient may also be in micro-encapsulated form, if appropriate, with one or more of the above-described excipients.

In some embodiments, liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils, cottonseed, groundnut, corn, germ, olive, castor oils, sesame oils, glycerol, tetrahydrofuryl alcohol, polyethylene glycols and fatty acid esters of sorbitan, and mixtures thereof.

In some embodiments, the emulsifiers are chosen from cottonseed, groundnut, corn, germ, olive, castor, and sesame oils.

Besides inert diluents, the oral compositions may also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Pharmaceutical compositions as described herein for rectal, vaginal, or urethral administration may be presented as a suppository, which may be prepared by mixing one or more compounds or salts as described herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, pharmaceutical compositions described herein may be formulated for delivery via a catheter, stent, wire, or other intraluminal device. Delivery via such devices may be especially useful for delivery to the bladder, urethra, ureter, rectum, or intestine.

Formulations suitable for vaginal administration also include pessaries, tampons, creams, gels, pastes, foams, or spray formulations containing such carriers as are known in the art to be appropriate.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may comprise excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound as described herein, excipients such as lactose, talc, silicic acid, aluminum hydroxide, calcium silicates, and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery to the body. Such dosage forms may be made by dissolving or dispersing the compound in the proper medium. Absorption enhancers may also be used to increase the flux across the skin. The rate of such flux may be controlled by either providing a rate controlling membrane or dispersing the compound in a polymer matrix or gel.

Ophthalmic formulations, eye ointments, powders, solutions, and the like, may also comprise at least one of the compounds or salts as described herein.

In some embodiments, pharmaceutical compositions as described herein suitable for parenteral administration comprise at least one compound of Formula I, or a pharmaceutically acceptable salt thereof, in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like.

In some embodiments, isotonic agents, such as sugars, sodium chloride, and the like may be included into the compositions. In addition, prolonged absorption of the injectable pharmaceutical form may be brought about by the inclusion of agents that delay absorption such as aluminum monostearate and gelatin.

In some cases, in order to prolong the effect of a drug, it may be advantageous to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

As further detailed below, the pharmaceutical compositions described herein may also comprise, or may be used in combination with, one or more known cytotoxic, vascular targeting agents or chemotherapeutic agents including, but not limited to, Xeloda™ (capecitabine), Paclitaxel™, FUDR (fluorouridine) Fludara™ (fludarabine phosphate), Gemzar™ (gemcitabine), methotrexate, cisplatin, carboplatin, adriamycin, avastin, tarceva, taxol, tamoxifen, Femora, temezolamide, cyclophosphamide, Erbitux, and Sutent.

In some embodiments, when pharmaceutically acceptable compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

The term "pharmaceutically acceptable prodrugs" as used herein represents those prodrugs of a compound of Formula I, or a pharmaceutically acceptable salt thereof, that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds and pharmaceutically acceptable salts described herein. A discussion is provided in Higuchi et al., "Prodrugs as Novel Delivery Systems," ACS Symposium Series, Vol. 14, and in Roche, E. B., ed. Bioreversible Carriers in Drug Design, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts.

In some embodiments, pharmaceutically acceptable acid addition salts include those formed with mineral acids such as hydrochloric acid and hydrobromic acid, and those formed with organic acids such as fumaric acid and maleic acid.

Compounds included in the present compositions, that are acidic in nature may react with any number of inorganic and organic bases to form pharmaceutically acceptable base salts. Bases may include, for example, the mineral bases, such as NaOH and KOH, but one of skill in the art would appreciate that other bases may also be used. See Ando et al., Remington: The Science and Practice of Pharmacy, 20th ed. 700-720 (Alfonso R. Gennaro ed.), 2000.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

In some embodiments, the pharmaceutically acceptable addition salts of the compounds described herein may also exist as various solvates, such as, for example, with water, methanol, ethanol, dimethylformamide, and the like. Mixtures of such solvates may also be prepared. The source of such solvate may be from the solvent of crystallization, inherent in the solvent of preparation or crystallization, or adventitious to such solvent.

Methods of Using the Heteroaryl Alkylbenzamides

In some embodiments, the compounds and pharmaceutically acceptable salts thereof described herein target cells which express HIF-1α and/or HIF-2α. In some embodiments, the compounds and pharmaceutically acceptable salts thereof described herein target cells which express HIF-1α. In some embodiments, the compounds and pharmaceutically acceptable salts thereof described herein target cells which express HIF-2α. In some embodiments, the compounds and pharmaceutically acceptable salts thereof described herein target cells which express HIF-1α and/or HIF-2α.

In some embodiments, the compounds and pharmaceutically acceptable salts thereof described herein target cells which do not have functional VHL.

In some embodiments, the compounds and pharmaceutically acceptable salts described herein may be used to treat cells, and more particularly, cancerous cells, expressing HIF-1α and/or HIF-2α. In some embodiments, the compounds and pharmaceutically acceptable salts described herein may be used to treat cells, and more particularly, cancerous cells, expressing HIF-1α. In some embodiments, the compounds and pharmaceutically acceptable salts described herein may be used to treat cells, and more particularly, cancerous cells, expressing HIF-2α. In some embodiments, the compounds and pharmaceutically acceptable salts described herein may be used to treat cells, and more particularly, cancerous cells, expressing HIF-1α and/or HIF-2α.

In some embodiments, the compounds and pharmaceutically acceptable salts thereof interfere with glycolysis.

In certain embodiments, the disease treated or prevented is cancer.

In some embodiments, the compounds and pharmaceutically acceptable salts described herein may be used to treat a disease mediated by defective pVHL protein, such as Von Hippel-Lindau disease (which may also be referred to as angiomatosis retinae, angiophakomatosis retinae et cerebelli, familial cerebelloretinal angiomatosis, cerebelloretinal hemangioblastomatosis, Hippel Disease, Hippel-Lindau syndrome, HLS, VHL, Lindau disease or retinocerebellar angiomatosis). In some embodiments, the compounds and pharmaceutically acceptable salts described herein may be used to treat a variety of malignant and/or benign tumors of the eye, brain, spinal cord, kidney, pancreas, and/or adrenal glands wherein individuals suffering from VHL may be disposed to such tumors. In some embodiments, the compounds and pharmaceutically acceptable salts described herein may be used to treat a disease mediated by defective pVHL protein, such as ngiomatosis, hemangioblastomas, pheochromocytoma, renal cell carcinoma, pancreatic cysts and café au lait spots.

Also provided is a method for treating a disease mediated by defective pVHL protein, comprising administering to a subject at least one compound of Formula I, or a pharmaceutically acceptable salt thereof, that is specifically cytotoxic to cells that have elevated HIF levels due to their increased rate and dependence on glucose uptake and glycolysis. In some embodiments, at least one compound of Formula I selectively disrupts glucose uptake and utilization in the subject. In some embodiments, at least one compound of Formula I, or a pharmaceutically acceptable salt thereof, inhibits HIF-mediated induction of PDK1.

Also provided is a method of targeting cells which have defective pVHL protein. In some embodiments, the cells are contacted with at least one compound of Formula I, or a pharmaceutically acceptable salt thereof, that selectively disrupts glucose uptake and utilization in the cells. In some embodiments, the compound of Formula I, or a pharmaceutically acceptable salt thereof, inhibits HIF-mediated induction of PDK1.

Also provided is a method for selectively killing cells which have defective pVHL protein. In some embodiments, the cells are contacted with at least one compound of Formula I, or a pharmaceutically acceptable salt thereof, that selectively disrupts glucose uptake and utilization in the cells. In some embodiments, at least one compound of Formula I, or a pharmaceutically acceptable salt thereof, inhibits HIF-mediated induction of PDK1.

Also provided is a method for treating a disease mediated by HIF-1α and/or HIF-2 α comprising administering to a subject at least one compound of Formula I, or a pharmaceutically acceptable salt thereof, that is specifically cytotoxic to cells that have elevated HIF levels due to their increased rate and dependence on glucose uptake and glycolysis. In some embodiments, at least one compound of Formula I, II, III, IV, V, or VI, or a pharmaceutically acceptable salt thereof, selectively disrupts glucose uptake and utilization in the subject. In some embodiments, at least one compound of Formula I, II, III, IV, V, or VI, or a pharmaceutically acceptable salt thereof, inhibits HIF-mediated induction of PDK1.

Also provided is a method for treating a disease mediated by cells comprising genetic or epigenetic alterations that make them highly dependent on aerobic glycolysis for energy production, comprising administering to a subject at least one compound of Formula I, II, III, IV, V, or VI, or a pharmaceutically acceptable salt thereof, that is specifically cytotoxic to cells comprising genetic or epigenetic alterations that make them highly dependent on aerobic glycolysis for energy production.

Also provided is a method for selectively killing cells comprising genetic or epigenetic alterations that make them highly dependent on aerobic glycolysis for energy production, comprising administering to the cells at least one compound of Formula I, II, III, IV, V, or VI, or a pharmaceutically acceptable salt thereof, that is specifically cytotoxic to cells comprising genetic or epigenetic alterations that make them highly dependent on aerobic glycolysis for energy production. In some embodiments, at least one compound of Formula I, II, III, IV, V, or VI, or a pharmaceutically acceptable salt thereof, selectively disrupts glucose uptake and utilization in cells comprising genetic or epigenetic alterations that make them highly dependent on aerobic glycolysis for energy production.

Also provided is a method for treating a disease mediated by GLUT1 comprising administering to a subject in need thereof at least one compound of Formula III, III, IV, V, or VI, or a pharmaceutically acceptable salt thereof. Also provided is a method for treating a disease mediated by GLUT1, comprising administering to a subject at least one compound of Formula I, II, III, IV, V, or VI, or a pharmaceutically acceptable salt thereof, that is specifically cytotoxic to cells that have elevated GLUT 1 levels due to their increased rate and dependence on glucose uptake and glycolysis. In some embodiments, at least one compound of Formula I, II, III, IV, V, or VI, or a pharmaceutically acceptable salt thereof, selectively disrupts glucose uptake and utilization in the subject. In some embodiments, at least one compound of Formula III, III, IV, V, or VI, or a pharmaceutically acceptable salt thereof, inhibits glucose transport by GLUT1.

Also provided is a method of identifying a compound as a candidate cancer therapy, comprising exposing a first population of cells that have elevated expression of GLUT1 but not GLUT2 to a test compound and assaying cytotoxicity of the test compound, exposing a second population of cells that have elevated expression of GLUT2 but not GLUT1 to the test compound and assaying cytotoxicity of the test compound, and identifying the test compound as a candidate cancer therapy if the test compound induces significantly higher cytotoxicity in the first population of cells than in the second population of cells. Also provided is at least one compound, or a pharmaceutically acceptable salt thereof, identified by such method.

The subject receiving treatment may be any mammal in need of such treatment. Such mammals include, e.g., humans, ovines, bovines, equines, porcines, canines, felines, non-human primate, mice, and rats. In some embodiments, the subject is a human. In some embodiments, the subject is a non-human mammal "Therapeutically-effective amount" refers to the concentration of a compound that is sufficient to elicit the desired therapeutic effect (e.g., treatment or prevention of a disease). It is generally understood that the effective amount of the compound will vary according to the weight, gender, age, and medical history of the subject. Other factors that influence the effective amount may include, but are not limited to, the severity of the patient's condition, the disorder being treated, the stability of the compound, and, if desired, another type of therapeutic agent being administered with the compounds and pharmaceutically acceptable salts described herein. A larger total dose may be delivered by multiple administrations of the agent. Methods to determine efficacy and dosage are known to those skilled in the art. See, e.g., Roden, *Harrison's Principles of Internal Medicine*, Ch. 3, McGraw-Hill, 2004.

Actual dosage levels of the active ingredients in the pharmaceutical compositions comprising at least one compound or pharmaceutically active salt as described herein may be varied so as to obtain an amount of the active ingredient that is effective to achieve the desired therapeutic response for a particular patient, composition, and mode of administration, without being toxic to the patient.

A physician or veterinarian having ordinary skill in the art can readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In general, a suitable daily dose of at least one compound of Formula III, III, IV, V, or VI, or a pharmaceutically acceptable salt thereof, will be that amount of the compound that is the lowest dose effective to produce a therapeutic effect. Such an effective dose will generally depend upon the factors described herein.

If desired, the effective daily dose of the active compound may be administered as one, two, three, four, five, six, or more sub-doses administered separately at appropriate intervals throughout the day, optionally, in unit dosage forms.

In some embodiments, the active compound may be administered two or three times daily. In another embodiment, the active compound is administered once daily.

The optimal frequency of administration and effective dosage will vary from one individual to another and will depend upon the particular disease being treated and may be determined by one skilled in the art.

In some embodiments, effective dosages of at least one compound of Formula I II, III, IV, V, or VI, or a pharmaceutically acceptable salt thereof, may range from as low as about 1 mg per day to as high as about 1000 mg per day, including all intermediate dosages there between.

In another embodiment, effective dosages may range from about 10 mg per day to about 100 mg per day, including all intermediate dosages there between. The compositions may be administered in a single dosage, or in multiple, divided dosages.

As described herein, at least one compound of Formula I, II, III, IV, V, or VI, may be used for treating or preventing cancer. In some embodiments, such methods may, further comprise administration of a chemotherapeutic agent.

Chemotherapeutic agents that may be coadministered with compounds and pharmaceutical compositions of Formula I, II, III, IV, V, or VI, may include: alemtuzumab, aminoglutethimide, amsacrine, anastrozole, asparaginase, Bacillus Calmette-Guérin, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, interleukin-2, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, sorafinib, streptozocin, sunitinib, suramin, tamoxifen, temozolomide, temsirolimus, teniposide, testosterone, thalidomide, thioguanine, thiotepa, titanocene dichloride, topotecan, tositumomab, trastuzumab, tretinoin, vatalanib, vinblastine, vincristine, vindesine, and vinorelbine.

Other useful chemotherapeutic agents for combination with the compounds as described herein include MDX-010; MAb, AME; ABX-EGF; EMD 72 000; apolizumab; labetuzumab; ior-t1; MDX-220; MRA; H-11 scFv; Oregovomab; huJ591 MAb, BZL; visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; Prostate cancer antibody; H22xKi-4; ABX-MA1; Imuteran; and Monopharm-C.

These chemotherapeutic agents may be categorized by their mechanism of action into, for example, the following groups: anti-metabolites/anti-cancer agents, such as pyrimidine analogs (e.g., 5-fluorouracil, floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (e.g., actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (e.g., L-asparaginase, which systemically metabolizes L-asparagine and deprives cells which do not have the capacity to synthesize their own asparagine); antiplatelet agents; antiproliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (e.g., trastuzumab and others listed above); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (e.g., cortisone, dexamethasone, hydrocortisone, methylpednisolone, prednisone, and prenisolone); growth factor signal transduction kinase inhibitors; mitochondrial dysfunction inducers and caspase activators; chromatin disruptors.

In some embodiments, pharmaceutical compositions comprising at least one compound of Formula I, II, III, IV, V, or VI, may be coadministered with chemotherapeutic agents either singly or in combination.

Combination therapies comprising at least one compound of Formula I, II, III, IV, V, or VI, or a pharmaceutically acceptable salt thereof, and a conventional chemotherapeutic agent may be advantageous over combination therapies known in the art because the combination allows the conventional chemotherapeutic agent to exert greater effect at lower dosage. In some embodiments, the effective dose ($ED_{50}$) for a chemotherapeutic agent, or combination of conventional chemotherapeutic agents, when used in combination with a compound of Formula I, II, III, IV, V, or VI, or a pharmaceutically acceptable salt thereof as described herein is at least 2 fold less than the $ED_{50}$ for the chemotherapeutic agent alone. In another embodiment, the $ED_{50}$ is about 5-fold less, about 10-fold less, and further about 25-fold less. Conversely, the therapeutic index (TI) for such chemotherapeutic agent or combination of such chemotherapeutic agent when used in combination with a compound or pharmaceutically acceptable salt described herein may be at least 2-fold greater than the TI for conventional chemotherapeutic regimen alone. In another embodiment, the TI is about 5-fold greater, about 10-fold greater, and further about 25-fold greater.

In some embodiments, the compounds and pharmaceutically acceptable salts thereof described herein may be administered in combination with radiation therapy.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analyses were carried out in the Campbell Microanalytical Laboratory, University of Otago, Dunedin, NZ. Melting points were determined on an Electrothermal 2300 Melting Point Apparatus. NMR spectra were obtained on a Bruker Avance 400 spectrometer at 400 MHz for $^1$H and 100 MHz for $^{13}$C spectra. Spectra were obtained in [$(CD_3)_2SO$] unless otherwise specified, and were referenced to $Me_4Si$. Chemical shifts and coupling constants were recorded in units of ppm and Hz, respectively. Assignments were determined using COSY, HSQC, and HMBC two-dimensional experiments. Low resolution mass spectra were gathered by direct injection of methanolic solutions into a Surveyor MSQ mass spectrometer using an atmospheric pressure chemical ionization (APCI) mode with a corona voltage of 50 V and a source temperature of 400° C. Solutions in organic solvents were dried with anhydrous $MgSO_4$. Solvents were evaporated under reduced pressure on a rotary evaporator. Thin-layer chromatography was carried out on aluminium-backed silica gel plates (Merck 60 $F_{254}$) with visualization of components by UV light (254 nm) or exposure to $I_2$. Column chromatography was carried out on silica gel (Merck 230-400 mesh). DCM refers to dichloromethane; DIEA refers to diisopropylethylamine; DME refers to dimethoxyethane, DMF refers to dry N,N-dimethylformamide; ether refers to diethyl ether; EtOAc refers to ethyl acetate; EtOH refers to ethanol; HBTU refers to O-benzotriazole-N,N,N',N'-tetramethyluronium hexafluorophosphate; MeOH refers to methanol; pet. ether refers to petroleum ether, boiling range 40-60° C.; THF refers to tetrahydrofuran dried over sodium benzophenone ketyl.

Method A

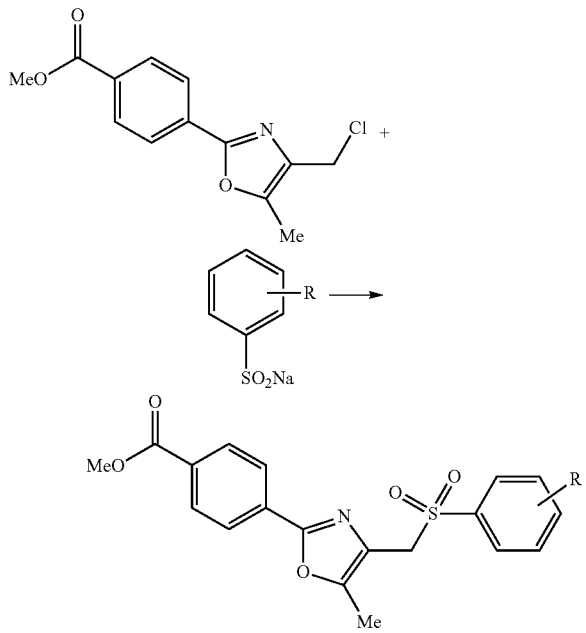

A mixture of chloride (1.0 mmol) and sodium arylsulfinate (1.1 mmol) in dry DMF (20 mL) was stirred at 70° C. for 3 h. The solvent was evaporated and the residue was suspended in EtOAc (100 mL) and washed with water (2×20 mL), washed with brine (20 mL) and dried. The solvent was evaporated and the residue purified by column chromatography to give benzoate.

Method B

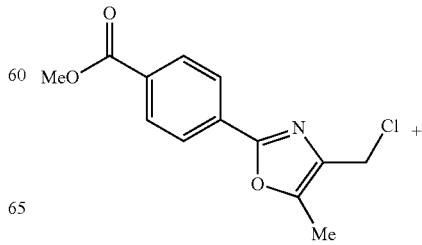

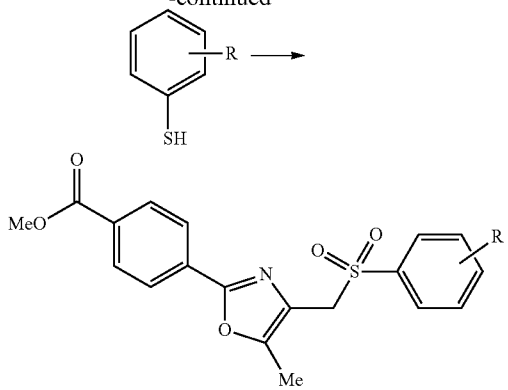

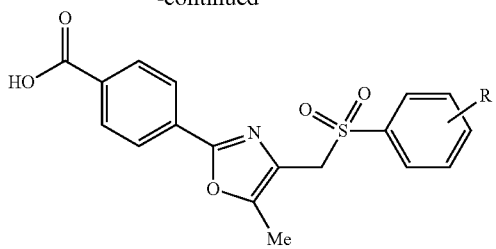

A mixture of benzoate (1.0 mmol) and 2 M NaOH (10 mL) in dioxane (10 mL) was stirred at reflux temperature for 2 h. The mixture was cooled and the organic solvent evaporated. The remaining mixture was diluted with water (40 mL) and washed with Et₂O (10 mL). The pH of the aqueous phase was adjusted to 2 with 6 M HCl and the mixture was stirred at 5° C. for 1 h. The precipitate was filtered, washed with water (10 mL) and dried to give acid.

Method E

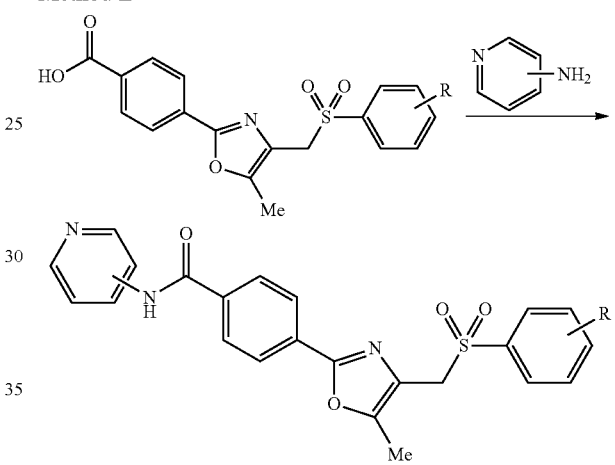

A mixture of chloride (1.0 mmol), arylthiol (1.1 mmol) and K₂CO₃ (1.1 mmol) in dry DMF (20 mL) was stirred at 70° C. for 16 h. The mixture was cooled to 5° C. and mCPBA (2.5 mmol) was added and the mixture stirred at 5° C. for 1 h. The mixture was poured into water (100 mL) and stirred for 30 min. The precipitate was filtered, washed with water and then partitioned between EtOAc (100 mL) and dilute aqueous NH₃ (2×50 mL). The organic fraction was washed with water (50 mL), washed with brine (30 mL) and dried. The solvent was evaporated and the residue purified by column chromatography to give benzoate.

Method C

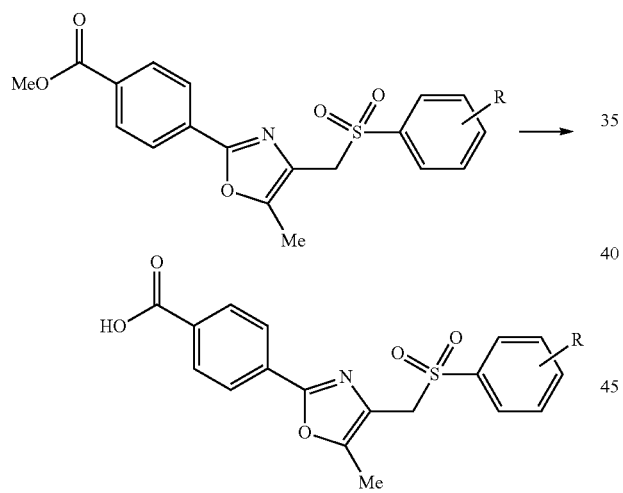

A mixture of benzoate (1.0 mmol) and 6 M HCl (10 mL) was stirred at reflux temperature for 16 h. The mixture was cooled and diluted with ice/water (40 ml) and stirred for 30 min. The precipitate was filtered, washed with water (20 mL) and dried to give the acid.

Method D

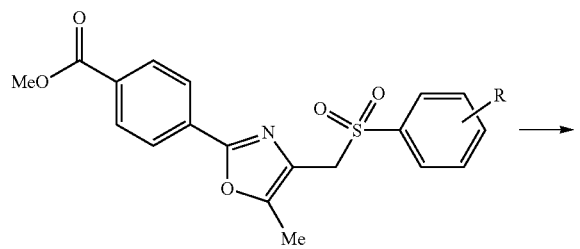

Oxalyl chloride (1.5 mmol) was added dropwise to a stirred suspension of benzoic acid (1.0 mmol) and DMF (2 drops) in dry THF (20 mL) and the solution was stirred at 20° C. for 2 h, then at 66° C. for 1 h. The solution was cooled to 20° C. and the solvent was evaporated. The residue was dissolved in dry pyridine (10 mL) and amine (1.1 mmol) was added and the solution stirred at 20° C. for 16 h. The solvent was evaporated and the residue suspended in ice/water (50 mL) for 1 h. The precipitate was filtered, washed with water (5 mL) and dried. The crude solid was purified by column chromatography to give benzamide.

Example 1

4-(5-Methyl-4-{[(4-methylphenyl)sulfonyl]methyl}-1,3-oxazol-2-yl)-N-(3-pyridinyl)benzamide (5)

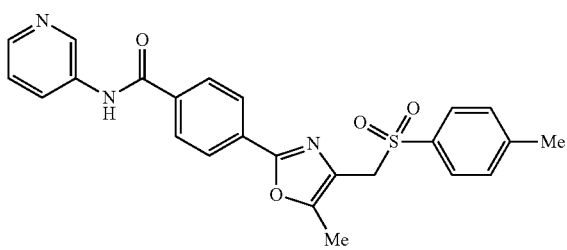 [SMILES: Cc1ccc(S(=O)(=O)Cc2nc(-c3ccc(C(=O)Nc4cccnc4)cc3)oc2C)cc1]

Methyl 4-(4,5-Dimethyl-3-oxido-1,3-oxazol-2-yl)benzoate (1). HCl gas was bubbled through a solution of methyl 4-formylbenzoate (8.20 g, 50.0 mmol) and 2,3-butanedione 2-oxime (5.05 g, 50 mmol) in HOAc (25 mL) at 0° C. and the mixture was stirred at 0° C. for 30 min. The mixture was diluted with Et₂O (300 mL) and the resulting precipitate was filtered, washed with Et₂O (50 mL) and dried in vacuo to give N-oxide 1 (12.05 g, 97%) as a white powder: mp (Et₂O) 127-128° C.; $^1$H NMR (CDCl₃) δ 8.44 (br d, J=8.8 Hz, 2 H, H-2, H-6), 8.23 (br d, J=8.8 Hz, 2 H, H-3, H-5), 3.98 (s, 3 H, OCH₃), 2.50 (s, 2 H, CH₃), 2.47 (s, 3H, CH₃); MS m/z 248.6 (mh⁺, 100%).

Methyl 4-[4-(Chloromethyl)-5-methyl-1,3-oxazol-2-yl] benzoate (2). POCl₃ (2.23 mL, 24.3 mmol) was added dropwise to a stirred solution of N-oxide 1 (5.0 g, 20.2 mmol) in dry DCM (100 mL) and the mixture stirred at 40° C. for 16 h. The solution was poured into a slurry of ice/1 M NaOH solution (100 mL) and the mixture stirred for 10 min. The mixture was extracted with DCM (3×50 mL), the combined organic extract dried and the solvent evaporated. The residue was purified by column chromatography, eluting with 20% EtOAc/pet. ether, to give benzoate 2 (4.12 g, 77%) as a white powder: mp (EtOAc) 127-128° C.; $^1$H NMR (CDCl₃) δ 8.06-8.12 (m, 4 H, H-2, H-3, H-5, H-6), 4.56 (s, 2 H, CH₂Cl), 3.94 (s, 3 H, OCH₃), 2.45 (s, 3 H, CH₃); MS m/z 266.6 (MH⁺, 100%). Anal. calcd for C₁₃H₁₂ClNO₃: C, 58.77; H, 4.55; N, 5.27. Found: C, 58.82; H, 4.43; N, 5.18%.

Methyl 4-(5-Methyl-4-{[(4-methylphenyl)sulfonyl]methyl}-1,3-oxazol-2-yl)benzoate (3). Method A. A mixture of chloride 2 (1.54 g, 5.8 mmol) and sodium 4-methylbenzenesulfinate (1.08 g, 6.1 mmol) gave benzoate 3 (1.96 g, 88%) as a white powder: mp (EtOAc) 177-178° C.; $^1$H NMR (CDCl₃) δ 8.08 (ddd, J=8.7, 2.0, 1.6 Hz, 2 H, H-2, H-6), 7.92 (ddd, J=8.7, 2.0, 1.6 Hz, 2 H, H-3, H-5), 7.69 (ddd, J=8.3, 1.9, 1.7 Hz, 2H, H-2', H-6'), 7.30 (br d, J=8.3Hz, 2 H, H-3', H-5'), 4.29 (s, 2 H, CH₂SO₂), 3.94 (s, 3 H, OCH₃), 2.43 (s, 3 H, CH₃), 2.31 (s, 3 H, CH₃); MS m/z 386.5 (MH₊, 100%). Anal. calcd for C₂₀H₁₉NO₅S: C, 62.32; H, 4.97; N, 3.63. Found: C, 62.59; H, 4.96; N, 3.71%.

4-(5-Methyl-4-{[(4-methylphenyl)sulfonyl]methyl}-1,3-oxazol-2-yl)benzoic Acid (4). Method C. Reaction of benzoate 3 (1.96 g, 5.1 mmol) and 6 M HCl (50 mL) gave acid 4 (1.83 g, 97%) as a white solid: mp (H₂O) 242-245° C.; $^1$H NMR δ 13.16 (br s, 1 H, CO₂H), 8.05 (ddd, J=8.6, 1.9, 1.5 Hz, 2 H, H-2, H-6), 7.92 (ddd, J=8.6, 1.9, 1.5 Hz, 2 H, H-3, H-5), 7.67 (br d, J=8.3Hz, 2 H, H-2', H-6'), 7.42 (br d, J=8.3Hz, 2 H, H-3', H-5'), 4.63 (s, 2 H, CH₂SO₂), 2.40 (s, 3 H, CH₃), 2.13 (s, 3 H, CH₃); MS m/z 372.8 (MH⁺, 100%). Anal. calcd for C₁₉H₁₇NO₅S: C, 61.44; H, 4.61; N, 3.77. Found: C, 61.67; H, 4.57; N, 3.79%.

4-(5-Methyl-4-{[(4-methylphenyl)sulfonyl]methyl}-1,3-oxazol-2-yl)-N-(3-pyridinyl)benzamide (5). Method E. Reaction of oxalyl chloride (100 λL, 1.1 mmol) and benzoic acid 4 (207 mg, 0.6 mmol) with subsequent coupling to 3-aminopyridine (58 mg, 0.6 mmol) gave benzamide 5 (148 mg, 59%) as a white powder: mp (EtOAc) 248-250° C.; $^1$H NMR δ 10.56 (s, 1 H, CONH), 8.94 (d, J=2.2Hz, 1 H, H-2'), 8.33 (dd, J=4.7, 1.5 Hz, 1 H, H-6'), 8.20 (ddd, J=8.3, 2.5, 1.5 Hz, 1 H, H-4'), 8.10 (br d, J=8.6 Hz, 2 H, H-2, H-6), 7.97 (br d, J=8.6 Hz, 2 H, H-3, H-5), 7.69 (br d, J=8.3Hz, 2 H, H-2'', H-6''), 7.38-7.45 (m, 3 H, H-5', H-3'', H-5''), 4.65 (s, 2 H, CH₂SO₂), 2.41 (s, 3 H, CH₃), 2.16 (s, 3 H, CH₃); $^{13}$C NMR δ 165.0, 157.9, 150.1, 144.7 (2), 144.5, 142.1, 135.6, 135.5, 129.7 (2), 129.3, 128.6 (2), 128.3 (2), 127.4, 126.1, 125.5 (2), 123.5, 53.0, 21.1, 9.7; MS m/z 448.7 (MH⁺, 100%). Anal. calcd for C₂₄H₂₁N₃O₄S: C, 64.41; H, 4.73; N, 9.39. Found: C, 64.18; H, 4.74; N, 9.39%.

Example 2

4-(5-Methyl-4-{[(4-methylphenyl)sulfonyl]methyl}-1,3-oxazol-2-yl)-N-(4-pyridinyl)benzamide (6)

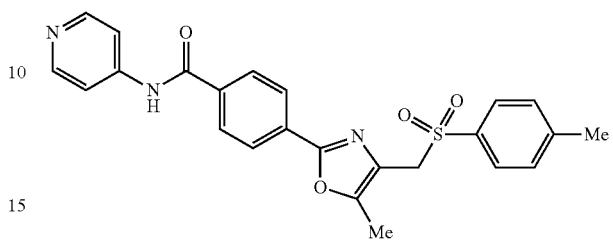

4-(5-Methyl-4-{[(4-methylphenyl)sulfonyl]methyl}-1,3-oxazol-2-yl)-N-(4-pyridinyl)benzamide (6). Method E. Reaction of oxalyl chloride (70.2 λL, 0.8 mmol) and benzoic acid 4 (200 mg, 0.5 mmol) with subsequent coupling to 4-aminopyridine (56 mg, 0.6 mmol) gave starting material (52 mg, 26%) and benzamide 6 (157 mg, 65%) as a white powder: mp (EtOAc) 229-231° C.; $^1$H NMR δ 10.69 (s, 1 H, CONH), 8.50 (dd, J=6.3, 1.5 Hz, 2 H, H-2', H-6'), 8.10 (dd, J=8.6, 1.8 Hz, 2 H, H-2, H-6), 7.97 (dd, J=8.6, 1.8 Hz, 2 H, H-3, H-5), 7.80 (dd, J=6.3, 1.5 Hz, 2 H, H-3', H-5'), 7.68 (br d, J=8.3Hz, 2 H, H-2'', H-6''), 7.43 (br d, J=8.3Hz, 2 H, H-3'', H-5''), 4.65 (s, 2 H, CH₂SO₂), 2.41 (s, 3 H, CH₃), 2.16 (s, 3 H, CH₃); $^{13}$C NMR δ 165.6, 157.9, 150.3 (2), 150.1, 145.8, 144.5, 135.6, 135.4, 129.7 (2), 129.5, 128.7 (2), 128.3 (2), 126.1, 125.5 (2), 114.1 (2), 53.0, 21.1, 9.7; MS m/z 448.7 (MH⁺, 100%). Anal. calcd for C₂₄H₂₁N₃O₄S.¼CH₃OH: C, 63.94; H, 4.87; N, 9.23. Found: C, 63.89; H, 4.86; N, 9.02%.

Example 3

N-Methyl-4-(5-methyl-4-{[(4-methylphenyl)sulfonyl]methyl}-1,3-oxazol-2-yl)-N-(3-pyridinyl)benzamide (7)

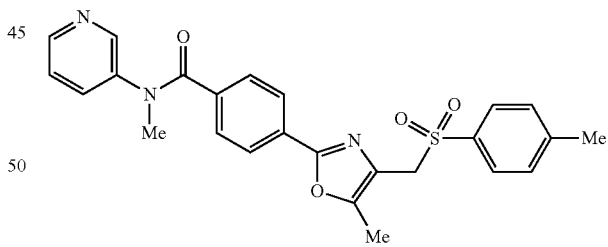

N-Methyl-4-(5-methyl-4-{[(4-methylphenyl)sulfonyl]methyl}-1,3-oxazol-2-yl)-N-(3-pyridinyl)benzamide (7). Method E. Reaction of oxalyl chloride (100 λL, 1.1 mmol) and benzoic acid 4 (275 mg, 0.7 mmol) with subsequent coupling to N-methyl-N-(3-pyridinyl)amine (88 mg, 0.8 mmol) gave benzamide 7 (237 mg, 69%) as a white powder: mp (MeOH) 195-197° C.; $^1$H NMR δ 8.37 (d, J=2.4 Hz, 1 H, H-2'), 8.35 (dd, J=4.7, 1.5 Hz, 1 H, H-6'), 7.72 (ddd, J=8.2, 2.4, 1.5 Hz, 1 H, H-4'), 7.67 (br d, J=8.5 Hz, 2 H, H-2, H-6), 7.63 (br d, J=8.2Hz, 2 H, H-2'', H-6''), 7.37-7.42 (m, J=8.2Hz, 4 H, H-3, H-5, H-3'', H-5''), 7.34 (ddd, J=8.2, 4.7, 1 H, H-5'), 4.58 (s, 2 H, CH₂SO₂), 3.42 (s, 3 H, NCH₃), 2.34 (s, 3 H, CH₃), 2.06 (s, 3 H, CH₃); $^{13}$C NMR δ 168.8, 157.8, 149.8, 148.1, 147.3, 144.4, 140.7, 137.4, 135.5, 134.2, 129.6 (2), 129.0 (2), 128.2 (2), 127.2, 125.9, 125.0 (2), 123.8, 52.9, 37.6, 21.0, 9.6; MS m/z 462.6 (MH$^+$, 100%). Anal. calcd for C$_{25}$H$_{23}$N$_3$O$_4$S: C, 65.06; H, 5.02; N, 9.10. Found: C, 64.90; H, 4.92; N, 8.83%.

Example 4

4-(5-Methyl-4-{[(4-methylphenyl)sulfonyl]methyl}-1,3-oxazol-2-yl)-N-(2-pyridinylmethyl)benzamide (8)

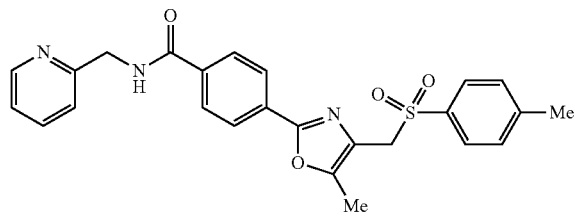

4-(5-Methyl-4-{[(4-methylphenyl)sulfonyl]methyl}-1,3-oxazol-2-yl)-N-(2-pyridinylmethyl)benzamide (8). Method E. Reaction of oxalyl chloride (75 λL, 0.9 mmol) and benzoic acid 4 (215 mg, 0 6 mmol) with subsequent coupling to 2-pyridinylmethylamine (68.2 λL, 0.6 mmol) gave benzamide 8 (221 mg, 83%) as a white powder: mp (EtOAc) 154-155° C.; $^1$H NMR δ 9.21 (t, J=6.0 Hz, 1 H, CONH), 8.52 (dd, J=4.8, 1.5 Hz, 1 H, H-6'), 8.04 (d, J=8.6 Hz, 2 H, H-2, H-6), 7.91 (d, J=8.6 Hz, 2 H, H-3, H-5), 7.77 (dt, J=7.8, 1.8 Hz, 1 H, H-4'), 7.67 (d, J =8.3Hz, 2 H, H-2", H-6"), 7.42 (d, J=8.3Hz, 2 H, H-3", H-5"), 7.35 (d, J=7.8 Hz, 1 H, H-3'), 7.27 (dd, J=7.7, 4.8 Hz, 1 H, H-5'), 4.63 (s, 2 H, CH$_2$SO$_2$), 4.59 (d, J=6.0 Hz, 2 H, CH$_2$N), 2.41 (s, 3 H, CH$_3$), 2.14 (s, 3 H, CH$_3$); $^{13}$C NMR δ 165.6, 158.6, 158.0, 149.9, 148.8, 144.5, 136.7, 135.6, 135.5, 129.6 (2), 128.8, 128.3 (2), 128.1 (2), 126.0, 125.4 (2), 122.1, 121.0, 53.0, 44.8, 21.0, 9.7; MS m/z 462.6 (MH$^+$, 100%). Anal. calcd for C$_{25}$H$_{23}$N$_3$O$_4$S: C, 65.06; H, 5.02; N, 9.10. Found: C, 65.03; H, 5.00; N, 9.11%.

Example 5

4-(5-Methyl-4-{[(4-methylphenyl)sulfonyl]methyl}-1,3-oxazol-2-yl)-N-(3-pyridinylmethyl)benzamide (9)

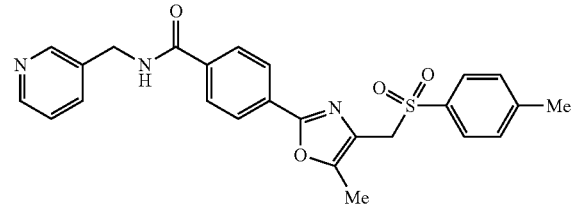 [SMILES: Cc1ccc(S(=O)(=O)Cc2nc(-c3ccc(C(=O)NCc4cccnc4)cc3)oc2C)cc1]

4-(5-Methyl-4-{[(4-methylphenyl)sulfonyl]methyl}-1,3-oxazol-2-yl)-N-(3-pyridinylmethyl)benzamide (9). Method E. Reaction of oxalyl chloride (195 λL, 2.2 mmol) and benzoic acid 4 (415 mg, 1.1 mmol) with subsequent coupling to 3-pyridinylmethylamine (125 λL, 1.2 mmol) gave benzamide 9 (406 mg, 79%) as a white powder: mp (EtOAc) 190-191° C.; $^1$H NMR δ 9.20 (t, J=5.8 Hz, 1 H, CONH), 8.57 (d, J=1.7 Hz, 1 H, H-2'), 8.47 (dd, J=4.8, 1.5 Hz, 1 H, H-6'), 8.00 (d, J=8.5 Hz, 2 H, H-2, H-6), 7.90 (d, J=8.4 Hz, 2 H, H-3, H-5), 7.74 (dt, J=7.8, 1.8 Hz, 1 H, H-4'), 7.67 (d, J=8.2Hz, 2 H, H-2", H-6"), 7.42 (d, J=8.2Hz, 2 H, H-3", H-5"), 7.36 (dd, J=7.8, 4.8Hz, 1 H, H-5'), 4.63 (s, 2 H, CH$_2$SO$_2$), 4.51 (d, J=5.8Hz, 2 H, CH$_2$N), 2.40 (s, 3 H, CH$_3$), 2.13 (s, 3 H, CH$_3$); $^{13}$C NMR δ 165.5, 158.0, 149.9, 148.9, 148.1, 144.5, 135.6, 135.4, 135.2, 134.9, 129.6 (2), 128.8, 128.3 (2), 128.1 (2), 126.0, 125.4 (2), 123.5, 53.0, 40.6, 21.0, 9.7; MS m/z 462.7 (MH$^+$, 100%). Anal. calcd for C$_{25}$H$_{23}$N$_3$O$_4$S: C, 65.06; H, 5.02; N, 9.10. Found: C, 64.79; H, 5.03; N, 9.15%.

Example 6

4-(5-Methyl-4-{[(4-methylphenyl)sulfonyl]methyl}-1,3-oxazol-2-yl)-N-(4-pyridinylmethyl)benzamide (10)

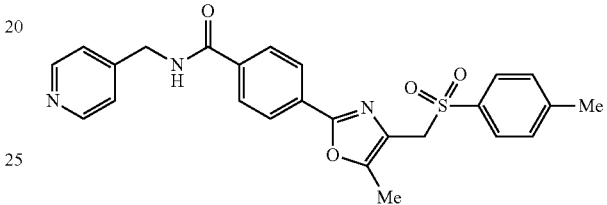

4-(5-Methyl-4-{[(4-methylphenyl)sulfonyl]methyl}-1,3-oxazol-2-yl)-N-(4-pyridinylmethyl)benzamide (10). Method E. Reaction of oxalyl chloride (178 λL, 2.0 mmol) and benzoic acid 4 (379 mg, 1.0 mmol) with subsequent coupling to 4-pyridinylmethylamine (114 λL, 1.1 mmol) gave benzamide 10 (336 mg, 71%) as a white powder: mp (EtOAc) 169-172° C.; $^1$H NMR δ 9.24 (t, J=5.9 Hz, 1 H, CONH), 8.50 (dd, J=4.4, 1.6Hz, 2 H, H-2', H-6'), 8.03 (dd, J=8.6, 1.8Hz, 2 H, H-2, H-6), 7.92 (dd, J=8.6, 1.8Hz, 2 H, H-3, H-5), 7.67 (d, J=8.3Hz, 2 H, H-2", H-6"), 7.42 (d, J=8.3Hz, 2 H, H-3", H-5"), 7.32 (dd, J=4.4, 1.6Hz, 2 H, H-3', H-5'), 4.63 (s, 2 H, CH$_2$SO$_2$), 4.51 (d, J=5.9Hz, 2 H, CH$_2$N), 2.41 (s, 3 H, CH$_3$), 2.14 (s, 3 H, CH$_3$); $^{13}$C NMR δ 165.7, 158.0, 150.0, 148.9 (2), 148.4, 144.5, 135.6, 135.3, 129.7 (2), 128.9, 128.3 (2), 128.1 (2), 126.0, 125.5 (2), 122.2 (2), 53.0, 41.8, 21.1, 9.7; MS m/z 462.8 (MH$^+$, 100%). Anal. calcd for C$_{25}$H$_{23}$N$_3$O$_4$S: C, 65.06; H, 5.02; N, 9.10. Found: C, 65.10; H, 4.96; N, 9.10%.

Example 7

N-Methyl-4-(5-methyl-4-{[(4-methylphenyl)sulfonyl]methyl}-1,3-oxazol-2-yl)-N-(3-pyridinylmethyl)benzamide (11)

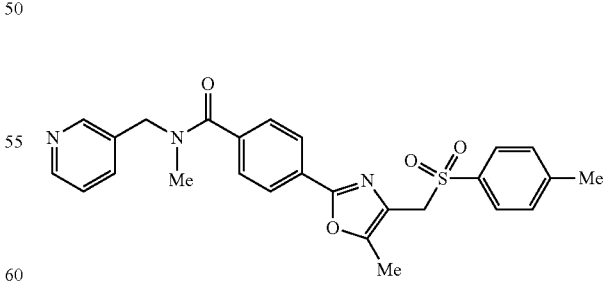

N-Methyl-4-(5-methyl-4-{[(4-methylphenyl)sulfonyl]methyl}-1,3-oxazol-2-yl)-N-(3-pyridinylmethyl)benzamide (11). Method E. Reaction of oxalyl chloride (132 λL, 1.5 mmol) and benzoic acid 4 (376 mg, 1.0 mmol) with subsequent coupling to N-methyl-N-(3-pyridinylmethyl)amine (51 mg, 1.1 mmol) gave benzamide 11 (322 mg, 67%) as a white powder: mp (EtOAc) 77-80° C.; $^1$H NMR δ 8.59 (br s, 1 H, H-2'), 8.52 (br d, J=4.5Hz, 1 H, H-6'), 7.87 (br d, J=7.6Hz, 2 H, H-2, H-6), 7.77 (br s, 1 H, H-4'), 7.66 (br d, J=8.2Hz, 2 H, H-2", H-6"), 7.58 (br s, 2 H, H-3, H-5), 7.38-7.44 (m, 3 H, H-5', H-3", H-5"), 4.71 (br s, 2 H, CH$_2$N), 4.62 (s, 2 H, CH$_2$SO$_2$), 2.90 (s, 3 H, NCH$_3$), 2.39 (s, 3H, CH$_3$), 2.11 (s, 3 H, CH$_3$); $^{13}$C NMR δ 169.7, 158.0, 149.7, 149.1, 148.6, 144.5, 137.6, 135.6, 135.5, 132.9, 129.6 (2), 128.2 (2), 127.8 (2), 127.4, 125.9, 125.5 (2), 123.7, 52.9, 47.8, 37.0, 21.0, 9.6; MS m/z 476.7 (MH$^+$, 100%). Anal. calcd for C$_{26}$H$_{25}$N$_3$O$_4$S: C, 65.67; H, 5.30; N, 8.84. Found: C, 65.46; H, 5.37; N, 8.67%.

Example 8

4-(5-Methyl-4-{[(4-methylphenyl)sulfonyl]methyl}-1,3-oxazol-2-yl)-N-[2-(3-pyridinyl)ethyl]benzamide (12)

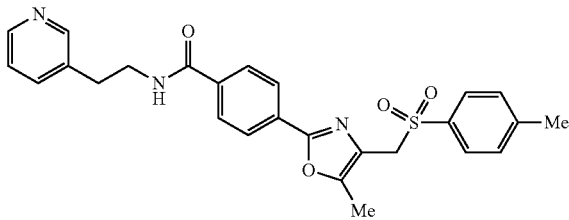 [SMILES: Cc1ccc(S(=O)(=O)Cc2nc(-c3ccc(C(=O)NCCc4cccnc4)cc3)oc2C)cc1]

4-(5-Methyl-4-{[(4-methylphenyl)sulfonyl]methyl}-1,3-oxazol-2-yl)-N-[2-(3-pyridinyl)ethyl]benzamide (12). Method E. Reaction of oxalyl chloride (71.2 μL, 0.82 mmol) and benzoic acid 4 (202 mg, 0.54 mmol) with subsequent reaction with 2-(3-pyridinyl)ethylamine (71 λL, 0.59 mmol) gave benzamide 12 (208 mg, 81%) as a white powder: mp (EtOAc) 207-208° C.; $^1$H NMR δ 8.68 (t, J=5.6Hz, 1 H, CONH), 8.46 (d, J=1.7Hz, 1 H, H-2'), 8.41 (dd, J=4.7, 1.6Hz, 1 H, H-6'), 7.93 (dd, J=8.6, 2.0Hz, 2 H, H-2, H-6), 7.87 (dd, J=8.6, 2.0Hz, 2 H, H-3, H-5), 7.65-7.69 (m, 3 H, H-4', H-2", H-6"), 7.42 (d, J=8.3Hz, 2 H, H-3", H-5"), 7.31 (ddd, J=7.8, 4.7, 0.7Hz, 1 H, H-5'), 4.62 (s, 2 H, CH$_2$SO$_2$), 3.54 (dt, J=7.0, 5.8 Hz, 2 H, CH$_2$N), 2.89 (t, J=7.1Hz, 2 H, CH$_2$), 2.40 (s, 3 H, CH$_3$), 2.13 (s, 3 H, CH$_3$); $^{13}$C NMR δ 165.4, 158.0, 149.9, 149.8, 147.4, 144.5, 136.2, 135.8, 135.6, 134.9, 129.6 (2), 128.7, 128.3 (2), 127.9 (2), 126.0, 125.4 (2), 123.4, 53.0, 40.4, 32.0, 21.0, 9.7; MS m/z 476.6 (MH$^+$, 100%). Anal. calcd for C$_{26}$H$_{25}$N$_3$O$_4$S: C, 65.67; H, 5.30; N, 8.84. Found: C, 65.53; H, 5.18; N, 8.75%.

Example 9

4-(5-Methyl-4-{[(4-methylphenyl)sulfonyl]methyl}-1,3-oxazol-2-yl)-N-(2-pyrazinylmethyl)benzamide (13)

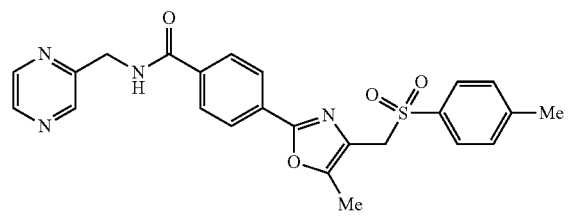 [SMILES: Cc1ccc(S(=O)(=O)Cc2nc(-c3ccc(C(=O)NCc4cnccn4)cc3)oc2C)cc1]

4-(5-Methyl-4-{[(4-methylphenyl)sulfonyl]methyl}-1,3-oxazol-2-yl)-N-(2-pyrazinylmethyl)benzamide (13). Method E. Reaction of oxalyl chloride (74 λL, 0.8 mmol) and benzoic acid 4 (209 mg, 0.6 mmol) with subsequent coupling to 2-pyrazinylmethylamine (90 mg, 0.6 mmol) gave benzamide 13 (192 mg, 74%) as a white powder: mp (EtOAc) 204-206° C.; $^1$H NMR δ 9.30 (t, J=5.8Hz, 1 H, CONH), 8.66 (d, J=1.5Hz, 1 H, H-3'), 8.59 (dd, J=2.6, 1.5Hz, 1 H, H-5'), 8.54 (d, J=2.6Hz, 1 H, H-6'), 8.02 (d, J=8.6Hz, 2 H, H-2, H-6), 7.90 (d, J=8.6Hz, 2 H, H-3, H-5), 7.67 (d, J=8.3Hz, 2 H, H-2", H-6"), 7.42 (d, J=8.3Hz, 2 H, H-3", H-5"), 4.62-4.66 (m, 4 H, CH$_2$SO$_2$, CH$_2$N), 2.41 (s, 3 H, CH$_3$), 2.14 (s, 3H, CH$_3$); $^{13}$C NMR δ 165.7, 158.0, 154.1, 149.9, 144.5, 143.9, 143.5, 143.2, 135.6, 135.3, 129.7 (2), 128.9, 128.3 (2), 128.1 (2), 126.0, 125.4 (2), 53.0, 42.9, 21.0, 9.7; MS m/z 433.6 (MH$^+$, 100%). Anal. calcd for C$_{24}$H$_{22}$N$_4$O$_4$S: C, 62.32; H, 4.79; N, 12.11. Found: C, 62.36; H, 4.67; N, 12.09%.

Example 10

N-[(1-Methyl-1H-imidazol-2-yl)methyl]-4-(5-methyl-4-{[(4-methylphenyl)sulfonyl]methyl}-1,3-oxazol-2-yl)benzamide (14)

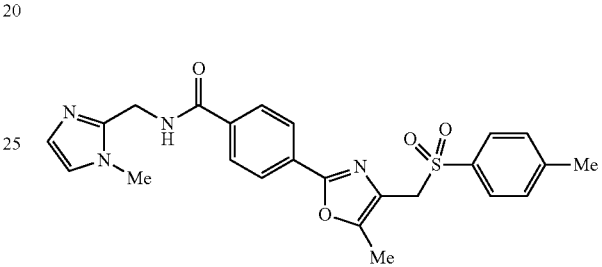

N-[(1-Methyl-1H-imidazol-2-yl)methyl]-4-(5-methyl-4-{[(4-methylphenyl)sulfonyl]methyl}-1,3-oxazol-2-yl)benzamide (14). Method E. Reaction of oxalyl chloride (75 λL, 0.86 mmol) and benzoic acid 4 (212 mg, 0.57 mmol) with subsequent coupling to (1-methyl-1H-imidazol-2-yl)methylamine (70 mg, 0.63 mmol) gave benzamide 14 (185 mg, 70%) as a white powder: mp (EtOAc) 190-192° C.; $^1$H NMR δ 9.05 (t, J=5.5Hz, 1 H, CONH), 8.00 (dd, J=8.6, 1.8Hz, 2 H, H-2, H-6), 7.87 (dd, J=8.6, 1.8Hz, 2H, H-3, H-5), 7.67 (d, J=8.3Hz, 2 H, H-2', H-6'), 7.42 (d, J=8.3Hz, 2 H, H-3', H-5'), 7.08 (d, J=1.1Hz, 1 H, H-5"), 6.80 (d, J=1.1Hz, 1 H, H-4"), 4.62 (s, 2 H, CH$_2$SO$_2$), 4.54 (d, J=5.5 Hz, 2 H, CH$_2$N), 3.66 (s, 3 H, NCH$_3$), 2.40 (s, 3 H, CH$_3$), 2.13 (s, 3 H, CH$_3$); $^{13}$C NMR δ 165.2, 158.0, 149.9, 144.5 (2), 135.6, 135.3, 129.6 (2), 128.8, 128.3 (2), 128.2 (2), 126.4, 126.0, 125.3 (2), 121.8, 53.0, 35.5, 32.4, 21.0, 9.6; MS m/z 462.5 (MH$^+$, 100%). Anal. calcd for C$_{24}$H$_{24}$N$_4$O$_4$S: C, 62.05; H, 5.21; N, 12.06. Found: C, 61.76; H, 5.09; N, 11.76%.

Example 11

N-[(1-Methyl-1H-imidazol-5-yl)methyl]-4-(5-methyl-4-{[(4-methylphenyl)sulfonyl]methyl}-1,3-oxazol-2-yl)benzamide (15)

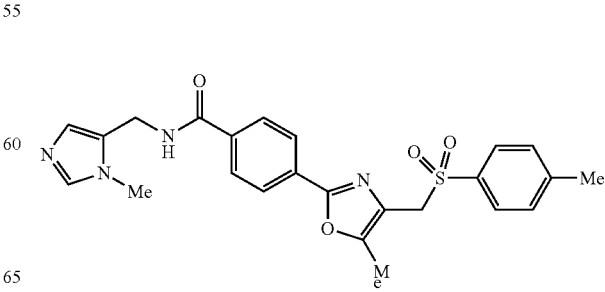

N-[(1-Methyl-1H-imidazol-5-yl)methyl]-4-(5-methyl-4-{[(4-methylphenyl)sulfonyl]methyl}-1,3-oxazol-2-yl)benzamide (15). Method E.

Reaction of oxalyl chloride (111 λL, 1.27 mmol) and benzoic acid 4 (318 mg, 0.85 mmol) with subsequent coupling to (1-methyl-1H-imidazol-5-yl)methylamine (104 mg, 0.94 mmol) gave benzamide 15 (325 mg, 82%) as a white powder: mp (EtOAc) 240-242° C.; $^1$H NMR δ 8.93 (t, J=5.3Hz, 1 H, CONH), 7.97 (br d, J=8.5Hz, 2 H, H-2, H-6), 7.87 (br d, J=8.5Hz, 2 H, H-3, H-5), 7.67 (br d, J=8.3 Hz, 2 H, H-2', H-6'), 7.54 (s, 1 H, H-2''), 7.42 (br d, J=8.3Hz, 2 H, H-3', H-5'), 6.84 (s, 1 H, H-4''), 4.62 (s, 2 H, CH$_2$SO$_2$), 4.48 (d, J=5.3Hz, 2 H, CH$_2$N), 3.62 (s, 3 H, NCH$_3$), 2.40 (s, 3 H, CH$_3$), 2.13 (s, 3 H, CH$_3$); $^{13}$C NMR δ 165.1, 157.9, 149.8, 144.4, 138.1, 135.5, 135.4, 129.5 (2), 128.7, 128.6, 128.1 (2), 128.0 (2), 127.7, 125.9, 125.2 (2), 52.8, 32.5, 30.9, 20.9, 9.5; MS m/z 465.5 (MH$^+$, 100%). Anal. calcd for C$_{24}$H$_{24}$N$_4$O$_4$S: C, 62.05; H, 5.21; N, 12.06. Found: C, 62.42; H, 5.24; N, 12.12%.

Example 12

4-{5-Methyl-4-[(phenylsulfonyl)methyl]-1,3-oxazol-2-yl}-N-(3-pyridinylmethyl)benzamide (18)

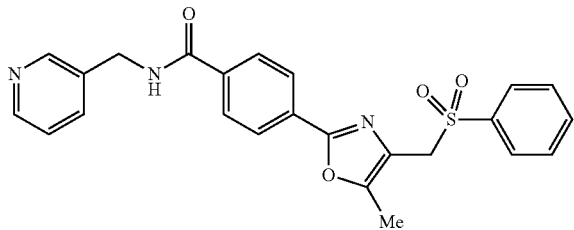 [SMILES: Cc1oc(-c2ccc(C(=O)NCc3cccnc3)cc2)nc1CS(=O)(=O)c1ccccc1]

Methyl 4-{5-methyl-4-[(phenylsulfonyl)methyl]-1,3-oxazol-2-yl}benzoate (16). Method A. Reaction of chloride 2 (267 mg, 1.0 mmol) and sodium benzenesulfinate (173 mg, 1.1 mmol) gave benzoate 16 (311 mg, 84%) as a white powder: mp (EtOAc) 159-161° C.; $^1$H NMR (CDCl$_3$) δ 8.07 (ddd, J=8.7, 1.9, 1.5 Hz, 2 H, H-2, H-6), 7.91 (ddd, J=8.7, 1.9, 1.5Hz, 2 H, H-3, H-5), 7.82 (ddd, J=8.2, 2.0, 1.2Hz, 2 H, H-2', H-6'), 7.64 (tt, J=7.5, 1.2Hz, 1 H, H-4'), 7.52 (br dd, J=8.2, 7.5Hz, 2 H, H-3', H-5'), 4.32 (s, 2 H, CH$_2$SO$_2$), 3.94 (s, 3 H, OCH$_3$), 2.32 (s, 3 H, CH$_3$); MS m/z 372.3 (MH$^+$, 100%). Anal. calcd for C$_{19}$H$_{17}$NO$_5$S: C, 61.44; H, 4.61; N, 3.77. Found: C, 61.75; H, 4.62; N, 3.75%.

4-{5-Methyl-4-[(phenylsulfonyl)methyl]-1,3-oxazol-2-yl}benzoic Acid (17). Method C. Reaction of benzoate 16 (290 mg, 0.78 mmol) and 6 M HCl (5 mL) gave acid 17 (278 mg, 100%) as a white solid: mp (H$_2$O) 284-287° C.; $^1$H NMR δ 12.68 (br s, 1 H, CO$_2$H), 8.04 (br d, J=8.4Hz, 2 H, H-2, H-6), 7.90 (br d, J=8.4 Hz, 2 H, H-3, H-5), 7.80 (br ddd, J=8.1, 1.9, 1.2Hz, 2 H, H-2', H-6'), 7.75 (tt, J=7.5, 1.2Hz, 1 H, H-4'), 7.62 (br dd, J=8.1, 7.4Hz, 2 H, H-3', H-5'), 4.68 (s, 2 H, CH$_2$SO$_2$), 2.13 (s, 3 H, CH$_3$); MS m/z 358.8 (MH$^+$, 100%).

4-{5-Methyl-4-[(phenylsulfonyl)methyl]-1,3-oxazol-2-yl}-N-(3-pyridinylmethyl)benzamide (18). Method E. Reaction of oxalyl chloride (102 λL, 1.17 mmol) and benzoic acid 17 (280 mg, 0.78 mmol) with subsequent coupling to 3-pyridinylmethylamine (87 λL, 0.86 mmol) gave benzamide 18 (169 mg, 48%) as a white powder: mp (EtOAc) 196-198° C.; $^1$H NMR δ 9.20 (t, J=5.9 Hz, 1 H, CONH), 8.57 (br s, 1 H, H-2'), 8.46 (br s, 1 H, H-6'), 8.00 (br dd, J=8.6, 1.8Hz, 2 H, H-2, H-6), 7.89 (br dd, J=8.6, 1.8Hz, 2 H, H-3, H-5), 7.80 (br d, J=8.5Hz, 2 H, H-2'', H-6''), 7.71-7.76 (m, 2 H, H-4', H-4''), 7.62 (br dd, J=8.2, 7.5 Hz, 2 H, H-3'', H-5''), 7.36 (dd, J=7.8, 4.8Hz, 1 H, H-5'), 4.68 (s, 2 H, CH$_2$SO$_2$), 4.50 (d, J=5.8Hz, 2 H, CH$_2$N), 2.13 (s, 3 H, CH$_3$); $^{13}$C NMR δ 165.4, 157.9, 149.9, 148.8, 148.0, 138.3, 135.3, 135.0, 134.8, 133.8, 129.1 (2), 128.7, 128.1 (2), 128.0 (2), 125.8, 125.3 (2), 123.4, 52.7, 40.4, 9.5; MS m/z 448.5 (MH$^+$, 100%). Anal. calcd for C$_{24}$H$_{21}$N$_3$O$_4$S: C, 64.41; H, 4.73; N, 9.39. Found: C, 64.23; H, 4.71; N, 9.37%.

Example 13

4-(4-{[(4-Chlorophenyl)sulfonyl]methyl}-5-methyl-1,3-oxazol-2-yl)-N-(3-pyridinylmethyl)benzamide (21)

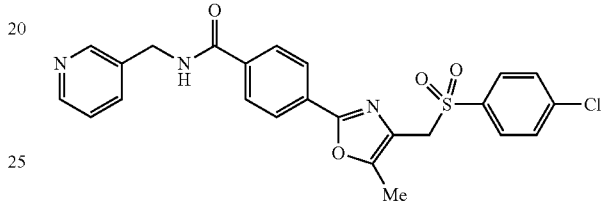

Methyl 4-(4-{[(4-Chlorophenyl)sulfonyl]methyl}-5-methyl-1,3-oxazol-2-yl)benzoate (19). Method A. Reaction of chloride 2 (268 mg, 1.0 mmol) and sodium 4-chlorobenzenesulfinate (198 mg, 1.0 mmol) gave benzoate 19 (273 mg, 67%) as a white powder: mp (EtOAc) 186-188° C.; $^1$H NMR (CDCl$_3$) δ 8.08 (ddd, J=8.7, 1.9, 1.6Hz, 2 H, H-2, H-6), 7.90 (ddd, J=8.7, 1.9, 1.6Hz, 2 H, H-3, H-5), 7.74 (ddd, J=8.7, 2.4, 2.0Hz, 2 H, H-2', H-6'), 7.49 (ddd, J=8.7, 2.4, 2.0Hz, 2 H, H-3', H-5'), 4.32 (s, 2 H, CH$_2$SO$_2$), 3.94 (s, 3 H, OCH$_3$), 2.37 (s, 3 H, CH$_3$); MS m/z 407.0 (MH$^+$, 100%), 409.0 (MH$^+$, 35%). Anal. calcd for C$_{19}$H$_{16}$ClNO$_5$S: C, 56.23; H, 3.97; N, 3.45. Found: C, 56.11; H, 3.80; N, 3.35%.

4-(4-{[(4-Chlorophenyl)sulfonyl]methyl}-5-methyl-1,3-oxazol-2-yl)benzoic Acid (20). Method C. Reaction of benzoate 19 (217 mg, 0.53 mmol) and 6 M HCl (5 mL) gave acid 20 (208 mg, 100%) as a white solid: mp (H$_2$O) 268-271° C.; $^1$H NMR [(CD$_3$)$_2$SO] δ 13.18 (br s, 1 H, CO$_2$H), 8.04 (dd, J=8.6, 1.8Hz, 2 H, H-2, H-6), 7.90 (br dd, J=8.6, 1.8Hz, 2 H, H-3, H-5), 7.81 (ddd, J=8.7, 2.4, 2.0 Hz, 2 H, H-2', H-6'), 7.70 (ddd, J=8.7, 2.4, 2.0Hz, 2 H, H-3', H-5'), 4.74 (s, 2 H, CH$_2$SO$_2$), 2.21 (s, 3 H, CH$_3$); MS m/z 393.2 (MH$^+$, 100%), 393.0 (MH$^+$, 35%). Anal. calcd for C$_{18}$H$_{14}$ClNO$_5$S: C, 55.18; H, 3.60; N, 3.57. Found: C, 55.22; H, 3.41; N, 3.47%.

4-(4-{[(4-Chlorophenyl)sulfonyl]methyl}-5-methyl-1,3-oxazol-2-yl)-N-(3-pyridinylmethyl)benzamide (21) Method E. Reaction of oxalyl chloride (60 λL, 0.69 mmol) and benzoic acid 20 (179 mg, 0.46 mmol) with subsequent coupling to 3-pyridinylmethylamine (51 λL, 0.50 mmol) gave benzamide 21 (183 mg, 85%) as a white powder: mp (EtOAc) 220-222° C.; $^1$H NMR δ 9.20 (t, J=5.8Hz, 1 H, CONH), 8.56 (d, J=1.6Hz, 1 H, H-2'), 8.51 (dd, J=4.7, 1.6Hz, 1 H, H-6'), 8.00 (d, J=8.6Hz, 2 H, H-2, H-6), 7.88 (d, J=8.6Hz, 2H, H-3, H-5), 7.81 (ddd, J=8.7, 2.4, 1.9Hz, 2 H, H-2'', H-6''), 7.74 (br dt, J=7.9, 1.8Hz, 1 H, H-4'), 7.70 (ddd, J=8.7, 2.4, 1.9Hz, 2 H, H-3'', H-5''), 7.36 (dd, J=7.9, 4.7Hz, 1 H, H-5'), 4.73 (s, 2 H, CH$_2$SO$_2$), 4.51 (d, J=5.8Hz, 2 H, CH$_2$N), 2.21 (s, 3 H, CH$_3$); $^{13}$C NMR δ 165.4, 158.0, 150.0, 148.8, 148.0, 139.0, 137.3, 135.4, 135.1, 134.8, 130.2 (2), 129.2 (2), 128.7, 128.0 (2), 125.6, 125.3 (2), 123.4, 52.7, 40.4, 9.7; MS m/z 483.3 (MH$^+$,

Example 14

4-(4-{[(4-tert-Butylphenyl)sulfonyl]methyl}-5-methyl-1,3-oxazol-2-yl)-N-(3-pyridinylmethyl)benzamide (24)

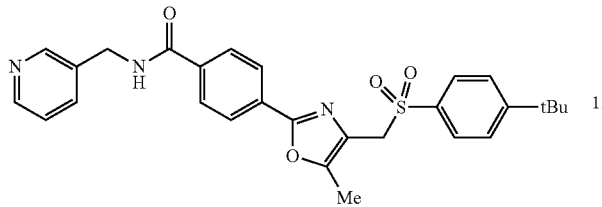

Methyl 4-(4-{[(4-tert-Butylphenyl)sulfonyl]methyl}-5-methyl-1,3-oxazol-2-yl)benzoate (22) A solution of $Na_2SO_3$ (126 mg, 1.0 mmol) and $Na_2CO_3$ (106 mg, 1.0 mmol) in water (2 mL) was added to a suspension of 4-tert-butylbenzenesulfonyl chloride (233 mg, 1.0 mmol) in water (5 mL) and the mixture was stirred at 100° C. for 2 h. A solution of chloride 2 (268 mg, 1.0 mmol) in EtOH (5 mL) was added and the mixture stirred at 100° C. for 16 h. The mixture was cooled and diluted with water (40 mL) and stirred for 15 min. The precipitate was filtered, washed with water (5 mL). The residue purified by column chromatography, eluting with a gradient (20-50%) of EtOAc/pet. ether, to give benzoate 22 (112 mg, 26%) as a white powder: mp (EtOAc) 190-192° C.; $^1$H NMR (CDCl$_3$) δ 8.05 (ddd, J=8.6, 1.8, 1.5Hz, 2 H, H-2, H-6), 7.89 (ddd, J=8.6, 1.8, 1.5Hz, 2 H, H-3, H-5), 7.71 (ddd, J=8.6, 2.2, 1.8Hz, 2 H, H-2', H-6'), 7.51 (ddd, J=8.6, 2.2, 1.8Hz, 2 H, H-3', H-5'), 4.30 (s, 2 H, CH$_2$SO$_2$), 3.94 (s, 3 H, OCH$_3$), 2.32 (s, 3 H, CH$_3$), 1.33 [s, 9 H, C(CH$_3$)$_3$]; MS m/z 428.5 (MH$^+$, 100%). Anal. calcd for $C_{23}H_{25}NO_5S$: C, 64.62; H, 5.89; N, 3.28. Found: C, 64.70; H, 5.94; N, 3.25%.

4-(4-{[(4-tert-Butylphenyl)sulfonyl]methyl}-5-methyl-1,3-oxazol-2-yl)benzoic Acid (23). Method C. Reaction of benzoate 22 (97 mg, 0.23 mmol) and 6 M HCl (5 mL) gave acid 23 (85 mg, 89%) as a white solid: mp (H$_2$O) 220-222° C.; $^1$H NMR δ 13.15 (br s, 1 H, CO$_2$H), 8.02 (dd, J=8.7, 1.9Hz, 2 H, H-2, H-6), 7.88 (ddd, J=8.7, 1.9, 1.5Hz, 2 H, H-3, H-5), 7.70 (ddd, J=8.6, 2.0, 1.9Hz, 2 H, H-2', H-6'), 7.63 (ddd, J=8.6, 2.0, 1.9Hz, 2 H, H-3', H-5'), 4.64 (s, 2 H, CH$_2$SO$_2$), 2.14 (s, 3 H, CH$_3$), 1.29 [s, 9 H, C(CH$_3$)$_3$]; MS m/z 415.5 (MH$^+$, 100%). Anal. calcd for $C_{22}H_{23}NO_5S \cdot H_2O$: C, 61.24; H, 5.84; N, 3.25. Found: C, 61.32; H, 5.50; N, 3.14%.

4-(4-{[(4-tert-Butylphenyl)sulfonyl]methyl}-5-methyl-1,3-oxazol-2-yl)-N-(3-pyridinylmethyl)benzamide (24). Method E. Reaction of oxalyl chloride (27 λL, 0.31 mmol) and benzoic acid 23 (85 mg, 0.21 mmol) with subsequent coupling to 3-pyridinylmethylamine (23 λL, 0.23 mmol) gave benzamide 24 (49 mg, 46%) as a white powder: mp (EtOAc) 177-180° C.; $^1$H NMR δ 9.20 (t, J=5.8Hz, 1 H, CONH), 8.57 (d, J=1.8Hz, 1 H, H-2'), 8.46 (dd, J=4.7, 1.5Hz, 1 H, H-6'), 7.98 (br d, J=8.5Hz, 2 H, H-2, H-6), 7.86 (br d, J=8.5Hz, 2 H, H-3, H-5), 7.73 (br dt, J=7.9, 1.9Hz, 1 H, H-4'), 7.70 (br dd, J=8.6, 1.9Hz, 2 H, H-2", H-6"), 7.63 (br dd, J=8.6, 1.9Hz, 2 H, H-3", H-5"), 7.36 (ddd, J=7.89, 4.7, 0.6Hz, 1 H, H-5'), 4.60 (s, 2 H, CH$_2$SO$_2$), 4.51 (d, J=5.8Hz, 2 H, CH$_2$N), 2.14 (s, 3 H, CH$_3$), 1.30 us, 9 H, C(CH$_3$)$_3$1; $^{13}$C NMR δ 165.4, 157.8, 157.0, 149.8, 148.7, 148.0, 135.4, 135.3, 135.0, 134.8, 128.7, 128.1 (2), 127.9 (2), 125.9 (2), 125.3 (2), 123.3, 52.9, 40.4, 34.8, 30.6 (3), 9.5, one resonance not observed; MS m/z 504.5 (MH$^+$, 100%). Anal. calcd for $C_{28}H_{29}N_3O_4S \cdot CH_3OH$: C, 65.03; H, 6.21; N, 7.84. Found: C, 65.03; H, 5.94; N, 7.99%.

Example 15

4-(4-{[(3,5-Dimethylphenyl)sulfonyl]methyl}-5-methyl-1,3-oxazol-2-yl)-N-(3-pyridinylmethyl)benzamide (27)

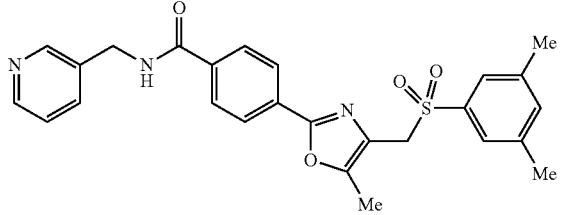 [SMILES: Cc1cc(C)cc(S(=O)(=O)Cc2nc(-c3ccc(C(=O)NCc4cccnc4)cc3)oc2C)c1]

Methyl 4-(4-{[(3,5-Dimethylphenyl)sulfonyl]methyl}-5-methyl-1,3-oxazol-2-yl)benzoate (25). A solution of $Na_2SO_3$ (308 mg, 2.4 mmol) and $Na_2CO_3$ (259 mg, 2.4 mmol) in water (5 mL) was added to a suspension of 3,5-dimethylbenzenesulfonyl chloride (500 mg, 2.4 mmol) in water (5 mL) and the mixture was stirred at 100° C. for 2 h. The mixture was cooled, filtered, and the filtrate was made acidic with 1 M HCl and chilled at 0° C. for 2 h. The precipitate was filtered, washed with water (1 mL) and dried. A mixture of chloride 2 (289 mg, 1.08 mmol) and crude sulfinic acid (184 mg, 1.08 mmol) in dry DMF (10 mL) was stirred at 100° C. for 16 h. The mixture was cooled and diluted with ice/water (50 mL) and stirred for 15 min. The precipitate was filtered, washed with water (5 mL). The residue purified by column chromatography, eluting with a gradient (50-100%) of EtOAc/pet. ether, to give benzoate 25 (388 mg, 90%) as a white powder: mp (EtOAc) 141-143° C.; $^1$H NMR (CDCl$_3$) δ 8.03 (ddd, J=8.6, 1.8, 1.5Hz, 2 H, H-2, H-6), 7.94 (ddd, J=8.6, 1.8, 1.5Hz, 2 H, H-3, H-5), 7.42 (br s, 2 H, H-2', H-6'), 7.25 (br s, 1 H, H-4'), 4.28 (s, 2 H, CH$_2$SO$_2$), 3.94 (s, 3 H, OCH$_3$), 2.35 (s, 3 H, CH$_3$), 2.33 (s, 6 H, 2×CH$_3$); MS m/z 400.5 (MH$^+$, 100%). Anal. calcd for $C_{21}H_{21}NO_5S$: C, 63.14; H, 5.30; N, 3.51. Found: C, 63.23; H, 5.28; N, 3.46%.

4-(4-{[(3,5-Dimethylphenyl)sulfonyl]methyl}-5-methyl-1,3-oxazol-2-yl)benzoic Acid (26). Method C. Reaction of benzoate 25 (346 mg, 0.87 mmol) and 6 M HCl (10 mL) gave acid 26 (335 mg, 100%) as a white solid: mp (H$_2$O) 265-268° C.; $^1$H NMR δ 13.16 (br s, 1 H, CO$_2$H), 8.05 (dd, J=8.5, 1.8Hz, 2 H, H-2, H-6), 7.93 (ddd, J=8.5, 1.8Hz, 2 H, H-3, H-5), 7.41 (br s, 2 H, H-2', H-6'), 7.37 (br s, 1 H, H-4'), 4.62 (s, 2 H, CH$_2$SO$_2$), 2.32 (s, 6 H, 2×CH$_3$), 2.19 (s, 3 H, CH$_3$); MS m/z 386.5 (MH$^+$, 100%). Anal. calcd for $C_{20}H_{19}NO_5S$: C, 62.32; H, 4.97; N, 3.63. Found: C, 62.59; H, 4.84; N, 3.58%.

-(4-{[(3,5-Dimethylphenyl)sulfonyl]methyl}-5-methyl-1,3-oxazol-2-yl)-N-(3-pyridinylmethyl)benzamide (27). Method E. Reaction of oxalyl chloride (106 λL, 1.21 mmol) and benzoic acid 26 (311 mg, 0.81 mmol) with subsequent coupling to 3-pyridinylmethylamine (91 λL, 0.89 mmol) gave benzamide 27 (302 mg, 78%) as a white powder: mp (EtOAc) 188-190° C.; $^1$H NMR δ 9.20 (t, J=5.8 Hz, 1 H, CONH), 8.57 (d, J=1.6Hz, 1 H, H-2'), 8.47 (dd, J=4.7, 1.5Hz, 1 H, H-6'), 8.00 (d, J=8.5Hz, 2 H, H-2, H-6), 7.91 (d, J=8.5Hz, 2 H, H-3, H-5), 7.74 (br d, J=7.8Hz, 1 H, H-4'), 7.41 (br s, 2

H, H-2", H-6"), 7.33-7.38 (m, 2 H, H-5', H-4"), 4.61 (s, 2 H, CH₂SO₂), 4.51 (d, J=5.8Hz, 2 H, CH₂N), 2.32 (s, 6 H, 2×CH₃), 2.19 (s, 3 H, CH₃); ¹³C NMR δ 165.6, 157.9, 150.0, 148.9, 148.1, 138.8, 138.5 (2), 135.4, 135.3, 135.2, 135.0, 134.9, 128.9, 128.1 (2), 125.6 (2), 125.4 (2), 123.4, 52.9, 40.5, 20.6 (2), 9.7; MS m/z 476.5 (MH⁺, 100%). Anal. calcd for C₂₆H₂₅N₃O₄S: C, 65.67; H, 5.30; N, 8.84. Found: C, 65.91; H, 5.38; N, 8.89%.

Example 16

4-(4-{[(4-Bromophenyl)sulfonyl]methyl}-5-methyl-1,3-oxazol-2-yl)-N-(3-pyridinylmethyl)benzamide (30)

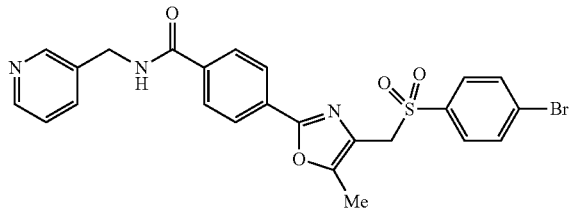 [SMILES: Cc1oc(-c2ccc(C(=O)NCc3cccnc3)cc2)nc1CS(=O)(=O)c1ccc(Br)cc1]

Methyl 4-(4-{[(4-Bromophenyl)sulfonyl]methyl}-5-methyl-1,3-oxazol-2-yl)benzoate (28). Method B. Reaction of chloride 2 (404 mg, 1.52 mmol), 4-bromobenzenethiol (317 mg, 1.60 mmol) and K₂CO₃ (202 mg, 1.60 mmol) in dry DMF (40 mL) with subsequent oxidation by mCPBA (1.31 g, 3.8 mmol) gave benzoate 28 (353 mg, 52%) as a white powder: mp (EtOAc) 186-188° C.; ¹H NMR (CDCl₃) δ 8.09 (ddd, J=8.6, 1.8, 1.5Hz, 2 H, H-2, H-6), 7.89 (ddd, J=8.6, 1.8, 1.5Hz, 2 H, H-3, H-5), 7.63-7.68 (m, 4 H, H-2', H-3', H-5', H-6'), 4.31 (s, 2 H, CH₂SO₂), 3.94 (s, 3 H, OCH₃), 2.38 (s, 3 H, CH₃); MS m/z 450.0 (MH⁺, 100%), 452.0 (MH⁺, 100%). Anal. calcd for C₁₉H₁₆BrNO₅S: C, 50.68; H, 3.58; N, 3.11. Found: C, 51.02; H, 3.62; N, 3.24%.

4-(4-{[(4-Bromophenyl)sulfonyl]methyl}-5-methyl-1,3-oxazol-2-yl)benzoic Acid (29). Method D. Reaction of benzoate 28 (320 mg, 0.71 mmol) and 2 M NaOH (10 mL) in dioxane (10 mL) gave acid 29 (216 mg, 70%) as a white solid: mp (DCM)>310° C.; ¹H NMR δ 13.15 (br s, 1 H, CO₂H), 7.93 (br d, J=8.3Hz, 2H, H-2, H-6), 7.84 (ddd, J=8.6, 2.3, 1.7Hz, 2 H, H-2', H-6'), 7.68-7.73 (m, 4 H, H-3, H-5, H-3', H-5'), 4.70 (s, 2 H, CH₂SO₂), 2.19 (s, 3 H, CH₃); MS m/z 437.0 (MH⁺, 100%), 439.0 (MH⁺, 100%). Anal. calcd for C₁₈H₁₄BrNO₅S.½CH₂Cl₂: C, 47.08; H, 3.12; N, 2.89. Found: C, 47.09; H, 2.80; N, 2.99%.

4-(4-{[(4-Bromophenyl)sulfonyl]methyl}-5-methyl-1,3-oxazol-2-yl)-N-(3-pyridinylmethyl)benzamide (30). Method E. Reaction of oxalyl chloride (61 λL, 0.70 mmol) and benzoic acid 29 (204 mg, 0.47 mmol) with subsequent couping to 3-pyridinylmethylamine (53 λL, 0.52 mmol) gave benzamide 30 (123 mg, 50%) as a white powder: mp (EtOAc) 224-227° C.; ¹H NMR δ 9.20 (t, J=5.9Hz, 1 H, CONH), 8.57 (d, J=1.7Hz, 1 H, H-2'), 8.47 (dd, J=4.7, 1.6Hz, 1 H, H-6'), 8.00 (d, J=8.6Hz, 2 H, H-2, H-6), 7.88 (d, J=8.6Hz, 2H, H-3, H-5), 7.85 (ddd, J=8.6, 2.3, 1.9Hz, 2 H, H-2", H-6"), 7.70-7.76 (m, 3H, H-4', H-3", H-5"), 7.36 (ddd, J=7.8, 4.7, 0.6Hz, 1 H, H-5'), 4.73 (s, 2 H, CH₂SO₂), 4.51 (d, J=5.9Hz, 2 H, CH₂N), 2.22 (s, 3 H, CH₃); ¹³C NMR δ 165.5, 158.1, 150.0, 148.9, 148.1, 137.8, 135.5, 135.2, 134.9, 132.3 (2), 130.4 (2), 128.8, 128.2, 128.1 (2), 125.7, 125.4 (2), 123.5, 52.8, 40.5, 9.7; MS m/z 526.1 (MH⁺, 100%), 528.1 (MH⁺, 100%). Anal. calcd for C₂₄H₂₀BrN₃O₄S.½H₂O: C, 52.95; H, 4.07; N, 7.72. Found: C, 52.74; H, 3.67; N, 7.60%.

Alternate preparation of 4-(4-{[(4-Bromophenyl)sulfonyl]methyl}-5-methyl-1,3-oxazol-2-yl)-N-(3-pyridinylmethyl)benzamide (30). Benzoic acid 29 (150 mg, 0.34 mmol) was dissolved in anhydrous DMF (5 mL), DIEA (0.12 mL, 0.69 mmol) and HBTU (171 mg, 0.45 mmol) were successively added and the reaction mixture was stirred at 20° C. for 10 min 3-Pyridinylmethanamine (0.14 mL, 1.4 mmol) was subsequently added and the reaction mixture was stirred at 20° C. for 1 h. The reaction mixture was diluted with EtOAc (150 mL), washed with H₂O (3×50 mL), washed with brine (50 mL) and dried. The solvent evaporated and the residue was purified by column chromatography, eluting with a gradient (0-10%) MeOH/EtOAc, to afford benzamide 30 (170 mg, 94%) as a white solid: mp (EtOAc) 225-226° C.; spectroscopically identical to the sample prepare above.

Example 17

4-(5-Methyl-4-{[(3-methylphenyl)sulfonyl]methyl}-1,3-oxazol-2-yl)-N-(3-pyridinylmethyl)benzamide (33)

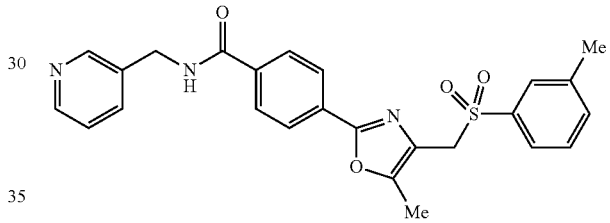

Methyl 4-(5-Methyl-4-{[(3-methylphenyl)sulfonyl]methyl}-1,3-oxazol-2-yl)benzoate (31). Method B. Reaction of chloride 2 (267 mg, 1.00 mmol), 3-methylbenzenethiol (130 mg, 1.05 mmol) and K₂CO₃ (133 mg, 2.5 mmol) in dry DMF (10 mL) with subsequent oxidation by mCPBA (0.86 g, 2.83 mmol) gave benzoate 31 (231 mg, 60%) as a white powder: mp (EtOAc) 161-163° C.; ¹H NMR (CDCl₃) δ 8.08 (ddd, J=8.6, 1.9, 1.5Hz, 2 H, H-2, H-6), 7.92 (ddd, J=8.6, 1.9, 1.5Hz, 2 H, H-3, H-5), 7.59-7.64 (m, 2 H, H-2', H-6'), 7.37-7.45 (m, 2 H, H-3', H-4'), 4.30 (s, 2 H, CH₂SO₂), 3.94 (s, 3 H, OCH₃), 2.38 (s, 3 H, CH₃), 2.33 (s, 3 H, CH₃); MS m/z 386.6 (MH⁺, 100%). Anal. calcd for C₂₀H₁₉NO₅S: C, 62.33; H, 4.97; N, 3.63. Found: C, 62.77; H, 4.94; N, 3.71%.

4-(5-Methyl-4-{[(3-methylphenyl)sulfonyl]methyl}-1,3-oxazol-2-yl)benzoic Acid (32). Method C. Reaction of benzoate 31 (217 mg, 0.56 mmol) and 6 M HCl (10 mL) gave acid 32 (173 mg, 83%) as a white solid: mp (H₂O) 287-290° C.; ¹H NMR δ 13.16 (br s, 1 H, CO₂H), 8.05 (br d, J=8.5Hz, 2 H, H-2, H-6), 7.92 (br d, J=8.5Hz, 2 H, H-3, H-5), 7.63 (br s, 1 H, H-2'), 7.54-7.59 (m, 2 H, H-4', H-6'), 7.50 (t, J=7.6Hz, 1 H, H-5'), 4.65 (s, 2 H, CH₂SO₂), 2.37 (s, 3 H, CH₃), 2.16 (s, 3 H, CH₃); MS m/z 372.6 (MH⁺, 100%). Anal. calcd for C₁₉H₁₇NO₅S: C, 61.74; H, 4.61; N, 3.77. Found: C, 61.51; H, 4.56; N, 3.80%.

4-(5-Methyl-4-{[(3-methylphenyl)sulfonyl]methyl}-1,3-oxazol-2-yl)-N-(3-pyridinylmethyl)benzamide (33). Method E. Reaction of oxalyl chloride (56 λL, 0.64 mmol) and benzoic acid 32 (158 mg, 0.43 mmol) with subsequent coupling to 3-pyridinylmethylamine (48 λL, 0.47 mmol) gave benzamide 33 (79 mg, 40%) as a white powder: mp (EtOAc) 179-

181° C.; $^1$H NMR δ 9.20 (t, J=5.8Hz, 1 H, CONH), 8.57 (d, J=1.8Hz, 1 H, H-2'), 8.47 (dd, J=4.7, 1.6Hz, 1 H, H-6'), 8.00 (d, J=8.5Hz, 2 H, H-2, H-6), 7.90 (br d, J=8.5Hz, 2 H, H-3, H-5), 7.74 (dt, J=7.9, 1.9Hz, 1 H, H-4'), 7.63 (br s, 1 H, H-2'') 7.53-7.60 (m, 2 H, H-4'', H-6''), 7.50 (t, J=7.6Hz, 1 H, H-5''), 7.36 (ddd, J=7.9, 4.7, 0.5Hz, 1 H, H-5'), 4.65 (s, 2 H, CH$_2$SO$_2$), 4.51 (d, J=5.8Hz, 2 H, CH$_2$N), 2.37 (s, 3 H, CH$_3$), 2.16 (s, 3 H, CH$_3$); $^{13}$C NMR δ 165.4, 157.9, 149.9, 148.8, 148.0, 139.0, 138.3, 135.3, 135.1, 134.8, 134.3, 128.9, 128.7, 128.3, 128.0 (2), 125.8, 125.3 (2), 125.2, 123.3, 52.8, 40.4, 20.6, 9.67; MS m/z 462.8 (MH$^+$, 100%). Anal. calcd for C$_{25}$H$_{23}$N$_3$O$_4$S: C, 64.06, 5.02; N, 9.10. Found: C, 64.76; H, 5.06; N, 9.05%.

Example 18

4-(4-{[(4-Methoxyphenyl)sulfonyl]methyl}-5-methyl-1,3-oxazol-2-yl)-N-(3-pyridinylmethyl)benzamide (36)

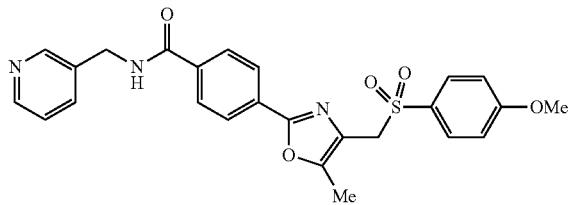 [SMILES: COc1ccc(S(=O)(=O)Cc2nc(-c3ccc(C(=O)NCc4cccnc4)cc3)oc2C)cc1]

Methyl 4-(4-{[(4-Methoxyphenyl)sulfonyl]methyl}-5-methyl-1,3-oxazol-2-yl)benzoate (34). Method B. Reaction of chloride 2 (320 mg, 1.20 mmol), 4-methoxybenzenethiol (187 mg, 1.32 mmol) and K$_2$CO$_3$ (182 mg, 1.44 mmol) in dry DMF (10 mL) with subsequent oxidation by mCPBA (1.04 g, 3.0 mmol) gave benzoate 34 (383 mg, 80%) as a white powder: mp (EtOAc) 197-199° C.; $^1$H NMR (CDCl$_3$) δ 8.08 (ddd, J=8.6, 1.9, 1.5Hz, 2 H, H-2, H-6), 7.93 (ddd, J=8.6, 1.9, 1.5Hz, 2 H, H-3, H-5), 7.72 (ddd, J=9.0, 2.9, 2.1Hz, 2 H, H-2', H-6'), 6.96 (ddd, J=9.0, 2.9, 2.0Hz, 2 H, H-3', H-5'), 4.29 (s, 2 H, CH$_2$SO$_2$), 3.94 (s, 3 H, OCH$_3$), 3.85 (s, 3 H, OCH$_3$), 2.33 (s, 3 H, CH$_3$); MS m/z 402.5 (MH$^+$, 100%). Anal. calcd for C$_{20}$H$_{19}$NO$_6$S: C, 59.84; H, 4.77; N, 3.49. Found: C, 59.83; H, 4.71; N, 3.45%.

4-(4-{[(4-Methoxyphenyl)sulfonyl]methyl}-5-methyl-1,3-oxazol-2-yl)benzoic Acid (35). Method D. Reaction of benzoate 34 (285 mg, 0.71 mmol) and 2 M NaOH (10 mL) in dioxane (10 mL) gave acid 35 (246 mg, 89%) as a white solid: mp (H$_2$O) 245-248° C.; $^1$H NMR [(CD$_3$)$_2$SO] δ 13.16 (br s, 1 H, CO$_2$H), 8.05 (dd, J=8.6, 1.8Hz, 2 H, H-2, H-6), 7.93 (dd, J=8.6, 1.8Hz, 2 H, H-3, H-5), 7.70 (ddd, J=9.0, 2.9, 2.0Hz, 2H, H-2', H-6'), 7.13 (ddd, J=9.0, 2.9, 2.0Hz, 2H, H-3', H-5'), 4.61 (s, 2 H, CH$_2$SO$_2$), 3.84 (s, 3 H, OCH$_3$), 2.14 (s, 3 H, CH$_3$); MS m/z 388.5 (MH$^+$, 100%). Anal. calcd for C$_{19}$H$_{17}$NO$_6$S: C, 58.91; H, 4.42; N, 3.62. Found: C, 58.86; H, 4.22; N, 3.54%.

4-(4-{[(4-Methoxyphenyl)sulfonyl]methyl}-5-methyl-1,3-oxazol-2-yl)-N-(3-pyridinylmethyl)benzamide (36). Method E. Reaction of oxalyl chloride (76 λL, 0.88 mmol) and benzoic acid 35 (226 mg, 0.58 mmol) with subsequent coupling to 3-pyridinylmethylamine (65 λL, 0.64 mmol) gave benzamide 36 (142 mg, 51%) as a white powder: mp (MeOH/EtOAc) 189-191° C.; $^1$H NMR δ 9.22 (t, J=5.8 Hz, 1H, CONH), 8.57 (d, J=1.7Hz, 1 H, H-2'), 8.47 (dd, J=4.7, 1.6Hz, 1 H, H-6'), 8.00 (dd, J=8.6, 1.8Hz, 2 H, H-2, H-6), 7.91 (dd, J=8.6, 1.8Hz, 2 H, H-3, H-5), 7.74 (ddd, J=8.0, 2.1, 1.4Hz, 1 H, H-4'), 7.70 (ddd, J=8.9, 3.0, 2.0Hz, 2 H, H-2'', H-6''), 7.36 (ddd, J=7.9, 4.7, 0.7Hz, 1 H, H-5'), 7.13 (ddd, J=8.9, 3.0, 2.0Hz, 2 H, H-3'', H-5''), 4.60 (s, 2 H, CH$_2$SO$_2$), 4.51 (d, J=5.8Hz, 2 H, CH$_2$N), 3.84 (s, 3 H, OCH$_3$), 2.13 (s, 3 H, CH$_3$); $^{13}$C NMR δ 165.5, 163.3, 157.9, 149.8, 148.9, 148.0, 135.3, 135.1, 134.8, 130.4 (2), 129.8, 128.8, 128.0 (2), 126.1, 125.3 (2), 123.4, 114.3 (2), 55.7, 53.0, 40.4, 9.6; MS m/z 477.6 (MH$^+$, 100%). Anal. calcd for C$_{25}$H$_{23}$N$_3$O$_5$S.½CH$_3$OH: C, 62.06; H, 5.11; N, 8.51. Found: C, 61.85; H, 4.88; N, 8.62%.

Example 19

4-(5-Methyl-4-{[(3-methoxyphenyl)sulfonyl]methyl}-1,3-oxazol-2-yl)-N-(3-pyridinylmethyl)benzamide (39)

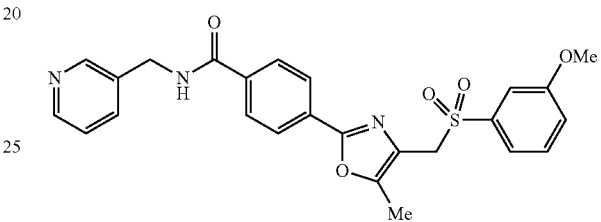

Methyl 4-(5-Methyl-4-{[(3-methoxyphenyl)sulfonyl]methyl}-1,3-oxazol-2-yl)benzoate (37). Method B. A mixture of chloride 2 (300 mg, 1.13 mmol), 3-methoxybenzenethiol (174 mg, 1.24 mmol) and K$_2$CO$_3$ (171 mg, 1.36 mmol) in dry DMF (10 mL) with subsequent oxidation by mCPBA (0.98 g, 2.83 mmol) gave benzoate 37 (240 mg, 53%) as a white powder: mp (EtOAc) 156-159° C.; $^1$H NMR (CDCl$_3$) δ 8.08 (ddd, J=8.6, 1.9, 1.5Hz, 2 H, H-2, H-6), 7.94 (ddd, J=8.6, 1.9, 1.5Hz, 2 H, H-3, H-5), 7.40-7.43 (m, 2 H, H-2', H-6'), 7.29-7.32 (m, 1H, H-4'), 7.14-7.18 (m, 1 H, H-5'), 4.32 (s, 2 H, CH$_2$SO$_2$), 3.94 (s, 3 H, OCH$_3$), 3.78 (s, 3 H, OCH$_3$), 2.34 (s, 3 H, CH$_3$); MS m/z 402.6 (MH$^+$, 100%). Anal. calcd for C$_{20}$H$_{19}$NO$_6$S.¼CH$_3$CO$_2$CH$_2$CH$_3$: C, 59.56; H, 5.00; N, 3.31. Found: C, 59.64; H, 4.70; N, 3.44%.

4-(5-Methyl-4-{[(3-methoxyphenyl)sulfonyl]methyl}-1,3-oxazol-2-yl)benzoic Acid (38) Method D. Reaction of benzoate 37 (213 mg, 0.53 mmol) and 2 M NaOH (10 mL) in dioxane (10 mL) gave acid 38 (160 mg, 78%) as a white solid: mp (H$_2$O) 280-283° C.; $^1$H NMR δ 13.12 (br s, 1H, CO$_2$H), 8.05 (dd, J=8.6, 1.8 Hz, 2 H, H-2, H-6), 7.93 (dd, J=8.6, 1.8Hz, 2 H, H-3, H-5), 7.53 (dd, J=8.9, 7.7 Hz, 1 H, H-5'), 7.35 (dt, J=7.7, 1.2Hz, 1 H, H-6'), 7.27-7.33 (m, 2 H, H-2', H-4'), 4.70 (s, 2 H, CH$_2$SO$_2$), 3.79 (s, 3 H, OCH$_3$), 2.18 (s, 3 H, CH$_3$); MS m/z 388.5 (MH$^+$, 100%). Anal. calcd for C$_{19}$H$_{17}$NO$_6$S.¼H$_2$O: C, 58.23; H, 4.50; N, 3.57. Found: C, 57.89; H, 4.37; N, 3.43%.

4-(5-Methyl-4-{[(3-methoxyphenyl)sulfonyl]methyl}-1,3-oxazol-2-yl)-N-(3-pyridinylmethyl)benzamide (39). Method E. Reaction of oxalyl chloride (50 λL, 0.57 mmol) and benzoic acid 38 (146 mg, 0.38 mmol) with subsequent coupling to 3-pyridinylmethylamine (43 λL, 0.42 mmol) gave benzamide 39 (47 mg, 26%) as a white powder: mp (EtOAc) 143-145° C.; $^1$H NMR δ 9.23 (t, J=5.8Hz, 1 H, CONH), 8.56 (d, J=1.6Hz, 1 H, H-2'), 8.46 (dd, J=4.7, 1.4Hz, 1 H, H-6'), 8.00 (br d, J=8.5Hz, 2 H, H-2, H-6), 7.91 (br d, J=8.5Hz, 2 H, H-3, H-5), 7.74 (br d, J=7.9Hz, 1 H, H-4'), 7.74 (br dd, J=8.9, 7.6Hz, 1 H, H-5''), 7.34-7.39 (m, 2H, H-5', H-2''), 7.25-7.29 (m, 2 H, H-4'', H-6''), 4.70 (s, 2 H, CH$_2$SO$_2$), 4.51 (d, J=5.8Hz, 2 H, CH₂N), 3.79 (s, 3 H, OCH₃), 2.17 (s, 3 H, CH₃); ¹³C NMR δ 165.5, 159.4, 158.0, 150.1, 148.9, 148.1, 139.7, 135.4, 135.2, 134.9, 130.4, 128.8, 128.1 (2), 125.9, 125.4 (2), 123.5, 120.3, 120.1, 112.8, 55.6, 52.7, 40.5, 9.7; MS m/z 478.6 (WE, 100%). Anal. calcd for $C_{25}H_{23}N_3O_5S \cdot \frac{1}{2}CH_3OH$: C, 62.06, 5.11; N, 8.51. Found: C, 62.23; H, 4.90; N, 8.66%.

Example 20

4-(4-{[(3,4-Dimethoxyphenyl)sulfonyl]methyl}-5-methyl-1,3-oxazol-2-yl)-N-(3-pyridinylmethyl)benzamide (42)

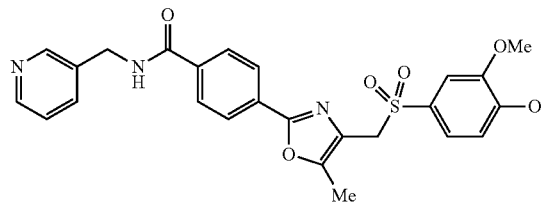

Methyl 4-(4-{[(3,4-Dimethoxyphenyl)sulfonyl]methyl}-5-methyl-1,3-oxazol-2-yl)benzoate (40). Method B. A mixture of chloride 2 (331 mg, 1.24 mmol), 3,4-dimethoxybenzenethiol (232 mg, 1.36 mmol) and K₂CO₃ (205 mg, 1.48 mmol) in dry DMF (10 mL) with subsequent oxidation by mCPBA (1.07 g, 3.10 mmol) gave benzoate 40 (375 mg, 70%) as a white powder: mp (EtOAc) 168-170° C.; ¹H NMR (CDCl₃) δ 8.09 (ddd, J=8.6, 1.9, 1.5Hz, 2 H, H-2, H-6), 7.95 (ddd, J=8.6, 1.9, 1.5Hz, 2 H, H-3, H-5), 7.43 (dd, J=8.5, 2.1Hz, 1 H, H-6'), 7.22 (d, J=2.1Hz, 1 H, H-2'), 6.93 (d, J=8.5Hz, 1 H, H-5'), 4.30 (s, 2 H, CH₂SO₂), 3.94 (s, 3 H, OCH₃), 3.93 (s, 3 H, OCH₃), 3.82 (s, 3 H, OCH₃), 2.36 (s, 3 H, CH₃); MS m/z 432.5 (MH⁺, 100%). Anal. calcd for $C_{21}H_{21}NO_7S$: C, 58.46; H, 4.91; N, 3.25. Found: C, 58.33; H, 4.93; N, 3.20%.

4-(4-{[(3,4-Dimethoxyphenyl)sulfonyl]methyl}-5-methyl-1,3-oxazol-2-yl)benzoic acid (41). Method D. Reaction of benzoate 40 (355 mg, 0.82 mmol) and 2 M NaOH (10 mL) in dioxane (10 mL) gave acid 41 (329 mg, 96%) as a white solid: mp (H₂O) 221-223° C.; ¹H NMR δ 13.16 (br s, 1 H, CO₂H), 8.05 (d, J=8.4Hz, 2 H, H-2, H-6), 7.94 (d, J=8.4Hz, 2 H, H-3, H-5), 7.33 (dd, J=8.5, 2.0Hz, 1 H, H-6'), 7.26 (d, J=2.0Hz, 1 H, H-2'), 7.14 (d, J=8.5Hz, 1 H, H-5'), 4.63 (s, 2 H, CH₂SO₂), 3.84 (s, 3 H, OCH₃), 3.76 (s, 3 H, OCH₃), 2.16 (s, 3 H, CH₃); MS m/z 418.6 (MH⁺, 100%). Anal. calcd for $C_{20}H_{19}NO_7S \cdot \frac{1}{2}H_2O$: C, 56.33; H, 4.73; N, 3.29. Found: C, 56.02; H, 4.59; N, 3.36%.

4-(4-{[(3,4-Dimethoxyphenyl)sulfonyl]methyl}-5-methyl-1,3-oxazol-2-yl)-N-(3-pyridinylmethyl)benzamide (42). Method E. Reaction of oxalyl chloride (92 λL, 1.06 mmol) and benzoic acid 41 (294 mg, 0.70 mmol) with subsequent coupling to 3-pyridinylmethylamine (78 λL, 0.77 mmol) gave benzamide 42 (263 mg, 74%) as a white powder: mp (EtOAc) 104-108° C.; ¹H NMR δ 9.23 (t, J=5.9 Hz, 1 H, CONH), 8.57 (d, J=1.6Hz, 1 H, H-2'), 8.46 (dd, J=4.7, 1.5Hz, 1 H, H-6'), 8.01 (d, J=8.5Hz, 2 H, H-2, H-6), 7.92 (d, J=8.5Hz, 2 H, H-3, H-5), 7.74 (br d, J=7.5Hz, 1 H, H-4'), 7.37 (dd, J=7.5, 4.8Hz, 1 H, H-5'), 7.33 (dd, J=8.5, 2.1Hz, 1 H, H-6"), 7.25 (d, J=2.1Hz, 1 H, H-2"), 7.14 (d, J=8.5Hz, 1 H, H-5"), 4.63 (s, 2 H, CH₂SO₂), 4.51 (d, J=5.8Hz, 2 H, CH₂N), 3.84 (s, 3 H, OCH₃), 3.76 (s, 3 H, OCH₃), 2.15 (s, 3 H, CH₃); ¹³C NMR δ 165.5, 157.9, 153.1, 149.9, 148.8, 148.6, 148.0, 135.3, 135.1, 134.8, 129.7, 128.8, 128.0 (2), 126.2, 125.3 (2), 123.4, 122.2, 111.2, 110.6, 55.9, 55.7, 52.9, 40.4, 9.6; MS m/z 508.7 (MH⁺, 100%). Anal. calcd for $C_{26}H_{25}N_3O_6S \cdot \frac{3}{4}CH_3OH$: C, 60.44, 5.31; N, 7.90. Found: C, 60.58; H, 5.17; N, 7.63%.

Example 21

4-(5-Methyl-4-{[(2,4-dimethylphenyl)sulfonyl]methyl}-1,3-oxazol-2-yl)-N-(3-pyridinylmethyl)benzamide (45).

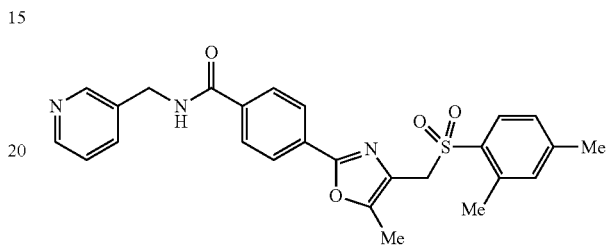

Methyl 4-(5-Methyl-4-{[(2,4-dimethylphenyl)sulfonyl]methyl}-1,3-oxazol-2-yl)benzoate (43). Method B. Reaction of chloride 2 (304 mg, 1.14 mmol), 2,4-dimethylbenzenethiol (174 mg, 1.26 mmol) and K₂CO₃ (173 mg, 1.37 mmol) in dry DMF (10 mL) with subsequent oxidation by mCPBA (984 mg, 2.85 mmol) gave benzoate 43 (136 mg, 30%) as a white powder: mp (EtOAc) 141-143° C.; ¹H NMR (CDCl₃) δ 8.06 (br d, J=8.6Hz, 2 H, H-2, H-6), 7.89 (br dd, J=8.6, 1.8 Hz, 2 H, H-3, H-5), 7.70 (br d, J=8.1Hz, 1 H, H-6'), 7.13 (br s, 1 H, H-3'), 7.06 (br d, J=8.1Hz, 1 H, H-5'), 4.32 (s, 2 H, CH₂SO₂), 3.94 (s, 3 H, OCH₃), 2.63 (s, 3 H, CH₃), 2.35 (s, 3 H, CH₃); MS m/z 400.6 (MH⁺, 100%). Anal. calcd for $C_{21}H_{21}NO_5S \cdot \frac{1}{4}CH_3CO_2CH_2CH_3$: C, 62.69; H, 5.50; N, 3.32. Found: C, 62.52; H, 5.27; N, 3.48%.

4-(5-Methyl-4-{[(2,4-dimethylphenyl)sulfonyl]methyl}-1,3-oxazol-2-yl)benzoic Acid (44). Method D. Reaction of benzoate 43 (131 mg, 0.34 mmol) and 1 M NaOH (10 mL) in dioxane (10 mL) gave acid 44 (109 mg, 83%) as a white solid: mp (H₂O) 235-238° C.; ¹H NMR δ 13.15 (br s, 1 H, CO₂H), 8.06 (br d, J=8.5Hz, 2 H, H-2, H-6), 7.90 (br d, J=8.5Hz, 2 H, H-3, H-5), 7.57 (d, J=8.1Hz, 1 H, H-6'), 7.28 (br s, 1 H, H-3'), 7.17 (br d, J=8.1Hz, 1 H, H-5'), 4.61 (s, 2 H, CH₂SO₂), 2.56 (s, 3 H, CH₃), 2.33 (s, 3 H, CH₃), 2.16 (s, 3H, CH₃); MS m/z 386.5 (MH⁺, 100%). Anal. calcd for $C_{20}H_{19}NO_5S \cdot \frac{3}{4}H_2O$: C, 62.69; H, 5.50; N, 3.32. Found: C, 62.52; H, 5.27; N, 3.48%.

4-(5-Methyl-4-{[(2,4-dimethylphenyl)sulfonyl]methyl}-1,3-oxazol-2-yl)-N-(3-pyridinylmethyl)benzamide (45). Method E. Reaction of oxalyl chloride (31 λL, 0.35 mmol) and benzoic acid 44 (92 mg, 0.24 mmol) with subsequent coupling to 3-pyridinylmethylamine (27 λL, 0.26 mmol) gave benzamide 45 (27 mg, 24%) as a clear gum: ¹H NMR δ 9.22 (t, J=5.8Hz, 1.H, CONH), 8.57 (d, J=1.5Hz, 1.H, H-2'), 8.47 (dd, J=4.7, 1.5Hz, 1 H, H-6'), 8.00 (d, J=8.4Hz, 2 H, H-2, H-6), 7.88 (d, J=8.4Hz, 2 H, H-3, H-5), 7.74 (br d, J=7.8Hz, 1 H, H-4'), 7.57 (d, J=8.1Hz, 1H, H-5") 7.37 (dd, J=7.8, 4.7Hz, 1 H, H-5'), 7.27 (br s, 1 H, H-3"), 7.18 (d, J=8.1Hz, 1 H, H-6"), 4.61 (s, 2 H, CH₂SO₂), 4.51 (d, J=5.8Hz, 2 H, CH₂N), 2.55 (s, 3 H, CH₃), 2.34 (s, 3 H, CH₃), 2.15 (s, 3 H, CH₃); MS m/z 476.6 (MH⁺, 100%). Anal. calcd for $C_{26}H_{25}N_3O_4S \cdot \frac{1}{2}CH_3CO_2CH_2CH_3$: C, 64.72, H, 5.63; N, 8.09. Found: C, 64.72; H, 5.60; N, 7.75%.

Example 22

4-(4-{[(4-Fluorophenyl)sulfonyl]methyl}-5-methyl-1,3-oxazol-2-yl)-N-(3-pyridinylmethyl)benzamide (48)

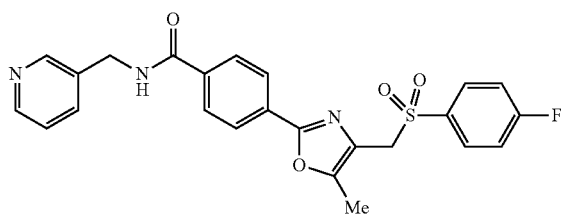 [SMILES: Cc1oc(-c2ccc(C(=O)NCc3cccnc3)cc2)nc1CS(=O)(=O)c1ccc(F)cc1]

Methyl 4-(4-{[(4-Fluorophenyl)sulfonyl]methyl}-5-methyl-1,3-oxazol-2-yl)benzoate (46). Method B. Reaction of chloride 2 (275 mg, 1.04 mmol), 4-methoxybenzenethiol (146 mg, 1.14 mmol) and $K_2CO_3$ (158 mg, 1.25 mmol) in dry DMF (10 mL) with subsequent oxidation by mCPBA (0.90 g, 2.6 mmol) gave benzoate 46 (249 mg, 61%) as a white powder: mp (EtOAc) 178-181° C.; $^1$H NMR (CDCl$_3$) δ 8.07 (ddd, J=8.6, 1.9, 1.5Hz, 2 H, H-2, H-6), 7.91 (ddd, J=8.6, 1.9, 1.5Hz, 2 H, H-3, H-5), 7.80-7.85 (m, 2 H, H-2', H-6'), 7.16-7.21 (m, 2 H, H-3', H-5'), 4.32 (s, 2 H, CH$_2$SO$_2$), 3.94 (s, 3 H, OCH$_3$), 2.33 (s, 3 H, CH$_3$); MS m/z 390.6 (WE, 100%). Anal. calcd for $C_{19}H_{16}FNO_5S$: C, 58.60; H, 4.14; N, 3.60. Found: C, 58.72; H, 4.00; N, 3.54%.

4-(4-{[(4-Fluorophenyl)sulfonyl]methyl}-5-methyl-1,3-oxazol-2-yl)benzoic Acid (47). Method D. Reaction of benzoate 46 (491 mg, 1.26 mmol) and 1 M NaOH (10 mL) in dioxane (10 mL) gave acid 47 (354 mg, 75%) as a white solid: mp (H$_2$O) 269-272° C.; $^1$H NMR δ 13.20 (br s, 1 H, CO$_2$H), 8.05 (d, J=8.5Hz, 2H, H-2, H-6), 7.91 (d, J=8.5Hz, 2 H, H-3, H-5), 7.84-7.89 (m, 2 H, H-2', H-6'), 7.47 (br t, J=8.8Hz, 2 H, H-3', H-5'), 4.74 (s, 2 H, CH$_2$SO$_2$), 2.06 (s, 3 H, CH$_3$); MS m/z 376.5 (WE, 100%). Anal. calcd for $C_{18}H_{14}FNO_5S$·¼H$_2$O: C, 56.91; H, 3.85; N, 3.69. Found: C, 57.15; H, 3.63; N, 3.59%.

4-(4-{[(4-Fluorophenyl)sulfonyl]methyl}-5-methyl-1,3-oxazol-2-yl)-N-(3-pyridinylmethyl)benzamide (48). Method E. Reaction of oxalyl chloride (118 λL, 1.35 mmol) and benzoic acid 47 (337 mg, 0.90 mmol) with subsequent coupling to 3-pyridinylmethylamine (101 λL, 0.99 mmol) gave benzamide 48 (325 mg, 78%) as a white powder: mp (EtOAc) 218-220° C.; $^1$H NMR δ 9.22 (t, J=5.9Hz, 1.H, CONH), 8.57 (d, J=1.6Hz, 1.H, H-2'), 8.47 (dd, J=4.7, 1.4Hz, 1 H, H-6'), 8.00 (d, J=8.5Hz, 2 H, H-2, H-6), 7.83-7.91 (m, 4 H, H-3, H-5, H-2", H-6"), 7.74 (br d, J=7.8Hz, 1 H, H-4'), 7.47 (br t, J=8.8Hz, 2 H, H-3", H-5"), 7.36 (dd, J=8.8, 4.7Hz, 1 H, H-5'), 4.73 (s, 2 H, CH$_2$SO$_2$), 4.51 (d, J=5.9Hz, 2H, CH$_2$N), 2.19 (s, 3 H, CH$_3$); $^{13}$C NMR δ 165.5, 165.2 (d, J=252.7), 158.1, 150.0, 148.9, 148.1, 135.4, 135.2, 134.9, 134.8 (d, J=2.9Hz), 131.6 (2, d, J=9.9Hz), 128.8, 128.1 (2), 125.8, 125.4 (2), 123.5, 116.4 (2, J=22.8Hz), 52.8, 40.5, 9.7; MS m/z 466.6 (MH$^+$, 100%). Anal. calcd for $C_{24}H_{20}FN_3O_4S$: C, 61.92; H, 4.33; N, 9.03. Found: C, 62.18; H, 4.38; N, 9.14%.

Example 23

4-[5-Methyl-4-({[4-(4-methyl-1-piperazinyl)phenyl]sulfonyl}methyl)-1,3-oxazol-2-yl]-N-(3-pyridinylmethyl)benzamide (49)

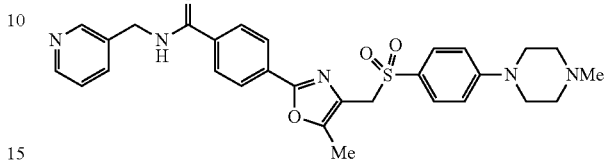

4-[5-Methyl-4-({[4-(4-methyl-1-piperazinyl)phenyl]sulfonyl}methyl)-1,3-oxazol-2-yl]-N-(3-pyridinylmethyl)benzamide (49). A mixture of fluoride 48 (112 mg, 0.24 mmol) and 1-methylpiperazine (1 mL) in DMSO (1 mL) was stirred in a sealed tube at 130° C. for 16 h. The solvent was evaporated and the residue was suspended in ice/water (50 mL) for 1 h. The mixture was partitioned between CHCl$_3$ (200 mL) and water (50 mL) and the solvent evaporated. The mixture was dissolved in EtOAc (5 mL) and the precipitated filtered to give benzamide 49 (41 mg, 31%) as a white powder: mp (EtOAc) 210-215° C.; $^1$H NMR δ 9.23 (s, 1 H, CONH), 8.56 (br s, 1 H, H-2'), 8.46 (dd, J=4.8, 1.6Hz, 1 H, H-6'), 8.00 (d, J=8.6Hz, 2 H, H-2, H-6), 7.91 (d, J=8.6Hz, 2 H, H-3, H-5), 7.73 (dt, J=8.0, 2.0Hz, 1 H, H-4'), 7.50 (d, J=9.1Hz, 2 H, H-3", H-5"), 7.36 (ddd, J=7.9, 4.7, 0.6Hz, 1 H, H-5'), 7.02 (d, J=9.1Hz, 2 H, H-2", H-6"), 4.49-4.53 (m, 4 H, CH$_2$SO$_2$, CH$_2$N), 3.30 (br t, J=4.9Hz, 4 H, 2×CH$_2$N), 2.40 (br t, J=4.9Hz, 4 H, 2×CH$_2$N), 2.20 (s, 3 H, CH$_3$), 2.12 (s, 3 H, CH$_3$); $^{13}$C NMR δ 165.5, 157.8, 154.0, 149.6, 148.8, 148.1, 135.3, 135.1, 134.9, 129.7 (2), 128.8, 128.0 (2), 126.4, 125.4 (2), 123.4 (2), 113.3 (2), 54.1 (2), 53.2, 46.4 (2), 45.6, 40.4, 9.6; MS m/z 546.8 (MH$^+$, 100%).

Example 24

4-[5-Methyl-4-({[4-(4-morpholinyl)phenyl]sulfonyl}methyl)-1,3-oxazol-2-yl]-N-(3-pyridinylmethyl)benzamide (50)

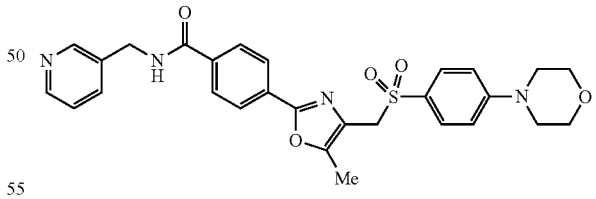

4-[5-Methyl-4-({[4-(4-morpholinyl)phenyl]sulfonyl}methyl)-1,3-oxazol-2-yl]-N-(3-pyridinylmethyl)benzamide (50). A mixture of fluoride 48 (103 mg, 0.22 mmol) and morpholine (2 mL) in DMSO (1 mL) was stirred in a sealed tube at 130° C. for 16 h. The solvent was evaporated and the residue was suspended in ice/water (50 mL) for 1 h. The precipitate was filtered, washed with water (5 mL) and dried. The crude solid was purified by column chromatography, eluting with a gradient (0-10%) of MeOH/EtOAc, to give benzamide 50 (83 mg, 71%) as a white powder: mp (EtOAc) 208-210° C.; $^1$H NMR δ 9.23 (s, 1 H, CONH), 8.57 (br s, 1 H, H-2'), 8.47 (br d, J=4.5Hz, 1 H, H-6'), 8.00 (br d, J=8.5Hz, 2 H, H-2, H-6), 7.91 (br d, J=8.5Hz, 2 H, H-3, H-5), 7.74 (br d, J=7.8Hz, 1 H, H-4'), 7.54 (d, J=9.0Hz, 2 H, H-3", H-5"), 7.37 (dd, J=7.8, 4.7Hz, 1 H, H-5'), 7.05 (d, J=9.0Hz, 2 H, H-2", H-6"), 4.49-4.54 (m, 4 H, CH$_2$SO$_2$, CH$_2$N), 3.72 (br t, J=4.8Hz, 4 H, 2×CH$_2$O), 3.27 (br t, J=4.8Hz, 4 H, 2×CH$_2$N), 2.13 (s, 3 H, CH$_3$); $^{13}$C NMR δ 165.5, 157.8, 154.2, 149.7, 148.8, 148.0, 135.3, 135.1, 134.8, 129.7 (2), 128.8, 128.0 (2), 126.4, 126.0, 125.4 (2), 123.4, 113.3 (2), 65.6 (2), 53.2, 46.7 (2), 40.4, 9.6; MS m/z 533.7 (MH$^+$, 100%). Anal. calcd for C$_{28}$H$_{28}$N$_4$O$_5$S: C, 63.14; H, 5.30; N, 10.52. Found: C, 62.94; H, 5.18; N, 10.51%.

Example 25

4-(4-{[(4-Methylphenyl)sulfonyl]methyl}-1,3-thiazol-2-yl)-N-(3-pyridinylmethyl)benzamide (54)

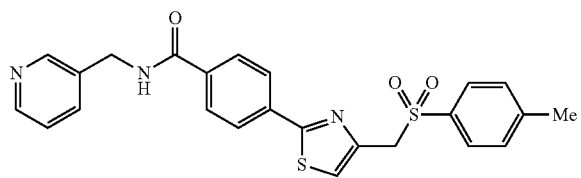 [SMILES: Cc1ccc(S(=O)(=O)Cc2csc(-c3ccc(C(=O)NCc4cccnc4)cc3)n2)cc1]

Methyl 4-[4-(Chloromethyl)-1,3-thiazol-2-yl]benzoate (51). A mixture of methyl 4-cyanobenzoate (5.0 g, 31.0 mmol) and O,O-diethyl hydrogen dithiophosphate (10.41 g, 62 mmol) in water (100 mL) was stirred at 80° C. for 16 h under N$_2$. The mixture was cooled to 20° C. and filtered. The precipitate was washed with water (50 mL) and dried under vacuum to give crude methyl 4-(aminocarbothioyl)benzoate (5.93 g, 98%) as a yellow powder: mp (water) 181-184° C.; $^1$H NMR δ 10.04 (br s, 1 H, NH$_2$), 9.65 (br s, 1 H, NH$_2$), 7.83-8.00 (m, 4 H, H-2, H-3, H-5, H-6), 3.88 (s, 3 H, OCH$_3$); MS m/z 196.5 (MH$^+$, 100%). A mixture of the crude benzoate (5.72 g, 29.2 mmol) and dichloroacetone (3.72 g, 29.3 mmol) in anhydrous DMF (50 mL) was stirred at 80° C. under N$_2$ for 16 h. The mixture was cooled to 20° C. and poured into ice/water (400 mL) and stirred for 30 min. The precipitate was filtered, washed with water (30 mL) and dried. The residue was purified by column chromatography, eluting with a gradient (10-20%) of EtOAc/pet. ether, to give benzoate 51 (5.40 g, 69%) as a white powder: mp (EtOAc/pet. ether) 110-111° C.; $^1$H NMR (CDCl$_3$) δ 8.11 (ddd, J=8.7, 2.0, 1.6Hz, 2 H, H-2, H-6), 8.02 (ddd, J=8.7, 2.0, 1.6Hz, 2 H, H-3, H-5), 7.38 (s, 1 H, H-5'), 4.76 (s, 2 H, CH$_2$Cl), 3.95 (s, 3 H, OCH$_3$); MS m/z 268.6 (MH$^+$, 100%). Anal. calcd for C$_{12}$H$_{10}$ClNO$_2$S: C, 53.83; H, 3.76; N, 5.23. Found: C, 53.77; H, 3.72; N, 5.03%.

Methyl 4-(4-{[(4-Methylphenyl)sulfonyl]methyl}-1,3-thiazol-2-yl)benzoate (52). Method A. Reaction of chloride 51 (402 mg, 1.5 mmol) and sodium 4-methylbenzenesulfinate (294 mg, 1.7 mmol) in dry DMF (10 mL) gave benzoate 52 (446 mg, 77%) as a white powder: mp (EtOAc) 160-161° C.; $^1$H NMR (CDCl$_3$) δ 8.05 (ddd, J=8.6, 1.9, 1.7Hz, 2.H, H-2, H-6), 7.77 (ddd, J=8.6, 1.9, 1.7Hz, 2 H, H-3, H-5), 7.64 (ddd, J=8.3, 1.9, 1.7Hz, 2 H, H-2", H-6"), 7.42 (s, 1 H, H-5'), 7.27 (br d, J=8.3Hz, 2 H, H-3", H-5"), 4.60 (s, 2 H, CH$_2$SO$_2$), 3.94 (s, 3 H, OCH$_3$), 2.41 (s, 3H, CH$_3$); MS m/z 388.6 (MH$^+$, 100%). Anal. calcd for C$_{19}$H$_{17}$NO$_4$S$_2$: C, 58.90; H, 4.42; N, 3.61. Found: C, 58.83; H, 4.33; N, 3.55%.

4-(4-{[(4-Methylphenyl)sulfonyl]methyl}-1,3-thiazol-2-yl)benzoic Acid (53). Method C. Reaction of benzoate 52 (407 mg, 1.05 mmol) and 6 M HCl (20 mL) gave acid 53 (392 mg, 100%) as a white solid: mp (H$_2$O) 270-272° C.; $^1$H NMR δ 13.15 (br s, 1 H, CO$_2$H), 8.01 (ddd, J=8.6, 1.9, 1.7Hz, 2 H, H-2, H-6), 7.83 (ddd, J=8.6, 1.9, 1.7Hz, 2 H, H-3, H-5), 7.70 (s, 1 H, H-5'), 7.65 (br d, J=8.3, 2 H, H-2", H-6"), 7.41 (br d, J=8.3Hz, 2 H, H-3", H-5"), 4.87 (s, 2 H, CH$_2$SO$_2$), 2.39 (s, 3H, CH$_3$); MS m/z 374.6 (MH$^+$, 100%). Anal. calcd for C$_{18}$H$_{15}$NO$_4$S$_2$: C, 57.89; H, 4.05; N, 3.75. Found: C, 57.89; H, 4.07; N, 3.63%.

4-(4-{[(4-Methylphenyl)sulfonyl]methyl}-1,3-thiazol-2-yl)-N-(3-pyridinylmethyl)benzamide (54). Method E. Reaction of oxalyl chloride (70 λL, 0.8 mmol) and benzoic acid 53 (200 mg, 0.54 mmol) with subsequent reaction with 3-pyridinylmethylamine (60 λL, 0.6 mmol) gave benzamide 54 (171 mg, 68%) as a white powder: mp (EtOAc) 178-181° C.; $^1$H NMR δ 9.19 (t, J=5.9Hz, 1 H, CONH), 8.57 (d, J=1.6Hz, 1 H, H-2"), 8.47 (dd, J=4.8, 1.5Hz, 1 H, H-6"), 7.97 (dd, J=6.7, 1.8Hz, 2 H, H-2, H-6), 7.81 (dd, J=6.7, 1.8Hz, 2 H, H-3, H-5), 7.74 (ddd J=8.1, 2.1, 1.6Hz, 1 H, H-4"), 7.68 (s, 1 H, H-5'), 7.65 (dd, J=8.3, 1.7Hz, 2 H, H-2", H-6"), 7.41 (br d, J=8.3Hz, 2 H, H-3", H-5"), 7.36 (ddd, J=8.1, 4.8, 0.7Hz, 1 H, H-5"), 4.87 (s, 2 H, CH$_2$SO$_2$), 4.51 (d, J=5.9Hz, 2 H, CH$_2$N), 2.40 (s, 3 H, CH$_3$); $^{13}$C NMR δ 165.7, 165.5, 148.9, 148.1, 145.2, 144.3, 135.9, 135.3, 135.2, 135.0, 134.9, 129.5 (2), 128.2 (2), 128.1 (2), 125.9 (2), 123.4, 122.2, 57.0, 40.5, 21.0; MS m/z 464.8 (MH$^+$, 100%). Anal. calcd for C$_{24}$H$_{21}$N$_3$O$_3$S$_2$: C, 62.18; H, 4.57; N, 9.06. Found: C, 62.30; H, 4.55; N, 9.10%.

Example 26

Alternate Preparation of 4-(5-Methyl-4-{[(4-methylphenyl)sulfonyl]methyl}-1,3-oxazol-2-yl)-N-(3-pyridinylmethyl)benzamide (9)

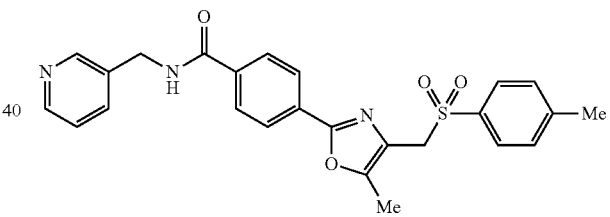

4-[4-(Hydroxymethyl)-5-methyl-1,3-oxazol-2-yl]benzoic Acid (55). Method D. Reaction of chloride 2 (500 mg, 1.88 mmol) and aqueous NaOH (2 M, 10 mL, 20 mmol) gave acid 55 (313 mg, 72%) as a cream solid: mp (EtOAc/MeOH) 240-242° C.; $^1$H NMR δ 13.18 (br s, 1H, CO$_2$H), 8.00-8.06 (m, 4 H, H-2, H-3, H-5, H-6), 5.11 (br s, 1 H, OH), 2.41 (s, 3 H, CH$_3$); MS m/z 234.5 (WE, 100%); HRMS calcd for C$_{12}$H$_{12}$NO$_4$: 234.0761. Found: 234.0760.

4-[4-(Hydroxymethyl)-5-methyl-1,3-oxazol-2-yl]-N-(3-pyridinylmethyl)benzamide (56). HBTU (170 mg, 0.45 mmol) was added to a solution of acid 55 (80 mg, 0.34 mmol) and diisopropylethylamine (0.13 mL, 0.69 mmol) in anhydrous DMF (7 mL). The solution was stirred at 20° C. for 10 min. 3-Pyridinylmethanamine (0.14 mL, 1.4 mmol) was then added and the reaction mixture was stirred at 20° C. for 1 h. It was the diluted with DCM (300 mL) and washed with H$_2$O (3×50 mL) and then washed with brine (50 mL). The combined organic phase was dried, filtered and the solvent evaporated. The residue was purified by column chromatography, eluting with 10% MeOH/DCM, to give amide 56 (65 mg, 59%) as a cream powder: mp (MeOH/DCM) 182-184° C.; $^1$H NMR δ 9.19 (t, J=5.7Hz, 1 H, NH), 8.57 (br s, 1 H, H-2'), 8.46

(br d, J=4.6Hz, 1 H, H-6'), 8.00 (s, 4 H, H-2, H-3, H-5, H-6), 7.74 (br d, J=7.8Hz, 1 H, H-4'), 7.36 (dd, J=7.8, 4.8Hz, 1 H, H-5'), 5.06 (t, J=5.6Hz, 1 H, OH), 4.51 (d, J=5.8Hz, 2 H, CH$_2$N), 4.39 (d, J=5.6Hz, 2 H, CH$_2$O), 2.41 (s, 3 H, CH$_3$); MS m/z 324.8 (MH$^+$, 100%); Anal. calcd for C$_{18}$H$_{17}$N$_3$O$_3$·¼H$_2$O: C, 65.94; H, 5.38; N, 12.82. Found: C, 66.06; H, 5.20; N, 12.85.

4-(5-Methyl-4-{[(4-methylphenyl)sulfonyl]methyl}-1,3-oxazol-2-yl)-N-(3-pyridinylmethyl)benzamide (9). A solution of alcohol 56 (163 mg, 0.5 mmol) in anhydrous DMF (7 mL) was cooled to 0° C. NEt$_3$ (0.14 mL, 1 mmol) and MsCl (47 λL, 0.6 mmol) were added successively and the reaction mixture was stirred at 0° C. for 1 h. K$_2$CO$_3$ (138 mg, 1 mmol) and 4-methylthiophenol (68 mg, 0.55 mmol) were added and the reaction mixture was stirred at 60° C. for 1 h. The reaction mixture was then cooled to 20° C. and partitioned between EtOAc (200 mL) and H$_2$O (50 mL). The organic fraction was washed with H$_2$O (2×50 mL), washed with brine (50 mL), and dried. The solvent was evaporated to give the crude sulfide (158 mg, 0.37 mmol) which was used without further purification. A solution of Oxone® (172 mg, 0.28 mmol) in H$_2$O (3 mL) was added at 0° C. to a stirred solution of crude sulfide (88 mg, 0.2 mmol) in MeOH (3 mL) and the reaction mixture was stirred for 1 h at 20° C. H$_2$O was added (50 mL), the mixture was extracted with DCM (3×50 mL) and the organic phase was washed with brine (50 mL), dried, and the solvent was evaporated. Remaining sulfide (70 mg, 0.16 mmol) was treated as described and the combined crude products were purified by column chromatography, eluting with 5% MeOH/EtOAc, to give sulfone 9 (65 mg, 28%) as a white powder: spectroscopically identical to the sample prepared above.

Example 27

N-Benzyl-4-(4-{[(4-bromophenyl)sulfonyl]methyl}-5-methyl-1,3-oxazol-2-yl)benzamide (57)

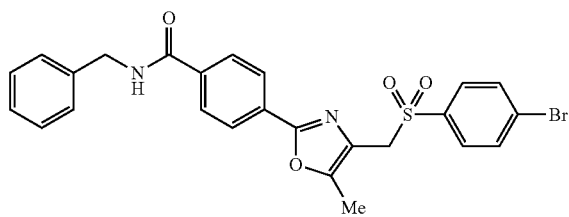 [SMILES: Cc1oc(-c2ccc(C(=O)NCc3ccccc3)cc2)nc1CS(=O)(=O)c1ccc(Br)cc1]

Benzoic acid 29 (150 mg, 0.34 mmol) was dissolved in anhydrous DMF (5 mL), DIEA (0.12 mL, 0.69 mmol) and HBTU (171 mg, 0.45 mmol) were successively added and the reaction mixture was stirred at 20° C. for 10 min. Benzylamine (0.16 mL, 1.4 mmol) was added and the reaction mixture was stirred at 20° C. for 1 h. The mixture was diluted with EtOAc (150 mL), washed with H$_2$O (3×50 mL), washed with brine (50 mL) and dried. The solvent evaporated and the residue was purified by column chromatography, eluting with a gradient (50-100%) of EtOAc/pet. ether followed by a gradient (1-4%) MeOH/DCM, to afford amide 57 (117 mg, 66%) as a white solid: mp (DCM/MeOH) 234-237° C.; $^1$H NMR δ (t, J=5.9Hz, 1H, CONH), 8.01 (br d, J=8.6Hz, 2 H, H-2, H-6), 7.87 (br d, J=8.7Hz, 2 H, H-3, H-5), 7.85 (dt, J=8.8, 2.1Hz, 2 H, H-2', H-6'), 7.72 (dt, J=8.7, 2.1Hz, 2 H, H-3', H-5'), 7.34 (s, 2 H, H-2", H-6"), 7.33 (s, 2 H, H-3", H-5"), 7.22-7.28 (m, 1 H, H-4"), 4.74 (s, 2 H, CH$_2$SO$_2$), 4.49 (d, J=5.9Hz, 2 H, CH$_2$NH), 2.21 (s, 3 H, CH$_3$); $^{13}$C NMR δ 165.3, 158.0, 150.0, 139.4, 137.7, 135.6, 132.2 (2), 130.3 (2), 128.6, 128.2 (2), 128.1, 128.0 (2), 127.2 (2), 126.7, 125.6, 125.3 (2), 52.6, 42.6, 9.7; MS m/z 526.5, 528.5 (MH$^+$, 100%). Anal. calcd for C$_{25}$H$_{21}$BrN$_2$O$_4$S: C, 57.15; H, 4.03; N, 5.33. Found: C, 57.34; H, 3.74; N, 5.50%.

Example 28

4-[4-({[4-(21-Amino-4,7,10,13,16,19-hexaoxahenicos-1-yl)phenyl]sulfonyl}methyl)-5-methyl-1,3-oxazol-2-yl]-N-(3-pyridinylmethyl)benzamide (61)

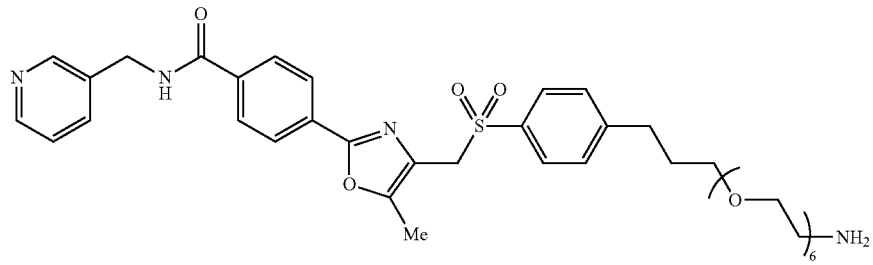

tert-Butyl 3,6,9,12,15,18-Hexaoxahenicos-20-yn-1-ylcarbamate (58). Mesyl chloride (1.78 mL, 23.0 mmol) was added dropwise to a stirred suspension of hexaethylene glycol (5.42 g, 19.2 mmol) and Ag$_2$O (4.67 g, 20.2 mmol) in dry DCM (50 mL) at 20° C. and the mixture was stirred at 20° C. for 3 days. The mixture was filtered through Celite® and the solvent evaporated. The residue was purified by column chromatography, eluting with a gradient (0-10%) of MeOH/EtOAc, to give 17-hydroxy-3,6,9,12,15-pentaoxaheptadec-1-yl methanesulfonate (3.52 g, 51%) as a colourless oil: $^1$H NMR (CDCl$_3$) δ 4.36-4.40 (m, 2 H, CH$_2$OSO$_2$), 3.76-3.78 (m, 2 H, CH$_2$O), 3.70-3.74 (m, 2 H, CH$_2$O), 3.64-3.67 (m, 16 H, 8×CH$_2$O), 3.59-3.62 (m, 2 H, CH$_2$O), 3.09 (s, 3 H, SO$_2$CH$_3$), 2.80 (br s, 1 H, OH); MS m/z 361.6 (MH$^+$, 100%). A mixture of the mesylate (3.52 g, 9.8 mmol) and NaN$_3$ (1.27 g, 19.5 mmol) in dry DMF (20 mL) was stirred at 110° C. for 2 h. The mixture was cooled to 20° C. and the solvent evaporated. The residue was purified by column chromatography, eluting with 10% MeOH/EtOAc, to give 17-azido-3,6,9,12,15-pentaoxaheptadecan-1-ol (2.98 g, 99%) as a colourless oil: $^1$H NMR (CDCl$_3$) δ3.71-3.74 (m, 2H, CH$_2$O), 3.65-3.69 (m, 18H, 9×CH$_2$O), 3.59-3.62 (m, 2H, CH$_2$O), 3.39 (br t, J=5.2Hz, 2H, CH$_2$N$_3$), 2.82 (br s, 1H, OH); MS m/z 308.5 (MH$^+$, 100%). A mixture of azide (2.98 g, 9.7 mmol) and Pd/C (100 mg) in EtOH (50 mL) was stirred under H$_2$ (60 psi) for 1 h. The mixture was filtered through Celite® and washed with EtOH (3×20 mL) and the solvent was evaporated. The crude residue was dissolved in DCM (50 mL) and di-tert-butyl dicarbonate (2.56 g, 11.7 mmol) in DCM (20 mL) was added dropwise and the solution was stirred at 20° C. for 16 h. The solvent was evaporated and residue was purified by column chromatography, eluting with 10% MeOH/EtOAc, to give tert-butyl 17-hydroxy-3,6,9,12,15-pentaoxaheptadec-1-ylcarbamate (2.97 g, 80%) as a colourless oil: $^1$H NMR (CDCl$_3$) δ 5.17 (br s, 1H, NHCO$_2$), 3.70-3.74 (m, 2 H, CH$_2$O), 3.60-3.68 (m, 18 H, 9×CH$_2$O), 3.54 (br t, J=5.1Hz, 2H, CH$_2$O), 3.31 (br q, J=5.1Hz, 2 H, CH$_2$N), 2.81 (br s, 1 H, OH), 1.44 [s, 9 H, C(CH$_3$)$_3$]; MS m/z 382.5 (MH$^+$, 100%). NaH (343 mg, 8.56 mmol) was added in small portions to a stirred solution of alcohol (2.97 g, 7.8 mmol) in THF (50 mL) at 0° C. and the resulting mixture stirred at 0° C. for 30 min. Propargyl bromide (0.87 mL, 7.8 mmol) was added followed by tetrabutylammonium iodide (29 mg, 78 μmol) and the mixture was stirred at 20° C. for 16 h. The reaction was quenched with sat. aq. NH$_4$Cl and extracted with EtOAc (4×50 mL). The combined organic fraction was washed with brine (50 mL), dried and the solvent evaporated. The residue was purified by column chromatography, eluting with 80% EtOAc/pet. ether, to give the acetylene 58 (2.56 g, 79%) as a colourless oil: $^1$H NMR (CDCl$_3$) δ 5.05 (br s, 1 H, NHCO$_2$), 4.20 (d, J=2.4Hz, 2 H, CH$_2$C≡C), 3.68-3.71 (m, 4 H, 2×CH$_2$O), 3.64-3.67 (m, 12H, 6×CH$_2$O), 3.60-3.63 (m, 4 H, 2×CH$_2$O), 3.54 (br t, J=5.2Hz, 2 H, CH$_2$O), 3.31 (br q, J=5.2Hz, 2 H, CH$_2$N), 2.42 (t, J=2.4Hz, 1 H, CH), 1.44 [s, 9 H, C(CH$_3$)$_3$]; MS m/z 420.7 (MH$^+$, 100%); HRMS calcd for C$_{20}$H$_{38}$N$_4$O$_8$S (MH$^+$): m/z 420.2592. found m/z 420.2590 (0.4 ppm).

tert-Butyl 21-[4-({[5-Methyl-2-(4-{[(3-pyridinylmethyl)amino]carbonyl}phenyl)-1,3-oxazol-4-yl]methyl}sulfonyl)phenyl]-3,6,9,12,15,18-hexaoxahenicos-20-yn-1-ylcarbamate (59). PdCl$_2$(PPh$_3$)$_2$ (14 mg, 0.02 mmol) was added to a stirred, degassed solution of bromide (100 mg, 0.19 mmol), acetylene 58 (105 mg, 0.25 mmol) and CuI (4 mg, 0.02 mmol) in a 1:1 mixture of NEt$_3$/DMF (5 mL), and the mixture was stirred in a sealed pressure vessel at 70° C. 16 h. The mixture was cooled to 20° C., diluted with EtOAc (200 mL) and washed with water (3×50 mL), washed with brine (50 mL) and dried. The solvent was evaporated and the residue purified by column chromatography, eluting with a gradient (0-5%) of MeOH/EtOAc, to give carbamate 59 (115 mg, 70%) as a white gum: $^1$H NMR δ 9.22 (t, J=5.9Hz, 1 H, CONH), 8.57 (br s, 1 H, H-2'), 8.47 (dd, J=4.6, 1.2Hz, 1 H, H-6'), 8.00 (br d, J=8.6Hz, 2 H, H-2, H-6), 7.89 (br d, J=8.6Hz, 2 H, H-3, H-5), 7.79 (dd, J=6.7, 1.9Hz, 2 H, H-2", H-6"), 7.74 (br d, J=7.8Hz, 1 H, H-4'), 7.68 (dd, J=6.7, 1.8Hz, 2 H, H-3", H-5"), 7.36 (dd, J=7.7, 4.8Hz, 1 H, H-5'), 6.73 (br t, J=5.4Hz, 1 H, NHCO$_2$), 4.74 (s, 2 H, CH$_2$SO$_2$), 4.51 (d, J=5.8 Hz, 2 H, CH$_2$NH), 4.45 (s, 2 H, CH$_2$C≡C), 3.62-3.65 (m, 2 H, CH$_2$O), 3.56-3.59 (m, 2 H, CH$_2$O), 3.46-3.53 (m, 16 H, CH$_2$O), 3.36 (t, J=6.1Hz, 2 H, H-20'''), 3.05 (q, J=6.1Hz, 2 H, H-21'''), 2.17 (s, 3 H, CH$_3$), 1.36 [s, 9 H, (CH$_3$)$_3$]; HRMS calcd for C$_{44}$H$_{57}$N$_4$O$_{12}$S (MH$^+$): m/z 865.3688. found m/z 865.3679.

tert-Butyl 21-[4-({[5-Methyl-2-(4-{[(3-pyridinylmethyl)amino]carbonyl}phenyl)-1,3-oxazol-4-yl]methyl}sulfonyl)phenyl]-3,6,9,12,15,18-hexaoxahenicos-1-ylcarbamate (60). A mixture of alkyne 59 (100 mg, 0.11 mmol) and 10% Pd/C (50 mg, 0.04 mmol) in MeOH (15 mL) was stirred at 20° C. under H$_2$ (60 psi) for 2.5 h. The mixture was filtered through Celite®, washed with MeOH (100 mL), the solvent was evaporated and the residue was dried to give the carbamate 60 (85 mg, 85%) as a white gum, which was used in the next step without further purification: $^1$H NMR δ 9.22 (t, J=5.8Hz, 1 H, CONH), 8.57 (d, J=1.8Hz, 1 H, H-2'), 8.46 (dd, J=4.7, 1.6Hz, 1 H, H-6'), 7.99 (br d, J=8.6Hz, 2 H, H-2, H-6), 7.89 (br d, J=8.6Hz, 2 H, H-3, H-5), 7.73 (dt, J=7.9 1.9Hz, 1 H, H-4'), 7.68 (br d, J=8.3Hz, 2 H, H-2", H-6"), 7.44 (br d, J=8.3Hz, 2 H, H-3", H-5"), 7.36 (ddd, J=7.9, 4.8, 0.6Hz, 1 H, H-5'), 6.73 (t, J=5.5Hz, 1 H, NHCO$_2$), 4.64 (s, 2 H, CH$_2$SO$_2$), 4.51 (d, J=5.8Hz, 2 H, CH$_2$NH), 3.43-3.50 (m, 20 H, CH$_2$O), 3.36 (br t, J=6.3Hz, 4 H, H-3''', H-20'''), 3.05 (br q, J=5.9Hz, 2 H, H-21'''), 2.71 (br t, J=7.6Hz, 2 H, H-1'''), 2.12 (s, 3 H, CH$_3$), 1.79 (br q, J=7.1Hz, 2 H, H-2'''), 1.36 [s, 9 H, (CH$_3$)$_3$].

4-[4-({[4-(21-Amino-4,7,10,13,16,19-hexaoxahenicos-1-yl)phenyl]sulfonyl}methyl)-5-methyl-1,3-oxazol-2-yl]-N-(3-pyridinylmethyl)benzamide (61). A solution of carbamate 60 (85 mg, 0.098 mmol) in a mixture of trifluoroacetic acid (2 mL) and anhydrous DCM (8 mL) was stirred at 20° C. for 1 h. The solvent was evaporated and the residue was purified by column chromatography, eluting with 10% MeOH/DCM containing 1% aqueous NH$_3$, to give amine 61 (56 mg, 75%) as a white gum: $^1$H NMR δ 9.22 (t, J=5.8Hz, 1 H, CONH), 8.56 (d, J=1.7Hz, 1 H, H-2'), 8.46 (dd, J=4.8, 1.6 Hz, 1 H, H-6'), 7.99 (br d, J=8.6Hz, 2 H, H-2, H-6), 7.89 (br d, J=8.6Hz, 2 H, H-3, H-5), 7.73 (dt, J=7.9, 1.9Hz, 1 H, H-4'), 7.68 (br d, J=8.3Hz, 2 H, H-2", H-6"), 7.44 (br d, J=8.3Hz, 2 H, H-3", H-5"), 7.36 (ddd, J=7.8, 4.8, 0.6Hz, 1 H, H-5'), 4.65 (s, 2 H, CH$_2$SO$_2$), 4.51 (d, J=5.8Hz, 2 H, CH$_2$NH), 3.49-3.50 (m, 20 H, CH$_2$O), 3.43-3.45 (m, 2 H, CH$_2$O), 3.33-3.36 (m, 2 H, CH$_2$O), 2.72 (t, J=7.3Hz, 2 H, H-1'''), 2.64 (t, J=5.6Hz, 2 H, H-21'''), 2.12 (s, 3 H, CH$_3$), 1.79 (br q, J=7.2Hz, 2 H, H-2'''), NH$_2$ not observed; $^{13}$C NMR δ 165.4, 157.9, 149.8, 148.8, 148.5, 148.0, 135.7, 135.3, 135.1, 134.8, 129.1 (2), 128.7, 128.3 (2), 128.0 (2), 125.9, 125.3 (2), 123.4, 72.6, 69.7 (7), 69.6, 69.5, 69.4, 68.9, 52.8, 41.1, 40.4, 31.4, 30.4, 9.5; HRMS calcd for C$_{39}$H$_{53}$N$_4$O$_{10}$S (MH$^+$): m/z 769.3477. found m/z 769.3492.

Example 29

4-[4-({[4-(21-Amino-4,7,10,13,16,19-hexaoxahenicos-1-yl)phenyl]sulfonyl}methyl)-5-methyl-1,3-oxazol-2-yl]-N-benzylbenzamide (63)

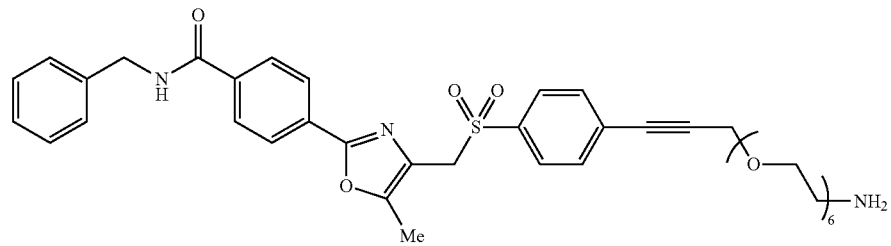

tert-Butyl 21-(4-{[(2-{4-[(Benzylamino)carbonyl]phenyl}-5-methyl-1,3-oxazol-4-yl)methyl]sulfonyl}phenyl)-3,6,9,12,15,18-hexaoxahenicos-1-ylcarbamate (62). PdCl$_2$(PPh$_3$)$_2$ (14 mg, 0.02 mmol) was added to a stirred, degassed solution of bromide (94 mg, 0.18 mmol), acetylene 58 (105 mg, 0.25 mmol) and CuI (4 mg, 0.02 mmol) in a 1:1 mixture of NEt$_3$/DMF (5 mL), and the mixture was stirred in a sealed pressure vessel at 70° C. 16 h. The mixture was cooled to 20° C., diluted with EtOAc (200 mL) and washed with water (3×50 mL), washed with brine (50 mL) and dried. The solvent was evaporated and the residue purified by column chromatography, eluting with 2% MeOH/EtOAc, to give carbamate 62 (55 mg, 35%) as a cream gum: $^1$H NMR δ 9.17 (t, J=6.0Hz, 1 H, CONH), 8.01 (br d, J=8.5Hz, 2 H, H-2, H-6), 7.89 (br d, J=8.5Hz, 2 H, H-3, H-5), 7.79 (br d, J=8.5Hz, 2 H, H-2", H-6"), 7.68 (br d, J=8.5Hz, 2 H, H-3", H-5"), 7.32-7.34 (m, 4 H, H-2', H-3', H-5', H-6'), 7.22-7.28 (m, 1 H, H-4'), 6.73 (br t, J=5.9 Hz Hz, 1 H, NHCO$_2$), 4.74 (s, 2 H, CH$_2$SO$_2$), 4.49 (d, J=6.0Hz, 2 H, CH$_2$NH), 4.45 (s, 2 H, CH$_2$C≡C), 3.62-3.65 (m, 2 H, CH$_2$O), 3.56-3.59 (m, 2 H, CH$_2$O), 3.48-3.52 (m, 16 H, CH$_2$O), 3.36 (t, J=6.1Hz, 2 H, H-20'''), 3.05 (q, J=6.1Hz, 2 H, H-21'''), 2.17 (s, 3 H, CH$_3$), 1.36 [s, 9 H, C(CH$_3$)$_3$]; HRMS calcd for C$_{45}$H$_{58}$N$_3$O$_{12}$S (MH$^+$): m/z 864.3736. found m/z 864.3711.

4-[4-({[4-(21-Amino-4,7,10,13,16,19-hexaoxahenicos-1-yl)phenyl]sulfonyl}methyl)-5-methyl-1,3-oxazol-2-A-N-benzylbenzamide (63). A solution of carbamate 62 (55 mg, 0.064 mmol) in a mixture of trifluoroacetic acid (2 mL) and anhydrous DCM (8 mL) was stirred at 20° C. for 1 h. The solvent was evaporated and the residue was purified by column chromatography, eluting with 10% MeOH/DCM containing 1% aqueous NH$_3$, to give the amine 63 (38 mg, 78%) as a white gum: $^1$H NMR δ 9.18 (t, J=5.9Hz, 1 H, CONH), 8.01 (br d, J=8.6Hz, 2 H, H-2, H-6), 7.89 (br d, J=8.6Hz, 2 H, H-3, H-5), 7.79 (br d, J=8.5Hz, 2 H, H-2", H-6"), 7.68 (br d, J=8.5Hz, 2 H, H-3", H-5"), 7.33-7.34 (m, 4 H, H-2', H-3', H-5', H-6'), 7.22-7.28 (m, 1 H, H-4'), 4.74 (s, 2 H, CH$_2$SO$_2$), 4.49 (d, J=5.9Hz, 2 H, CH$_2$NH), 4.45 (s, 2 H, CH$_2$C≡C), 3.62-3.65 (m, 2 H, CH$_2$O), 3.56-3.59 (m, 2 H, CH$_2$O), 3.50-3.52 (m, 16 H, CH$_2$O), 3.38 (t, J=5.7 H, 2H, CH$_2$O), 2.69 (t, J=5.5Hz, 2 H, H-21'''), 2.17 (s, 3 H, CH$_3$), NH$_2$ not observed; $^{13}$C NMR δ 165.4, 158.1, 150.1, 139.5, 138.2, 135.7, 132.0 (2), 128.7, 128.6, 128.3 (2), 128.1 (2), 127.4, 127.2 (2), 126.8 (2), 125.7, 125.4 (2), 90.1, 84.1, 71.7, 69.8 (6), 69.7, 69.6, 69.5, 68.8, 58.0, 52.7, 42.7, 40.8, 9.7; HRMS calcd for C$_{40}$H$_{50}$N$_3$O$_{10}$S (MH$^+$): m/z 764.3211. found m/z 769.3227.

Example 30

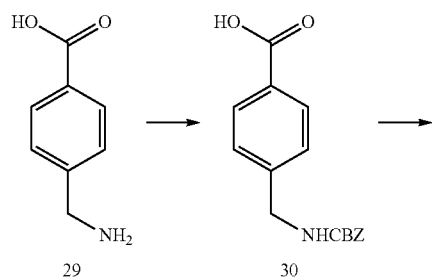

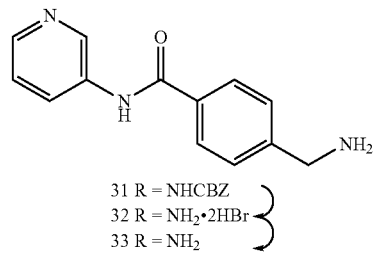

31 R = NHCBZ
32 R = NH$_2$·2HBr
33 R = NH$_2$ 4-(Benzyloxycarbonylamino)methyl)benzoic acid (30). Benzyl chloroformate (10.3 mL, 72.7 mmol) and 2 M NaOH solution (33 mL, 66 mmol) were simultaneously added dropwise to a stirred solution of 4-aminomethylbenzoic acid (29) (10.0 g, 66.2 mmol) in 2 M NaOH solution (33 mL) and THF (30 mL) at 0° C. The mixture was stirred at 20° C. for 16 h, then the organic solvent was evaporated and the residue acidified with 2 M HCl until the pH of the mixture was 2-3. The precipitate was filtered, washed with water (250 mL), washed with EtOH (50 mL), and finally washed with Et$_2$O (100 mL). The solid was dried under vacuum to give acid 2 (16.43 g, 87%) as a white powder: mp 190-192° C. [lit. (Loge et. al., J. Enzyme Inhibit. Med. Chem. 2002, 17, 381-390) mp (toluene) 194-195° C.; $^1$H NMR δ 7.85 (br d, 2 H, H-2, H-6), 7.82 (br t, J=6.1Hz, 1 H, NHCO$_2$), 7.30-7.40 (m, 5 H, H-2', H-3', H-4', H-5', H-6'), 7.27 (br d, J=8.2Hz, 2 H, H-3, H-5), 5.05 (s, 2H, OCH$_2$), 4.24 (d, J=6.1Hz, 2 H, CH$_2$N).

Benzyl 4-(pyridine-3-ylcarbamoyl)benzylcarbamate (31). Reaction of benzoic acid 30 (10.0 g, 35.0 mmol) and oxalyl chloride (4.58 mL, 52.5 mmol), with subsequent reaction with 3-aminopyridine (3.62 g, 38.5 mmol) gave carbamate 31 (7.82 g, 62%) as a white solid: mp (EtOH) 207-210° C.; $^1$H NMR δ 10.37 (s, 1 H, NHCO), 8.92 (d, J=2.3Hz, 1 H, H-2'), 8.31 (dd, J=4.7, 1.5Hz, 1 H, H-6'), 8.18 (ddd, J=8.34, 2.5, 1.5Hz, 1 H, H-4'), 7.93 (br d, J=8.3Hz, 2 H, H-2, H-6), 7.89 (br t, J=6.0Hz, 1 H, NHCO$_2$), 7.41 (br d, J=8.3Hz, 2 H, H-3, H-5), 7.31-7.39 (m, 6 H, H-5', H-2", H-3", H-4", H-5", H-6"), 5.06 (s, 2 H, CH$_2$O), 4.30 (d, J=6.2Hz, 2 H, CH$_2$N). Anal. Calcd for C$_{21}$H$_{19}$N$_3$O$_3$: C, 69.79; H, 5.30; N, 11.63. Found: C, 69.60; H, 5.40; N, 11.63%.

4-(Aminomethyl)-N-(3-pyridinyl)benzamide dihydrobromide (32). Reaction of carbamate 31 (2.2 g, 6.1 mmol) gave benzamide 32 (2.35 g, 99%) as a white solid: mp (EtOAc) 292-296° C.; $^1$H NMR δ 11.06 (s, 1H, NHCO), 9.35 (d, J=2.2Hz, 1 H, H-2'), 8.70 (ddd, J=8.5, 2.2, 1.1Hz, 1 H, H-4'), 8.64 (br d, J=5.4Hz, 1 H, H-6'), 8.31 (br s, 3 H, NH$_2$.HBr), 8.09 (br d, J=8.2Hz, 2 H, H-2, H-6), 7.96 (dd, J=8.6, 5.4Hz, 1 H, H-5'), 7.67 (d, J=8.4Hz, 2 H, H-3, H-5), 5.95 (br s, 1 H, pyrN.HBr), 4.16 (q, J=5.8Hz, 2 H, CH$_2$N); Anal. Calcd for C$_{13}$H$_{15}$Br$_2$N$_3$O: C, 40.13; H, 3.89; N, 10.80. Found: C, 39.99; H, 3.94; N, 10.36%.

4-(Aminomethyl)-N-(3-pyridinyl)benzamide (33). A suspension of dihydrobromide salt 32 (1 mmol) in dilute aqueous ammonia solution (50 mL) was extracted into CHCl$_3$ (3×50 mL), the organic fraction dried and the solvent evaporated to give crude benzamide 33 which was used directly.

Example 31

N-(3-Pyridinyl)-4-{[(3-pyridylsulfonyl)amino]methyl}benzamide II-1

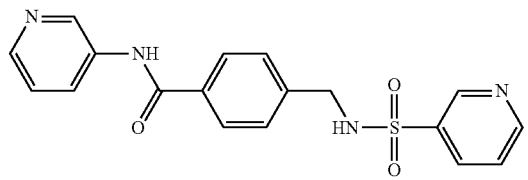 [SMILES: O=C(Nc1cccnc1)c1ccc(CNS(=O)(=O)c2cccnc2)cc1]

A mixture of 4-(aminomethyl)-N-(3-pyridinyl)benzamide (33) (217 mg, 1.0 mmol) and 2-pyridylsulfonyl chloride (170 mg, 1.0 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-20%) of MeOH/EtOAc, to give benzamide 6 (213 mg, 60%) as a white powder: mp (MeOH/EtOAc) 189-191° C.; $^1$H NMR δ 10.37 (s, 1 H, NHCO), 8.95 (br s, 2 H, H-2', H-2''), 8.80 (d, J=4.6Hz, 1 H, H-6'), 8.52 (br s, 1 H, H-6''), 8.34 (br s, 1 H, NHSO$_2$), 8.14-8.21 (m, 2 H, H-4', H-4''), 7.90 (d, J=8.3Hz, 2 H, H-2, H-6), 7.60 (dd, J=7.9, 4.6Hz, 1 H, H-5''), 7.38-7.44 (m, 3 H, H-3, H-5, H-5'), 4.18 (s, 2 H, CH$_2$N); $^{13}$C NMR δ 165.5, 152.9, 147.0, 144.5, 142.0, 141.4, 137.1, 134.4, 133.1, 127.7 (2), 127.5 (2), 127.3, 124.2, 123.6 (2), 45.7; MS m/z 369.6 (MH$^+$, 100%). Anal. calcd for C$_{18}$H$_{16}$N$_4$O$_3$S.½H$_2$O: C, 57.28; H, 4.54; N, 14.85. Found: C, 57.50; H, 4.33; N, 14.82%.

Example 32

4-({[(6-Chloro-3-pyridinyl)sulfonyl]amino}methyl)-N-(3-pyridinyl)benzamide II-2

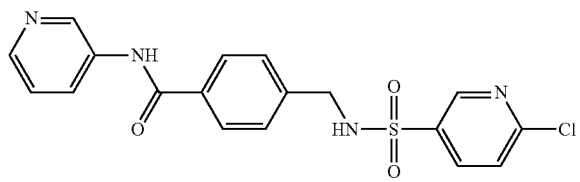 [SMILES: O=C(Nc1cccnc1)c1ccc(CNS(=O)(=O)c2ccc(Cl)nc2)cc1]

A mixture of 4-(aminomethyl)-N-(3-pyridinyl)benzamide (33) (250 mg, 1.1 mmol) and 6-chloro-3-pyridinesulfonyl chloride (233 mg, 1.1 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-30%) of MeOH/EtOAc, to give benzamide I-2 (279 mg, 63%) as a white powder: mp (MeOH/EtOAc) 226-228° C.; $^1$H NMR δ 10.36 (s, 1 H, NHCO), 8.93 (d, J=2.2Hz, 1 H, H-2'), 8.75 (dd, J=2.6, 0.6Hz, 1 H, H-2''), 8.61 (br s, 1 H, NHSO$_2$), 8.32 (dd, J=4.6, 1.5Hz, 1 H, H-6'), 8.10-8.20 (m, 2 H, H-4', H-6''), 7.90 (br d, J=8.3Hz, 2 H, H-2, H-6), 7.72 (dd, J=8.4, 0.6Hz, 1 H, H-5''), 7.36-7.42 (m, 3 H, H-3, H-5, H-5'), 4.19 (s, 2 H, CH$_2$N); $^{13}$C NMR δ 165.4, 153.6, 147.7, 144.6, 142.0, 141.2, 137.9, 136.6, 135.8, 133.1, 127.8 (2), 127.6 (2), 127.3, 125.0, 123.5, 45.7; MS m/z 404.0 (MH$^+$, 100%), 406.0 (MH$^+$, 60%). Anal. calcd for C$_{18}$H$_{15}$ClN$_4$O$_3$S: C, 53.67; H, 3.75; N, 13.91. Found: C, 53.37; H, 3.81; N, 14.03%.

Example 33

4-({[(6-Phenoxy-3-pyridinyl)sulfonyl]amino}methyl)-N-(3-pyridinyl)benzamide II-3

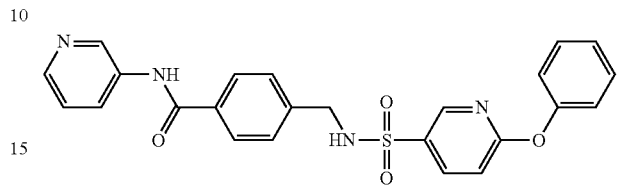

A mixture of 4-(aminomethyl)-N-(3-pyridinyl)benzamide (33) (464 mg, 2.0 mmol) and 6-phenoxy-3-pyridinesulfonyl chloride (606 mg, 2.2 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-20%) of MeOH/EtOAc, to give benzamide 1-3 (405 mg, 43%) as a white powder: mp (MeOH/EtOAc) 203-205° C.; $^1$H NMR δ 10.40 (s, 1 H, CONH), 8.95 (d, J=2.4Hz, 1 H, H-2'), 8.61 (t, J=6.4Hz, 1 H, NHSO$_2$), 8.42 (dd, J=2.5, 0.4Hz, 1 H, H-2''), 8.32 (dd, J=4.7, 1.4 Hz, 1 H, H-6'), 8.21 (ddd, J=8.3, 2.5, 1.5Hz, 1 H, H-4'), 8.12 (dd, J=8.7, 2.5, 1 H, H-6''), 7.90 (br d, J=8.3Hz, 2 H, H-2, H-6), 7.37-7.43 (m, 5 H, H-3, H-5, H-3''', H-5'''), 7.25 (tt, J=7.4, 1.0Hz, 1 H, H-4''), 7.12-7.17 (m, 3 H, H-5'', H-2''', H-6'''), 4.17 (d, J=6.4Hz, 2 H, CH$_2$N); $^{13}$C NMR δ 165.4, 165.0, 152.9, 146.4, 144.5, 141.9, 141.4, 138.6, 135.8, 132.9, 132.1, 129.8 (2), 127.7 (2), 127.6 (2), 127.3, 125.3, 123.5, 121.5 (2), 111.5, 45.7; MS m/z 461.5 (MH$^+$, 100%). Anal. calcd for C$_{24}$H$_{20}$N$_4$O$_4$: C, 62.60; H, 4.38; N, 12.17. Found: C, 62.48; H, 4.41; N, 12.14%.

Example 34

N-(3-Pyridinyl)-4-{[(2-thienylsulfonyl)amino]methyl}benzamide II-4

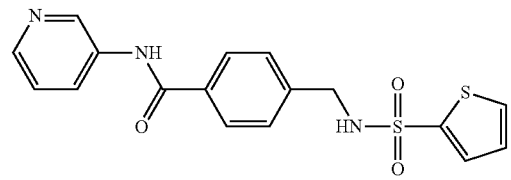

A mixture of 4-(aminomethyl)-N-(3-pyridinyl)benzamide (33) (256 mg, 1.1 mmol) and 2-thienylsulfonyl chloride (206 mg, 1.1 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with EtOAc, to give benzamide I-4 (318 mg, 75%) as a white powder: mp (EtOAc) 185-188° C.; $^1$H NMR δ 10.38 (s, 1H, NHCO), 8.93 (d, J=2.2Hz, 1 H, H-2''), 8.46 (br s, 1 H, NHSO$_2$), 8.31 (dd, J=4.7, 1.5Hz, 1 H, H-6''), 8.19 (ddd, J=8.2, 2.5, 1.5Hz, 1 H, H-4''), 7.90-7.95 (m, 3 H, H-2, H-6, H-5'), 7.61 (dd, J=3.7, 1.3 Hz, 1

H, H-3'), 7.43 (br d, J=8.3Hz, 2 H, H-3, H-5), 7.39 (ddd, J=8.2, 4.7, 0.5 Hz, 1 H, H-5"), 7.18 (dd, J=5.0, 3.7Hz, 1 H, H-4'), 4.17 (s, 2 H, CH$_2$N); $^{13}$C NMR δ 165.4, 144.4, 141.9, 141.5, 141.4, 135.7, 133.0, 132.4, 131.5, 127.6 (2), 127.5, 127.3 (2), 127.2, 123.4, 45.8; MS m/z 374.6 (MH$^+$, 100%). Anal. calcd for C$_{17}$H$_{15}$N$_3$O$_3$S$_2$: C, 54.67; H, 4.05; N, 11.25. Found: C, 55.23; H, 4.11; N, 11.32%.

Example 35

N-(3-Pyridinyl)-4-{[(3-thienylsulfonyl)amino]methyl}benzamide II-5

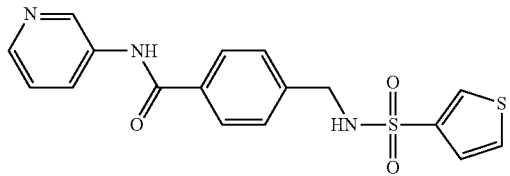 [SMILES: O=C(Nc1cccnc1)c1ccc(CNS(=O)(=O)c2ccsc2)cc1]

A mixture of 4-(aminomethyl)-N-(3-pyridinyl)benzamide (33) (235 mg, 1.0 mmol) and 3-thienylsulfonyl chloride (208 mg, 1.1 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-10%) of MeOH/EtOAc, to give benzamide 1-5 (259 mg, 67%) as a white powder: mp (EtOAc) 207-210° C.; $^1$H NMR δ 10.40 (s, 1 H, CONH), 8.93 (d, J=2.2Hz, 1 H, H-2"), 8.31 (dd, J=4.7, 1.5Hz, 1 H, H-6"), 8.23 (br t, J=6.3 Hz, 1 H, NHSO$_2$), 8.17-8.21 (m, 2 H, H-2', H-4"), 7.92 (dd, J=8.3, 1.7Hz, 2 H, H-2, H-6), 7.75 (dd, J=5.1, 1.3Hz, 1 H, H-5'), 7.42 (br d, J=8.4Hz, 2 H, H-3, H-5), 7.39 (dd, J=8.2, 4.7Hz, 1 H, H-5"), 7.35 (dd, J=5.1, 1.3Hz, 1 H, H-4'), 4.13 (d, J=6.3Hz, 2 H, CH$_2$N); $^{13}$C NMR δ 165.5, 144.5, 141.9, 141.8, 140.5, 135.7, 132.9, 130.4, 129.0, 127.6 (2), 127.3 (2), 127.2, 125.1, 123.4, 45.7; MS m/z 374.6 (MH$^+$, 100%). Anal. calcd for C$_{17}$H$_{15}$N$_3$O$_3$S$_2$: C, 54.67; H, 4.05; N, 11.25. Found: C, 54.86; H, 3.95; N, 11.06%.

Example 36

4-({[(1,2-Dimethyl-1H-imidazol-5-yl)sulfonyl]amino}methyl)-N-(3-pyridinyl)benzamide II-6

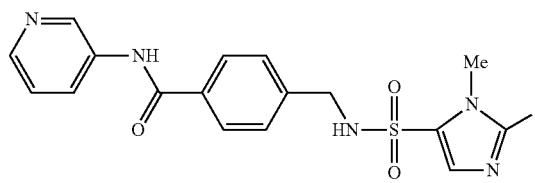

A mixture of 4-(aminomethyl)-N-(3-pyridinyl)benzamide (33) (341 mg, 1.5 mmol) and 1,2-dimethyl-1H-imidazole-5-sulfonyl chloride (292 mg, 1.5 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-20%) of MeOH/EtOAc, to give benzamide I-6 (201 mg, 35%) as a white powder: mp (MeOH/EtOAc) 238-240° C.; $^1$H NMR δ 10.37 (s, 1 H, CONH), 8.92 (br s, 1 H, H-2'), 8.31 (dd, J=4.7, 1.5 Hz, 1 H, H-6'), 8.18 (ddd, J=8.3, 2.5, 1.5Hz, 1 H, H-4'), 7.97 (br s, 1 H, NHSO$_2$), 7.91 (br dd, J=8.3, 1.7Hz, 2 H, H-2, H-6), 7.61 (s, 1 H, H-5"), 7.44 (br d, J=8.3Hz, 2 H, H-3, H-5), 7.39 (ddd, J=8.3, 4.6, 0.6Hz, 1 H, H-5'), 4.10 (br d, J=6.0Hz, 2 H, CH$_2$N), 3.58 (s, 3 H, NCH$_3$), 2.30 (s, 3 H, CH$_3$); $^{13}$C NMR δ 165.7, 146.4, 144.5, 142.5, 142.0, 137.1, 135.8, 132.9, 127.5 (2), 127.4 (2), 127.3, 124.7, 123.5, 45.7, 32.8, 12.4; MS m/z 386.6 (MH$^+$, 100%). Anal. calcd for C$_{18}$H$_{19}$N$_5$O$_3$S: C, 56.09; H, 4.97; N, 18.17. Found: C, 56.15; H, 5.08; N, 18.00%.

Example 37

N-(3-pyridinyl)-4-{[(4H-1,2,4-triazol-3-ylsulfonyl)amino]methyl}benzamide II-7

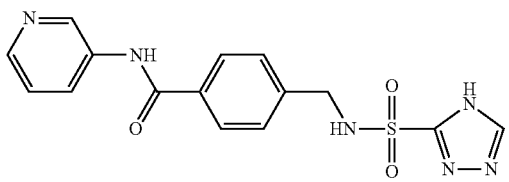 [SMILES: O=C(Nc1cccnc1)c1ccc(CNS(=O)(=O)c2nnc[nH]2)cc1]

A mixture of 4-(aminomethyl)-N-(3-pyridinyl)benzamide (33) (295 mg, 1.3 mmol) and 4H-1,2,4-triazole-3-sulfonyl chloride (218 mg, 1.3 mmol) in dry pyridine (10 mL) was stirred at 20° C. for 16 h. The solvent was evaporated and the residue stirred in ice/water (20 mL) for 1 h. The precipitate was filtered, washed with water (5 mL) and dried. The crude solid was purified by column chromatography, eluting with a gradient (0-25%) of MeOH/EtOAc, to give benzamide 11-7 (176 mg, 38%) as a white powder: mp (MeOH/EtOAc) 266-269° C.; $^1$H NMR δ 14.79 (s, 1 H, NH), 10.39 (s, 1 H, CONH), 8.94 (d, J=2.2Hz, 1 H, H-2"), 8.78 (s, 1 H, H-5'), 8.71 (br s, 1 H, NHSO$_2$), 8.31 (dd, J=4.7, 1.5Hz, 1 H, H-6"), 8.19 (ddd, J=8.3, 2.5, 1.5Hz, 1 H, H-4"), 7.93 (d, J=8.3Hz, 2 H, H-2, H-6), 7.46 (br d, J=8.3Hz, 2 H, H-3, H-5), 7.39 (dd, J=8.3, 4.7Hz, 1 H, H-5"), 4.30 (br d, J=4.7Hz, 2 H, CH$_2$N); $^{13}$C NMR δ 165.6, 161.8, 145.7, 144.5, 142.0, 135.8, 133.1, 127.7 (2), 127.3 (2), 127.2, 123.5, 45.9, 1 resonance not observed; MS m/z 359.6 (MH$^+$, 100%). Anal. calcd for C$_{15}$H$_{14}$N$_6$O$_3$S: C, 50.27; H, 3.94; N, 23.45. Found: C, 50.35; H, 3.82; N, 23.42%.

Example 38

N-(3-Pyridinyl)-4-{[(2-furanylsulfonyl)amino]methyl}benzamide II-8

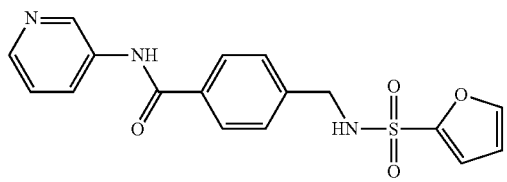 [SMILES: O=C(Nc1cccnc1)c1ccc(CNS(=O)(=O)c2ccco2)cc1]

A mixture of 4-(aminomethyl)-N-(3-pyridinyl)benzamide (33) (259 mg, 1.1 mmol) and 2-furanylsulfonyl chloride (209 mg, 1.2 mmol) in dry pyridine (10 mL) was stirred at 20° C.

for 16 h. The solvent was evaporated and the residue stirred in ice/water (20 mL) for 1 h. The precipitate was filtered, washed with water (5 mL) and dried. The crude solid was purified by column chromatography, eluting with a gradient (0-10%) of MeOH/EtOAc, to give benzamide 1-8 (248 mg, 61%) as a white powder: mp (EtOAc) 178-180° C.; $^1$H NMR δ 10.40 (s, 1 H, CONH), 8.93 (d, J=2.2Hz, 1 H, H-2"), 8.69 (t, J=6.2Hz, 1 H, NHSO$_2$), 8.31 (dd, J=4.7, 1.5Hz, 1 H, H-6"), 8.19 (ddd, J=8.3, 2.5, 1.5Hz, 1 H, H-4"), 7.94 (dd, J=1.8, 0.9Hz, 1 H, H-5'), 7.92 (br dd, J=8.3, 1.6Hz, 2 H, H-2, H-6), 7.37-7.43 (m, 3 H, H-3, H-5, H-5"), 7.08 (dd, J=3.4, 0.9Hz, 1 H, H-3"), 6.65 (dd, J=3.4, 1.8Hz, 1 H, H-4"), 4.20 (d, J=6.2Hz, 2 H, CH$_2$N); $^{13}$C NMR δ 165.5, 148.8, 146.8, 144.5, 141.9, 141.7, 135.7, 133.0, 127.7 (2), 127.2 (3), 123.4, 115.5, 111.3, 45.4; MS m/z 378.5 (MH$^+$, 100%). Anal. calcd for C$_{17}$H$_{15}$N$_3$O$_4$S: C, 57.13; H, 4.23; N, 11.76. Found: C, 57.40; H, 4.19; N, 11.74%.

Example 39

Synthesis of 4-(5-Methyl-4-((piperidin-4-ylsulfonyl) methyl)oxazol-2-yl)-N-(pyridin-3-ylmethyl)benzamide trifluoroacetic acid salt Step 1: Synthesis of tert-butyl 4-thioxopiperidine-1-carboxylate

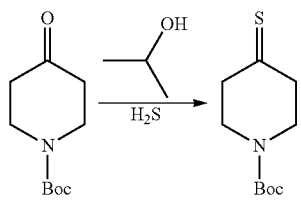

Hydrogen sulfide gas was bubbled into a solution of tert-butyl 4-oxopiperidine-1-carboxylate (2 g, 10.05 mmol, 1.00 equiv) in isopropanol (20 mL) contained in a 100-mL 3-necked round-bottom flask. The resulting solution was stirred at room temperature for 2 h. The reaction mixture was concentrated and the crude product was used in the next step directly without purification.

Step 2: Synthesis of tert-butyl 4-mercaptopiperidine-1-carboxylate

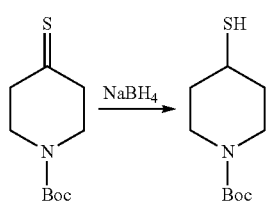

To a solution of crude tert-butyl 4-thioxopiperidine-1-carboxylate (2 g, 9.30 mmol, 1.00 equiv) in ethanol (20 mL) contained in a 100-mL 3-necked round-bottom flask under nitrogen was added sodium borohydride (570 mg, 15.00 mmol, 1.50 equiv) in several portions. The resulting solution was stirred at 80° C. for 2 h. The reaction mixture was then quenched by the addition of 30 mL of water after it was cooled to room temperature with a water bath. The solution was extracted with 3×30 mL of ether and the organic layers combined. The combined organic layer was washed with 2×50 mL of brine, dried over anhydrous sodium sulfate and concentrated under vacuum to give 2.34 g of crude tert-butyl 4-mercaptopiperidine-1-carboxylate as yellow oil.

Step 3: Synthesis of tert-butyl 4-((2-(4-(methoxycarbonyl)phenyl)-5-methyloxazol-4-yl)methylthio)piperidine-1-carboxylate

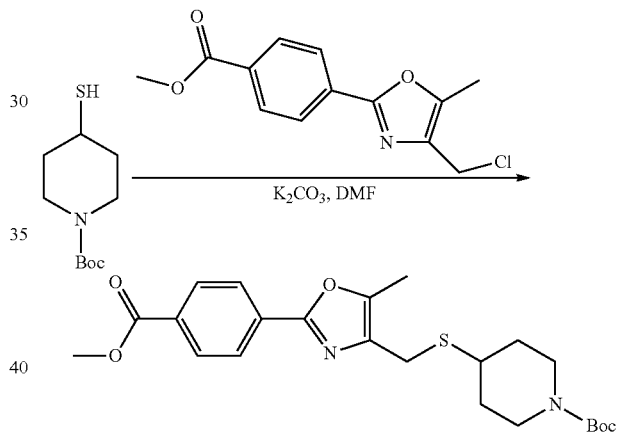

A mixture of the crude tert-butyl 4-mercaptopiperidine-1-carboxylate (2.34 g, 10.78 mmol, 1.20 equiv), methyl 4-(4-(chloromethyl)-5-methyloxazol-2-yl)-benzoate (2.33 g, 8.79 mmol, 1.00 equiv) and potassium carbonate (1.74 g, 12.39 mmol, 1.50 equiv) in N,N-dimethylformamide (23.4 mL) was stirred overnight in a 100-mL round-bottom flask at 50° C. The reaction mixture was then quenched by the addition of 30 mL of water. The resulting solution was extracted with 3×30 mL of ethyl acetate and the organic layers combined. The organic layer was washed with 2×40 mL of brine, dried over anhydrous sodium sulfate and concentrated under vacuum. The residue was eluted with ethyl acetate/petroleum ether (1:30-1:5) on a silica gel column to give 920 mg (23%) of tert-butyl 4-((2-(4-(methoxycarbonyl-phenyl)-5-methyloxazol-4-yl)methylthio)piperidine-1-carboxylate as a yellow solid. LC-MS: (ES, m/z): 447 [M+H]$^+$, 347, 271, 146, 105.

Step 4: Synthesis of tert-butyl 4-((2-(4-(methoxycarbonyl)phenyl)-5-methyloxazol-4-yl)methylsulfonyl)piperidine-1-carboxylate

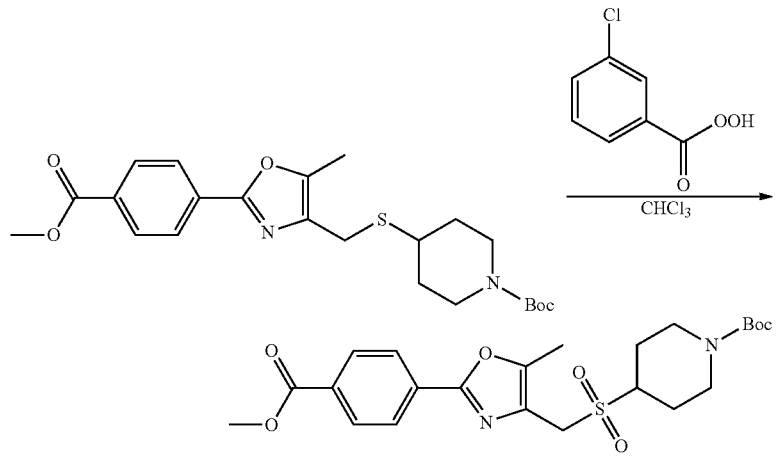

To a solution of tert-butyl 4-((2-(4-(methoxycarbonyl)-phenyl)-5-methyloxazol-4-yl)methylthio)piperidine-1-carboxylate (920 mg, 2.06 mmol, 1.00 equiv) in chloroform (10 mL) placed in a 100-mL round-bottom flask was added m-chloroperbenzoic acid (1.78 g, 10.35 mmol, 2.50 equiv) at 0° C. in small portions. The resulting solution was stirred at 0° C. in an ice/water bath for 1 h. The mixture was washed with 2×20 mL of aqueous sodium bisulfite solution, 2×20 mL of saturated aqueous sodium bicarbonate solution and 2×20 mL of brine. The organic layer was dried over anhydrous sodium sulfate and concentrated under vacuum to give 0.98 g (99%) of tert-butyl 4-((2-(4-(methoxycarbonyl)-phenyl)-5-methyloxazol-4-yl)methylsulfonyl)piperidine-1-carboxylate as a white solid. LC-MS: (ES, m/z): 479 [M+H]$^+$, 423, 379.

Step 5: Synthesis of 4-(4-((1-(tert-butoxycarbonyl)piperidin-4-ylsulfonyl)methyl)-5-methyloxazol-2-yl)benzoic acid

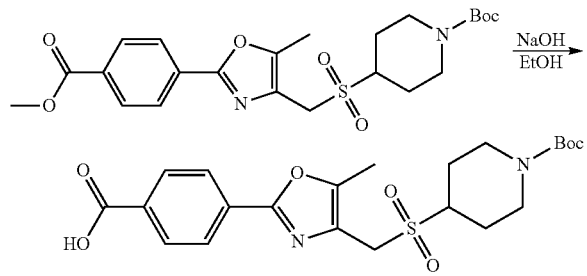

A solution of tert-butyl 4-((2-(4-(methoxycarbonyl)phenyl)-5-methyloxazol-4-yl)methylsulfonyl) piperidine-1-carboxylate (980 mg, 2.05 mmol, 1.00 equiv), sodium hydroxide (120 mg, 3.00 mmol, 1.50 equiv) in ethanol (10 mL) was stirred at 50° C. overnight in a 100-mL round-bottom flask. The reaction mixture was concentrated under vacuum and quenched by the addition of 30 mL of water/ice. The pH value of the solution was adjusted to 3 with the addition of 3M hydrochloric acid. The precipitate was collected by filtration and dried to give 0.76 g (80%) of 4-(4-((1-(tert-butoxycarbonyl)piperidin-4-ylsulfonyl) methyl)-5-methyloxazol-2-yl) benzoic acid as a white solid. LC-MS: (ES, m/z): 409 [M-C$_4$H$_9$+H]$^+$.

Step 6: Synthesis of tert-butyl 4-((5-methyl-2-(4-(pyridin-3-ylmethylcarbamoyl)phenyl) oxazol-4-yl)methylsulfonyl)piperidine-1-carboxylate

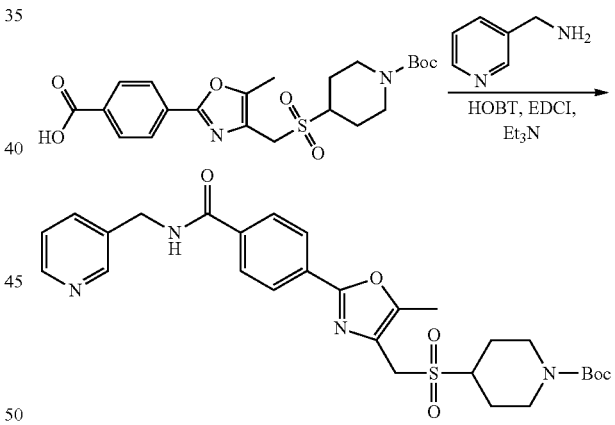

Triethylamine (440 mg, 4.36 mmol, 3.00 equiv) was added dropwise with stirring to a solution of pyridin-3-ylmethanamine (170 mg, 1.57 mmol, 1.10 equiv), 4-(4-((1-(tert-butoxycarbonyl)piperidin-4-ylsulfonyl)methyl)-5-methyloxazol-2-yl)benzoic acid (670 mg, 1.44 mmol, 1.00 equiv), EDCI (330 mg, 1.73 mmol, 1.20 equiv) and HOBT (230 mg, 1.70 mmol, 1.20 equiv) in N,N-dimethylformamide (10 mL) contained in a 50-mL round-bottom flask. The resulting solution was stirred overnight at room temperature. The reaction was then quenched by the addition of 30 mL of water/ice. The precipitate was collected by filtration and dried in an oven under reduced pressure to give 0.74 g (93%) of tert-butyl 4-((2-(4-((pyridin-3-ylmethyl)carbamoyl)phenyl)-5-methyloxazol-4-yl)methylsulfonyl)piperidine-1-carboxylate as a yellow solid. LC-MS: (ES, m/z): 555 [M+H]$^+$, 455.

91

Step 7: Synthesis of 4-(5-methyl-4-((piperidin-4-ylsulfonyl)methyl)oxazol-2-yl)-N-(pyridine-3-ylmethyl)benzamide trifluoroacetic acid salt

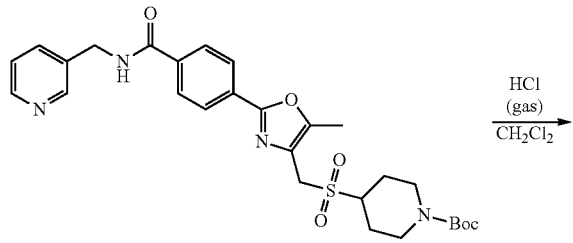

Example 1

Hydrogen chloride gas was bubbled into a solution of tert-butyl 4-((2-(4-((pyridin-3-ylmethyl)carbamoyl)phenyl)-5-methyloxazol-4-yl)methylsulfonyl)piperidine-1-carboxylate (740 mg, 1.34 mmol, 1.00 equiv) in dichloromethane (50 mL) kept at 0° C. in a 100-mL 3-necked round-bottom flask for 3 h. The resulting solution was stirred for another 3 h at 0° C. The solids were collected by filtration. The crude product (560 mg) was purified by Prep-HPLC with the following conditions: Column, SunfireC18.19*150; mobile phase, CH3CN/0.05% aqueous TFA solution; Detector, 254 nm. The fractions containing the pure product were combined and concentrated in vacuum to give 109.9 mg (14%) of 4-(5-methyl-4-((piperidin-4-ylsulfonyl)methyl)oxazol-2-yl)-N-(pyridin-3-ylmethyl)benzamide trifluoroacetic acid salt as a white solid. LC-MS: (ES, m/z): 455 [M+H]$^+$, 270, 228. $^1$H-NMR: $^1$HNMR (400 MHz, CD$_3$OD) δ 8.79 (1H, s), 8.68-8.67 (1H, d), 8.37-8.35 (1H, d), 8.14-8.12 (1H, d), 8.02-8.00 (1H, d), 7.86-7.83 (1H, t), 4.84-4.74 (1H, s), 4.51 (1H, s), 3.61-3.57 (3H, q), 3.15-3.09 (2H, t), 2.51-2.47 (4H, d), 2.10-2.07 (2H, q).

92

Example 40

Synthesis of 4-(5-Methyl-4-((1-methylpiperidin-4-ylsulfonyl)methyl)oxazol-2-yl)-N-(pyridin-3-ylmethyl)benzamide Step 1: Synthesis of 4-(5-methyl-4-((1-methylpiperidin-4-ylsulfonyl)methyl)oxazol-2-yl)-N-(pyridin-3-ylmethyl)benzamide

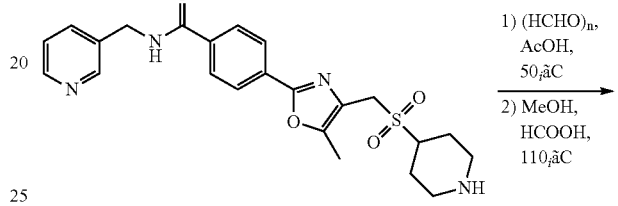

Example 2

4-(5-Methyl-4-((piperidin-4-ylsulfonyl)methyl)oxazol-2-yl)-N-(pyridin-3-ylmethyl)benzamide (350 mg, 0.77 mmol, 1.00 equiv) and polyoxymethylene (460 mg, 15.33 mmol, 20.00 equiv) was added into a 100-mL round-bottom flask containing a mixture of methanol (10 mL), acetic acid (1 mL) and formic acid (100 mL). The resulting solution was stirred overnight at 50° C. Formic acid (100 mL) was again added and the reaction mixture was stirred for another 24 h at 110° C. The resulting mixture was concentrated under vacuum. The crude product (300 mg) was purified by Prep-HPLC chromatography with the following conditions: (1#-Pre-HPLC-005(waters)): Column, XbridgeRP 19*150; mobile phase: Phase A: water with 0.05% TFA Phase B: CH$_3$CN Gradient: 5%-20%; Detector, UV (254/220 nm) to give 200 mg of product as its trifluoroacetic acid salt. The salt was dissolved in 20 mL of water and the pH value of the solution was adjusted to 10 with 1M sodium hydroxide solution. The resulting solution was extracted with 3×30 mL of dichloromethane and the organic layers combined. The organic layer was washed with 3×20 mL of water, dried over anhydrous sodium sulfate and then concentrated under vacuum to give 100 mg (28%) of 4-(5-methyl-4-((1-methylpiperidin-4-ylsulfonyl)methyl)oxazol-2-yl)-N-(pyridin-3-ylmethyl)benzamide as a white solid. LC-MS: (ES, m/z): 469 [M+H]$^+$, 256, 235. $^1$HNMR (400 MHz, CD$_3$OD) δ 8.59 (1H, s), 8.47-8.46 (1H, d), 8.11-8.09 (2H, d), 8.00-7.98 (2H, d), 7.90-7.88 (1H, d), 7.46-7.43 (1H, t), 4.45 (2H, s), 4.41 (2H, s), 3.21-3.15 (1H, m), 3.06-3.03 (2H, d), 2.50 (3H, s), 2.30 (3H, s), 2.26-2.23 (2H, d), 2.12-2.06 (2H, m), 1.96-1.87 (2H, m).

Example 41

Synthesis of 4-[5-Methyl-4-([[4-(pyrrolidin-1-yl) cyclohexane]sulfonyl]methyl]-1,3-oxazol-2-yl]-N-(pyridin-3-ylmethyl)benzamide trifluoroacetic acid salt

Step 1: Synthesis of tert-butyl N-(4-hydroxycyclohexyl)carbamate

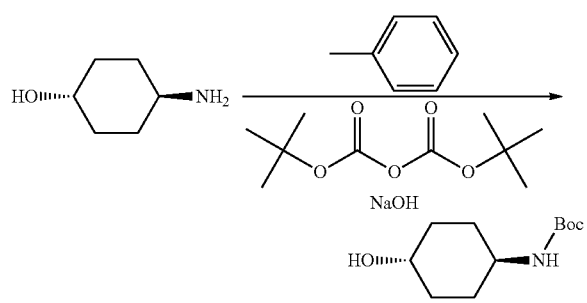

To a solution of 4-aminocyclohexan-1-ol (25 g, 217.06 mmol, 1.00 equiv) and di-tert-butyl dicarbonate (47.39 g, 217.14 mmol, 1.00 equiv) in toluene (250 mL) maintained under an inert atmosphere of nitrogen was added an aqueous sodium hydroxide (10.43 g, 260.77 mmol, 1.20 equiv) solution dropwise with stirring. The resulting solution was stirred overnight at room temperature. The solid was collected by filtration then dried to give 40 g (86%) of tert-butyl N-(4-hydroxycyclohexyl)carbamate as a white solid.

Step 2: Synthesis of tert-butyl N-[4-(methanesulfonyloxy)cyclohexyl]carbamate

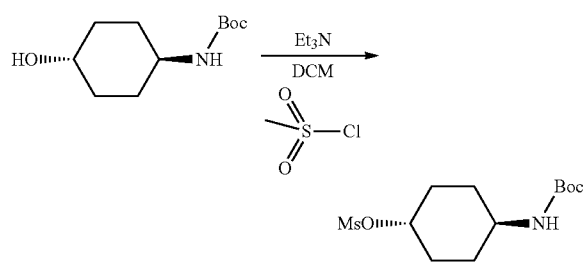

To a solution of tert-butyl N-(4-hydroxycyclohexyl)carbamate (15 g, 69.67 mmol, 1.00 equiv) and triethylamine (15.5 g, 153.18 mmol, 2.00 equiv) in dichloromethane (150 mL) was added methanesulfonyl chloride (9.6 g, 83.81 mmol, 1.21 equiv) dropwise with stiffing at 0° C. The resulting solution was stirred for 10 min at 0° C. and warmed to room temperature overnight. Water (100 mL) was added to quench the reaction. The resulting mixture was extracted with 3×200 mL of dichloromethane. The combined organic layers was washed with brine, dried over anhydrous sodium sulfate and concentrated under vacuum to give 7 g (34%) of tert-butyl N-[4-(methanesulfonyloxy)cyclohexyl]carbamate as a white solid.

Step 3: Synthesis of methyl 4-[4-[(acetylsulfanyl) methyl]-5-methyl-1,3-oxazol-2-yl]benzoate

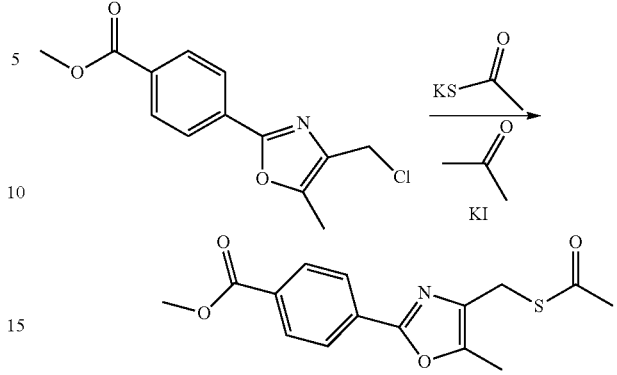

A solution of methyl 4-[4-(chloromethyl)-5-methyl-1,3-oxazol-2-yl]benzoate (5 g, 18.82 mmol, 1.00 equiv), potassium ethanethioate (2.68 g, 23.47 mmol, 1.25 equiv) and potassium iodide (120 mg, 0.72 mmol, 0.04 equiv) in acetone (40 mL) was stirred at 35° C. for 30 min. Water (50 mL) was added to quench the reaction. The resulting solution was extracted with 3×100 mL of ethyl acetate. The combined organic layers was washed with 2×200 mL of brine, dried over anhydrous sodium sulfate and concentrated under vacuum to give 6.03 g of crude methyl 4-[4-[(acetylsulfanyl) methyl]-5-methyl-1,3-oxazol-2-yl]benzoate as a white solid.

Step 4: Synthesis of methyl 4-[5-methyl-4-(sulfanylmethyl)-1,3-oxazol-2-yl]benzoate

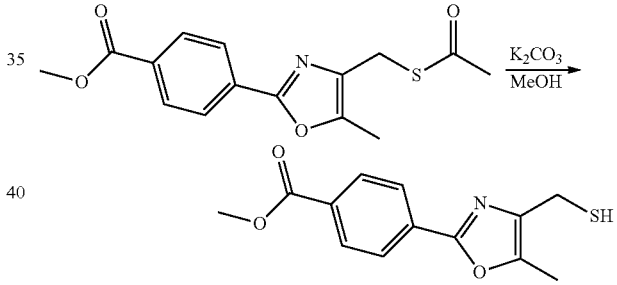

A mixture of methyl 4-[4-[(acetylsulfanyl)methyl]-5-methyl-1,3-oxazol-2-yl]benzoate (4.29 g, 14.05 mmol, 1.00 equiv) and potassium carbonate (4.85 g, 34.84 mmol, 3.00 equiv) in methanol (50 mL) was stirred at 35° C. under an inert atmosphere of nitrogen for 30 min Water (100 mL) was then added and the resulting solution was extracted with 3×150 mL of dichloromethane. The combined organic layers was washed with 2×300 mL of brine, dried over anhydrous sodium sulfate and concentrated under vacuum to yield 3.8 g of crude methyl 4-[5-methyl-4-(sulfanylmethyl)-1,3-oxazol-2-yl]benzoate as a white solid. LC-MS: (ES, m/z): 305 [M+CH$_3$CN+H]$^+$, 264 [M+H]$^+$, 230.

Step 5: Synthesis of methyl 4-(4-[[(4-[[(tert-butoxy) carbonyl]amino]cyclohexyl)sulfanyl]methyl]-5-methyl-1,3-oxazol-2-yl)benzoate

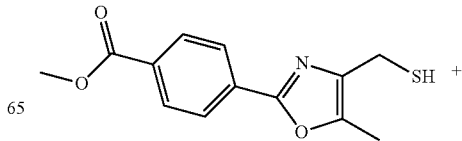

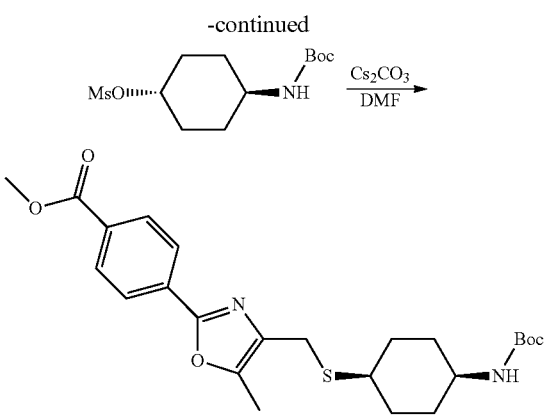

Into a 100-mL 3-necked round-bottom flask purged and maintained with an inert atmosphere of nitrogen, was placed A mixture of methyl 4-[5-methyl-4-(sulfanylmethyl)-1,3-oxazol-2-yl]benzoate (3 g, 11.39 mmol, 1.00 equiv), cescium carbonate (5.13 g, 15.70 mmol, 1.39 equiv) and tert-butyl N-[4-(methanesulfonyloxy)cyclohexyl]carbamate (3.22 g, 10.98 mmol, 1.20 equiv) in N,N-dimethylformamide (30 mL) was stirred at 50° C. for 3 h. The reaction was quenched by the addition of 50 mL of water and the resulting solution was extracted with 3×60 mL of ethyl acetate. The organic combined layers was washed with 2×200 mL of brine, dried over anhydrous sodium sulfate and concentrated under vacuum. The residue was purified on\ a silica gel column eluted with ethyl acetate/petroleum ether (1:15-1:5). The collected fractions were combined and concentrated under vacuum to give 760 mg (14%) of methyl 4-(4-[[(4-[[(tert-butoxy)carbonyl]amino]cyclohexyl)sulfanyl]methyl]-5-methyl-1,3-oxazol-2-yl)benzoate as a yellow solid. LC-MS: (ES, m/z): 461 [M+H]$^+$, 405, 361, 271, 230, 115.

Step 6: Synthesis of methyl 4-(4-[[(4-[[(tert-butoxy)carbonyl]amino]cyclohexane)sulfonyl]methyl]-5-methyl-1,3-oxazol-2-yl)benzoate

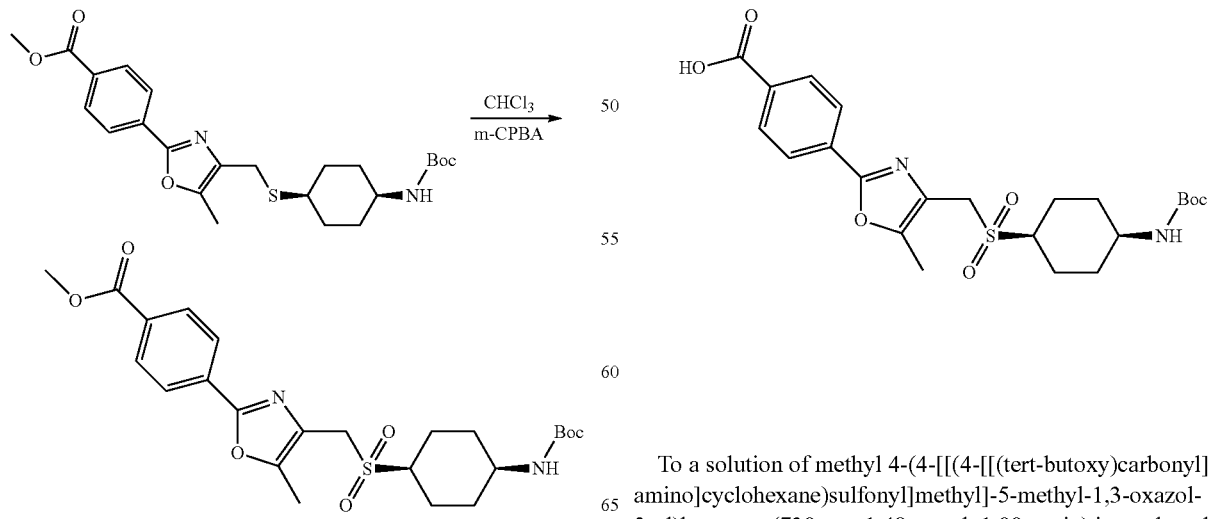

A mixture of methyl 4-(4-[[(4-[[(tert-butoxy)carbonyl]amino]cyclohexyl)sulfanyl]methyl]-5-methyl-1,3-oxazol-2-yl)benzoate (760 mg, 1.65 mmol, 1.00 equiv) and 3-chlorobenzene-1-carboperoxoic acid (1.42 g, 8.23 mmol, 2.50 equiv) in chloroform (30 mL) was stirred at 0° C. for 30 min. The resulting mixture was washed successively with 2×100 mL of aqueous sodium bisulphite solution, 2×100 mL of aqueous sodium bicarbonate solution and 2×100 mL of brine. The organic layer was dried over anhydrous sodium sulfate and concentrated under vacuum to give 730 mg (90%) of methyl 4-(4-[[(4-[[(tert-butoxy)carbonyl]amino]cyclohexane)sulfonyl]methyl]-5-methyl-1,3-oxazol-2-yl)benzoate as a yellow solid. LC-MS: (ES, m/z): 437 M-C$_4$H$_8$+H$^+$, 393.

Step 7: Synthesis of 4-(4-[[(4-[[(tert-butoxy)carbonyl]amino]cyclohexane)sulfonyl]methyl]-5-methyl-1,3-oxazol-2-yl)benzoic acid

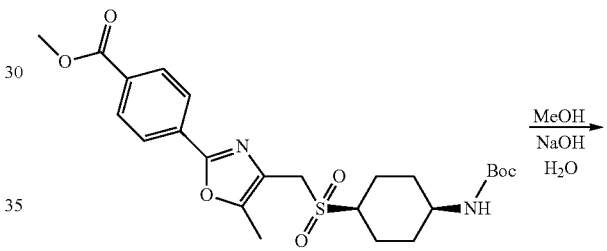

To a solution of methyl 4-(4-[[(4-[[(tert-butoxy)carbonyl]amino]cyclohexane)sulfonyl]methyl]-5-methyl-1,3-oxazol-2-yl)benzoate (730 mg, 1.48 mmol, 1.00 equiv) in methanol (20 mL) was added a solution of sodium 'hydroxide (180 mg, 4.50 mmol, 3.00 equiv) in water (5 mL). The resulting solution was stirred at 50° C. for 2.5 h and then concentrated under vacuum. A mixture of ice/water (50 mL) was added and the pH value of the solution was adjusted to 3 with 3M hydrochloric acid. The precipitate was collected by filtration, washed with water and dried in a vacuum oven to give 0.43 g (61%) of 4-(4-[[(4-[[(tert-butoxy)carbonyl]amino]cyclohexane)sulfonyl]methyl]-5-methyl-1,3-oxazol-2-yl)benzoic acid as a yellow solid. LC-MS: (ES, m/z): 479-56 [M+H]+

Step 8: Synthesis of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate

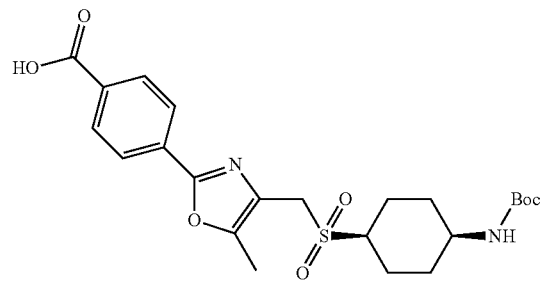

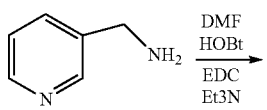

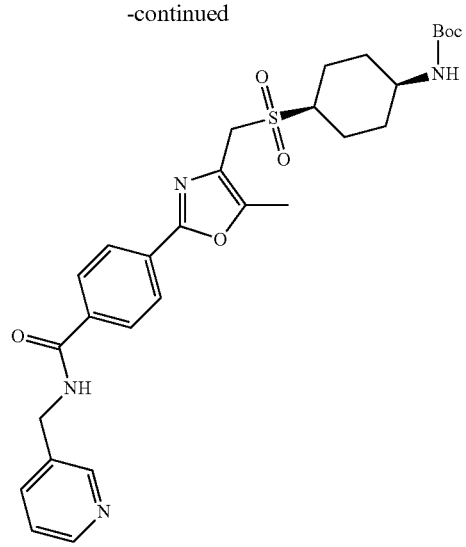

A solution of 4-(4-[[(4-[[(tert-butoxy)carbonyl]amino]cyclohexane)sulfonyl]methyl]-5-methyl-1,3-oxazol-2-yl)benzoic acid (430 mg, 0.90 mmol, 1.00 equiv), pyridin-3-ylmethanamine (120 mg, 1.11 mmol, 1.20 equiv), EDC (510 mg, 3.29 mmol, 3.00 equiv), 1H-1,2,3-benzotriazol-1-ol (150 mg, 1.11 mmol, 1.20 equiv) and triethylamine (270 mg, 2.67 mmol, 3.00 equiv) in N,N-dimethylformamide (20 mL) was stirred overnight at room temperature. The reaction was then quenched by the addition of 60 mL of water/ice. The solid was collected by filtration, washed with water and dried in a vacuum oven to give 430 mg (84%) of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate as a yellow solid. LC-MS: (ES, m/z): 569 [M+H]+, 513, 469, 347, 306.

Step 9: Synthesis of 4-(4-(((1s,4s)-4-aminocyclohexylsulfonyl)methyl)-5-methyloxazol-2-yl)-N-(pyridin-3-ylmethyl)benzamide hydrochloride

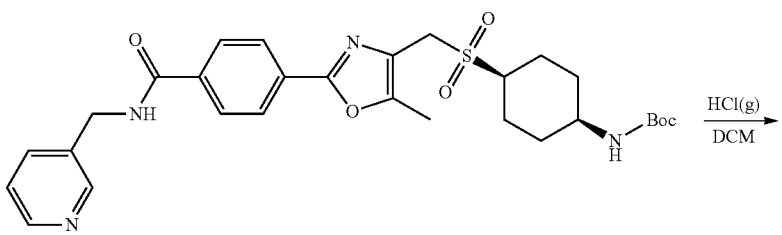

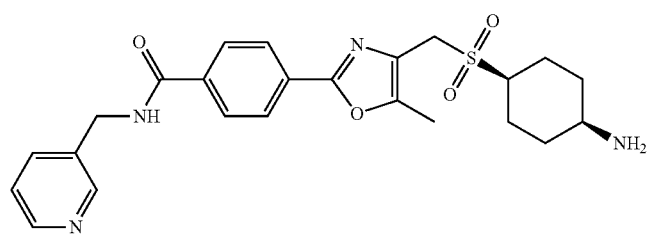

Example 3

Hydrogen chloride gas was bubbled into a solution of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate (430 mg, 0.76 mmol, 1.00 equiv) in dichloromethane (20 mL). The resulting solution was stirred at 0° C. for 2 h. The resulting mixture was concentrated under vacuum. The crude product (80 mg) was dissolved in distilled water and dried under lyophilization conditions to give 49 mg (13%) of 4-(4-(((1s,4s)-4-aminocyclohexylsulfonyl)methyl)-5-methyloxazol-2-yl)-N-(pyridin-3-ylmethyl)benzamide hydrochloride as a white solid. LC-MS: (ES, m/z): 469 [M+H]$^+$, 276, 256. $^1$H-NMR: $^1$HNMR (400 MHz, CD$_3$OD, ppm) δ 9.41-9.39 (1H, t), 8.91 (1H, s), 8.80-8.79 (1H, d), 8.65-8.63 (1H, d), 8.13-8.02 (5H, m), 4.81-4.80 (2H, s), 4.49 (2H, s), 3.41 (1H, s), 3.33 (2H, s), 2.51 (3H, s), 2.34-2.31 (2H, s), 2.12-2.02 (4H, m), 1.98-1.94 (3H, s).

Example 42

Synthesis of 4-[5-methyl-4-([[4-(pyrrolidin-1-yl)cyclohexane]sulfonyl]methyl)-1,3-oxazol-2-yl]-N-(pyridin-3-ylmethyl)benzamide as the trifluoroacetic acid salt N,N-dimethylformamide (10 mL) was stirred at 70° C. for 4 h. The reaction was quenched by the addition of 30 mL of water and the resulting solution was extracted with 3×40 mL of dichloromethane. The combined organic layers was washed with 2×100 mL of aqueous sodium chloride solution, dried over anhydrous sodium sulfate and concentrated under vacuum. The crude product (100 mg) was purified by Prep-HPLC with the following conditions (2#-Waters 2767-1 (HPLC-07)): Column, SunFire Prep C18, 19*150 mm 5 um; mobile phase, WATER WITH 0.05% TFA and CH3CN (5% CH3CN up to 25% in 13 min, up to 100% in 2 min, down to 5% in 2 min); Detector, UV 220 nm to give 31.3 mg (16%) of 4-[5-methyl-4-([[4-(pyrrolidin-1-yl)cyclohexane]sulfonyl]methyl)-1,3-oxazol-2-yl]-N-(pyridin-3-ylmethyl)benzamide as the trifluoroacetic acid salt that was a white solid. LC-MS: (ES, m/z): 523 [M+H]$^+$, 283, 262. $^1$H-NMR[400Hz, CD$_3$OD, ppm] δ 8.90 (1H, s), 8.79-8.78 (2H, d), 8.63-8.61 (1H, d), 8.13-8.11 (2H, d), 8.08-8.01 (3H, d), 4.79 (2H, s), 4.51 (2H, s), 3.66 (2H, s), 3.46-3.32 (1H, d), 3.28-3.25 (1H, m), 3.18-3.11 (2H, m), 2.51 (5H, s), 2.16-1.99 (10H, m).

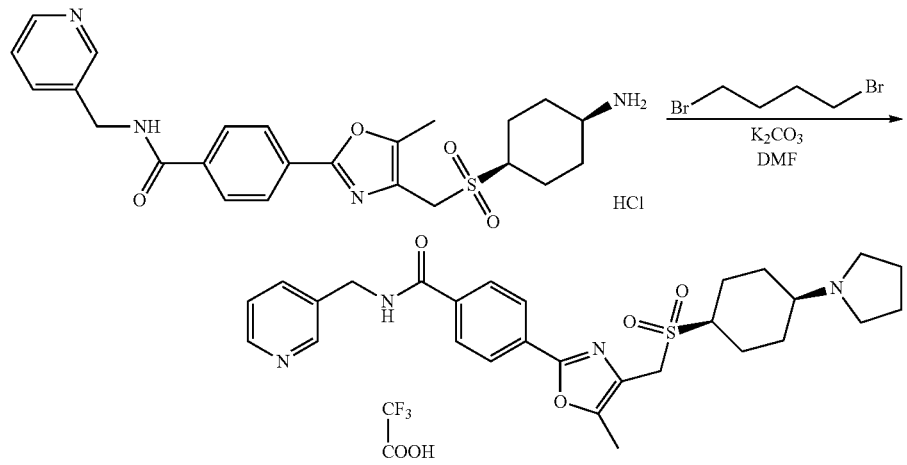

Example 4

A solution of 4-(4-(((1S,4S)-4-aminocyclohexylsulfonyl)methyl)-5-methyloxazol-2-yl)-N-(pyridin-3-ylmethyl)benzamide hydrochloride (140 mg, 0.30 mmol, 1.00 equiv) (Example 3), 1,4-dibromobutane (60 mg, 0.28 mmol, 1.20 equiv) and potassium carbonate (140 mg, 1.01 mmol, 4.00 equiv) in Example 43

Synthesis of 4-[5-Methyl-4-([[4-(piperidin-1-yl)cyclohexane]sulfonyl]methyl)-1,3-oxazol-2-yl]-N-(pyridin-3-ylmethyl)benzamide trifluoroacetic acid salt

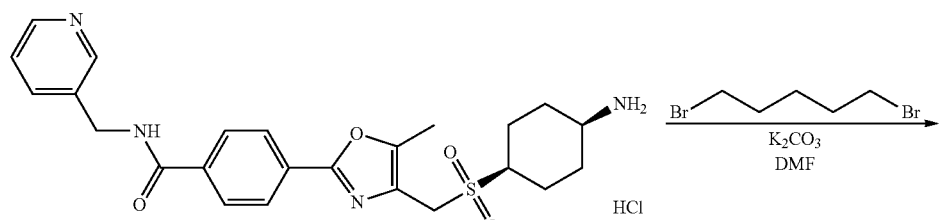

Example 3

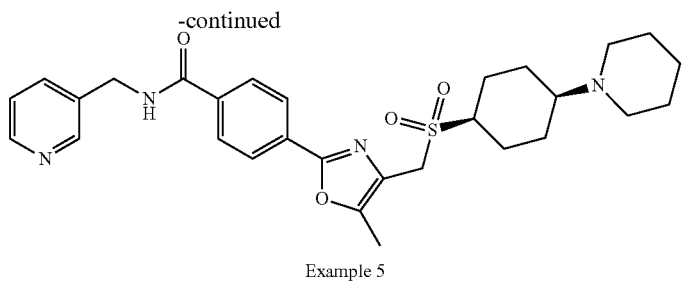

Example 5

A solution of 4-(4-(((1S,4S)-4-aminocyclohexylsulfonyl)methyl)-5-methyloxazol-2-yl)-N-(pyridin-3-ylmethyl)benzamide hydrochloride (100 mg, 0.21 mmol, 1.00 equiv), 1,5-dibromopentane (40 mg, 0.17 mmol, 1.20 equiv) and potassium carbonate (30 mg, 0.22 mmol, 4.00 equiv) in N,N-dimethylformamide (7 mL) was stirred at 70° C. for 4 h. The reaction was then quenched by the addition of 43 mL of water and the resulting solution was extracted with 3×40 mL of dichloromethane. The combined organic layers was washed with 2×100 mL of aqueous sodium chloride solution, dried over anhydrous sodium sulfate and concentrated under vacuum. The crude product (90 mg) was purified by Prep-HPLC with the following conditions (2#-Waters 2767-1 (HPLC-07)): Column, SunFire Prep C18, 19*150 mm 5 um; mobile phase, WATER WITH 0.05% TFA and CH3CN (5% CH3CN up to 15% in 2 min, up to 45% in 8 min, up to 100% in 1 min, down to 5% in 1 min); Detector, UV 220 nm, to yield 8.8 mg (8%) of 4-[5-methyl-4-([[4-(piperidin-1-yl)cyclohexane]sulfonyl]methyl)-1,3-oxazol-2-yl]-N-(pyridin-3-ylmethyl)benzamide as the trifluoroacetic acid salt that was a white solid. LC-MS: (ES, m/z): 537 [M+H]$^+$, 290, 269. $^1$H-NMR (400Hz, CD$_3$OD, ppm) δ 8.59 (1H, s), 8.47-8.46 (1H, d), 8.11-8.09 (2H, d), 7.99-7.97 (2H, d), 7.90-7.88 (1H, d), 7.46-7.43 (1H, m), 4.65 (2H, s), 4.43 (2H, s), 2.56 (4H, s), 2.50 (4H, s), 2.39 (3H, s), 2.09-2.01 (2H, m), 1.91-1.85 (2H, m), 1.71-1.63 (7H, m), 1.48 (3H, s).

Example 44

Synthesis of 4-(4-[[(4-Aminocyclohexane)sulfonyl]methyl]-5-methyl-1,3-oxazol-2-yl)-N-(pyridin-3-ylmethyl)benzamide trifluoroacetic acid salt Step 1: Synthesis of 4-[[(tert-butoxy)carbonyl]amino]cyclohexyl acetate

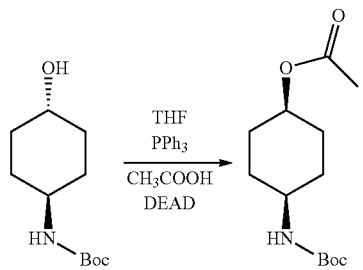 [SMILES: CC(C)(C)OC(=O)N[C@H]1CC[C@H](O)CC1 ; CC(=O)O[C@H]1CC[C@@H](NC(=O)OC(C)(C)C)CC1]

To a solution of tert-butyl N-(4-hydroxycyclohexyl)carbamate (15 g, 69.67 mmol, 1.00 equiv), acetic acid (16.7 g, 278.09 mmol, 4.00 equiv) and triphenylphosphane (73 g, 278.32 mmol, 4.00 equiv). In tetrahydrofuran (200 mL) was added diethyl azodicarboxylate (48.55 g, 278.78 mmol, 4.00 equiv) dropwise with stiffing at 0° C. The resulting solution was stirred overnight at room temperature and then 200 mL of aqueous sodium bicarbonate solution was added. The resulting mixture was extracted with 3×100 mL of ethyl acetate. The combined organic layers was dried over anhydrous sodium sulfate and concentrated under vacuum. The crude product was triturated with 500 mL of a 1:1 mixture of ether and hexane. The solid triphenylphosphine oxide was removed by filtration. The filtrate was concentrated under vacuum and purified on a silica gel column eluted with ethyl acetate/petroleum ether (1:15) to give 3.8 g (21%) of 4-[[(tert-butoxy)carbonyl]amino]cyclohexyl acetate as a white solid.

Step 2: Synthesis of tert-butyl N-(4-hydroxycyclohexyl)carbamate

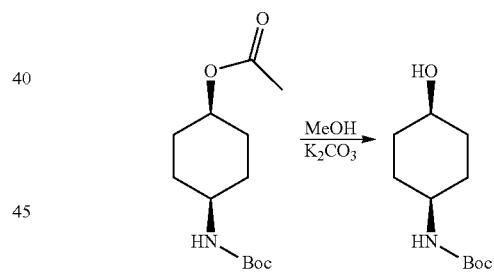

A mixture of 4-[[(tert-butoxy)carbonyl]amino]cyclohexyl acetate (2.43 g, 9.44 mmol, 1.00 equiv), methanol (30 mL) and potassium carbonate (2 g, 14.37 mmol, 1.50 equiv) was stirred overnight at 25° C. The resulting mixture was concentrated under vacuum. Water (50 mL) was added and the resulting solution was extracted with 3×70 mL of dichloromethane. The organic layers were combined and washed with 2×200 mL of brine. The organic layer was dried over anhydrous sodium sulfate and concentrated under vacuum to give 2.19 g of crude tert-butyl N-(4-hydroxycyclohexyl)carbamate as yellow oil.

Step 3: Synthesis of tert-butyl N-[4-(methanesulfonyloxy)cyclohexyl]carbamate

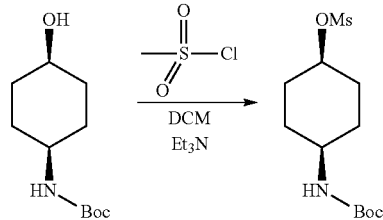

To a solution of tert-butyl N-(4-hydroxycyclohexyl)carbamate (3.8 g, 17.65 mmol, 1.00 equiv) and triethylamine (3.9 g, 38.54 mmol, 2.20 equiv) in dichloromethane (40 mL) was added methanesulfonyl chloride (2.43 g, 21.21 mmol, 1.21 equiv) dropwise with stirring at 0° C. The reaction mixture was stirred overnight at room temperature. Water (50 mL) was added to quench the reaction. The resulting mixture was extracted with 3×50 mL of dichloromethane. The combined organic layers was washed with 2×200 mL of brine, dried over anhydrous sodium sulfate and concentrated under vacuum to give 3.0 g (58%) of tert-butyl N-[4-(methanesulfonyloxy)cyclohexyl]carbamate as a white solid.

Step 4: Synthesis of methyl 4-(4-[[(4-[[(tert-butoxy)carbonyl]amino]cyclohexyl)sulfanyl]methyl]-5-methyl-1,3-oxazol-2-yl)benzoate

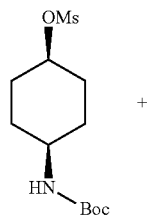

+

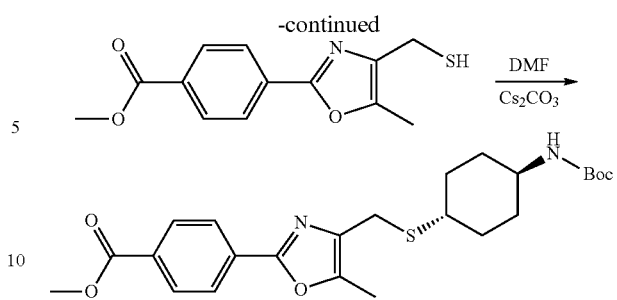

A solution of tert-butyl N-[4-(methanesulfonyloxy)cyclohexyl]carbamate (2.24 g, 7.64 mmol, 1.00 equiv), methyl 4-[5-methyl-4-(sulfanylmethyl)-1,3-oxazol-2-yl]benzoate (3.0 g, 11.39 mmol, 1.20 equiv) and cesium carbonate (5.55 g, 16.98 mmol, 2.00 equiv) in N,N-dimethylformamide (30 mL) was stirred at 50° C. under nitrogen atmosphere for 3 h. Water (100 mL) was added to quench the reaction. The resulting solution was extracted with 3×80 mL of ethyl acetate. The combined organic layers was washed with 2×200 mL of brine, dried over anhydrous sodium sulfate and concentrated under vacuum. The residue was purified on a silica gel column eluted with ethyl acetate/petroleum ether (1:15-2:1) to give 960 mg (27%) of methyl 4-(4-[[(4-[[(tert-butoxy)carbonyl]amino]cyclohexyl)sulfanyl]methyl]-5-methyl-1,3-oxazol-2-yl)benzoate as a yellow solid. LC-MS: (ES, m/z): 461 $[M+H]^+$, 405, 271, 230, 102.

Step 5: Synthesis of methyl 4-(4-[[(4-[[(tert-butoxy)carbonyl]amino]cyclohexane)sulfonyl]methyl]-5-methyl-1,3-oxazol-2-yl)benzoate

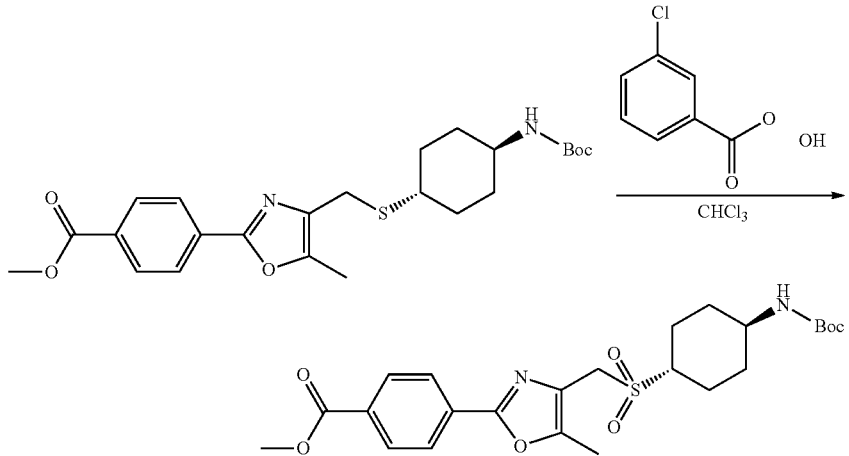

To a solution of methyl 4-(4-[[(4-[[(tert-butoxy)carbonyl]amino]cyclohexyl)sulfanyl]methyl]-5-methyl-1,3-oxazol-2-yl)benzoate (960 mg, 2.08 mmol, 1.00 equiv) in chloroform (30 mL) was added m-chloroperbenzoic acid (1.8 g, 10.43 mmol, 2.50 equiv) in small portions at 0° C. The resulting solution was stirred at 0° C. for 30 min. The reaction mixture was washed with 2×100 mL of aqueous sodium bisulphite solution, 2×100 mL of aqueous sodium bicarbonate solution and 2×100 mL of brine. The organic layer was dried over anhydrous sodium sulfate and concentrated under vacuum to give 950 mg (93%) of methyl 4-(4-[[(4-[[(tert-butoxy)carbonyl]amino]cyclohexane)sulfonyl]methyl]-5-methyl-1,3-oxazol-2-yl)benzoate as a yellow solid. LC-MS: (ES, m/z): 437 $[M-C_4H_8+H]^+$, 393, 230.

Step 6: Synthesis of 4-(4-[[(4-[[(tert-butoxy)carbonyl]amino]cyclohexane)sulfonyl]methyl]-5-methyl-1,3-oxazol-2-yl)benzoic acid

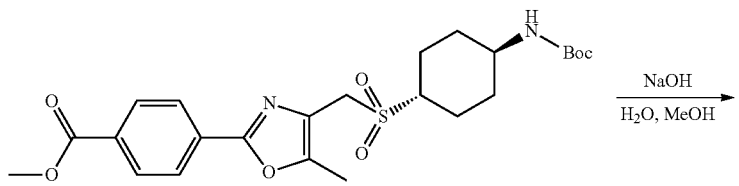

To a solution of methyl 4-(4-[[(4-[[(tert-butoxy)carbonyl]amino]cyclohexane) sulfonyl]methyl]-5-methyl-1,3-oxazol-2-yl)benzoate (950 mg, 1.93 mmol, 1.00 equiv) in methanol (30 mL) was added a solution of sodium hydroxide (230 mg, 5.75 mmol, 3.00 equiv) in water (5 mL). The reaction mixture was stirred overnight at 50° C. and then concentrated under vacuum. A mixture of water/ice (60 mL) was added and the pH value of the solution was adjusted to 3 with 3M hydrochloric acid. The precipitate was collected by filtration and dried in a vacuum oven to give 800 mg (87%) of 4-(4-[[(4-[[(tert-butoxy)carbonyl]amino]cyclohexane)sulfonyl]methyl]-5-methyl-1,3-oxazol-2-yl)benzoic acid as a white solid. LC-MS: (ES, m/z): 479 [M+H]$^+$, 423, 379, 279, 141, 115.

Step 7: Synthesis of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate

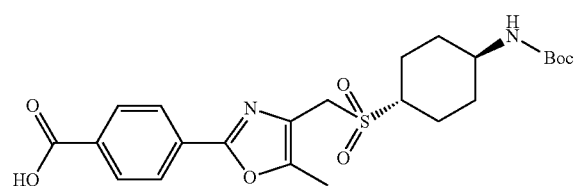

+

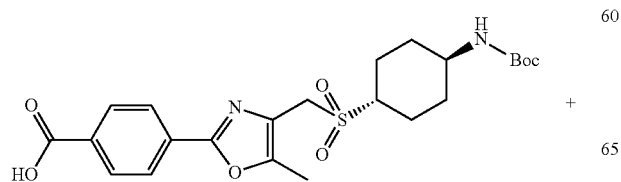

-continued

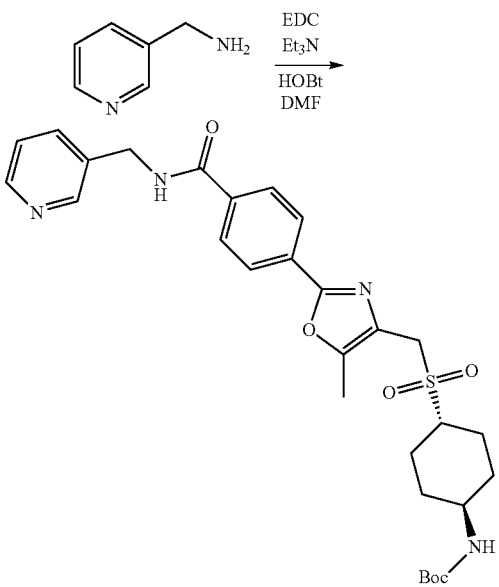

To a solution of 4-(4-[[(4-[[(tert-butoxy)carbonyl]amino] cyclohexane)sulfonyl]methyl]-5-methyl-1,3-oxazol-2-yl)

benzoic acid (800 mg, 1.67 mmol, 1.00 equiv), pyridin-3-ylmethanamine (220 mg, 2.03 mmol, 1.20 equiv), EDC (950 mg, 6.12 mmol, 3.00 equiv) and 1H-1,2,3-benzotriazol-1-ol (270 mg, 2.00 mmol, 1.20 equiv) in N,N-dimethylformamide (20 mL) was added triethylamine (510 mg, 5.04 mmol, 3.00 equiv) dropwise with stirring. The resulting solution was stirred for 3 h at 30° C. and then quenched by the addition of 100 mL of water/ice. The solid was collected by filtration and dried in a vacuum oven to give 790 mg (83%) of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate as a yellow solid. LC-MS: (ES, m/z): 569 [M+H]$^+$, 513, 469, 306, 115.

Step 8: Synthesis of 4-(4-[[[(4-aminocyclohexane)sulfonyl]methyl]-5-methyl-1,3-oxazol-2-yl)-N-(pyridin-3-ylmethyl)benzamide trifluoroacetic acid salt

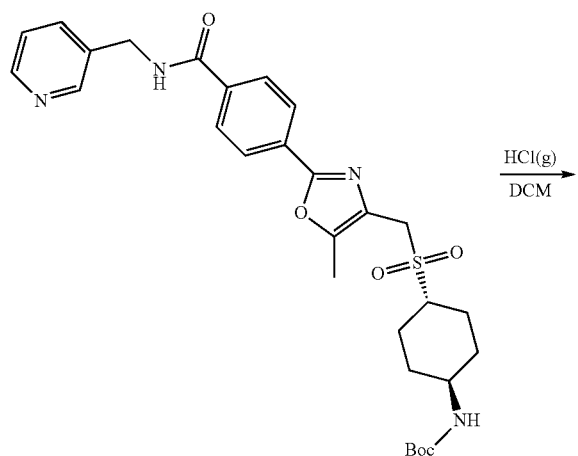

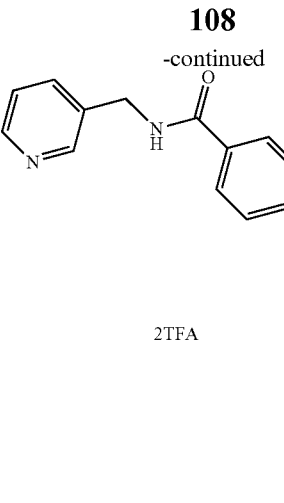

Example 6

Hydrogen chloride gas was bubbled into a solution of tert-butyl N-(4-[[(5-methyl-2-[4-[(pyridin-3-ylmethyl)carbamoyl]phenyl]-1,3-oxazol-4-yl)methane]sulfonyl]cyclohexyl)carbamate (790 mg, 1.39 mmol, 1.00 equiv) in dichloromethane (30 mL, 0.35 mmol, 0.25 equiv). The resulting solution was stirred for 3 h at 0° C. then concentrated under vacuum. The crude product (100 mg) was purified by Prep-HPLC with the following conditions (1#-Pre-HPLC-005 (Waters)): Column, Xbridge Prep C18, 5 um, 19*150 mm; mobile phase, WATER WITH 0.05% TFA and CH3CN (10.0% CH3CN up to 35.0% in 12 min, up to 100.0% in 1 min); Detector, UV 254 nm. 33.1 mg product was obtained. This resulted in 33.1 mg (3%) of 4-(4-[[[(4-aminocyclohexane)sulfonyl]methyl]-5-methyl-1,3-oxazol-2-yl)-N-(pyridin-3-ylmethyl)benzamide, a white solid as the trifluoroacetic acid salt. LC-MS: (ES, m/z): 469 [M+H]$^+$, 297, 277. $^1$H-NMR (400 MHz, CD$_3$OD, ppm) δ 8.89 (1H, s), 8.79-8.77 (1H, d), 8.61-8.59 (1H, d), 8.13-8.11 (2H, d), 8.06-8.01 (3H, m), 4.79 (2H, s), 4.44 (2H, s), 3.22-3.16 (2H, t), 2.46-2.43 (5H, d), 2.25-2.23 (2H, d), 1.80-1.71 (2H, m), 1.54-1.45 (2H, m).

Example 45

4-[5-Methyl-4-([[4-(pyrrolidin-1-yl)cyclohexane]sulfonyl]methyl)-1,3-oxazol-2-yl]-N-(pyridin-3-ylmethyl)benzamide trifluoroacetate

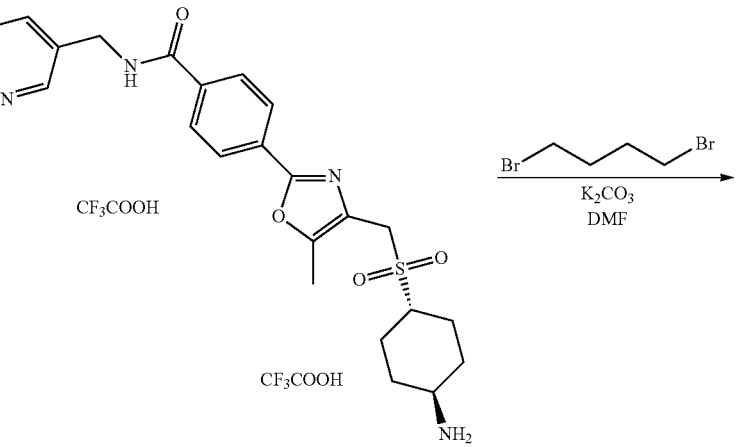

Example 6

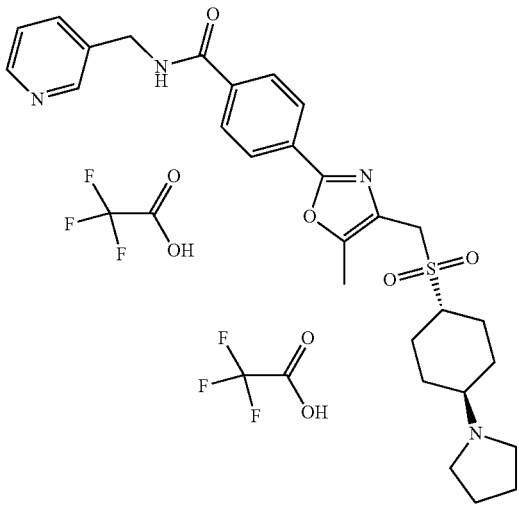

Example 7

A mixture of 4-(4-[[(4-aminocyclohexane)sulfonyl]methyl]-5-methyl-1,3-oxazol-2-yl)-N-(pyridin-3-ylmethyl)benzamide ditrifluoroacetate (100 mg, 0.20 mmol, 1.00 equiv), potassium (120 mg, 0.86 mmol, 4.00 equiv) and 1,4-dibromobutane (55 mg, 0.25 mmol, 1.20 equiv) in N,N-dimethylformamide (20 mL) was stirred overnight at 70° C. The reaction was then quenched by the addition of 40 mL of water and then extracted with 3×50 mL of dichloromethane. The organic combined layers was washed with 2×200 mL of brine, dried over anhydrous sodium sulfate and concentrated under vacuum. The crude product (120 mg) was purified by Prep-HPLC with the following conditions (1#-Pre-HPLC-005(Waters)): Column, Xbridge Prep C18, Sum, 19*150 mm; mobile phase, WATER WITH 0.05% TFA and CH3CN (10.0% CH3CN up to 30.0% in 12 min, up to 100.0% in 1 min); Detector, UV 254 nm, to give 34.2 mg (23%) of 4-[5-methyl-4-([[4-(pyrrolidin-1-yl)cyclohexane]sulfonyl]methyl)-1,3-oxazol-2-yl]-N-(pyridin-3-ylmethyl)benzamide, a white oil as its trifluoroacetic acid salt. LC-MS: (ES, m/z): 523[M+H]$^+$, 283, 263. $^1$H-NMR (400 MHz, CD$_3$OD, ppm) δ 8.90 (1H, s), 8.80-8.78 (1H, d), 8.63-8.61 (1H, d), 8.14-8.11 (2H, d), 8.08-8.01 (3H, t), 4.80 (2H, s), 4.45 (2H, s), 3.66 (2H, s), 2.47-2.40 (7H, m), 2.17 (2H, s), 2.03-2.00 (2H, d), 1.77-1.71 (2H, m), 1.62-1.57 (2H, m).

Example 46

4-[5-Methyl-4-([[4-(piperidin-1-yl)cyclohexane]sulfonyl]methyl)-1,3-oxazol-2-yl]-N-(pyridin-3-ylmethyl)benzamide

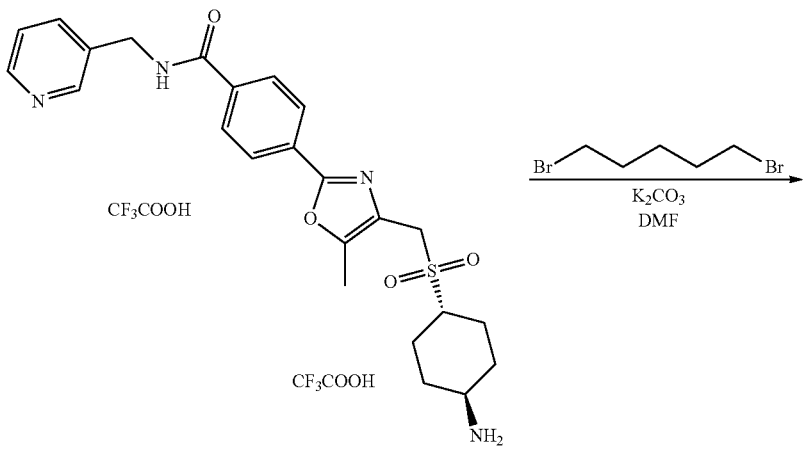

Example 6

-continued

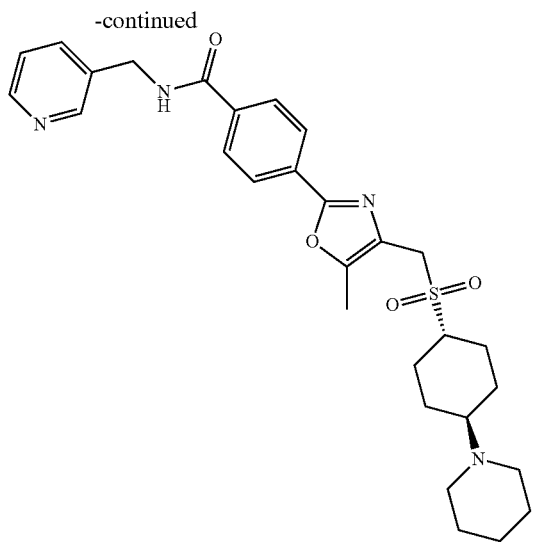

Example 8

A mixture of 4-(4-((trans-4-aminocyclohexylsulfonyl)methyl)-5-methyloxazol-2-yl)-N-(pyridin-3-ylmethyl)benzamide bistrifluoroacetate (170 mg, 0.33 mmol, 1.00 equiv), potassium carbonate (200 mg, 1.44 mmol, 4.00 equiv), 1,5-dibromopentane (99 mg, 0.43 mmol, 1.20 equiv) in N,N-dimethylformamide (20 mL) was stirred overnight at 70° C. Water (40 mL) was added and the resulting solution was extracted with 3×50 mL of dichloromethane. The combined organic layers was washed with brine, dried over anhydrous sodium sulfate and concentrated under vacuum. The crude product (120 mg) was purified by Prep-HPLC with the following conditions (1#-Pre-HPLC-005(Waters)): Column, SunFire Prep C18, 5 um, 19*150 mm; mobile phase, WATER WITH 0.05% TFA and CH3CN (17.0% CH3CN up to 40.0% in 12 min, up to 100.0% in 1 min); Detector, UV 254/220 nm, to yield 12.6 mg (7%) of 4-[5-methyl-4-([[4-(piperidin-1-yl)cyclohexane]sulfonyl]methyl)-1,3-oxazol-2-yl]-N-(pyridin-3-ylmethyl)benzamide as a white solid. LC-MS: (ES, m/z): 537 [M+H]+, 290, 263. $^1$H-NMR (400 MHz, CD$_3$OD, ppm) δ 8.59 (1H, s), 8.47-8.46 (1H, d), 8.12-8.10 (2H, d), 8.00-7.98 (2H, d), 7.90-7.88 (1H, d), 7.46-7.43 (1H, t), 4.65 (2H, s), 4.40 (2H, s), 3.14-3.07 (1H, m), 2.62 (4H, s), 2.50 (3H, s), 2.41-2.38 (3H, d), 2.16-2.13 (2H, d), 1.70-1.64 (6H, m), 1.49-1.37 (4H, m).

Example 47

Synthesis of 4-[4-([[(1S,3S)-3-Aminocyclopentane]sulfonyl]methyl)-5-methyl-1,3-oxazol-2-yl]-N-(pyridin-3-ylmethyl)benzamide bis-trifluoroacetic acid salt Step 1: Synthesis of tert-butyl N-hydroxycarbamate

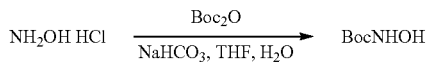

To a mixture of di-tert-butyl dicarbonate (12 g, 54.98 mmol, 0.33 equiv) and aqueous sodium carbonate solution (w/w=0.176) (117.6 g) in tetrahydrofuran (100 mL) was added a solution of hydroxylamine hydrochloride (11.6 g, 166.93 mmol, 1.00 equiv) in water (100 mL) dropwise with stirring at room temperature. The resulting solution was stirred overnight at room temperature. Water (100 mL) was added and the mixture was extracted with 3×150 mL of ethyl acetate. The combined organic layers was dried over anhydrous sodium sulfate and concentrated under vacuum to give 15 g (67%) of tert-butyl N-hydroxycarbamate as a white solid.

Step 2: Synthesis of tert-butyl 2-oxa-3-azabicyclo[2.2.1]hept-5-ene-3-carboxylate

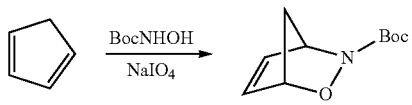

To a solution of tert-butyl N-hydroxycarbamate (9.2 g, 69.10 mmol, 1.00 equiv) and cyclopenta-1,3-diene (20.2 g, 305.59 mmol, 4.42 equiv) in methanol (600 mL) was added of a solution of sodium periodate (17 g, 79.48 mmol, 1.15 equiv) in water (180 mL) dropwise at 0° C. with stirring in 30 min. The reaction mixture was stirred for another 30 min at 0° C. and then diluted with 600 mL of water. The solution was extracted with 3×300 mL of ethyl acetate. The combined organic layers was washed with 2×200 mL of brine, dried over anhydrous sodium sulfate and concentrated under vacuum to give 9.1 g (67%) of tert-butyl 2-oxa-3-azabicyclo[2.2.1]hept-5-ene-3-carboxylate as a white solid. $^1$HNMR (400 MHz, D$_2$O, ppm) δ 6.42 (2H, s), 5.22 (1H, s), 4.99 (1H, s), 1.99 (1H, d, J=8.4Hz), 1.73 (1H, d, J=8.4Hz), 1.47 (9H, s).

Step 3: Synthesis of tert-butyl N-[(1S,3R)-3-hydroxycyclopentyl]carbamate

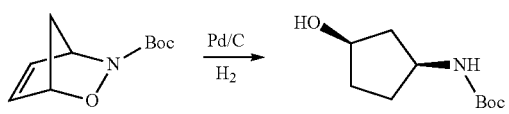 [SMILES: CC(C)(C)OC(=O)N1OC2C=CC1C2 ; "Pd/C" ; "H2" ; CC(C)(C)OC(=O)N[C@H]1CC[C@@H](O)C1]

A mixture of tert-butyl 2-oxa-3-azabicyclo[2.2.1]hept-5-ene-3-carboxylate (8.0 g, 40.56 mmol, 1.00 equiv) and palladium on carbon (0.5 g) catalyst in methanol (100 mL) was stirred under an atmosphere of hydrogen atmosphere at 60° C. for 48 h. The reaction mixture was cooled to room temperature and the catalyst was removed by filtration. The catalyst was washed with 3×10 mL of MeOH. The combined filtrate and washings was concentrated under vacuum to give 6.5 g (80%) of tert-butyl N-[(1S,3R)-3-hydroxycyclopentyl]carbamate as a white solid. $^1$HNMR (400 MHz, D$_2$O, ppm) δ 4.72 (1H, s), 4.55 (1H, s), 1.92-1.87 (3H, m), 1.76-1.60 (3H, m), 1.50 (9H, s).

Step 4: Synthesis of tert-butyl N-[(1S,3R)-3-(methane sulfonyloxy)cyclopentyl]carbamate

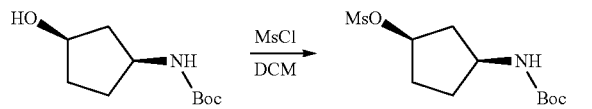

To a solution of tert-butyl N-[(1S,3R)-3-hydroxycyclopentyl]carbamate (3.0 g, 14.91 mmol, 1.00 equiv) and triethylamine (3.0 g, 29.65 mmol, 1.99 equiv) in dichloromethane (50 mL) was added methanesulfonyl chloride (2.2 g, 19.21 mmol, 1.29 equiv) dropwise with stiffing at 0-5° C. After addition was completed, the reaction mixture was warmed to room temperature and stirred at room temperature for 2 h. The mixture was diluted with 50 mL of water and extracted with 2×50 mL of ethyl acetate. The combined organic layers was washed with 2×30 mL of brine, dried over anhydrous sodium sulfate and concentrated under vacuum to give 3.8 g (91%) of tert-butyl N-[(1S,3R)-3-(methane sulfonyloxy)cyclopentyl] carbamate as a white solid.

Step 5: Synthesis of methyl 4-[4-[(acetylsulfanyl) methyl]-5-methyl-1,3-oxazol-2-yl]benzoate

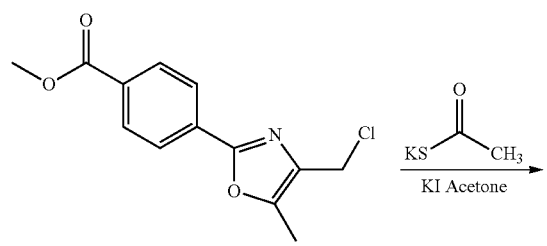

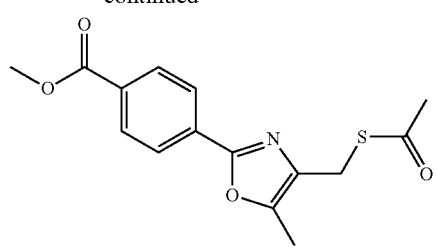

A solution of methyl 4-[4-(chloromethyl)-5-methyl-1,3-oxazol-2-yl]benzoate (10 g, 37.64 mmol, 1.00 equiv), potassium ethanethioate (5 g, 43.78 mmol, 1.16 equiv) and potassium iodide (300 mg, 1.81 mmol, 0.05 equiv) in acetone (160 mL) was stirred at 35° C. under nitrogen for 30 min. The product was precipitated by the addition of 250 mL water. The precipitate was collected by filtration, washed with water and dried in a vacuum oven to give 10.5 g (91%) of methyl 4-[4-[(acetylsulfanyl)methyl]-5-methyl-1,3-oxazol-2-yl] benzoate as a white solid.

Step 6: Synthesis of methyl 4-[5-methyl-4-(sulfanylmethyl)-1,3-oxazol-2-yl]benzoate

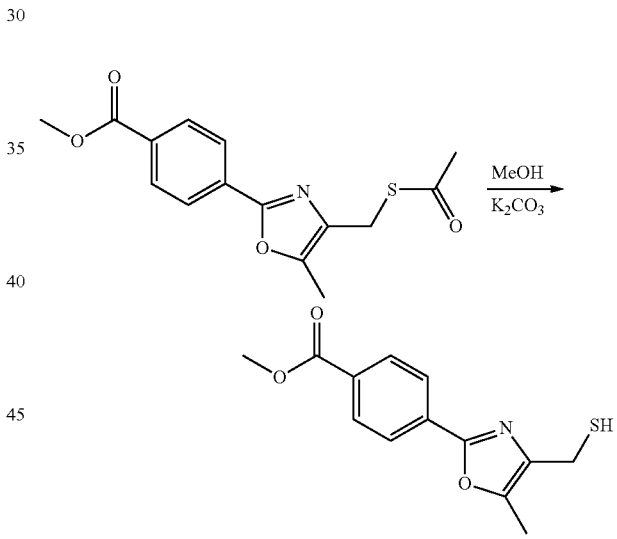

A mixture of methyl 4-[4-[(acetylsulfanyl)methyl]-5-methyl-1,3-oxazol-2-yl]benzoate (10.5 g, 34.39 mmol, 1.00 equiv) and potassium carbonate (12.3 g, 89.00 mmol, 2.59 equiv) in methanol (200 mL) was stirred at 35° C. under an inert atmosphere of nitrogen for 30 min. Water (200 mL) was added and the resulting solution was extracted with 3×100 mL of dichloromethane. The combined organic layers was washed with 3×50 mL of brine, dried over anhydrous sodium sulfate and concentrated under vacuum. To afford 8.4 g (93%) of methyl 4-[5-methyl-4-(sulfanylmethyl)-1,3-oxazol-2-yl] benzoate as a white solid. LC-MS-: (ES, m/z): 305 [M+CH$_3$CN+H]$^+$, 264 [M+H]$^+$, 230.

Step 7: Synthesis of methyl 4-[4-([[(1S,3S)-3-[[(tert-butoxy)carbonyl]amino]cyclopentyl]sulfanyl]methyl)-5-methyl-1,3-oxazol-2-yl]benzoate

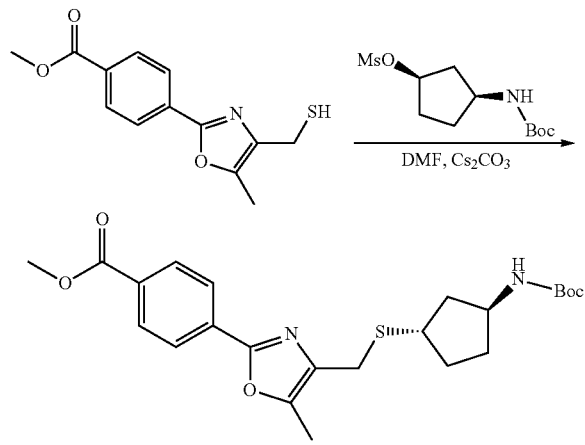

To a solution of methyl 4-[5-methyl-4-(sulfanylmethyl)-1,3-oxazol-2-yl]benzoate (920 mg, 3.49 mmol, 1.00 equiv) in N,N-dimethylformamide (20 mL) maintained under an inert atmosphere of nitrogen was added cescium carnonate (2.3 g). The mixture was stirred for 20 min then tert-butyl N-[(1S,3R)-3-(methanesulfonyloxy)cyclopentyl]carbamate (1.0 g, 3.58 mmol, 1.02 equiv) was added. The resulting solution was stirred at 35° C. for 50 min then the product was precipitated by the addition of 50 mL water. The precipitate was collected by filtration, washed with water and then dried under vacuum to give 1.37 g (88%) of methyl 4-[4-([[(1S,3S)-3-[[(tert-butoxy)carbonyl]amino]cyclopentyl]sulfanyl]methyl)-5-methyl-1,3-oxazol-2-yl]benzoate as a white solid. LC-MS: (ES, m/z): 447 [M+H]$^+$, 391, 271, 230, 115.

Step 8: Synthesis of methyl 4-[4-([[(1S,3S)-3-[[(tert-butoxy)carbonyl]amino]cyclopentane]sulfonyl]methyl)-5-methyl-1,3-oxazol-2-yl]benzoate

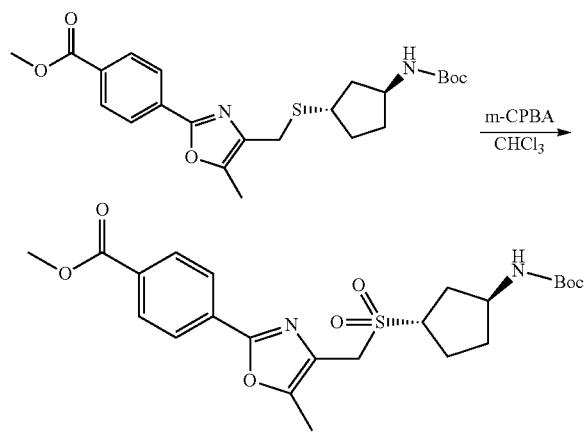

To a solution of methyl 4-[4-([[(1S,3S)-3-[[(tert-butoxy)carbonyl]amino]cyclopentyl]sulfanyl]methyl)-5-methyl-1,3-oxazol-2-yl]benzoate (1.3 g, 2.91 mmol, 1.00 equiv) in chloroform (30 mL) maintained under nitrogen at 0-5° C. was added m-chloroperbenzoic acid (1.25 g, 7.24 mmol, 2.49 equiv) in several batches. The resulting solution was stirred for 2 h at 0-5° C. then quenched by the addition of saturated aqueous sodium bisulphite solution (20 mL) and aqueous sodium carbonate solution (20 mL). The resulting mixture was extracted with 60 mL of chloroform. The organic layer was washed with 3×20 mL of brine, dried over anhydrous sodium sulfate and concentrated under vacuum to give 1.28 g (92%) of methyl 4-[4-([[(1S,3S)-3-[[(tert-butoxy)carbonyl]amino]cyclopentane]sulfonyl]methyl)-5-methyl-1,3-oxazol-2-yl]benzoate as a white solid. LC-MS: (ES, m/z): 479 [M+H]$^+$, 423.

Step 9: Synthesis of 4-[4-([[(1S,3S)-3-[[(tert-butoxy)carbonyl]amino]cyclopentane]sulfonyl]methyl)-5-methyl-1,3-oxazol-2-yl]benzoic acid

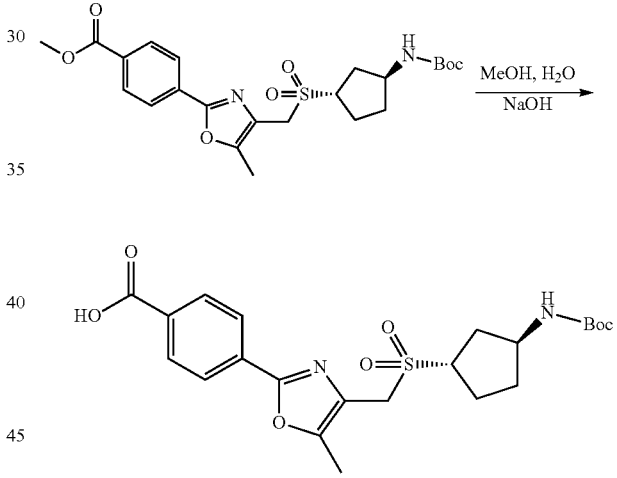

To a solution of methyl 4-[4-([[(1S,3S)-3-[[(tert-butoxy)carbonyl]amino]cyclopentane]sulfonyl]methyl)-5-methyl-1,3-oxazol-2-yl]benzoate (1.28 g, 2.67 mmol, 1.00 equiv) in methanol (30 mL) was added a solution of sodium hydroxide (640 mg, 16.00 mmol, 5.98 equiv) in water (6 mL). The resulting solution was stirred at 50° C. for 2 h. The pH value of the solution was adjusted to 2-3 with 2N hydrochloric acid. The precipitate was collected by filtration, washed with 3×20 mL of water and dried in a vacuum oven to give 1.1 g (89%) of 4-[4-([[(1S,3S)-3-[[(tert-butoxy)carbonyl]amino]cyclopentane]sulfonyl]methyl)-5-methyl-1,3-oxazol-2-yl]benzoic acid as a white solid. LC-MS: (ES, m/z): 465 [M+H]$^+$, 409.

Step 10: Synthesis of tert-butyl N-[(1S,3S)-3-[[(5-methyl-2-[4-[(pyridin-3-ylmethyl)carbamoyl]phenyl]-1,3-oxazol-4-yl)methane]sulfonyl]cyclopentyl]carbamate

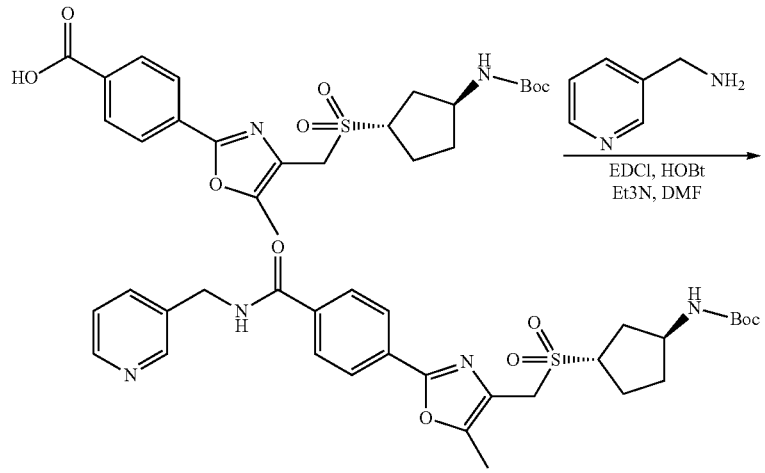

A solution of 4-[4-([[(1S,3S)-3-[[(tert-butoxy)carbonyl]amino]cyclopentane]sulfonyl]methyl)-5-methyl-1,3-oxazol-2-yl]benzoic acid (1.1 g, 2.37 mmol, 1.00 equiv), EDCI (600 mg, 3.13 mmol, 1.32 equiv), HOBt (420 mg, 3.11 mmol, 1.31 equiv), triethylamine (720 mg, 7.12 mmol, 3.00 equiv) and pyridin-3-ylmethanamine (500 mg, 4.62 mmol, 1.95 equiv) in N,N-dimethylformamide (30 mL) was stirred at 35° C. overnight. The product was precipitated by the addition of 80 mL water. The precipitate was collected by filtration, washed with water and dried under vacuum to give 1.0 g (76%) of tert-butyl N-[(1S,3S)-3-[[(5-methyl-2-[4-[(pyridin-3-ylmethyl)carbamoyl]phenyl]-1,3-oxazol-4-yl)methane]sulfonyl]cyclopentyl]carbamate as a white solid. LC-MS: (ES, m/z): 555 [M+H]$^+$, 499, 306, 264.

Step 11: Synthesis of 4-[4-([[(1S,3S)-3-aminocyclopentane]sulfonyl]methyl)-5-methyl-1,3-oxazol-2-yl]-N-(pyridin-3-ylmethyl)benzamide bis-trifluoroacetic acid salt Hydrogen chloride gas was bubbled into a solution of tert-butyl N-[(1S,3S)-3-[[(5-methyl-2-[4-[(pyridin-3-ylmethyl)carbamoyl]phenyl]-1,3-oxazol-4-yl)methane]sulfonyl]cyclopentyl]carbamate (1.0 g, 1.80 mmol, 1.00 equiv) in dichloromethane (20 mL). The resulting solution was stirred for 2 h at 0-5° C. then concentrated under vacuum. The crude product (300 mg) was purified by Prep-HPLC with the following conditions (1#-Pre-HPLC-005(Waters)): Column, SunFire Prep C18, 19*150 mm 5 um; mobile phase, WATER WITH 0.05% TFA and CH3CN (5% CH3CN up to 25% in 12 min, up to 100% in 1 min); Detector, uv 254 nm, to give 200 mg (16%) of 4-[4-([[(1S,3S)-3-aminocyclopentane]sulfonyl]methyl)-5-methyl-1,3-oxazol-2-yl]-N-(pyridin-3-ylmethyl)benzamide bis-trifluoroacetic acid salt as a white solid. LC-MS: (ES, m/z): 455 [M+H]$^+$, 290, 245. $^1$HNMR (400 MHz, D$_2$O ppm) δ 8.66 (1H, s), 8.59 (H, d, J=5.6Hz), 8.47 (1H, d, J=8.0Hz), 7.94-7.91 (1H, m), 7.85 (2H, d, J=8.4Hz), 7.73 (2H, d, J=8.4Hz), 4.65 (2H, s), 4.37 (2H, s), 3.92-3.84 (1H, m), 3.73-3.69 (1H, m), 2.52-2.45 (1H, m), 2.28 (3H, s), 2.24-2.18 (2H, m), 2.12-2.03 (2H, m), 1.73-1.68 (1H, m).

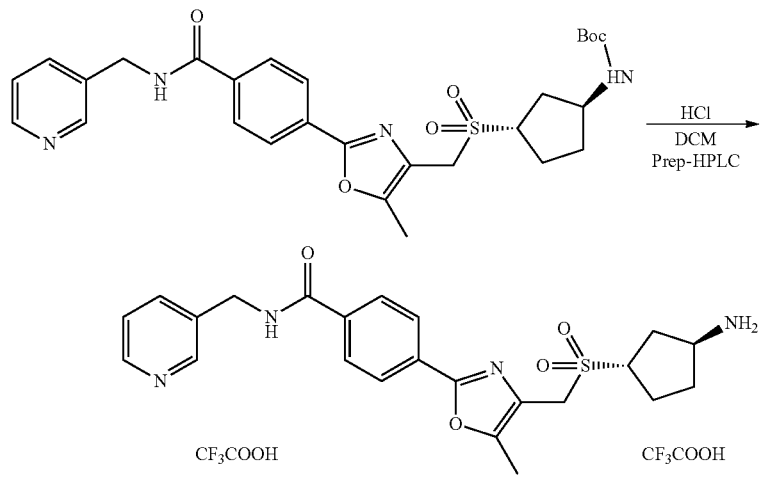

Example 9

Example 48

Synthesis of 4-[5-Methyl-4-([[(1S,3S)-3-(pyrrolidin-1-yl)cyclopentane]sulfonyl]methyl)-1,3-oxazol-2-yl]-N-(pyridin-3-ylmethyl)benzamide

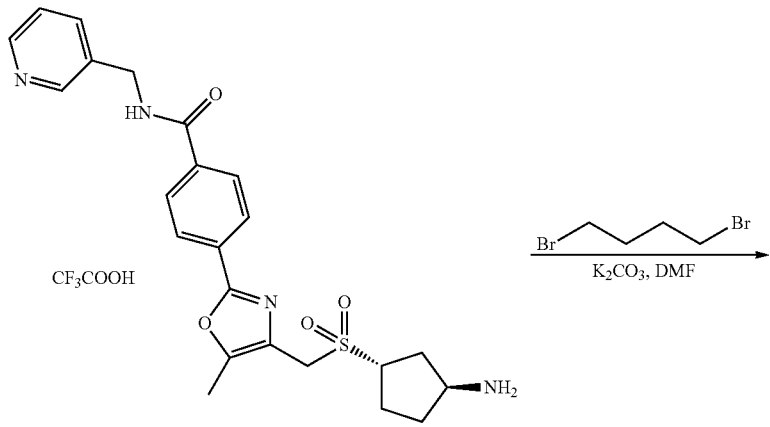

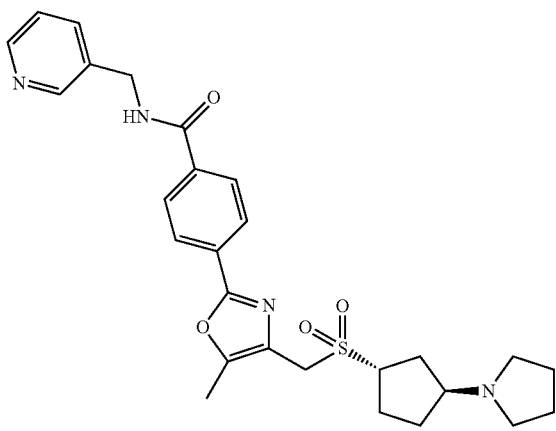

Example 10

A solution of 4-[4-([[(1S,3S)-3-aminocyclopentane]sulfonyl]methyl)-5-methyl-1,3-oxazol-2-yl]-N-(pyridin-3-ylmethyl)benzamide trifluoroacetic acid (350 mg, 0.72 mmol, 1.00 equiv), 1,4-dibromobutane (180 mg, 0.84 mmol, 1.18 equiv) and potassium carbonate (250 mg, 1.81 mmol, 2.53 equiv) in N,N-dimethylformamide (20 mL) was stirred overnight at 70° C. The resulting solution was diluted with 60 mL of water then extracted with 2×30 mL of ethyl acetate. The combined organic layers was washed with 2×50 mL of brine, dried over anhydrous sodium sulfate and concentrated under vacuum. The crude product (300 mg) was purified by Prep-HPLC with the following conditions (2#-Waters 2767-2 (HPLC-08)): Column, Xbridge Prep C18, 5 um, 19*150 mm;

mobile phase, Water with 50 mmolNH4HCO3 and CH3CN (10.0% CH3CN up to 25.0% in 2 min, up to 40.0% in 8 min, up to 100.0% in 1 min, down to 10.0% in 2 min); Detector, UV 254 nm, to yield 50 mg (14%) of 4-[5-methyl-4-([[(1S,3S)-3-(pyrrolidin-1-yl)cyclopentane]sulfonyl]methyl)-1,3-oxazol-2-yl]-N-(pyridin-3-ylmethyl)benzamide as a white solid. LC-MS: (ES, m/z): 509 [M+H]$^+$, 296, 275. $^1$H-NMR: (400 MHz, CD$_3$OD, ppm) δ 8.60 (1H, s), 8.46 (1H, d, J=4.8Hz), 8.12-8.10 (2H, m), 7.98 (2H, d, J=8.4Hz), 7.88 (1H, d, J=7.6Hz), 7.46-7.43 (1H, m), 4.65 (2H, s), 4.40 (2H, s), 3.86-3.78 (1H, m), 2.81-2.74 (1H, m), 2.62 (4H, s), 2.50 (3H, s), 2.40-2.23 (2H, m), 2.13-2.00 (3H, m), 1.83 (4H, s), 1.69-1.59 (1H, m).

Example 49

Synthesis of 4-[5-Methyl-4-([[(1S,3S)-3-(piperidin-1-yl)cyclopentane]sulfonyl]methyl)-1,3-oxazol-2-yl]-N-(pyridin-3-ylmethyl)benzamide bis-trifluoroacetic acid salt A solution of 4-[4-([[(1S,3S)-3-aminocyclopentane]sulfonyl]methyl)-5-methyl-1,3-oxazol-2-yl]-N-(pyridin-3-ylmethyl)benzamide trifluoroacetate (350 mg, 0.72 mmol, 1.00 equiv), 1,5-dibromopentane (200 mg, 0.88 mmol, 1.23 equiv) and potassium carbonate (300 mg, 2.17 mmol, 3.04 equiv) in N,N-dimethylformamide (20 mL) was stirred overnight at 70° C. The reaction mixture was diluted with 60 mL of water then extracted with 2×30 mL of ethyl acetate. The combined organic layers was washed with 2×50 mL of brine, dried over anhydrous sodium sulfate and concentrated under vacuum. The crude product (300 mg) was purified by Prep-HPLC with the following conditions (1#-Pre-HPLC-005(Waters)): Column, SunFire Prep C18, 19*150 mm 5 um; mobile phase, WATER WITH 0.05% TFA and CH3CN (5.0% CH3CN up to 25.0% in 12 min, up to 100.0% in 1 min); Detector, UV 254/220 nm, to give 60 mg (11%) of 4-[5-methyl-4-([[(1S,3S)-3-(piperidin-1-yl)cyclopentane]sulfonyl]methyl)-1,3-oxazol-2-yl]-N-(pyridin-3-ylmethyl)benzamide bis-trifluoroacetic acid salt as a white solid. LC-MS: (ES, m/z): 523 [M+H]$^+$, 263. $^1$H-NMR: (400 MHz, D$_2$O, ppm) δ 8.70 (1H, s), 8.61 (1H, d, J=5.6Hz), 8.50 (1H, d, J=8.0Hz), 7.96 (3H, d,

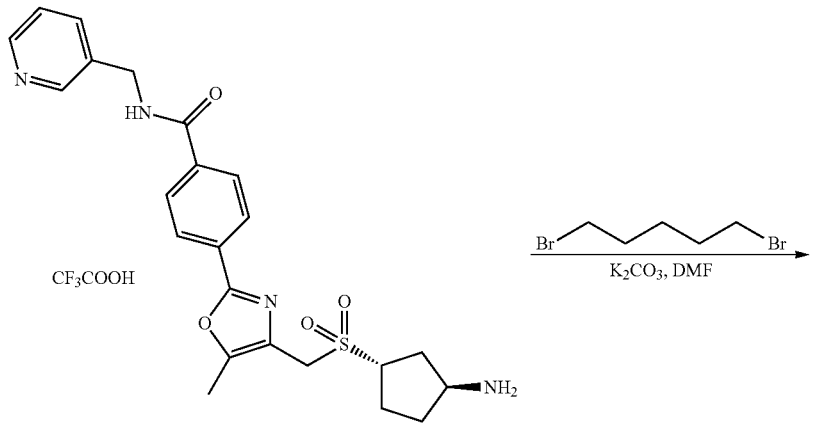

Example 9

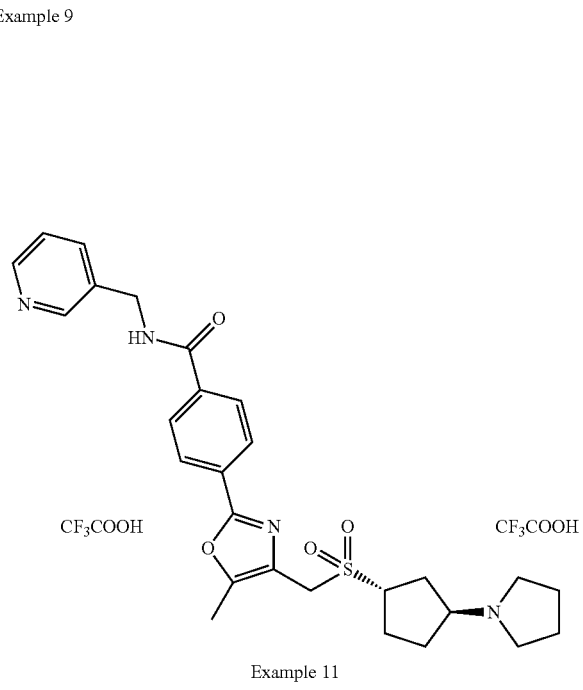

Example 11

J=7.2Hz), 7.81 (2H, d, J=8.0Hz), 4.70 (2H, s), 4.44 (2H, s), 3.91-3.90 (1H, m), 3.63-3.44 (3H, m), 2.89-2.85 (2H, m), 2.59-2.58 (1H, m), 2.35 (3H, s), 2.32-2.15 (3H, m), 2.05-1.99 (1H, m), 1.85-1.53 (7H, m).

Example 50

Synthesis of 4-[4-([[(1R,3S)-3-Aminocyclopentane]sulfonyl]methyl)-5-methyl-1,3-oxazol-2-yl]-N-(pyridin-3-ylmethyl)benzamide hydrochloride Step 1: Synthesis of tert-butyl N-[(1S,3S)-3-iodocyclopentyl]carbamate

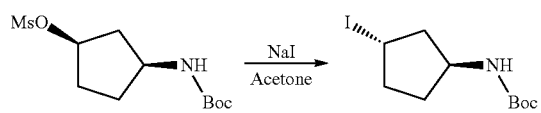 [SMILES: CC(C)(C)OC(=O)N[C@H]1CC[C@@H](OS(C)(=O)=O)C1 ; "NaI" ; CC(C)(C)OC(=O)N[C@H]1CC[C@H](I)C1]

A solution of tert-butyl N-[(1S,3R)-3-(methanesulfonyloxy)cyclopentyl]carbamate (2.1 g, 7.52 mmol, 1.00 equiv) and sodium iodide (7 g, 46.70 mmol, 6.21 equiv) in acetone (40 mL) was stirred at 50° C. for 30 min. The reaction mixture was diluted with 100 mL of water then extracted with 2×30 mL of ethyl acetate. The combined organic layers was washed with 2×50 mL of brine, dried over anhydrous sodium sulfate and concentrated under vacuum. The residue was purified on a silica gel column with ethyl acetate/petroleum ether (1/5) to give 1.0 g (43%) of tert-butyl N-[(1S,3S)-3-iodocyclopentyl]carbamate as a white solid.

Step 2: Synthesis of methyl 4-[4-([[(1R,3S)-3-[[(tert-butoxy)carbonyl]amino]cyclopentyl]sulfanyl]methyl)-5-methyl-1,3-oxazol-2-yl]benzoate

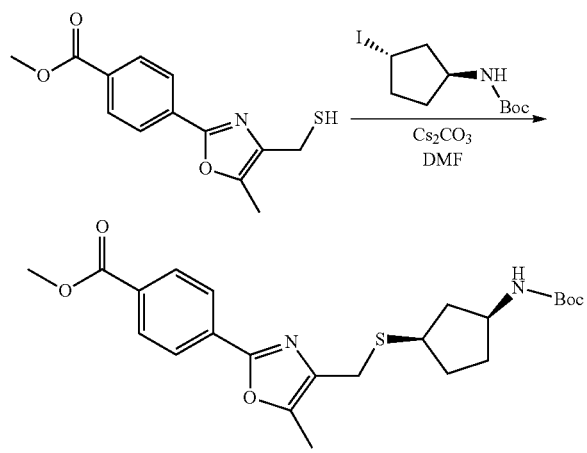

To a solution of methyl 4-[5-methyl-4-(sulfanylmethyl)-1,3-oxazol-2-yl]benzoate (870 mg, 3.30 mmol, 1.00 equiv) in N,N-dimethylformamide (20 mL) maintained under an atmosphere of nitrogen at 35° C. was added cesium carbonate (2.5 g, 7.65 mmol, 2.32 equiv). After stirring at 35° C. for 20 min, tert-butyl N-[(1S,3S)-3-iodocyclopentyl]carbamate (1.25 g, 4.02 mmol, 1.22 equiv) was then added. The resulting solution was allowed to stir for 50 min at 35° C. under nitrogen after which the product was precipitated by the addition of 50 mL water. The solid was collected by filtration, washed with water then dried in a vacuum oven to give 1.35 g (91%) of methyl 4-[4-([[(1R,3S)-3-[[(tert-butoxy)carbonyl]amino]cyclopentyl]sulfanyl]methyl)-5-methyl-1,3-oxazol-2-yl]benzoate as a white solid.

Step 3: Synthesis of methyl 4-[4-([[(1R,3S)-3-[[(tert-butoxy)carbonyl]amino]cyclopentane]sulfonyl]methyl)-5-methyl-1,3-oxazol-2-yl]benzoate

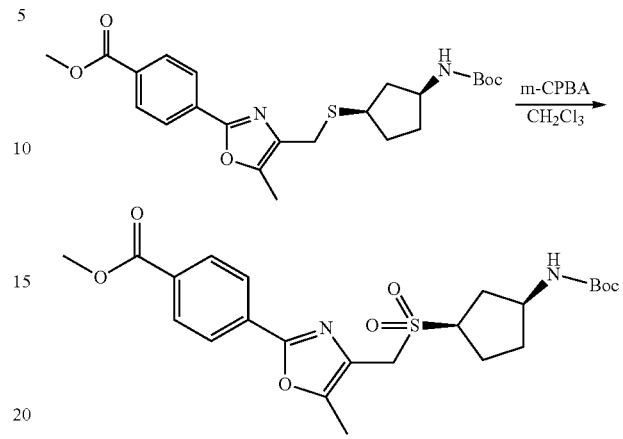

To a solution of methyl 4-[4-([[(1R,3S)-3-[[(tert-butoxy)carbonyl]amino]cyclopentyl]sulfanyl]methyl)-5-methyl-1,3-oxazol-2-yl]benzoate (1.3 g, 2.91 mmol, 1.00 equiv) in chloroform (50 mL) at 0-5° C. was added m-chloroperbenzoic acid (1.25 g, 7.24 mmol, 2.49 equiv) in several batches. The resulting solution was stirred at 0~5° C. for 2 h. Saturated aqueous sodium bisulphite solution (20 mL) and saturated sodium carbonate solution (20 mL) were added to quench the reaction. The resulting solution was extracted with 2×30 mL of chloroform. The combined organic layers was washed with 3×20 mL of brine, dried over anhydrous sodium sulfate and concentrated under vacuum to give 1.2 g (86%) of methyl 4-[4-([[(1R,3S)-3-[[(tert-butoxy)carbonyl]amino]cyclopentane]sulfonyl]methyl)-5-methyl-1,3-oxazol-2-yl]benzoate as a white solid.

Step 4: Synthesis of 4-[4-([[(1R,3S)-3-[[(tert-butoxy)carbonyl]amino]cyclopentane]sulfonyl]methyl)-5-methyl-1,3-oxazol-2-yl]benzoic acid

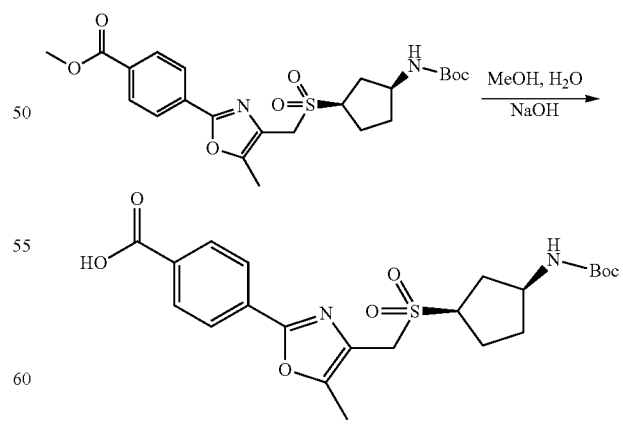

To a solution of methyl 4-[4-([[(1R,3S)-3-[[(tert-butoxy)carbonyl]amino]cyclopentane]sulfonyl]methyl)-5-methyl-1,3-oxazol-2-yl]benzoate (1.2 g, 2.51 mmol, 1.00 equiv) in methanol (30 mL) was added a solution of sodium hydroxide (640 mg, 16.00 mmol, 6.38 equiv) in water (6 mL). The resulting solution was stirred at 50° C. for 2 h. The product was precipitated by adjusting the pH of the solution to 2-3 with 2N hydrochloric acid. The solid was collected by filtration, washed with 3×20 mL of water and dried in an oven to give 1.0 g (86%) of 4-[4-([[(1R,3S)-3-[[(tert-butoxy)carbonyl]amino]cyclopentane]sulfonyl]methyl)-5-methyl-1,3-oxazol-2-yl]benzoic acid as a white solid.

Step 5: Synthesis of tert-butyl N-[(1S,3R)-3-[[(5-methyl-2-[4-[(pyridin-3-ylmethyl)carbamoyl]phenyl]-1,3-oxazol-4-yl) methane]sulfonyl]cyclopentyl]carbamate

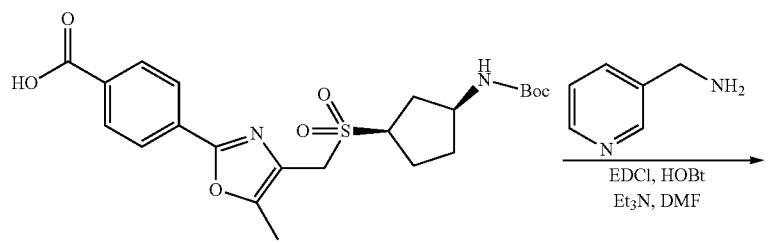

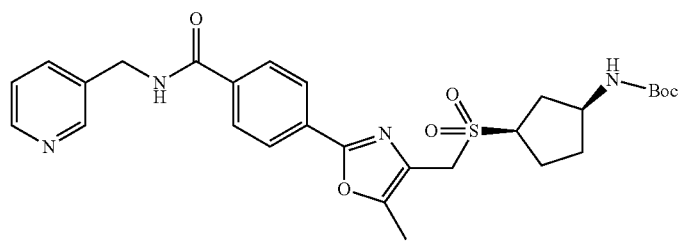

A solution of 4-[4-([[(1R,3S)-3-[[(tert-butoxy)carbonyl]amino]cyclopentane]sulfonyl]methyl)-5-methyl-1,3-oxazol-2-yl]benzoic acid (1.0 g, 2.15 mmol, 1.00 equiv), EDCI (540 mg, 2.82 mmol, 1.31 equiv), HOBt (380 mg, 2.81 mmol, 1.31 equiv), triethylamine (650 mg, 6.42 mmol, 2.98 equiv) and pyridin-3-ylmethanamine (300 mg, 2.77 mmol, 1.29 equiv) in N,N-dimethylformamide (30 mL) was stirred overnight at 35° C. The product was precipitated by the addition of 80 mL water. The solid was collected by filtration, washed with 2×30 mL of water and dried in a vacuum oven to give 1.0 g (84%) of tert-butyl N-[(1S,3R)-3-[[(5-methyl-2-[4-[(pyridin-3-ylmethyl)carbamoyl]phenyl]-1,3-oxazol-4-yl) methane]sulfonyl]cyclopentyl]carbamate as a white solid.

Step 6: Synthesis of 4-[4-([[(1R,3S)-3-aminocyclopentane]sulfonyl]methyl)-5-methyl-1,3-oxazol-2-yl]-N-(pyridin-3-ylmethyl)benzamide hydrochloride

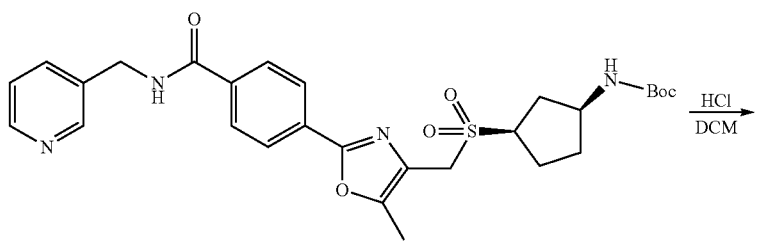

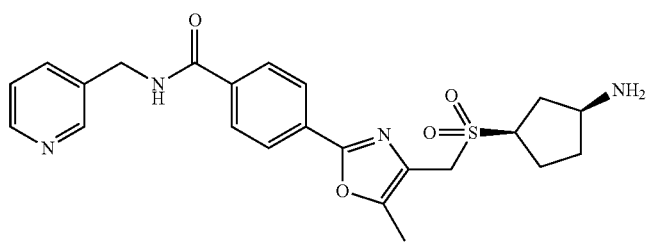

Example 12

Excess hydrogen chloride gas was bubbled into a solution of tert-butyl N-[(1S,3R)-3-[[(5-methyl-2-[4-[(pyridin-3-yl-methyl)carbamoyl]phenyl]-1,3-oxazol-4-yl)methane]sulfonyl]cyclopentyl]carbamate (1.0 g, 1.81 mmol, 1.00 equiv) in dichloromethane (20 mL) at 0-5° C. The mixture was stirred at 0-5° C. for 2 h then concentrated under vacuum to give 0.9 g of a white solid. The crude product was purified by Prep-HPLC with the following conditions (1#-Pre-HPLC-005 (Waters)): Column, Xbridge Prep C18, 5 um, 19*150 mm; mobile phase, WATER WITH 50 mLNH4CO3 and CH3CN (7.0% CH3CN up to 17.0% in 2 min, up to 32.0% in 8 min, up to 100.0% in 1 min); Detector, uv 254/220 nm, to give 450 mg (51%) of 4-[4-([[(1R,3S)-3-aminocyclopentane]sulfonyl]methyl)-5-methyl-1,3-oxazol-2-yl]-N-(pyridin-3-ylmethyl)benzamide hydrochloride as a white solid. LC-MS: (ES, m/z): 455 [M+H]$^+$, 249, 228. $^1$H-NMR (400 MHz, CD$_3$OD, ppm) δ 8.59 (1H, s), 8.48-8.46 (1H, m), 8.13-8.10 (2H, m), 7.98 (2H, d, J=8.4Hz), 7.88 (1H, d, J=8.0Hz), 7.47-7.43 (1H, m), 4.65 (2H, s), 4.40 (2H, s) 3.77-3.73 (1H, m), 3.43-3.33 (1H, m), 2.50 (3H, s), 2.48-2.25 (2H, m), 2.16-1.87 (3H, m), 1.67-1.62 (1H, m).

Example 51

Synthesis of 4-[5-Methyl-4-([[(1R,3S)-3-(pyrrolidin-1-yl)cyclopentane]sulfonyl]methyl)-1,3-oxazol-2-yl]-N-(pyridin-3-ylmethyl)benzamide A mixture of 4-[4-([[(1R,3S)-3-aminocyclopentane]sulfonyl]methyl)-5-methyl-1,3-oxazol-2-yl]-N-(pyridin-3-ylmethyl)benzamide hydrochloride (300 mg, 0.61 mmol, 1.00 equiv), potassium carbonate (250 mg, 1.81 mmol, 2.95 equiv) and 1,4-dibromobutane (160 mg, 0.75 mmol, 1.22 equiv) in N,N-dimethylformamide (20 mL) was stirred overnight at 70° C. The reaction mixture was diluted with 60 mL of water then extracted with 2×30 mL of ethyl acetate. The combined organic layers was washed with 2×50 mL of brine, dried over anhydrous sodium sulfate and concentrated under vacuum. The crude product (300 mg) was purified by Prep-HPLC with the following conditions (1#-Pre-HPLC-005(Waters)): Column, Xbridge Prep C18, 5 um, 19*150 mm; mobile phase, WATER WITH 50 mLNH4CO3 and CH3CN (17.0% CH3CN up to 35.0% in 12 min, up to 100.0% in 1 min); Detector, UV 254/220 nm, to give 30 mg (10%) of 4-[5-methyl-4-([[(1R,3S)-3-(pyrrolidin-1-yl)cyclopentane]sulfonyl]methyl)-1,3-oxazol-2-yl]-N-(pyridin-3-ylmethyl)benzamide as a white solid. LC-MS: (ES, m/z): 509 [M+H]$^+$, 275. $^1$H-NMR: (400 MHz, CD$_3$OD, ppm) δ 8.59 (1H, s), 8.46 (1H, d, J=4.0Hz), 8.10 (2H, d, J=8.4Hz), 7.98 (2H, d, J=8.4Hz), 7.88 (1H, d, J=7.6Hz), 7.46-7.43 (1H, m), 4.69 (2H, s), 4.39 (2H, s), 3.76-3.73 (1H, m), 2.72-2.64 (5H, m), 2.50-2.43 (4H, m), 2.28-2.25 (1H, m), 2.12-1.96 (4H, m), 1.83 (4H, s), 1.73-1.67 (1H, m).

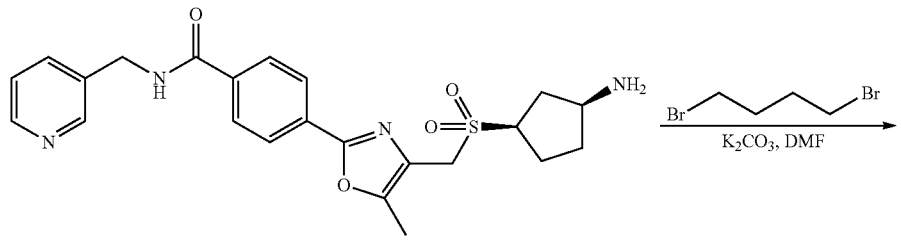

Example 12

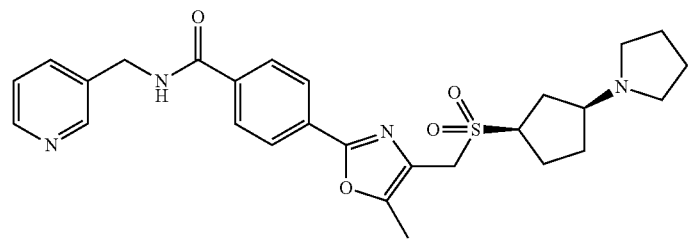

Example 13

Example 52

Synthesis of 4-[5-Methyl-4-([[(1R,3S)-3-(piperidin-1-yl)cyclopentane]sulfonyl]methyl)-1,3-oxazol-2-yl]-N-(pyridin-3-ylmethyl)benzamide

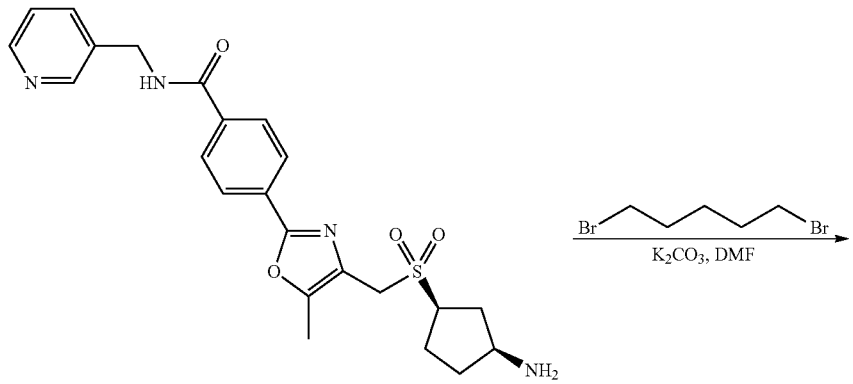

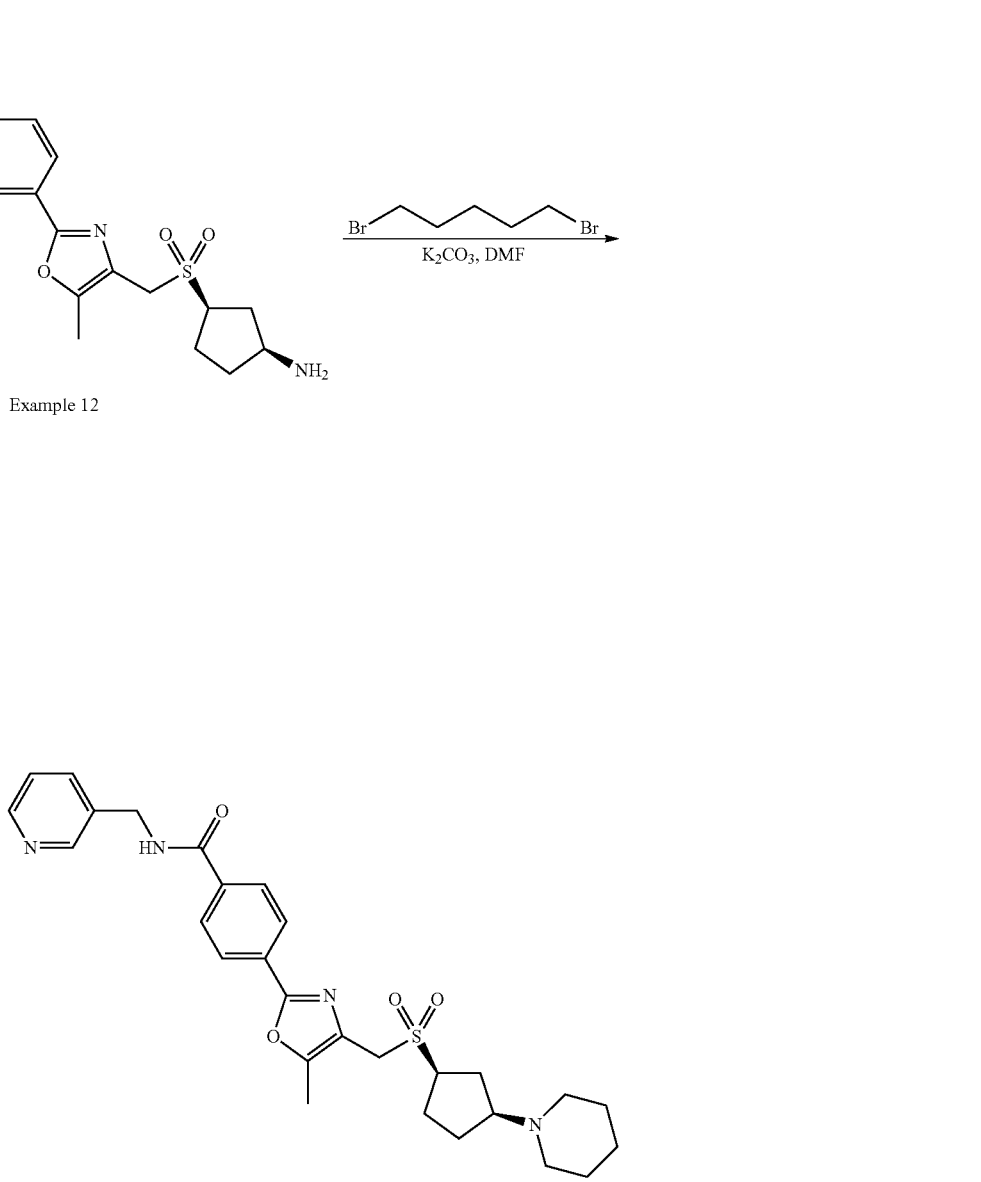

A mixture of 4-[4-([[(1R,3S)-3-aminocyclopentane]sulfonyl]methyl)-5-methyl-1,3-oxazol-2-yl]-N-(pyridin-3-ylmethyl)benzamide hydrochloride (300 mg, 0.61 mmol, 1.00 equiv), potassium carbonate (250 mg, 1.81 mmol, 2.95 equiv) and 1,5-dibromopentane (170 mg, 0.75 mmol, 1.22 equiv) in N,N-dimethylformamide (20 mL) was stirred overnight at 70° C. Water (60 mL) was then added and the resulting solution was extracted with 2×30 mL of ethyl acetate. The combined organic layers was washed with 2×50 mL of brine, dried over anhydrous sodium sulfate and concentrated under vacuum. The crude product (310 mg) was purified by Prep-HPLC with the following conditions (2#-Waters 2767-1 (HPLC-07)): Column, Xbridge Prep C18, 5 um, 19*150 mm; mobile phase, WATER WITH 50 mLNH4CO3 and CH3CN (17.0% CH3CN up to 40.0% in 16 min, up to 100.0% in 1 min); Detector, UV 254 nm, to give 50 mg (16%) of 4-[5-methyl-4-([[(1R,3 S)-3-(piperidin-1-yl)cyclopentane]sulfonyl]methyl)-1,3-oxazol-2-yl]-N-(pyridin-3-ylmethyl)benzamide as a white solid. LC-MS: (ES, m/z): 523 [M+H]$^+$, 283. $^1$H-NMR: (400 MHz, CD$_3$OD, ppm) δ 8.59 (1H, s), 8.46 (1H, d, J=4.4Hz), 8.10 (2H, d, J=8.4Hz), 7.98 (2H, d, J=8.4Hz), 7.88 (1H, d, J=8.0Hz), 7.46-7.43 (1H, m), 4.65 (2H, s), 4.40 (2H, s), 3.76-3.68 (1H, m), 2.79 (1H, s), 2.58-2.44 (8H, m), 2.28-2.21 (1H, m), 2.10-2.02 (2H, m), 1.98-1.90 (1H, m), 1.71-1.63 (5H, m), 1.50 (2H, s).

Example 53

Synthesis of 4-(5-methyl-4-[[1-(2-methylpropyl)piperidine-4-sulfonyl]methyl]-1,3-oxazol-2-yl)-N-(pyridin-3-ylmethyl)benzamide

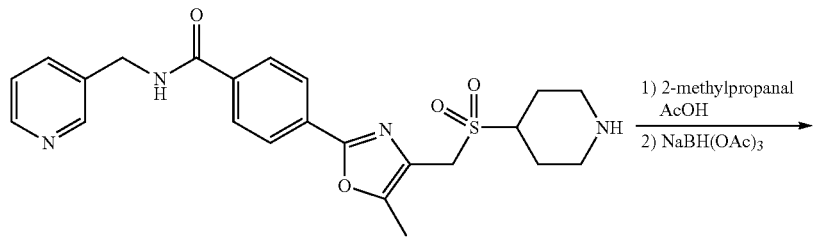

Example 1

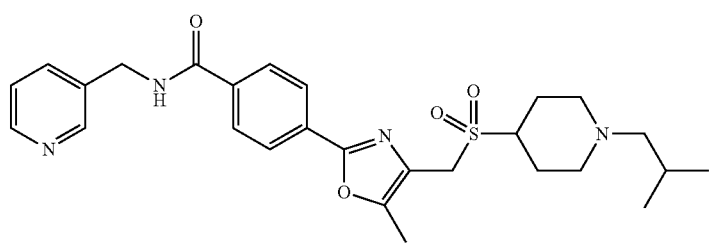

Example 15

A solution of 4-[5-methyl-4-[(piperidine-4-sulfonyl)methyl]-1,3-oxazol-2-yl]-N-(pyridin-3-ylmethyl)benzamide (300 mg, 0.66 mmol, 1.00 equiv), acetic acid (59.3 mg, 0.99 mmol, 1.50 equiv) and 2-methylpropanal (57 mg, 0.79 mmol, 1.20 equiv) in 1,2-dichloroethane (3 mL) was stirred at room temperature for 4 h. Sodium triacetoxyborohydride (420 mg, 1.98 mmol, 3.00 equiv) was added in small batches and the resulting solution was stirred overnight at 30° C. The resulting mixture was concentrated under vacuum and the residue was diluted with 2 mL of methanol. The solution was loaded onto a C18 column and eluted with acetonitrile/water to give 200 mg (59%) of 4-(5-methyl-4-[[1-(2-methylpropyl) piperidine-4-sulfonyl]methyl]-1,3-oxazol-2-yl)-N-(pyridin-3-ylmethyl)benzamide as a white solid. LC-MS (ES, m/z): 511 [M+H]$^+$, 306, 256; $^1$HNMR (300 MHz, CD3OD, ppm) δ 8.60 (s, 1H), 8.47 (d, 1H), 8.11 (d, 2H), 7.99 (d, 2H), 7.89 (d, 1H), 7.47-7.43 (m, 1H), 4.65 (s, 2H), 4.41 (s, 2H), 3.33-3.08 (m, 3H), 2.50.

Example 54

Synthesis of 4-[4-[(1-cyclopentylpiperidine-4-sulfonyl)methyl]-5-methyl-1,3-oxazol-2-yl]-N-(pyridin-3-ylmethyl)benzamide

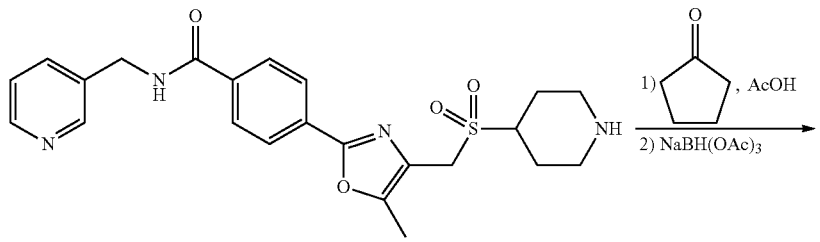

Example 1

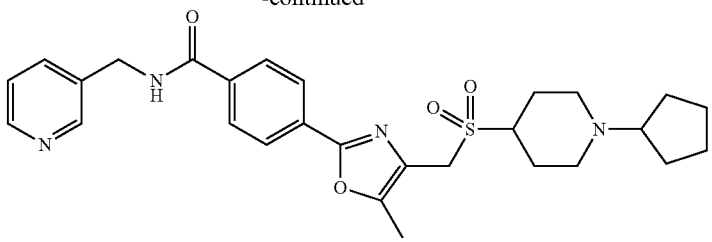

Example 16

A solution of 4-[5-methyl-4-[(piperidine-4-sulfonyl)methyl]-1,3-oxazol-2-yl]-N-(pyridin-3-ylmethyl)benzamide (300 mg, 0.66 mmol, 1.00 equiv), cyclopentanone (84 mg, 1.00 mmol, 1.51 equiv) and acetic acid (60 mg, 1.00 mmol, 1.51 equiv) in 1,2-dichloroethane (10 mL) was stirred at room temperature for 4 h. Sodium triacetoxyborohydride (420 mg, 1.98 mmol, 3.00 equiv) was added and the resulting solution was stirred overnight at room temperature. The resulting mixture was concentrated under vacuum and the residue was eluted with water/acetonitrile (95:5-20:80) on a C18 column to give 240 mg (70%) of 4-[4-[(1-cyclopentylpiperidine-4-sulfonyl)methyl]-5-methyl-1,3-oxazol-2-yl]-N-(pyridin-3-ylmethyl)benzamide as a colorless solid. LC-MS- (ES, m/z): 523 [M+H]$^+$, 262; 1HNMR (400 MHz, CD3OD, ppm) δ 8.60 (s, 1H), 8.48 (d, 1H), 8.11 (d, 2H), 7.99 (d, 2H), 7.89 (d, 1H), 7.45 (m, 1H), 4.65 (s, 2H), 4.46 (s, 2H), 3.49 (d, 2H), 3.37 (t, 1H), 3.02 (t, 1H), 2.58-2.55 (m, 2H), 2.51 (s, 3H), 2.37 (d, 2H), 2.06-1.96 (m, 4H), 1.83-1.70 (m, 2H), 1.69-1.51 (m, 4H).

Example 55

Synthesis of 4-[4-[(1-cyclohexylpiperidine-4-sulfonyl)methyl]-5-methyl-1,3-oxazol-2-yl]-N-(pyridin-3-ylmethyl)benzamide A solution of 4-[5-methyl-4-[(piperidine-4-sulfonyl)methyl]-1,3-oxazol-2-yl]-N-(pyridin-3-ylmethyl)benzamide (300 mg, 0.66 mmol, 1.00 equiv), cyclohexanone (98 mg, 1.00 mmol, 1.51 equiv) and acetic acid (120 mg, 2.00 mmol, 3.03 equiv) in 1,2-dichloroethane (10 mL) was stirred for 4 h at room temperature. To this was added sodium triacetoxyborohydride (420 mg, 1.98 mmol, 3.00 equiv). The resulting solution was stirred overnight at room temperature and then concentrated under vacuum. The residue was purified on a silica gel column with water/acetonitrile (95/5-20/80) to give 350 mg (99%) of 4-[4-[(1-cyclohexylpiperidine-4-sulfonyl)methyl]-5-methyl-1,3-oxazol-2-yl]-N-(pyridin-3-ylmethyl)benzamide as a white solid. LC-MS (ES, m/z): 537 [M+H]$^+$; $^1$HNMR (300 MHz, CD$_3$OD, ppm) δ 8.60 (s, 1H), 8.47 (d, 1H), 8.11 (d, 2H), 8.00 (d, 2H), 7.89 (d, 1H), 7.47-7.43 (m, 1H), 4.65 (s, 2H), 4.40 (s, 2H), 3.14 (d, 3H), 2.50 (d, 3H), 2.41-2.33 (m, 3H), 2.25 (d, 2H), 1.92-1.83 (m, 6H), 1.67 (d, 1H), 1.29-1.09 (m, 5H).

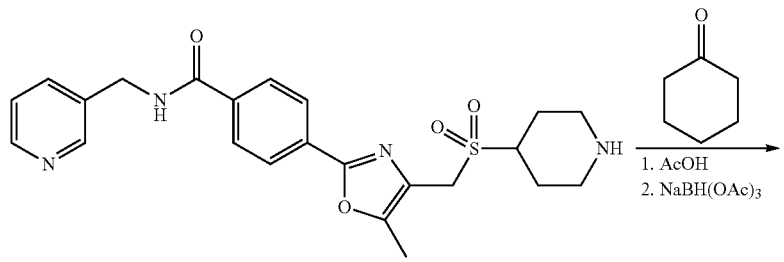

Example 1

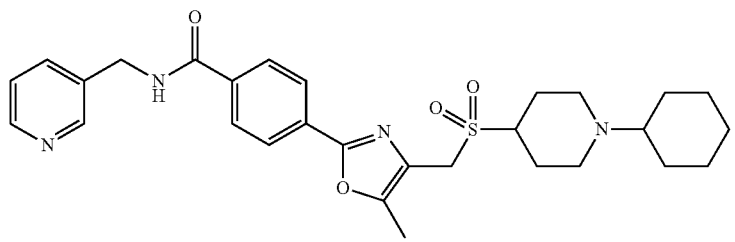

Example 17

Example 56

Synthesis of 4-(5-methyl-4-(p-tolylthiomethyl)oxazol-2-yl)-N-(pyridin-3-ylmethyl)benzamide Step 1: Synthesis of methyl 4-(5-methyl-4-(p-tolylthiomethyl)oxazol-2-yl)benzoate

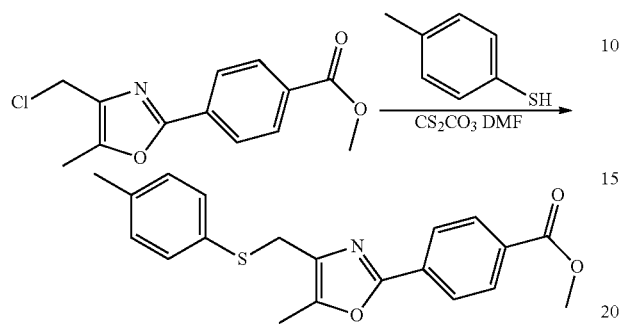

A solution of methyl 4-(4-(chloromethyl)-5-methyloxazol-2-yl)benzoate (6 g, 22.64 mmol, 1.00 equiv), 4-methylbenzenethiol (4.2 g, 33.87 mmol) and cesium carbonate (8.8 g, 26.99 mmol, 1.19 equiv) in N,N-dimethylformamide (120 mL) was stirred under nitrogen overnight at 50° C. The reaction mixture was diluted with 100 mL of water and extracted with 3×150 mL of ethyl acetate. The combined organic layers was washed with 3×50 mL of brine, dried over anhydrous sodium sulfate and concentrated under vacuum. The residue was triturated with 2×50 mL of hexane. The solid was collected by filtration and dried in vacuum to yield 6.2 g (78%) of methyl 4-(5-methyl-4-(p-tolylthiomethyl)oxazol-2-yl)benzoate as a yellow solid. LC-MS: (ES, m/z): 395 [M+CH$_3$CN+H]$^+$, 354 [M+H]$^+$, 271, 203, 126, 120.

Step 2: Synthesis of 4-(5-methyl-4-(p-tolylthiomethyl)oxazol-2-yl)benzoic acid

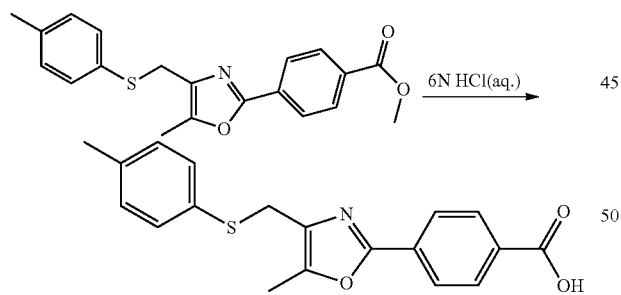

A mixture of methyl 4-(5-methyl-4-(p-tolylthiomethyl)oxazol-2-yl)benzoate (3.1 g, 8.78 mmol, 1.00 equiv) in 6N hydrochloric acid (90 mL) was stirred overnight at 90° C. The reaction mixture was diluted with 150 mL of water and extracted with 3×150 mL of ethyl acetate. The combined organic layers was washed with 3×50 mL of brine, dried over anhydrous sodium sulfate and concentrated under vacuum to give 2.2 g (74%) of 4-(5-methyl-4-(p-tolylthiomethyl)oxazol-2-yl)benzoic acid as a white solid. LC-MS: (ES, m/z): 381 [M+CH$_3$CN+H]$^+$, 340 [M+H]$^+$, 257, 216, 189, 146, 105. H-NMR: $^1$HNMR (400 MHz, CDCl$_3$, ppm) δ 8.18-8.09 (dd, 4H), 7.30-7.28 (d, 2H), 7.10-7.08 (d, 2H), 3.95 (s, 2H), 2.32 (s, 3H), 2.08 (s, 3H).

Step 3: Synthesis of 4-(5-methyl-4-(p-tolylthiomethyl)oxazol-2-yl)-N-(pyridin-3-ylmethyl)benzamide

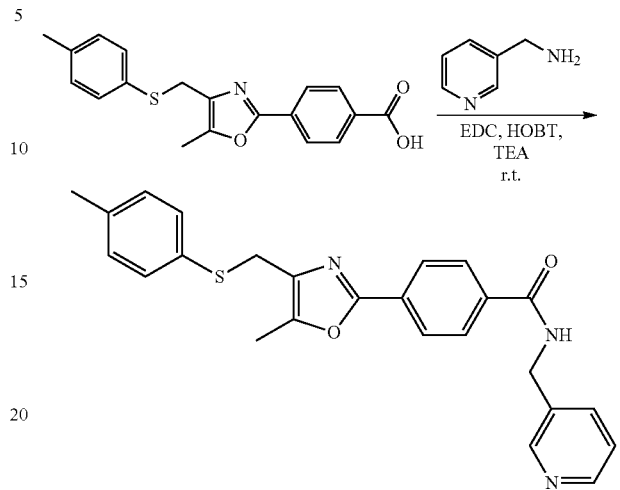

A solution of 4-(5-methyl-4-(p-tolylthiomethyl)oxazol-2-yl)benzoic acid (500 mg, 1.47 mmol, 1.00 equiv), EDCI (340 mg, 1.78 mmol, 1.21 equiv), 1H-1,2,3-benzotriazol-1-ol (240 mg, 1.78 mmol, 1.21 equiv), pyridin-3-ylmethanamine (190 mg, 1.76 mmol, 1.19 equiv) and triethylamine (450 mg, 4.46 mmol, 3.02 equiv) in N,N-dimethylformamide (10 mL) was stirred overnight at room temperature. The resulting solution was diluted with 20 mL of an ice/water mixture. The precipitate was collected by filtration, washed with 3×10 mL of hexane and 4×10 mL of 66% aqueous methanol to give 0.33 g (52%) of 4-(5-methyl-4-(p-tolylthiomethyl)oxazol-2-yl)-N-(pyridin-3-ylmethyl)benzamide as a white solid. LC-MS: (ES, m/z): 471 [M+CH$_3$CN+H]$^+$, 430 [M+H]$^+$, 347, 306. $^1$HNMR (400 MHz, DMSO-d6, ppm) δ 9.22-9.20 (s, 1H), 8.57 (s, 1H), 8.46 (d, 1H), 8.02-7.97 (t, 4H), 7.75-7.73 (d, 1H), 7.38-7.35 (t, 1H), 7.30-7.28 (d, 2H), 7.14-7.13 (d, 2H), 4.52-4.51 (d, 2H), 4.07 (s, 2H), 2.27 (s, 3H), 2.17 (s, 3H).

Example 57

Synthesis of 4-(5-methyl-4-(p-tolyloxymethyl)oxazol-2-yl)-N-(pyridin-3-ylmethyl)benzamide Step 1: Synthesis of methyl 4-(5-methyl-4-(p-tolyloxymethyl)oxazol-2-yl)benzoate

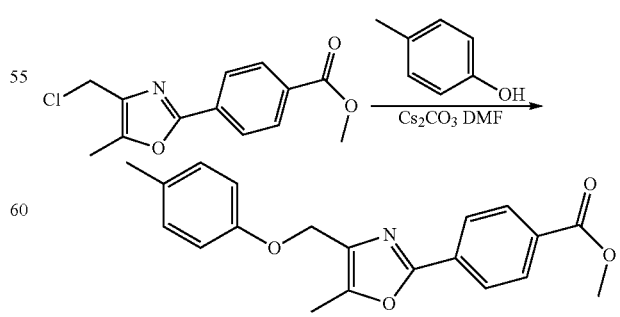

A solution of methyl 4-(4-(chloromethyl)-5-methyloxazol-2-yl)benzoate (3.1 g, 11.70 mmol, 1.00 equiv), p-cresol (2.0 g, 18.52 mmol, 1.58 equiv), Cs2CO3 (4.5 g, 13.80 mmol, 1.18 equiv) in N,N-dimethylformamide (60 mL) was stirred under nitrogen overnight at 50° C. The resulting solution was diluted with 100 mL of water and extracted with 3×100 mL of ethyl acetate. The combined organic layers was washed with 3×50 mL of brine, dried over anhydrous sodium sulfate and concentrated under vacuum to give 3.7 g (94%) of methyl 4-(5-methyl-4-(p-tolyloxymethyl)oxazol-2-yl)benzoate as a yellow solid. LC-MS: (ES, m/z): 379 [M+CH$_3$CN+H]$^+$, 338 [M+H]$^+$, 271, 230, 203, 146, 91.

Step 2: Synthesis of 4-(5-methyl-4-(p-tolyloxymethyl)oxazol-2-yl)benzoic acid

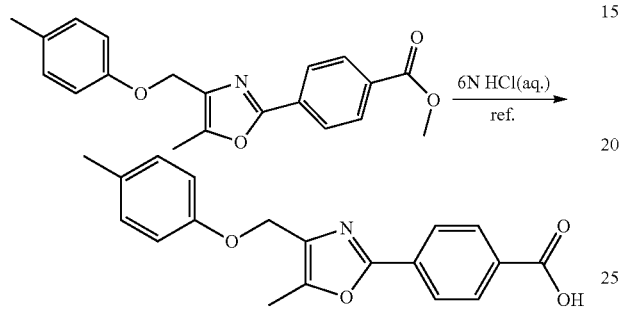

A mixture of methyl 4-(5-methyl-4-(p-tolyloxymethyl)oxazol-2-yl)benzoate (1.0 g, 2.97 mmol, 1.00 equiv) in 6N hydrochloric acid (30 mL) was stirred overnight at 90° C. The reaction mixture was diluted with 50 mL of water then extracted with 3×150 mL of ethyl acetate. The combined organic layers was washed with 3×50 mL of brine, dried over anhydrous sodium sulfate and concentrated under vacuum to give 0.24 g (25%) of 4-(5-methyl-4-(p-tolyloxymethyl)oxazol-2-yl)benzoic acid as a gray solid. LC-MS: (ES, m/z): 324 [M+H]$^+$, 302, 265, 120. H-NMR: $^1$HNMR (400 MHz, CDCl$_3$, ppm) δ 8.15-8.13 (d, 2H), 8.06-8.04 (d, 2H), 6.94-6.91 (m, 4H), 3.79 (s, 2H), 2.44 (s, 3H,), 2.26 (s, 3H).

Step 3: Synthesis of 4-(5-methyl-4-(p-tolyloxymethyl)oxazol-2-yl)-N-(pyridin-3-ylmethyl)benzamide

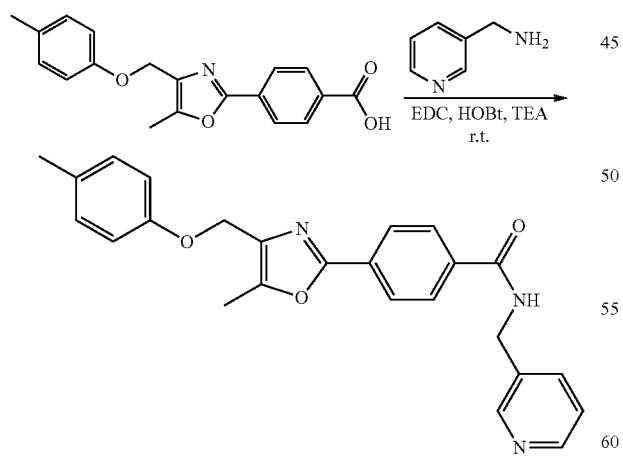

Example 19

A solution of 4-(5-methyl-4-(p-tolyloxymethyl)oxazol-2-yl)benzoic acid (460 mg, 1.42 mmol, 1.00 equiv), EDCI (320 mg, 1.68 mmol, 1.18 equiv), HOBT (240 mg, 1.78 mmol, 1.25 equiv), pyridin-3-ylmethanamine (180 mg, 1.67 mmol, 1.17 equiv) and triethylamine (440 mg, 4.36 mmol, 3.06 equiv) in N,N-dimethylformamide (6 mL) was stirred overnight at room temperature. The resulting solution was diluted with 20 mL of ice/water. The solid was collected by filtration and washed with 3×10 mL of hexane. The crude product was purified on a silica gel column eluted with chloroform/methanol (50:1-20:1) to give 0.33 g (56%) of 4-(5-methyl-4-(p-tolyloxymethyl)oxazol-2-yl)-N-(pyridin-3-ylmethyl)benzamide as a gray solid. LC-MS: (ES, m/z): 414 [M+H]$^+$. $^1$HNMR (400 MHz, DMSO-d6, ppm) δ 9.16 (s, 2H), 8.56 (s, 1H), 8.46 (s, 1H), 8.00-7.95 (m, 3H), 7.75 (d, 1H), 7.34 (m, 1H), 6.86-6.81 (m, 2H), 6.68 (d, 1H), 4.50 (d, 2H), 3.78 (s, 2H), 2.50 (s, 3H), 2.14 (s, 3H).

Example 58

Synthesis of 4-(4-((4-(((dimethylamino)methyl)phenylsulfonyl)methyl)-5-methyloxazol-2-yl)-N-(pyridin-3-ylmethyl)benzamide trifluoroacetic acid salt Step 1: Synthesis of (4-bromophenyl)-N,N-dimethylmethanamine

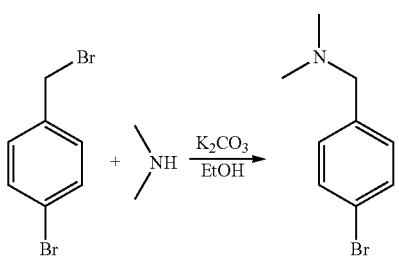

A solution of 1-bromo-4-(bromomethyl)benzene (20 g, 80.65 mmol, 1.00 equiv), dimethylamine (13.20 g, 96.80 mmol, 1.20 equiv, 33%) and potassium carbonate (13.36 g, 96.81 mmol, 1.20 equiv) in ethanol (200 mL) was stirred overnight at 50° C. The solid material was removed by filtration and the filtrate was concentrated under vacuum. The residue was dissolved in 200 mL of water and extracted with 3×200 mL of dichloromethane. The combined organic layer was washed with 3×200 mL of brine, dried over anhydrous sodium sulfate and concentrated under vacuum. The residue was purified on a silica gel column eluted with dichloromethane/methanol (20:1) to give 10 g (58%) of (4-bromophenyl)-N,N-dimethylmethanamine as a yellow oil. LC-MS: (ES, m/z): 255 [M+CH$_3$CN+H]$^+$, 214 [M+H]$^+$, 169.

Step 2: Synthesis of lithium 4-((dimethylamino)methyl)benzenesulfinate

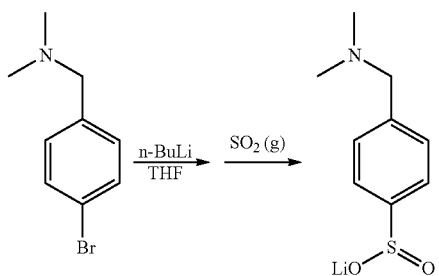

To a solution of (4-bromophenyl)-N,N-dimethylmethanamine (4.26 g, 20.00 mmol, 1.00 equiv) in tetrahydrofuran (60 mL) maintained under nitrogen at −78° C. was added in 30 min a 2.5M solution of n-butyllithium (8.8 mL, 1.10 equiv) in hexane dropwise with stirring. The resulting solution was stirred at −78° C. for 2 h. Sulfur dioxide gas was then bubbled into the solution at −78° C. for 1 h. Ether (200 mL) was added and the precipitate was collected by filtration. The solid was washed with ether and dried in vacuum to give 4 g (98%) of lithium 4-((dimethylamino)methyl)benzenesulfinate as a yellow solid.

Step 3: Synthesis of 4-(4-((4-((dimethylamino)methyl) phenylsulfonyl)methyl)-5-methyloxazol-2-yl) benzoate

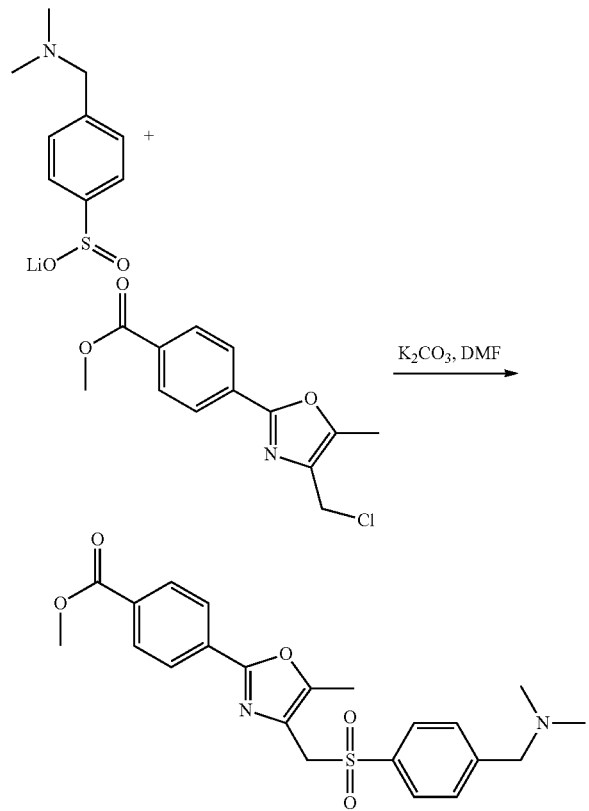

A mixture of methyl 4-(4-(chloromethyl)-5-methyloxazol-2-yl)benzoate (2.65 g, 10.00 mmol, 1.00 equiv), lithium 4-((dimethylamino)methyl)benzenesulfinate (3.075 g, 15.00 mmol, 1.50 equiv) and potassium carbonate (1.38 g, 10.00 mmol, 1.00 equiv) in N,N-dimethylformamide (100 mL) was stirred overnight at 70° C. Water (150 mL) was added and the resulting solution was extracted with 3×200 mL of ethyl acetate. The combined organic layers was washed with 3×200 mL of brine, dried over anhydrous sodium sulfate and concentrated under vacuum to yield 0.9 g (16%) of methyl 4-(4-((4-((dimethylamino)methyl)phenylsulfonyl)methyl)-5-methyloxazol-2-yl)benzoate as a light yellow solid. LC-MS: (ES, m/z): 429 [M+H]$^+$, 175, 120.

Step 4: Synthesis of 4-(4-((4-((dimethylamino)methyl)phenylsulfonyl)methyl)-5-methyloxazol-2-yl) benzoic acid hydrochloride

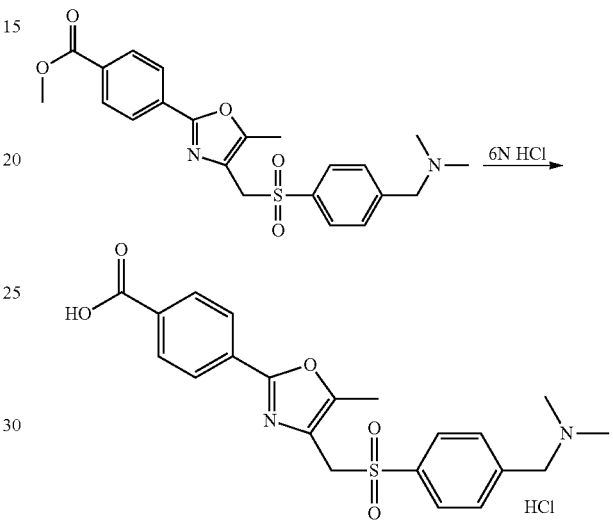

A solution of methyl 4-(4-((4-((dimethylamino)methyl) phenylsulfonyl)methyl)-5-methyloxazol-2-yl)benzoate (900 mg, 1.56 mmol, 1.00 equiv, 74%) in 6N hydrochloric acid (25 mL) was refluxed overnight. The resulting solution cooled to room temperature and then diluted with 30 mL of water/ice. The solid was removed by filtration out and washed with 3×20 mL of water. The filtrate and washings were combined and concentrated in vacuum to give 0.6 g (84%) of 4-(4-((4-((dimethylamino)methyl)phenylsulfonyl)methyl)-5-methyloxazol-2-yl)benzoic acid hydrochloride as a yellow solid. LC-MS: (ES, m/z): 415 [M+H]$^+$, 395, 120.

Step 5: Synthesis of 4-(4-((4-((dimethylamino)methyl)phenylsulfonyl)methyl)-5-methyloxazol-2-yl)-N-(pyridin-3-ylmethyl)benzamide trifluoroacetic acid salt

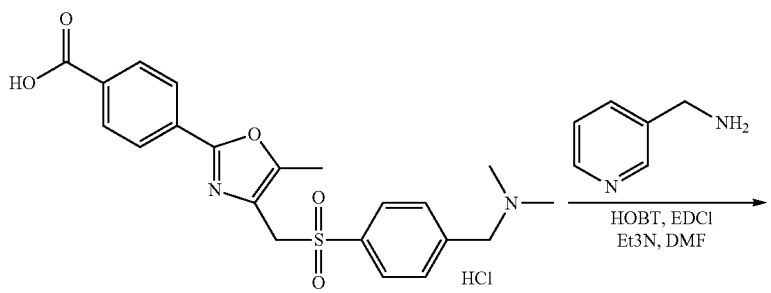

-continued

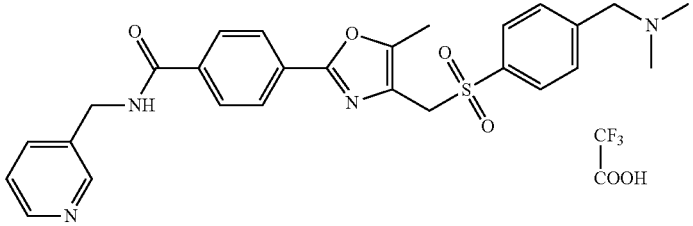

Example 20

To a solution of 4-(4-((4-((dimethylamino)methyl)phenylsulfonyl)methyl)-5-methyloxazol-2-yl)benzoic acid hydrochloride (540 mg, 1.20 mmol, 1.00 equiv), pyridin-3-ylmethanamine (155.52 mg, 1.44 mmol, 1.20 equiv), HOBt (194.4 mg, 1.44 mmol, 1.20 equiv) and EDCI (275 mg, 1.44 mmol, 1.20 equiv) in N,N-dimethylformamide (10 mL) was added triethylamine (363.6 mg, 3.60 mmol, 3.01 equiv) dropwise with stiffing. The reaction mixture was stirred overnight at room temperature and then diluted with 20 mL of ice-water. The resulting solution was extracted with 3×100 mL of ethyl acetate. The combined organic layers was washed with 3×100 mL of brine, dried over anhydrous sodium sulphate and concentrated under vacuum. The crude product (350 mg) was purified by Prep-HPLC with the following conditions (1#-Pre-HPLC-005(Waters)): Column, Atlantis T3, 5 um, 19*150 mm; mobile phase, WATER WITH 0.05% TFA and CH$_3$CN (10% CH$_3$CN up to 30% in 12 min, up to 100% in 1 min); Detector, uv 254/220 nm, to give 159 mg (21%) of 4-(4-((4-((dimethylamino)methyl)phenylsulfonyl)methyl)-5-methyloxazol-2-yl)-N-(pyridin-3-ylmethyl)benzamide trifluoroacetic acid salt as a yellow solid. LC-MS: (ES, m/z): 505 [M+H]$^+$, 274, 253. $^1$HNMR (400 MHz, CD$_3$OD, ppm) δ 8.84 (s, 1H), 8.73 (s, 1H), 8.50-8.48 (d, 1H), 7.99-7.97 (d, 7H), 7.76-7.74 (d, 2H), 4.77 (s, 2H), 4.60 (s, 2H), 4.44 (s, 2H), 2.87 (s, 6H), 2.31 (s, 3H).

Example 59

Synthesis of 4-(5-methyl-4-((4-(piperidin-1-ylmethyl)phenylsulfonyl)methyl)oxazol-2-yl)-N-(pyridin-3-ylmethyl)benzamide TFA salt Step 1: Synthesis of lithium 4-(piperidin-1-ylmethyl)benzenesulfinate

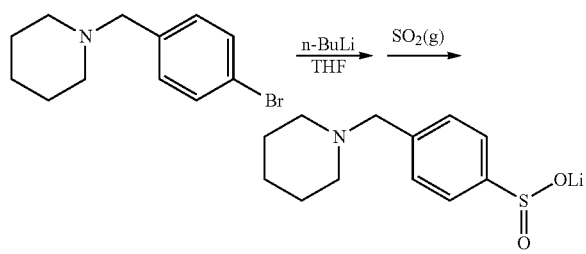

To a solution of 1-(4-bromobenzyl)piperidine (5 g, 19.76 mmol, 1.00 equiv) in tetrahydrofuran (50 mL) maintained under nitrogen at −78° C. was added in 30 min a 2.5M solution of n-butyllithium (8.7 mL, 1.10 equiv) in hexane dropwise with stirring. The resulting solution was stirred at −78° C. for 2 h. Sulfur dioxide gas was then bubbled into the solution at −78° C. for 1 h. Sulfur dioxide gas was then bubbled into the solution at −78° C. for 1 h. Ether (200 mL) was added and the precipitate was collected by filtration. The solid was washed with ether and dried in vacuum to give 4.8 g (99%) of lithium 4-(piperidin-1-ylmethyl)benzenesulfinate as a yellow solid.

Step 2: Synthesis of 4-(5-methyl-4-((4-(piperidin-1-ylmethyl)phenylsulfonyl)methyl)oxazol-2-yl)benzoate

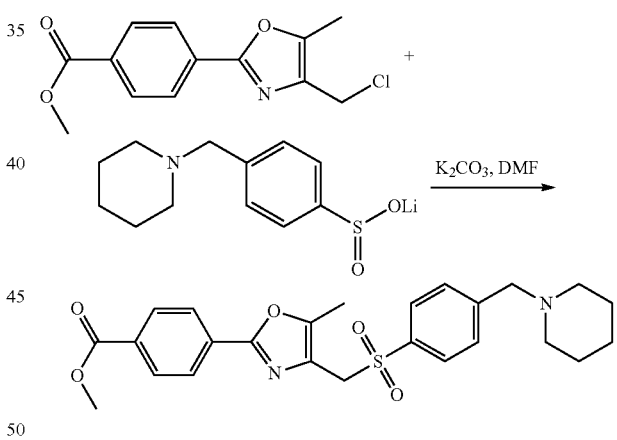

A mixture of methyl 4-(4-(chloromethyl)-5-methyloxazol-2-yl)benzoate (2.65 g, 10.00 mmol, 1.00 equiv), lithium 4-(piperidin-1-ylmethyl)benzenesulfinate (4.8 g, 19.59 mmol, 2.00 equiv) and potassium carbonate (1.38 g, 10.00 mmol, 1.00 equiv) in N,N-dimethylformamide (100 mL) was stirred overnight at 70° C. Water (150 mL) was added and the resulting solution was extracted with 3×200 mL of ethyl acetate. The combined organic layers was washed with 3×200 mL of brine, dried over anhydrous sodium sulfate and concentrated under vacuum to yield 4 g (53%) of methyl 4-(5-methyl-4-((4-(piperidin-1-ylmethyl)phenylsulfonyl)methyl)oxazol-2-yl)benzoate as a yellow solid. LC-MS: (ES, m/z): 510 [M+CH$_3$CN+H]$^+$, 469 [M+H]$^+$, 120.

Step 3: Synthesis of 4-(5-methyl-4-((4-(piperidin-1-ylmethyl)phenylsulfonyl)methyl)oxazol-2-yl)benzoic acid hydrochloride

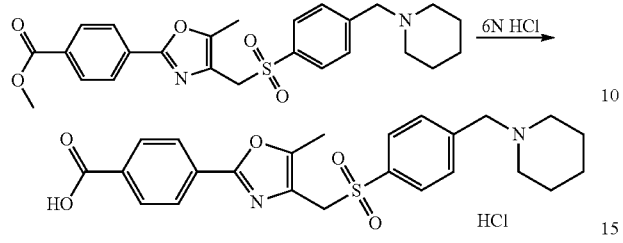

A solution of methyl 4-(5-methyl-4-((4-(piperidin-1-ylmethyl)phenylsulfonyl)methyl)oxazol-2-yl)benzoate (2 g, 2.65 mmol, 1.00 equiv, 62%) in 6N hydrochloric acid (50 mL) was refluxed overnight. The resulting mixture was concentrated under vacuum and the residue was washed with 20 mL of ethyl acetate and 20 mL of ether. The solid was dried in a vacuum oven to give 1.2 g (68%) of 4-(5-methyl-4-((4-(piperidin-1-ylmethyl)phenylsulfonyl)methyl)oxazol-2-yl)benzoic acid hydrochloride as an off-white solid. LC-MS: (ES, m/z): 496 [M+CH$_3$CN+H]$^+$, 455 [M+H]$^+$

Step 4: Synthesis of 4-(5-methyl-4-((4-(piperidin-1-ylmethyl)phenylsulfonyl)methyl)oxazol-2-yl)-N-(pyridin-3-ylmethyl)benzamide TFA salt

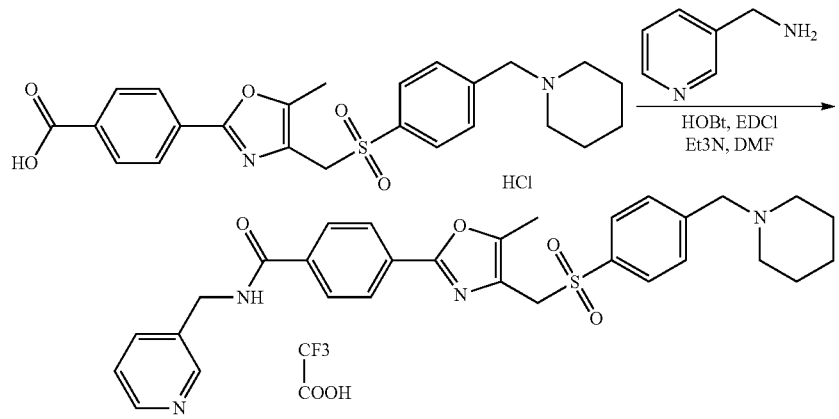

Example 21

To a solution of 4-(5-methyl-4-((4-(piperidin-1-ylmethyl)phenylsulfonyl)methyl)oxazol-2-yl)benzoic acid hydrochloride (1.02 g, 1.54 mmol, 1.00 equiv, 74%), pyridin-3-ylmethanamine (199.8 mg, 1.85 mmol, 1.20 equiv), HOBt (249.8 mg, 1.85 mmol, 1.20 equiv) and EDCI (353.4 mg, 1.85 mmol, 1.20 equiv) in N,N-dimethylformamide (10 mL) was added triethylamine (467.2 mg, 4.63 mmol, 3.00 equiv) dropwise with stirring. The reaction mixture was stirred overnight at room temperature and then diluted with 20 mL of ice-water. The solid was collected by filtration. The crude product (350 mg) was purified by Prep-HPLC with the following conditions (1#-Pre-HPLC-005(Waters)): Column, SunFire Prep C18, 5 um, 19*150 mm; mobile phase, WATER WITH 0.05% TFA and CH$_3$CN (10% CH$_3$CN up to 30% in 12 min, up to 100% in 1 min); Detector, uv 254/220 nm, to give 161.1 mg (16%) of 4-(5-methyl-4-((4-(piperidin-1-ylmethyl)phenylsulfonyl)methyl)oxazol-2-yl)-N-(pyridin-3-ylmethyl)benzamide TFA salt as an off-white solid. LC-MS: (ES, m/z): 545 [M+H]$^+$, 294, 273, 192. $^1$HNMR (400 MHz, CD$_3$OD, ppm) δ 8.83 (s, 1H), 8.72-8.71 (d, 1H), 8.46-8.44 (d, 1H), 8.01-7.91 (m, 7H), 7.76-7.75 (d, 2H), 4.76 (s, 2H), 4.60 (s, 2H), 4.42 (s, 2H), 3.45-3.42 (d, 2H), 3.02-2.99 (d, 2H), 2.32 (s, 3H), 1.96-1.73 (m, 5H), 1.52 (s, 1H)

Example 60

Synthesis of 4-(5-methyl-4-((4-(morpholinomethyl)phenylsulfonyl)methyl)oxazol-2-yl)-N-(pyridin-3-ylmethyl)benzamide Step 1: Synthesis of lithium 4-(morpholinomethyl)benzenesulfinate

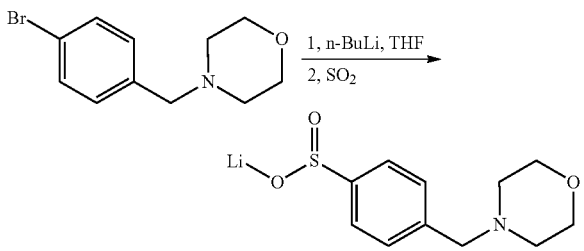

To a solution of 4-(4-bromobenzyl)morpholine (5.0 g, 19.61 mmol, 1.00 equiv) in tetrahydrofuran (60 mL) maintained under nitrogen at −78° C. was added in 30 min a 2.5M solution of n-butyllithium (8.8 mL, 1.10 equiv) in hexane dropwise with stirring. The resulting solution was stirred at −78° C. for 2 h. Sulfur dioxide gas was then bubbled into the solution at −78° C. for 1 h. The reaction mixture was warmed naturally to room temperature and the product was precipitated by the addition of 50 mL of ether. The solids were collected by filtration, washed with hexane (30 mL) and dried in a vacuum oven to produce 3.2 g (66%) of lithium 4-(morpholinomethyl)benzenesulfinate as a white solid.

Step 2: Synthesis of 4-(5-methyl-4-((4-(morpholinomethyl)phenylsulfonyl)methyl)oxazol-2-yl)benzoate

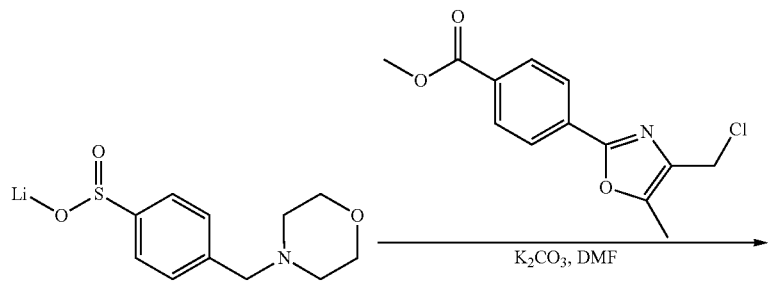

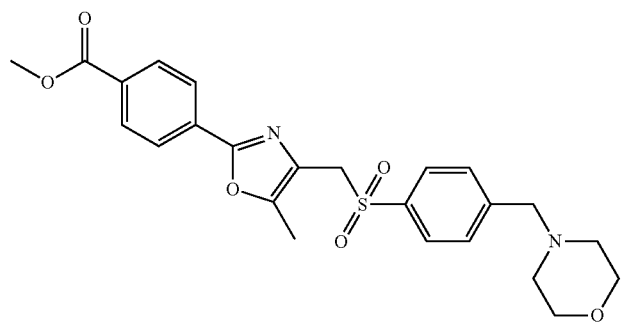

A mixture of lithium 4-(morpholinomethyl)benzenesulfinate (2.0 g, 8.10 mmol, 1.43 equiv), methyl 4-(4-(chloromethyl)-5-methyloxazol-2-yl)benzoate (1.5 g, 5.66 mmol, 1.00 equiv) and potassium carbonate (780 mg, 5.65 mmol, 1.00 equiv) in N,N-dimethylformamide (60 mL) was stirred overnight at 70° C. The reaction mixture was cooled to room temperature and the product was precipitated by the addition of 150 mL of ice and water. The solid was collected by filtration, washed with 2×20 mL of water and dried in a vacuum oven to afford 1.5 g (57%) of methyl 4-(5-methyl-4-((4-(morpholinomethyl)phenylsulfonyl)methyl)oxazol-2-yl) benzoate as a white solid. LC-MS: (ES, m/z): 512 [M+CH₃CN+H]⁺, 471 [M+H]⁺. ¹HNMR (400 MHz, DMSO-d6, ppm) δ 8.04 (d, J=8.0Hz, 2H), 7.90 (d, J=8.0Hz, 2H), 7.72 (d, J=7.6Hz, 2H), 7.52 (d, J=7.6Hz, 2H), 4.67 (s, 2H), 3.88 (s, 3H), 3.55 (s, 6H), 3.31-3.29 (d, 4H), 2.32 (s, 4H), 2.15 (s, 3H).

Step 3: Synthesis of 4-(5-methyl-4-((4-(morpholinomethyl)phenylsulfonyl)methyl)oxazol-2-yl)benzoic acid

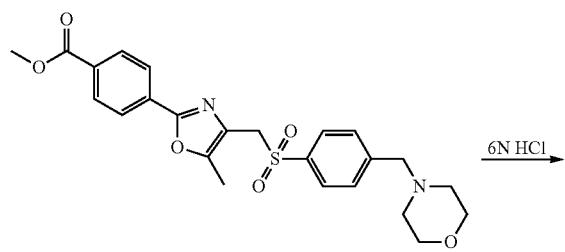

-continued

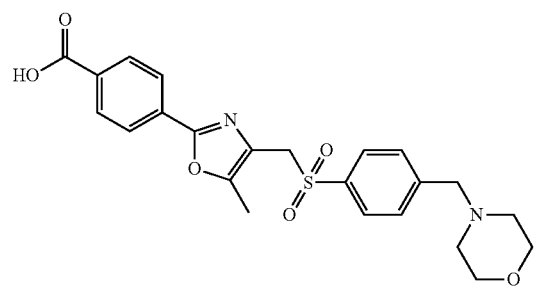

A solution of methyl 4-(5-methyl-4-((4-(morpholinomethyl)phenylsulfonyl)methyl)oxazol-2-yl)benzoate (1 g, 2.13 mmol, 1.00 equiv) in 6N hydrochloric acid (40 mL) was refluxed for 8 h. The reaction mixture was cooled to room temperature naturally and then diluted with 100 mL of water/ice. The precipitate was collected by filtration, washed with 2×20 mL of water and dried in a vacuum oven to give 0.7 g (72%) of 4-(5-methyl-4-((4-(morpholinomethyl)phenylsulfonyl)methyl)oxazol-2-yl)benzoic acid as a white solid.

Step 4: Synthesis of 4-(5-methyl-4-((4-(morpholinomethyl)phenylsulfonyl)methyl)oxazol-2-yl)-N-(pyridin-3-ylmethyl)benzamide

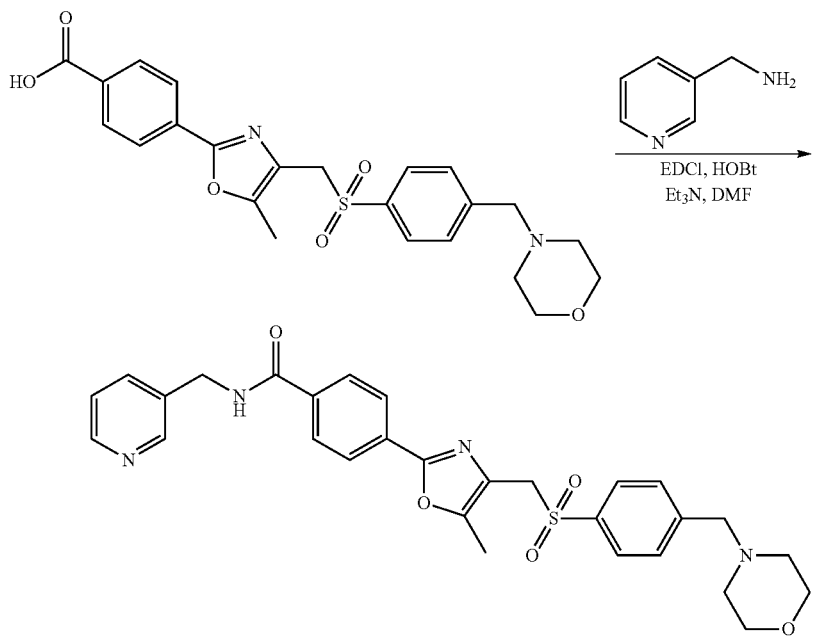

Example 22

To a solution of 4-(5-methyl-4-((4-(morpholinomethyl)phenylsulfonyl)methyl)oxazol-2-yl)benzoic acid (490 mg, 1.07 mmol, 1.00 equiv), EDCI (250 mg, 1.31 mmol, 1.22 equiv), HOBt (180 mg, 1.33 mmol, 1.24 equiv), triethylamine (330 mg, 3.27 mmol, 3.04 equiv) and pyridin-3-ylmethanamine (330 mg, 3.06 mmol, 2.84 equiv) in N,N-dimethylformamide (20 mL) was stirred overnight at room temperature. The product was precipitated by the addition of 60 mL ice/water. The solid was collected by filtration and washed with water (1×20 mL) and dried in an oven under reduced pressure to give 0.40 g (68%) of 4-(5-methyl-4-((4-(morpholinomethyl)phenylsulfonyl)methyl)oxazol-2-yl)-N-(pyridin-3-ylmethyl)benzamide as a white solid. LC-MS: (ES, m/z): 547 [M+H]$^+$. $^1$HNMR (400 MHz, DMSO-d6, ppm) δ 9.22 (s, 1H), 8.57 (s, 1H), 8.46 (s, 1H), 7.98 (d, J=7.6Hz, 2H), 7.86 (d, J=7.6Hz, 2H), 7.74-7.72 (m, 3H), 7.53 (d, J=7.6Hz, 2H), 7.36 (s, 1H), 4.67 (s, 2H), 4.51 (d, J=4.0Hz, 2H), 3.55 (s, 6H), 2.32 (s, 4H), 2.15 (s, 3H).

Example 61

Synthesis of 4-(5-methyl-4-((4-(2-morpholinoethyl)phenylsulfonyl) methyl)oxazol-2-yl)-N-(pyridin-3-ylmethyl)benzamide trifluoroacetic acid salt Step 1: Synthesis of 2-(4-bromophenyl)acetyl chloride

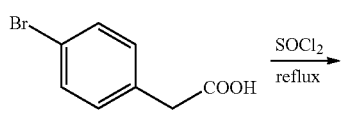

-continued

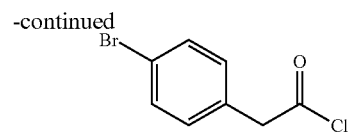

A solution of 2-(4-bromophenyl)acetic acid (20.0 g, 93.46 mmol, 1.00 equiv) in thionyl chloride (40 mL) was refluxed for 2 h. The resulting mixture was concentrated under vacuum to give 20 g (92%) of 2-(4-bromophenyl)acetyl chloride as a white solid.

Step 2: Synthesis of 2-(4-bromophenyl)-1-morpholinoethanone

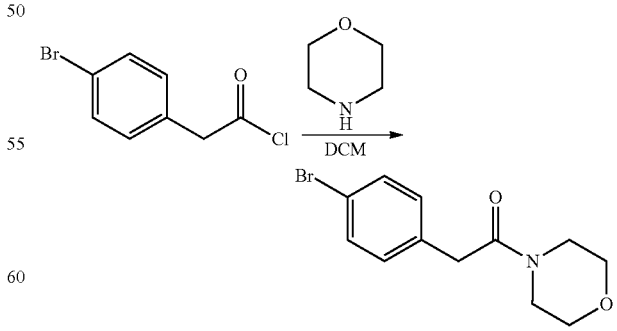

To a solution of morpholine (16 g, 183.91 mmol, 1.98 equiv) in dichloromethane (50 mL) at 0-5° C. was added a solution of 2-(4-bromophenyl)acetyl chloride (21.5 g, 92.67 mmol, 1.00 equiv) in dichloromethane (20 mL) dropwise with stirring. The reaction mixture was stirred for another hour at 0~5° C. The reaction mixture was warmed to room temperature and diluted with 30 mL of dichloromethane. The mixture was washed with 3×50 mL of brine, dried over anhydrous sodium sulfate and concentrated under vacuum to give 19.5 g (74%) of 2-(4-bromophenyl)-1-morpholinoethanone as a white solid. LC-MS: (ES, m/z): 284 [M+H]⁺.

Step 3: Synthesis of 4-(4-bromophenethyl)morpholine

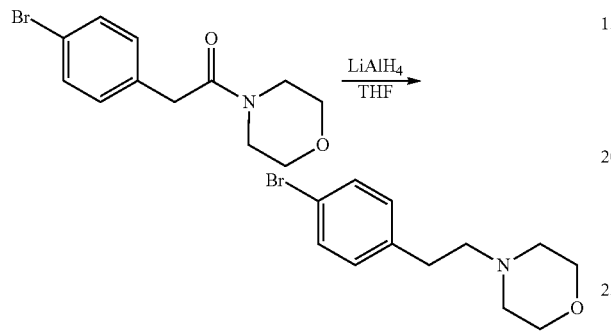

To a mixture of lithium aluminum hydride (3.35 g, 88.16 mmol, 2.00 equiv) in tetrahydrofuran (100 mL) maintained under nitrogen at −30° C. was added a solution of 2-(4-bromophenyl)-1-morpholinoethanone (12.5 g, 44.17 mmol, 1.00 equiv) in tetrahydrofuran (30 mL) dropwise with stirring. The reaction mixture was stirred at −30° C. for 30 min and then at room temperature for 2 h. The reaction was then quenched sequentially by the addition of 3.5 mL of water, 10 mL of 15% aqueous sodium hydroxide solution and 3.5 mL of water. The solid was removed by filtration. The filtrate was extracted with 1×150 mL of ethyl acetate. The organic layer was collected then washed with 2×30 mL of brine, dried over anhydrous sodium sulfate and concentrated under vacuum to give 11.5 g (97%) of 4-(4-bromophenethyl)morpholine as a white solid. LC-MS: (ES, m/z): 311 [M+CH₃CN+H]⁺, 270 [M+H]⁺, 130, 102.

Step 4: Synthesis of lithium 4-(2-morpholinoethyl)benzenesulfinate

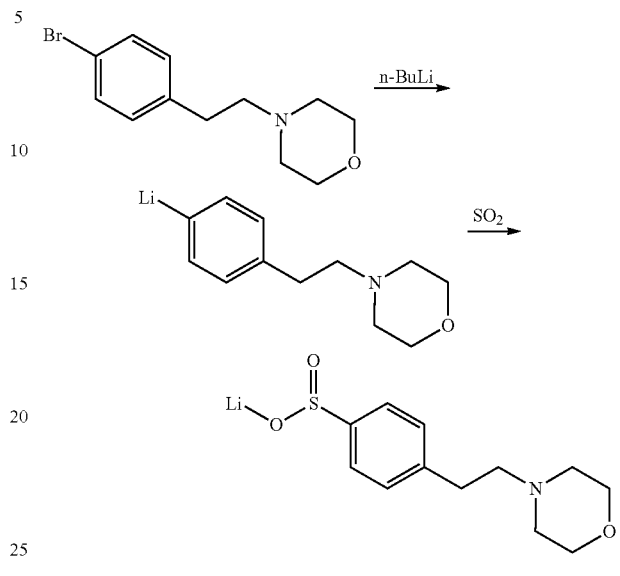

To a solution of 4-(4-bromophenethyl)morpholine (5.0 g, 18.59 mmol, 1.00 equiv) in tetrahydrofuran (70 mL) maintained under nitrogen at −78° C. was added a. To this was added a 2.5M solution of n-butyllithium (8.2 mL) dropwise with stirring at −78° C. The resulting solution was stirred for another 2 h at −78° C. Dry sulfur dioxide gas was then bubbled into the solution at −78° C. for 1 h. The reaction mixture was warmed to room temperature then diluted with 50 mL of ether to precipitate out the product. The solid was collected by filtration, washed with 1×20 mL of ether and dried in a vacuum oven to give 3.5 g (72%) of lithium 4-(2-morpholinoethyl)benzenesulfinate as a white solid.

Step 5: Synthesis of methyl 4-(5-methyl-4-((4-(2-morpholinoethyl)phenylsulfonyl)methyl)oxazol-2-yl)benzoate

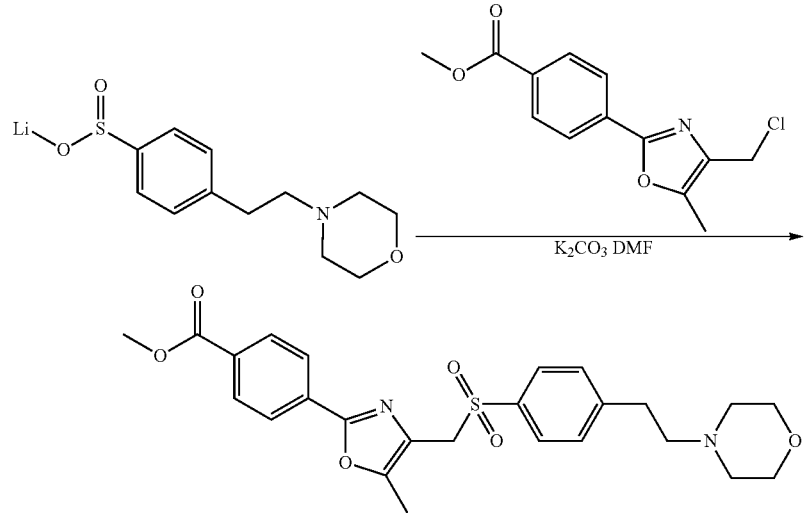

A mixture of lithium 4-(2-morpholinoethyl)benzenesulfinate (2.0 g, 7.66 mmol, 1.00 equiv), methyl 4-(3-(chloromethyl)-4-methylcyclopenta-1,3-dienyl)benzoate (1.5 g, 5.66 mmol, 0.74 equiv) and potassium carbonate (800 mg, 5.80 mmol, 0.76 equiv) in N,N-dimethylformamide (60 mL) was stirred under nitrogen overnight at 70° C. The reaction mixture was cooled to room temperature and the product was precipitated by the addition of 150 mL of ice and water. The solid was collected by filtration, washed with 1×20 mL of water and dried in a vacuum oven to give 2.1 g (57%) of methyl 4-(5-methyl-4-((4-(2-morpholinoethyl)phenylsulfonyl)methyl)oxazol-2-yl)benzoate as a white solid. LC-MS: (ES, m/z): 485 [M+H]$^+$, 437, 279, 130, 115.

Step 6: Synthesis of 4-(5-methyl-4-((4-(2-morpholinoethyl)phenylsulfonyl)methyl)oxazol-2-yl)benzoic acid hydrochloride

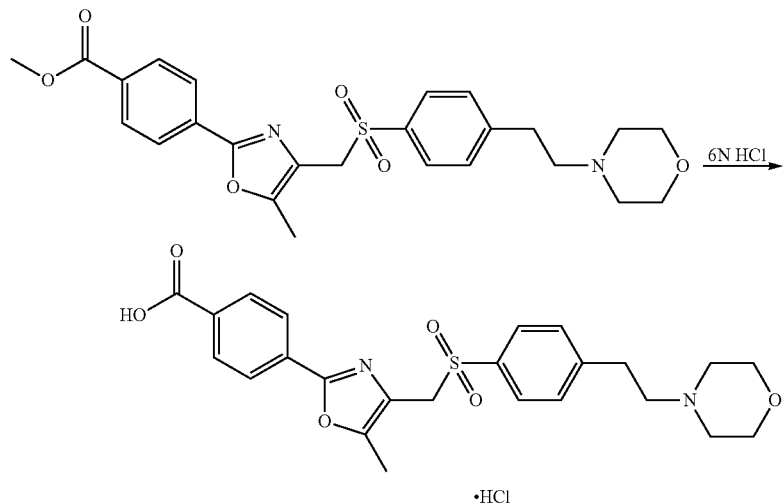

A solution of methyl 4-(5-methyl-4-((4-(2-morpholinoethyl)phenylsulfonyl)methyl)oxazol-2-yl)benzoate (600 mg, 1.24 mmol, 1.00 equiv) in 6N hydrochloric acid (30 mL) was refluxed for 8 h. The reaction mixture was cooled to room temperature and concentrated under vacuum to give 0.6 g (96%) of 4-(5-methyl-4-((4-(2-morpholinoethyl)phenylsulfonyl)methyl)oxazol-2-yl)benzoic acid hydrochloride as a white solid.

Step 7: Synthesis of 4-(5-methyl-4-((4-(2-morpholinoethyl)phenylsulfonyl)methyl)oxazol-2-yl)-N-(pyridin-3-ylmethyl)benzamide trifluoroacetic acid salt

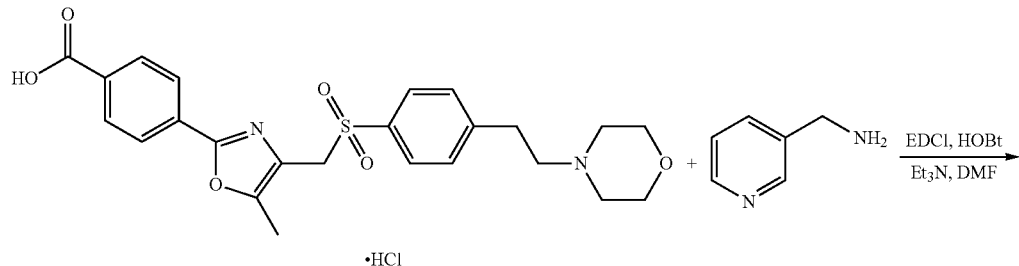

-continued

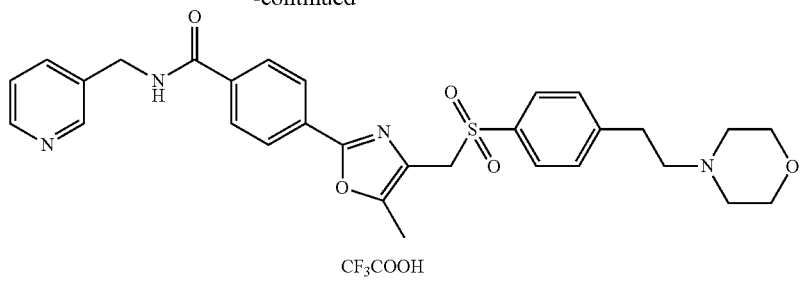

Example 23

A solution of 4-(5-methyl-4-((4-(2-morpholinoethyl)phenylsulfonyl)methyl)oxazol-2-yl)benzoic acid (600 mg, 1.28 mmol, 1.00 equiv), EDCI (290 mg, 1.52 mmol, 1.19 equiv), HOBt (210 mg, 1.56 mmol, 1.22 equiv), triethylamine (390 mg, 3.86 mmol, 3.02 equiv) and pyridin-3-ylmethanamine (170 mg, 1.57 mmol, 1.23 equiv) in N,N-dimethylformamide (30 mL) was stirred overnight at room temperature. The product was precipitated by the addition of 100 mL of ice/water. The solid was collected by filtration, washed with 1×30 mL of water and dried in a vacuum oven. The crude product (350 mg) was purified by Prep-HPLC with the following conditions (2#-Waters 2767-2(HPLC-08)): Column, SunFire Prep C18, 19*150 mm 5 um; mobile phase, WATER WITH 0.05% TFA and CH$_3$CN (10% CH3CN up to 30% in 12 min); Detector, UV 220 nm, to give 95 mg (11%) of 4-(5-methyl-4-((4-(2-morpholinoethyl)phenylsulfonyl)methyl)oxazol-2-yl)-N-(pyridin-3-ylmethyl)benzamide trifluoroacetic acid salt as a white solid. LC-MS: (ES, m/z): 561 [M+H]$^+$, 323, 302, 281. $^1$HNMR (400 MHz, D$_2$O, ppm) δ 8.75 (s, 1H), 8.67 (d, J=5.2Hz, 1H), 8.56 (d, J=8.0Hz, 1H), 8.00 (t, J=7.2Hz, 1H), 7.88-7.82 (m, 4H), 7.66 (d, J=7.6Hz, 2H), 7.45 (d, J=7.6Hz, 2H), 4.75 (s, 2H), 4.52 (s, 2H), 4.03 (d, J=12.8Hz, 2H), 3.72 (t, J=12.4Hz, 1H), 3.48 (d, J=12.4Hz, 2H), 3.33-3.29 (m, 2H), 3.14-3.10 (m, 4H), 1.97 (s, 3H).

Example 62

Synthesis of 4-(5-methyl-4-((4-(3-morpholinopropyl) phenylsulfonyl)methyl)oxazol-2-yl)-N-(pyridin-3-ylmethyl)benzamide acid trifluoroacetic acid salt Step 1: Synthesis of dimethyl 2-(4-bromobenzyl)malonate

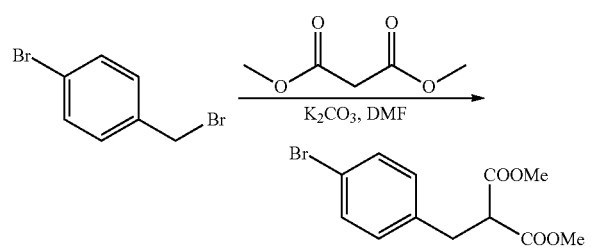

A mixture of dimethyl malonate (42.6 g, 322.73 mmol, 4.00 equiv) and potassium carbonate (22.3 g, 161.59 mmol, 2.00 equiv) in N,N-dimethylformamide (200 mL) was stirred for 30 min at 50° C. A solution of 1-bromo-4-(bromomethyl) benzene (20 g, 80.65 mmol, 1.00 equiv) in N,N-dimethylformamide (80 mL) was then added dropwise with stirring to the reaction mixture. The resulting solution was stirred at 50° C. for 2 h. Water (100 mL) was added and the mixture was extracted with 1×400 mL of ethyl acetate. The organic layer was washed with 2×100 mL of brine, dried over anhydrous sodium sulfate and concentrated under vacuum to give 22 g (91%) of dimethyl 2-(4-bromobenzyl)malonate as a white solid. LC-MS: (ES, m/z): 301 [M+H]$^+$, 126, 120.

Step 2: Synthesis of 2-(4-bromobenzyl)malonic acid

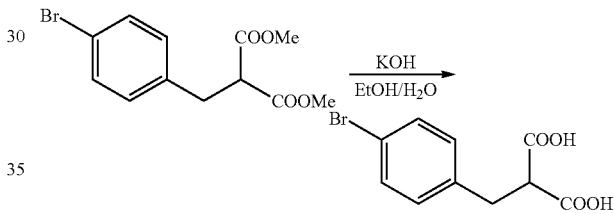

A mixture of dimethyl 2-(4-bromobenzyl)malonate (22 g, 73.33 mmol, 1.00 equiv) and potassium hydroxide (12.3 g, 219.64 mmol, 3.00 equiv) in ethanol (140 mL) and water (140 mL) was stirred at 60° C. overnight. The resulting solution was diluted with 300 mL of ice and water then extracted with 1×500 mL of ethyl acetate. The organic layer was washed with 2×150 mL of brine, dried over anhydrous sodium sulfate and concentrated under vacuum to give 18.2 g (91%) of 2-(4-bromobenzyl)malonic acid as a white solid.

Step 3: Synthesis of 3-(4-bromophenyl)propanoic acid

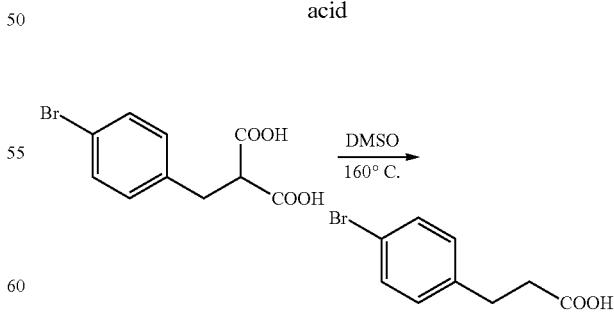

A solution of 2-(4-bromobenzyl)malonic acid (18 g, 66.18 mmol, 1.00 equiv) in dimethylsulfoxide (50 mL) was stirred at 160° C. for 2 h. The reaction mixture was cooled to room temperature and the product was precipitated by the addition of 200 mL ice and water. The solid was collected by filtration, washed with 1×50 mL of water and dried in a vacuum oven to give 14.8 g (98%) of 3-(4-bromophenyl)propanoic acid as a white solid. LC-MS: (ES, m/z): 229 [M+H]$^+$. $^1$HNMR (400 MHz, DMSO-d6, ppm): δ 7.45 (d, J=8.0Hz, 2H), 7.21 (d, J=8.0Hz, 2H), 2.82-2.77 (m, 2H), 2.55-2.51 (m, 2H).

Step 4: Synthesis of 3-(4-bromophenyl)propanoyl chloride

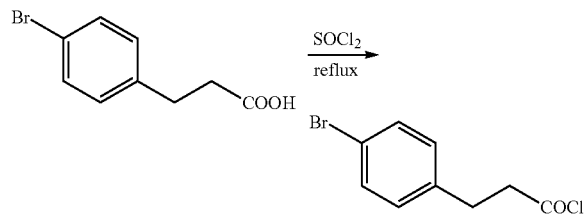

A solution of 3-(4-bromophenyl)propanoic acid (14.5 g, 63.60 mmol, 1.00 equiv) in thionyl chloride (80 mL) was refluxed for 2 h. The reaction mixture was cooled to room temperature and then concentrated under vacuum to give 15.5 g (99%) of 3-(4-bromophenyl)propanoyl chloride as a light yellow oil.

Step 5: Synthesis of 3-(4-bromophenyl)-1-morpholinopropan-1-one

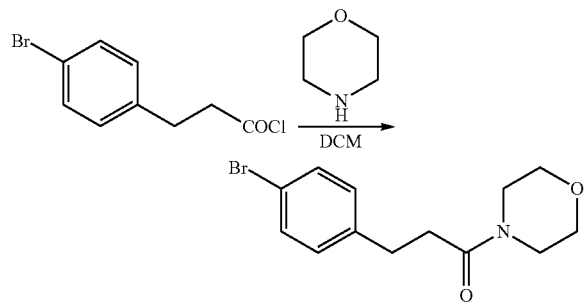

To a solution of morpholine (11 g, 126.44 mmol, 2.01 equiv) in dichloromethane (60 mL) 0~5° C. was added a solution of 3-(4-bromophenyl)propanoyl chloride (15.5 g, 63.01 mmol, 1.00 equiv) in dichloromethane (30 mL) dropwise with stirring. The resulting solution was stirred at 0~5° C. for 1 h. The reaction mixture was warmed to room temperature. The resulting solution was diluted with 40 mL of water. The mixture was extracted with dichloromethane 2×100 mL. The combined organic layers was washed with 3×50 mL of brine, dried over anhydrous sodium sulfate and concentrated under vacuum to give 17.4 g (93%) of 3-(4-bromophenyl)-1-morpholinopropan-1-one as a white solid.

Step 6: Synthesis of 4-(3-(4-bromophenyl)propyl)morpholine

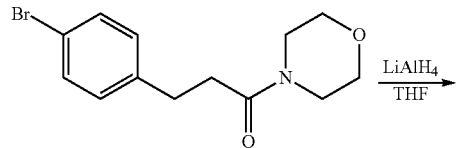

To a mixture of lithium aluminum hydride (4.4 g, 115.79 mmol, 2.00 equiv) in tetrahydrofuran (120 mL) maintained under nitrogen at −30° C. was added a solution of 3-(4-bromophenyl)-1-morpholinopropan-1-one (17.2 g, 57.91 mmol, 1.00 equiv) in tetrahydrofuran (80 mL) dropwise with stirring. The resulting solution was stirred at −30° C. for 30 min and at room temperature for 2 h. The reaction was quenched by the sequential addition of 4.4 mL of water, 13 mL of 15% aqueous sodium hydroxide solution and 4.4 mL of water. The solid was removed by filtration and the filtrate was extracted with 1×350 mL of ethyl acetate. The organic layer was washed with 2×50 mL of brine, dried over anhydrous sodium sulfate and concentrated under vacuum to afford 13.5 g (82%) of 4-(3-(4-bromophenyl)propyl)morpholine as a light yellow oil.

Step 7: Synthesis of lithium 4-(3-morpholinopropyl)benzenesulfinate

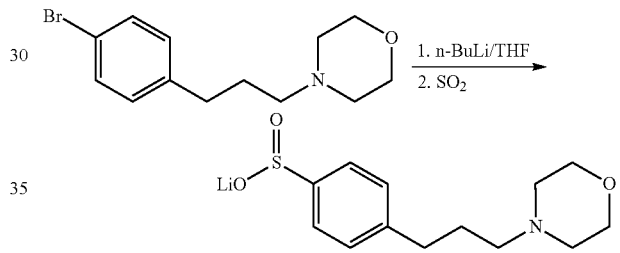

To a solution of 4-(3-(4-bromophenyl)propyl)morpholine (5.0 g, 17.67 mmol, 1.00 equiv) in tetrahydrofuran (80 mL) maintained under nitrogen at −78° C. was added in 30 min a 2.5M solution of n-butyllithium (8.0 mL) in hexane dropwise with stirring. The resulting solution was stirred at −78° C. for 2 h. Sulfur dioxide gas was then bubbled into the solution at −78° C. for 1 h and then warmed naturally to room temperature. The resulting solution was diluted with 60 mL of ether to precipitate out the product. The solid was collected by filtration, washed with 2×20 mL of ether and dried in a vacuum oven to give 4.1 g (84%) of lithium 4-(3-morpholinopropyl) benzenesulfinate as a white solid.

Step 8: Synthesis of 4-(5-methyl-4-((4-(3-morpholinopropyl)phenylsulfonyl) methyl)oxazol-2-yl)benzoate

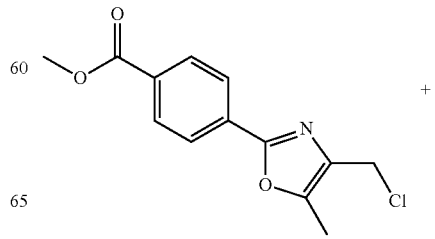

-continued

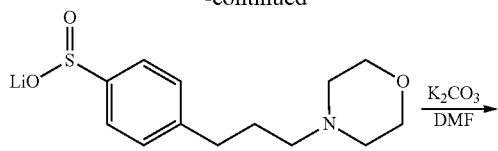

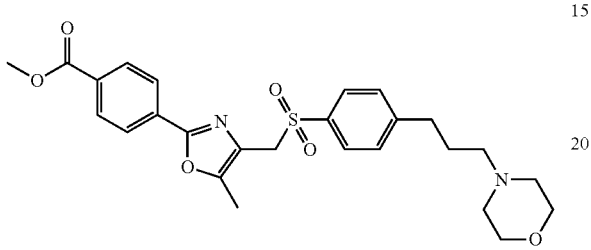

A mixture of methyl 4-(4-(chloromethyl)-5-methyloxazol-2-yl)benzoate (2.0 g, 7.55 mmol, 1.00 equiv), lithium 4-(3-morpholinopropyl)benzenesulfinate (4.0 g, 14.55 mmol, 1.93 equiv) and potassium carbonate (1.35 g, 9.78 mmol, 1.30 equiv) in N,N-dimethylformamide (50 mL) was stirred overnight at 70° C. The product was precipitated by the addition of 150 mL ice and water after the reaction was cooled to room temperature. The solid was collected by filtration, washed with 2×15 mL of water and dried in a vacuum oven to give 2.8 g (74%) of methyl 4-(5-methyl-4-((4-(3-morpholinopropyl)phenylsulfonyl)methyl)oxazol-2-yl)benzoate as a white solid. LC-MS: (ES, m/z): 499 [M+H]$^+$, 115.

Step 9: Synthesis of methyl-4-((4-(3-morpholinopropyl)phenylsulfonyl)methyl)oxazol-2-yl)benzoic acid hydrochloride

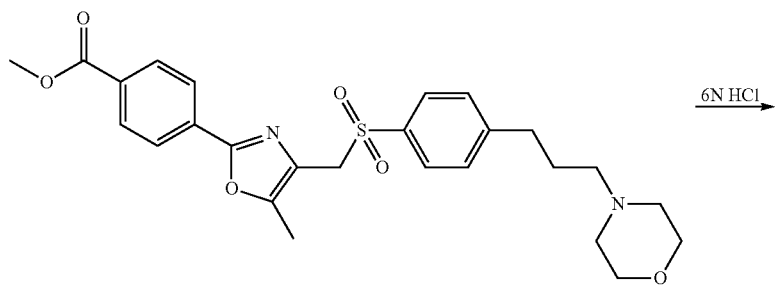

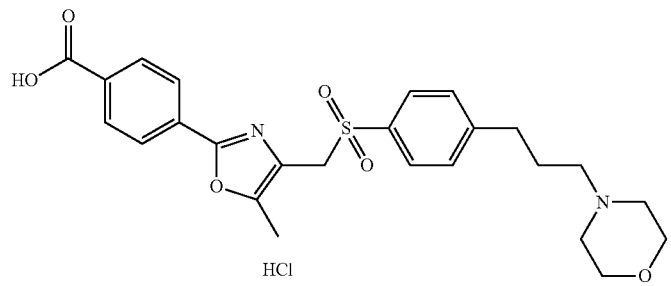

A solution of methyl 4-(5-methyl-4-((4-(3-morpholinopropyl)phenylsulfonyl)methyl)oxazol-2-yl)benzoate (2.0 g, 4.02 mmol, 1.00 equiv) in 6N hydrochloric acid (80 mL) was refluxed overnight. The reaction mixture was cooled to room temperature and concentrated under vacuum to give 2.0 g (96%) of 4-(5-methyl-4-((4-(3-morpholinopropyl)phenylsulfonyl)methyl)oxazol-2-yl)benzoic acid hydrochloride as a white solid. LC-MS: (ES, m/z): 485 [M+H]⁺.

Step 10: Synthesis of 4-(5-methyl-4-((4-(3-morpholinopropyl) phenylsulfonyl)methyl)oxazol-2-yl)-N-(pyridin-3-ylmethyl)benzamide acid trifluoroacetic acid salt

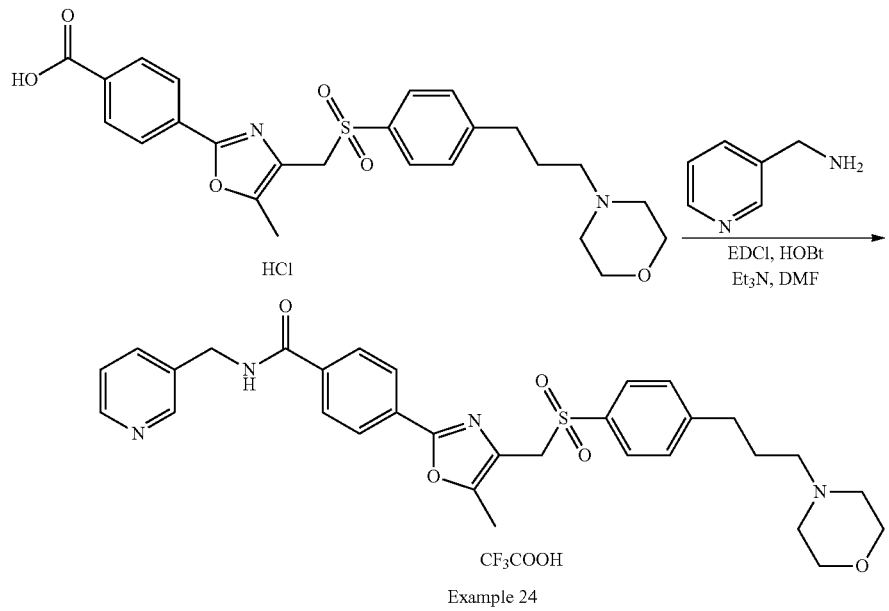

Example 24

A solution of 4-(5-methyl-4-((4-(3-morpholinopropyl) phenylsulfonyl)methyl)oxazol-2-yl)benzoic acid hydrochloride (1.5 g, 2.88 mmol, 1.00 equiv), EDCI (660 mg, 3.46 mmol, 1.20 equiv), HOBt (460 mg, 3.41 mmol, 1.18 equiv), triethylamine (1.16 g, 11.49 mmol, 3.98 equiv) and pyridin-3-ylmethanamine (380 mg, 3.52 mmol, 1.22 equiv) in N,N-dimethylformamide (40 mL) was stirred overnight at 25~30° C. The resulting solution was diluted with 100 mL of water and extracted with 1×100 mL of ethyl acetate. The organic layer was washed with 3×50 mL of brine, dried over anhydrous sodium sulfate and concentrated under vacuum. The crude product (550 mg) was purified by Prep-HPLC with the following conditions (1#-Pre-HPLC-005(Waters)): Column, Xbridge Prep C18, 5 um, 19*150 mm; mobile phase, WATER WITH 0.05% TFA and CH3CN (10% CH3CN up to 30% in 12 min, up to 100% in 1 min); Detector, uv 220/254 nm, to give 400 mg (20%) of 4-(5-methyl-4-((4-(3-morpholinopropyl) phenylsulfonyl)methyl)oxazol-2-yl)-N-(pyridin-3-ylmethyl)benzamide acid trifluoroacetic acid salt as a white solid. LC-MS: (ES, m/z): 575 [M+H]⁺, 288, 126. ¹HNMR (400 MHz, DMSO-d6, ppm): δ 8.79 (m, 1H), 8.70 (d, J=4.8Hz, 1H), 8.31 (d, J=8.0Hz, 1H), 7.98 (d, J=8.8Hz, 2H), 7.92 (d, J=8.4Hz, 2H), 7.87-7.84 (m, 1H), 7.72 (d, J=8.0Hz, 2H), 7.48 (d, J=8.4Hz, 2H), 4.62 (s, 4H), 3.98-3.94 (m, 2H), 3.64 (s, 2H), 3.42-3.39 (m, 2H), 3.12-3.00 (m, 4H), 2.78-2.73 (m, 2H), 2.09 (s, 3H), 2.00-1.92 (m, 2H).

Example 63

Synthesis of 4-(5-methyl-4-((piperidin-4-ylsulfonyl) methyl)oxazol-2-yl)-N-(2-(pyridin-3-yl)ethyl)benzamide Step 1: Synthesis of 2-(pyridin-3-yl)ethanamine

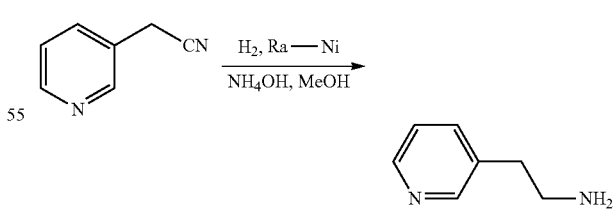

A mixture of 2-(pyridin-3-yl)acetonitrile (1 g, 8.47 mmol, 1.00 equiv), Raney nickel (1 g, 17.24 mmol, 1.00 equiv) and ammonium hydroxide (3 mL) in methanol (15 mL) was stirred under 1 atmosphere of hydrogen at room temperature overnight. The catalyst was removed by filtration through a pad of Celite and washed with several portions of methanol. The filtrate and washings were combined and concentrated under vacuum to give 940 mg (45%) of 2-(pyridin-3-yl)ethanamine as a yellow oil. LC-MS: (ES, m/z): 164 [M+CH$_3$CN+H]$^+$, 123 [M+H]$^+$, 106.

Step 2: Synthesis of 4-((2-(4-(((2-(pyridin-3-yl)ethyl)carbamoyl)phenyl)-5-methyloxazol-4-yl)methylsulfonyl)piperidine-1-carboxylate

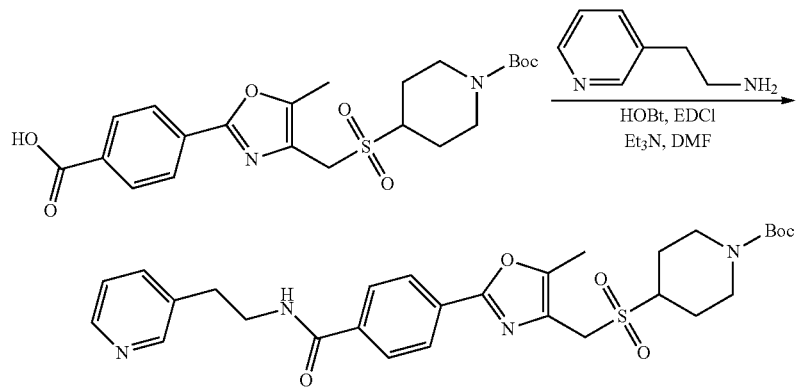

To a solution of 2-(pyridin-3-yl)ethanamine (940 mg, 7.70 mmol, 5.00 equiv), 4-(4-(((1-(tert-butoxycarbonyl)piperidin-4-yl)sulfonyl)methyl)-5-methyloxazol-2-yl)benzoic acid (700 mg, 1.51 mmol, 1.00 equiv), HOBt (250 mg, 1.85 mmol, 1.20 equiv), EDCI (350 mg, 1.83 mmol, 1.20 equiv) in N,N-dimethylformamide (20 mL) at 30° C. was added triethylamine (460 mg, 4.55 mmol, 3.00 equiv) dropwise with stirring. The reaction mixture was stirred at 30° C. overnight and then quenched by the addition of 30 mL of water/ice. The precipitate was collected by filtration, washed with water and dried in a vacuum oven to give 840 mg (98%) of tert-butyl 4-((2-(4-(((2-(pyridin-3-yl)ethyl)carbamoyl)phenyl)-5-methyloxazol-4-yl)methylsulfonyl)piperidine-1-carboxylate as a yellow solid. LC-MS: (ES, m/z): 569 [M+H]$^+$, 469, 361, 320, 169, 126. $^1$HNMR (400 MHz, DMSO-d6, ppm) δ 8.73 (s, 1H), 8.50-8.45 (d, 2H), 7.99-7.94 (d, 5H), 7.74 (s, 1H), 7.38 (s, 1H), 4.54 (s, 3H), 4.07 (s, 3H), 3.54 (s, 3H), 2.90 (m, 6H), 2.50-2.45 (s, 6H), 2.11 (s, 3H), 1.48-1.41 (s, 16H).

Step 3: Synthesis of 4-(5-methyl-4-((piperidin-4-ylsulfonyl)methyl)oxazol-2-yl)-N-(2-(pyridin-3-yl)ethyl)benzamide Excess hydrogen chloride gas was bubbled into a solution of tert-butyl 4-((2-(4-(((2-(pyridin-3-yl)ethyl)carbamoyl)phenyl)-5-methyloxazol-4-yl)methylsulfonyl)piperidine-1-carboxylate (840 mg, 1.48 mmol, 1.00 equiv) in dichloromethane (20 mL) maintained at 0° C. in a water/ice bath. The reaction mixture was stirred at 0° C. for another 2 h. The pH value of the solution was adjusted to 10 with 1M sodium hydroxide solution. Water (400 mL) was then added and the resulting solution was extracted with 5×200 mL of dichloromethane. The combined organic layers was washed with 2×600 mL of brine, dried over anhydrous sodium sulfate and concentrated under vacuum to give 420 mg (61%) of 4-(5-methyl-4-((piperidin-4-ylsulfonyl)methyl)oxazol-2-yl)-N-(2-(pyridin-3-yl)ethyl)benzamide as a white solid. LC-MS: (ES, m/z): 469 [M+H]$^+$, 320, 235. $^1$HNMR (400 MHz, CD$_3$OD, ppm) δ 8.47 (s, 1H), 8.42-8.40 (d, 1H), 8.09-8.07 (d, 2H), 7.90-7.88 (d, 2H), 7.81-7.79 (d, 1H), 7.42-7.39 (t, 1H), 4.45 (s, 2H), 3.70-3.66 (t, 2H), 3.43-3.39 (m, 3H), 3.03-2.99 (t, 2H), 2.88-2.82 (m, 2H), 2.50 (s, 3H), 2.34-2.31 (d, 2H), 1.91-1.88 (m, 2H).

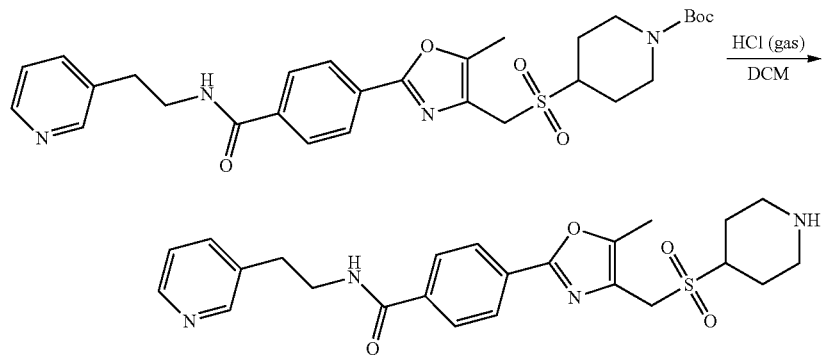

Example 25

Example 64

Synthesis of 4-[5-methyl-4-[(1-methylpiperidine-4-sulfonyl)methyl]-1,3-oxazol-2-yl]-N-[2-(pyridin-3-yl)ethyl]benzamide

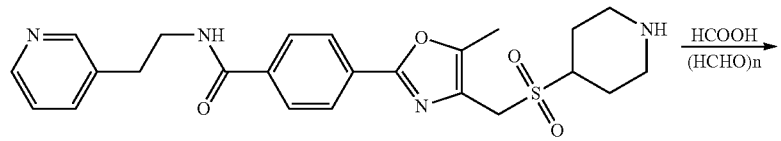

Example 25

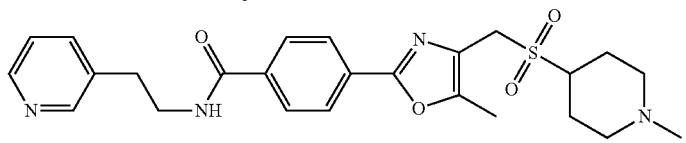

Example 26

A solution of 4-[5-methyl-4-[(piperidine-4-sulfonyl)methyl]-1,3-oxazol-2-yl]-N-[2-(pyridin-3-yl)ethyl]benzamide (322 mg, 0.69 mmol, 1.00 equiv) and paraformaldehyde (0.21 g, 10.00 equiv) in formic acid (15 mL) was stirred overnight at 110° C. The resulting mixture was concentrated under vacuum and the crude product (320 mg) was purified by Prep-HPLC with the following conditions (1#-Pre-HPLC-001(SHIMADZU)): Column, SunFire Prep C18, 19*150 mm 5um; mobile phase, CH3CN/H2O (5% up to 60% in 12 min, up to 100% in 1 min, down to 5% in 1 min); Detector, UV 254 nm, to give 36.5 mg (11%) of 4-[5-methyl-4-[(1-methylpiperidine-4-sulfonyl)methyl]-1,3-oxazol-2-yl]-N-[2-(pyridin-3-yl)ethyl]benzamide as a white solid. LC-MS: (ES, m/z): 483 [M-PH]+, 242. $^1$HNMR (400 MHz, CD$_3$OD, ppm): δ 8.47 (s, 1H), 8.42-8.40 (s, 1H), 8.08-8.06 (d, 2H), 7.90-7.88 (d, 2H), 7.81-7.79 (d, 1H), 7.42-7.39 (m, 1H), 4.41 (s, 2H), 3.69-3.66 (t, 2H), 3.21-3.06 (m, 1H), 3.06-2.99 (m, 4H), 2.50 (s, 3H), 2.30 (s, 3H), 2.26-2.23 (m, 2H), 2.12-2.06 (m, 2H), 1.95-1.87 (m, 2H).

Example 65

Synthesis of 4-[5-methyl-4-[3-(piperidin-4-yloxy) propyl]-1,3-oxazol-2-yl]-N-(pyridin-3-ylmethyl) benzamide trifluoroacetate

Step 1: Synthesis of 4-(4-(3-tert-butoxy-2-(tert-butoxycarbonyl)-3-oxopropyl)-5-methyloxazol-2-yl) benzoate

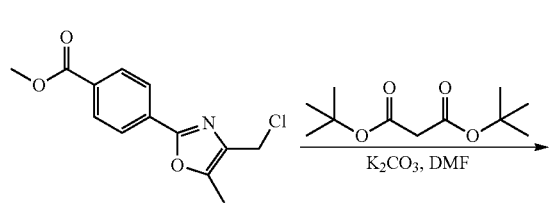

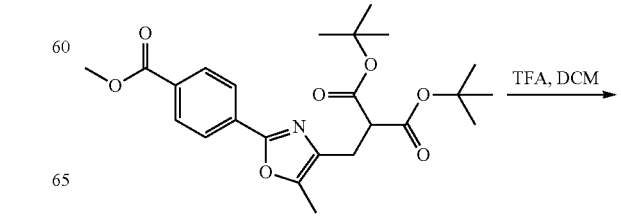

A mixture of di-tert-butyl malonate (4.3 g, 19.91 mmol, 1.99 equiv) and potassium carbonate (2.8 g, 20.29 mmol, 2.03 equiv) in N,N-dimethylformamide (30 mL) was stirred at 65° C. for 30 min A solution of methyl 4-(4-(chloromethyl)-5-methyloxazol-2-yl)benzoate (2.65 g, 10.00 mmol, 1.00 equiv) in N,N-dimethylformamide (5 mL) was then added dropwise with stirring to the reaction mixture. The resulting solution was stirred at 65° C. overnight and then quenched with 60 mL of ice and water. The mixture was extracted with 2×50 mL of ethyl acetate. The combined organic layers was washed with 3×30 mL of brine, dried over anhydrous sodium sulfate and concentrated under vacuum to give 4.0 g (90%) of methyl 4-(4-(3-tert-butoxy-2-(tert-butoxycarbonyl)-3-oxopropyl)-5-methyloxazol-2-yl)benzoate as a light yellow solid. LC-MS: (ES, m/z): 446 [M+H]+, 390, 334, 272, 230, 115.

Step 2: Synthesis of 2-((2-(4-(methoxycarbonyl) phenyl)-5-methyloxazol-4-yl)methyl)malonic acid

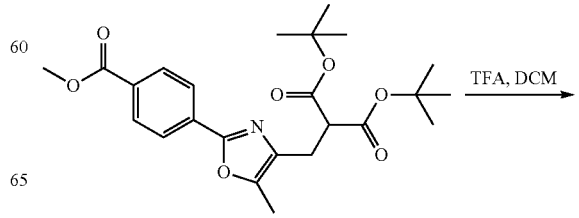

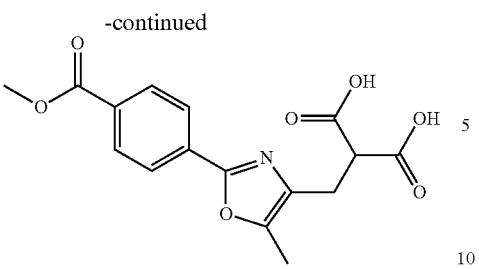

To a solution of methyl 4-(4-(3-tert-butoxy-2-(tert-butoxycarbonyl)-3-oxopropyl)-5-methyloxazol-2-yl)benzoate (4.0 g, 8.99 mmol, 1.00 equiv) in dichloromethane (20 mL) was added trifluoroacetic acid (20 mL). The reaction mixture was stirred overnight at 35° C. and then concentrated under vacuum to remove dichloromethane. Saturated sodium bicarbonate solution was added to the residue until the pH value of the solution was adjusted to 2-3. The resulting solution was extracted with 200 mL of ethyl acetate. The organic layer was washed with 2×50 mL of brine, dried over anhydrous sodium sulfate and concentrated under vacuum to yield 3.0 g (100%) of 2-((2-(4-(methoxycarbonyl)phenyl)-5-methyloxazol-4-yl)methyl)malonic acid as a light yellow solid. LC-MS: (ES, m/z): 334 [M+H]$^+$, 272, 115.

Step 3: Synthesis of 3-[2-[4-(methoxycarbonyl)phenyl]-5-methyl-1,3-oxazol-4-yl]propanoic acid

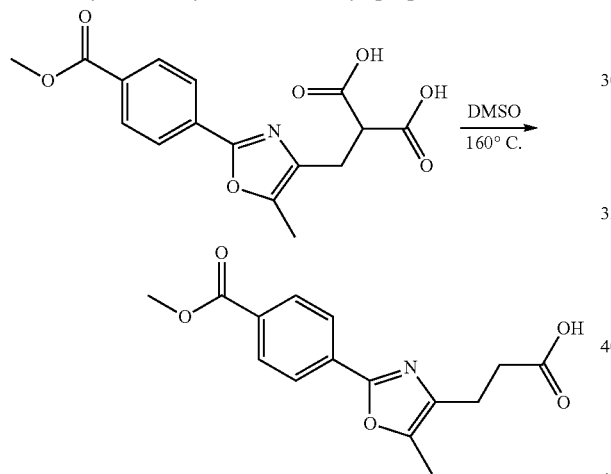

A solution of 2-([2-[4-(methoxycarbonyl)phenyl]-5-methyl-1,3-oxazol-4-yl]methyl)propanedioic acid (2.0 g, 6.00 mmol, 1.00 equiv) in dimethylsulfoxide (30 mL) was stirred at 160° C. for 30 min. The reaction mixture was cooled to room temperature and the product was precipitated by the addition of 150 mL ice and water. The solid was collected by filtration, washed with 1×50 mL of water and dried in vacuum to give 1.5 g (86%) of 3-[2-[4-(methoxycarbonyl)phenyl]-5-methyl-1,3-oxazol-4-yl]propanoic acid as a white solid. LC-MS: (ES, m/z): 290 [M+H]$^+$, 272, 146, 120.

Step 4: Synthesis of methyl 4-[4-(3-hydroxypropyl)-5-methyl-1,3-oxazol-2-yl]benzoate

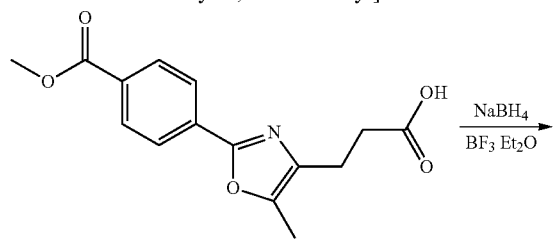

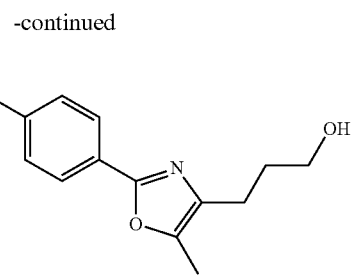

Boron trifluoride etherate (4 g) was added dropwise with stirring to a mixture of sodium borohydride (720 mg, 19.03 mmol, 2.02 equiv) in tetrahydrofuran (35 mL) maintained under nitrogen at 0° C. The resulting solution was warmed to room temperature and stirred for 2 h. The above mixture was cooled to 0° C. then 3-[2-[4-(methoxycarbonyl)-phenyl]-5-methyl-1,3-oxazol-4-yl]propanoic acid (2.72 g, 9.40 mmol, 1.00 equiv) was added in several batches. The reaction mixture was stirring at room temperature overnight and then quenched with 5 mL of methanol and 60 mL of water. The resulting solution was extracted with 50 mL of ethyl acetate. The organic layer was dried over anhydrous calcium chloride and concentrated under vacuum to give 2.2 g (85%) of methyl 4-[4-(3-hydroxypropyl)-5-methyl-1,3-oxazol-2-yl]benzoate as a white solid. LC-MS: (ES, m/z): 276 [M+H]$^+$, 146, 115.

Step 5: Synthesis of -[4-[3-(methanesulfonyloxy)propyl]-5-methyl-1,3-oxazol-2-yl]benzoate

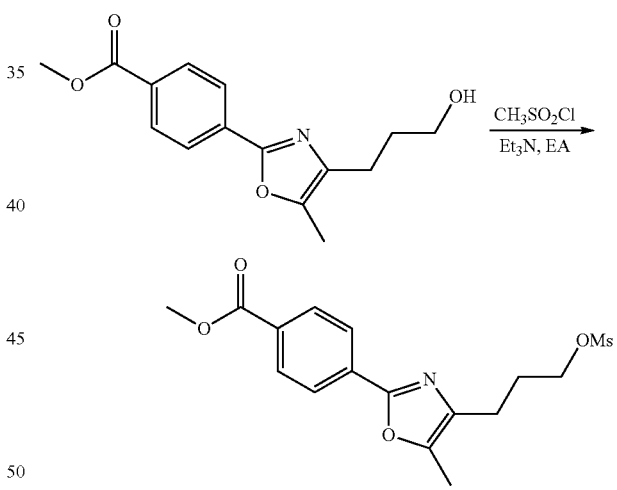

To a solution of methyl 4-[4-(3-hydroxypropyl)-5-methyl-1,3-oxazol-2-yl]benzoate (500 mg, 1.82 mmol, 1.00 equiv) and triethylamine (370 mg, 3.66 mmol, 2.01 equiv) in ethyl acetate (20 mL) at −5° C. was added methane sulfonyl chloride (0.27 g) dropwise with stirring. The resulting solution was warmed to room temperature naturally and stirred at room temperature for 1 h. Water (20 mL) was added and the mixture was extracted with 1×30 mL of ethyl acetate. The organic layer was washed sequentially with 1×10 mL of 1 N hydrochloric acid, 1×10 mL of 5% sodium bicarbonate solution and 1×30 mL of brine. The organic layer was dried over anhydrous sodium sulfate and concentrated under vacuum to give 0.55 g (86%) of methyl 4-[4-[3-(methanesulfonyloxy)propyl]-5-methyl-1,3-oxazol-2-yl]benzoate as a white solid. LC-MS: (ES, m/z): 354 [M+H]$^+$, 258, 146, 105.

Step 6: Synthesis of 4-(4-(3-(1-(tert-butoxycarbonyl) piperidin-4-yloxy)propyl)-5-methyloxazol-2-yl)benzoic acid

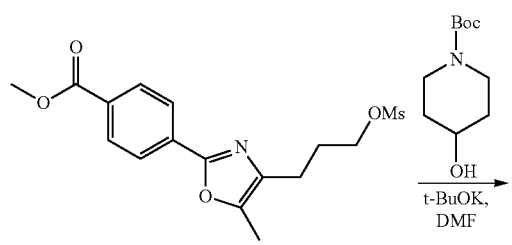

equiv) in 20 min. The resulting solution was stirred at 35° C. for another 35 min then the reaction was quenched with 50 mL of water. The pH value of the solution was adjusted to 2-3 with 2N hydrochloric acid. The resulting solution was extracted with 50 mL of ethyl acetate. The organic layer was washed with 2×50 mL of brine, dried over anhydrous sodium sulfate and concentrated under vacuum to give 1.0 g of crude 4-(4-(3-(1-(tert-butoxycarbonyl)piperidin-4-yloxy)propyl)-5-methyloxazol-2-yl)benzoic acid as a white solid. LC-MS: (ES, m/z): 445[M+H]$^+$, 389, 115.

Step 7: Synthesis of tert-butyl 4-[3-(5-methyl-2-[4-[(pyridin-3-ylmethyl)carbamoyl]phenyl]-1,3-oxazol-4-yl)propoxy]piperidine-1-carboxylate

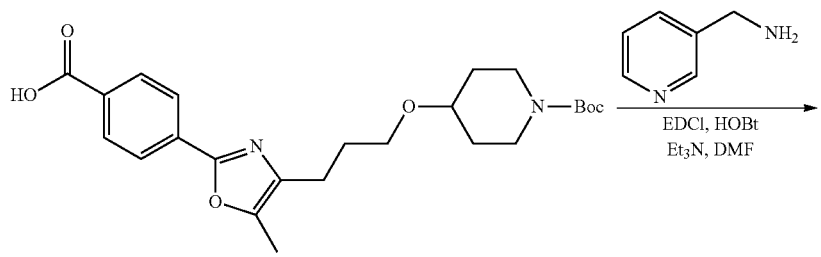

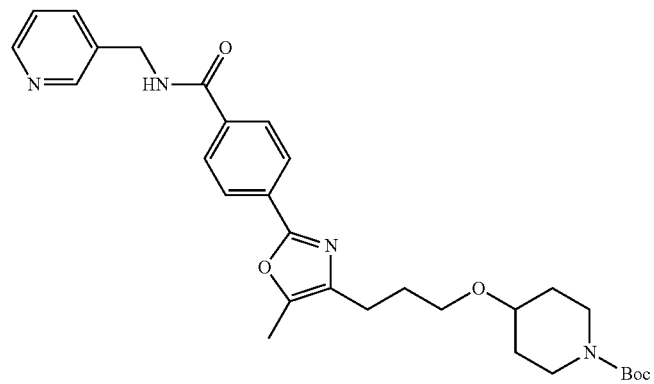

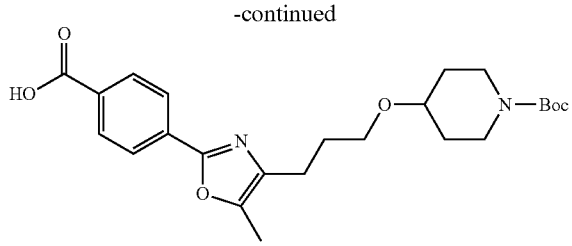

-continued

To a solution of methyl 4-[4-[3-(methanesulfonyloxy)propyl]-5-methyl-1,3-oxazol-2-yl]benzoate (630 mg, 1.78 mmol, 1.00 equiv) and tert-butyl 4-hydroxypiperidine-1-carboxylate (1 g, 4.97 mmol, 2.79 equiv) in N,N-dimethylformamide (20 mL) maintained under nitrogen at 35° C. was added potassium tert-butoxide (350 mg, 3.12 mmol, 1.75

A solution of 4-[4-[3-([1-[(tert-butoxy)carbonyl]piperidin-4-yl]oxy)propyl]-5-methyl-1,3-oxazol-2-yl]benzoic acid (1.0 g, 2.25 mmol, 1.00 equiv), EDCI (560 mg, 2.92 mmol, 1.30 equiv), HOBt (400 mg, 2.96 mmol, 1.32 equiv), triethylamine (800 mg, 7.91 mmol, 3.51 equiv) and pyridin-3-ylmethanamine (480 mg, 4.44 mmol, 1.97 equiv) in N,N-dimethylformamide (30 mL) was stirred at 35° C. overnight. The product was precipitated by the addition of 50 mL of ice/water. The solid was collected by filtration, washed with 3×30 mL of water and dried in a vacuum oven to give 0.8 g (67%) of tert-butyl 4-[3-(5-methyl-2-[4-[(pyridin-3-ylmethyl)carbamoyl]phenyl]-1,3-oxazol-4-yl)propoxy]piperidine-1-carboxylate as a white solid LC-MS-PH: (ES, m/z): 535 [M+H]$^+$, 435, 367, 352, 239, 102.

Step 8: Synthesis of 4-[5-methyl-4-[3-(piperidin-4-yloxy)propyl]-1,3-oxazol-2-yl]-N-(pyridin-3-ylmethyl)benzamide trifluoroacetate

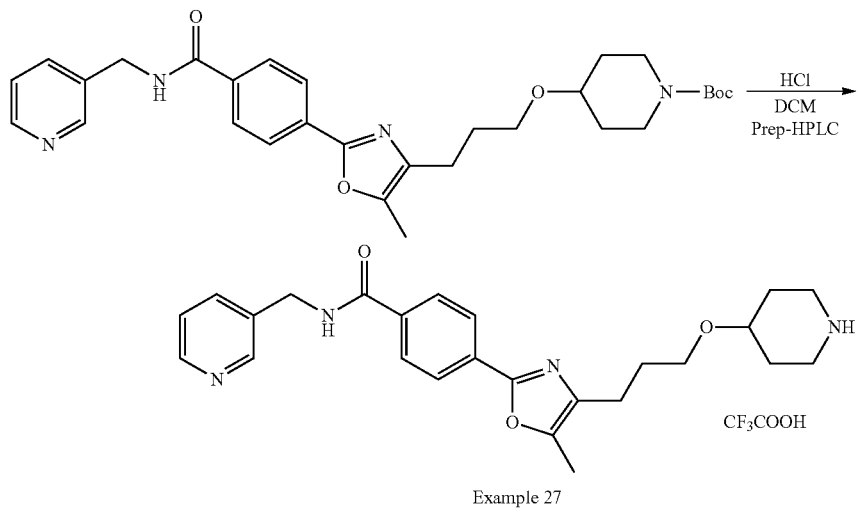

Example 27

Excess hydrogen chloride gas was bubbled into a solution of tert-butyl 4-[3-(5-methyl-2-[4-[(pyridin-3-ylmethyl)carbamoyl]phenyl]-1,3-oxazol-4-yl)propoxy]piperidine-1-carboxylate (700 mg, 1.31 mmol, 1.00 equiv) in dichloromethane (20 mL) at 0° C. The resulting solution was stirred at 0° C. for 2 h and then concentrated under vacuum. The crude product (500 mg) was purified by Prep-HPLC with the following conditions (Waters-1): Column, Xbridge C1819*150; mobile phase, 0.05% TFA/water; Detector, UV 220 nm, to yield 27.3 mg (4%) of 4-[5-methyl-4-[3-(piperidin-4-yloxy)propyl]-1,3-oxazol-2-yl]-N-(pyridin-3-ylmethyl)benzamide trifluoroacetate as a white solid. LC-MS: (ES, m/z): 435 [M+H]$^+$, 352, 306, 239, 218. $^1$H-NMR (400 MHz, D$_2$O, ppm) δ 8.71 (s, 1H), 8.63 (d, J=5.6Hz, 1H), 8.52 (d, J=8.0Hz, 1H), 7.99-7.95 (m, 2H), 7.84 (d, J=8.4Hz, 2H), 3.63-3.61 (m, 1H), 3.50-3.47 (m, 2H), 3.28-3.25 (m, 2H), 3.01-2.96 (m, 2H), 2.57-2.53 (m, 2H), 2.28 (s, 2H), 2.03-2.00 (m, 2H), 1.84-1.71 (m, 2H), 1.68-1.65 (m, 2H)

Example 66

Synthesis of 4-(5-methyl-4-((4-(trifluoromethyl)phenylsulfonyl)methyl)oxazol-2-yl)-N-(pyridin-3-ylmethyl)benzamide Step 1: Synthesis of lithium 4-(trifluoromethyl)benzenesulfinate

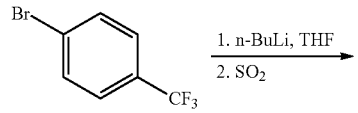

-continued

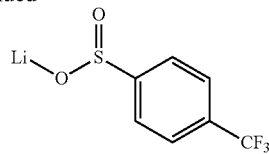

To a solution of 1-bromo-4-(trifluoromethyl)benzene (5.0 g, 22.32 mmol, 1.00 equiv, 100%) in tetrahydrofuran (50 mL) maintained under nitrogen at −78° C. was added a 2.5M n-butyllithium solution in hexane (9.8 mL) dropwise with stirring. The resulting solution was stirred at −78° C. for 2 h then sulfur dioxide gas was bubbled continuously for 1 h into the reaction mixture. The solution was warmed naturally to 25° C. then 50 mL of ether was added. The solid was collected by filtration, washed with 30 mL of hexane then dried in a vacuum oven to give 3.5 g (73%) of lithium 4-(trifluoromethyl)benzenesulfinate as a white solid.

Step 2: Synthesis of methyl 4-(5-methyl-4-((4-(trifluoromethyl)phenylsulfonyl)methyl)oxazol-2-yl)benzoate 171
-continued

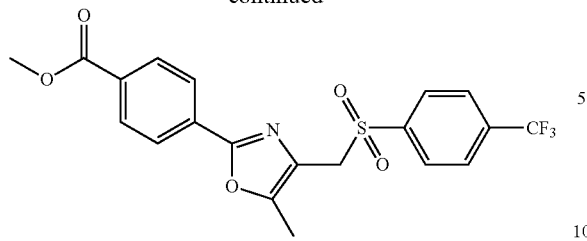

172
-continued

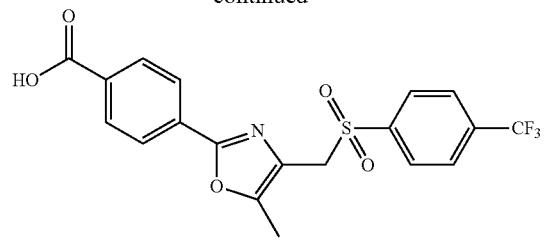

A mixture of lithium 4-(trifluoromethyl)benzenesulfinate (700 mg, 3.24 mmol, 1.72 equiv, 100%), methyl 4-(4-(chloromethyl)-5-methyloxazol-2-yl)benzoate (500 mg, 1.89 mmol, 1.00 equiv) and potassium carbonate (0.35 g) in N,N-dimethylformamide (25 mL) was stirred overnight at 70° C. The reaction mixture was cooled to room temperature then quenched by the addition of 60 mL of water and ice. The solid was collected by filtration, washed with 2×20 mL of water and dried in a vacuum oven to yield 0.7 g (85%) of methyl 4-(5-methyl-4-((4-(trifluoromethyl)phenylsulfonyl)methyl)oxazol-2-yl)benzoate as a white solid. LC-MS: (ES, m/z): 481 [M+CH$_3$CN+H]$^+$, 440 [M+H]$^+$, 271, 146, 105.

A solution of methyl 4-(5-methyl-4-((4-(trifluoromethyl)phenylsulfonyl)methyl)oxazol-2-yl)benzoate (700 mg, 1.59 mmol, 1.00 equiv) in 6N hydrochloric acid (30 mL) was refluxed for 8 h. The reaction mixture was cooled to room temperature and diluted with 100 g of water/ice. The solid was collected by filtration, washed with 2×20 mL of water and dried in a vacuum oven to afford 0.6 g (89%) of 4-(5-methyl-4-((4-(trifluoromethyl)phenylsulfonyl)methyl)oxazol-2-yl)benzoic acid as a white solid.

Step 4: Synthesis of 4-(5-methyl-4-((4-(trifluoromethyl)phenylsulfonyl)methyl)oxazol-2-yl)-N-(pyridin-3-ylmethyl)benzamide

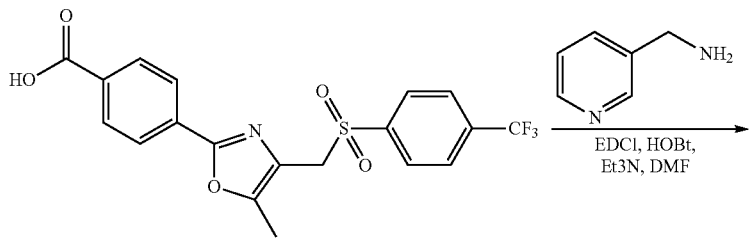

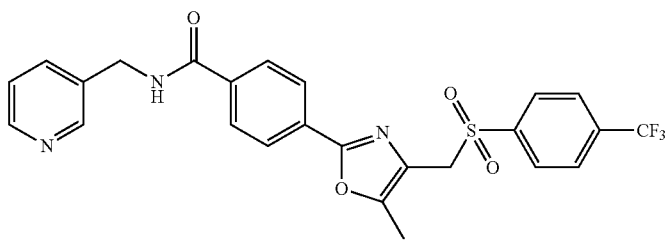

Example 28

Step 3: Synthesis of 4-(5-methyl-4-((4-(trifluoromethyl)phenylsulfonyl)methyl)oxazol-2-yl)benzoic acid A solution of 4-(5-methyl-4-((4-(trifluoromethyl)phenylsulfonyl)methyl)oxazol-2-yl)benzoic acid (420 mg, 0.99 mmol, 1.00 equiv), EDCI (230 mg, 1.20 mmol, 1.22 equiv), HOBt (170 mg, 1.26 mmol, 1.27 equiv), triethylamine (300 mg, 2.97 mmol, 3.01 equiv) and pyridin-3-ylmethanamine (140 mg, 1.30 mmol, 1.31 equiv) in N,N-dimethylformamide (20 mL) was stirred overnight at room temperature. The product was precipitated by the addition 60 mL of water/ice. The solid was collected by filtration, washed with 2×20 mL of water and dried in a vacuum oven to give 0.20 g (39%) of 4-(5-methyl-4-((4-(trifluoromethyl)phenylsulfonyl)methyl)oxazol-2-yl)-N-(pyridin-3-ylmethyl)benzamide as a white solid. LC-MS: (ES, m/z): 557 [M+CH$_3$CN+H]$^+$, 516 [M+H]$^+$, 102. $^1$HNMR (400 MHz, CDCl$_3$, ppm) δ 9.22 (s, 1H), 8.57 (s, 1H), 8.47 (s, 1H), 8.06-7.89 (m, 6H), 7.82 (d, J=8.0Hz, 1H), 7.73 (d, J=7.6Hz, 1H), 7.38-7.36 (m, 1H), 4.84 (s, 2H), 4.51 (d, J=5.2Hz, 2H), 2.24 (s, 3H).

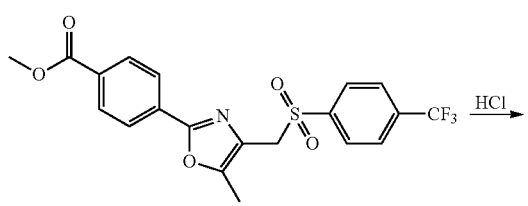

Example 67

Synthesis of 4-(4-(cyclohexylsulfonylmethyl)-5-methyloxazol-2-yl)-N-(pyridin-3-ylmethyl)benzamide

Step 1: Synthesis of methyl 4-(4-(cyclohexylthiomethyl)-5-methyloxazol-2-yl)benzoate

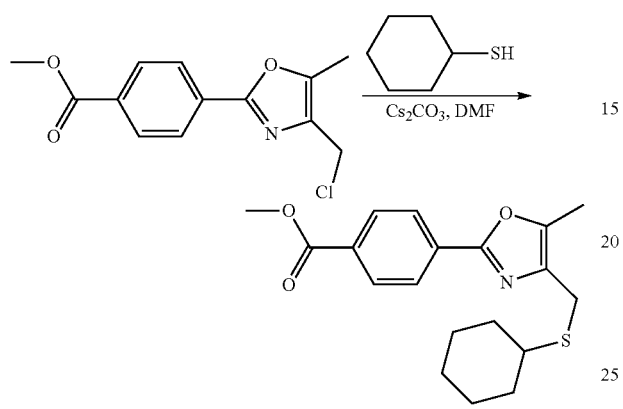

A solution of methyl 4-(4-(chloromethyl)-5-methyloxazol-2-yl)benzoate (6.0 g, 22.64 mmol, 1.00 equiv), cyclohexanethiol (3.9 g, 33.62 mmol, 1.50 equiv) and cesium carbonate (11.1 g, 34.05 mmol, 1.50 equiv) in N,N-dimethylformamide (60 mL) was stirred under nitrogen overnight at 50° C. The reaction was then quenched by the addition of 30 mL of water. The precipitate was collected by filtration and washed with 3×10 mL of hexane to give 4.5 g (58%) of methyl 4-(4-(cyclohexylthiomethyl)-5-methyloxazol-2-yl)benzoate as a white solid after drying under vacuum.

Step 2: Synthesis of methyl 4-(4-(cyclohexylsulfonylmethyl)-5-methyloxazol-2-yl)benzoate

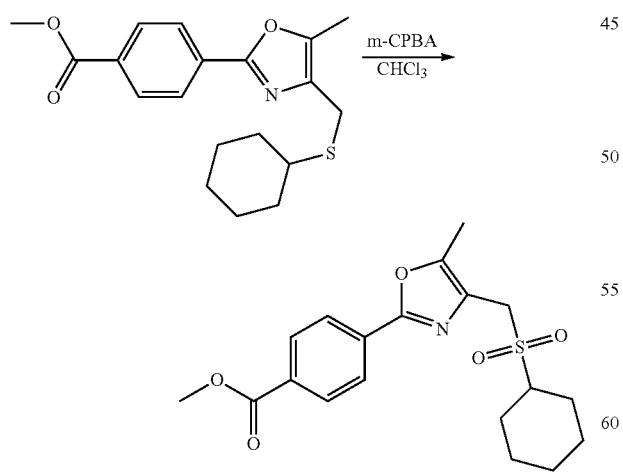

To a solution of methyl 4-(4-(cyclohexylthiomethyl)-5-methyloxazol-2-yl)benzoate (2.0 g, 5.80 mmol, 1.00 equiv) in chloroform (20 mL) at 0~5° C. was added 3-chloroperoxybenzoic acid (2.5 g, 14.53 mmol, 2.50 equiv), in portions in 1.5 h. The resulting solution was stirred at 0~5° C. for 1 h. The reaction mixture was diluted with 100 mL of dichloromethane then washed sequentially with 3×100 mL of aqueous sodium bisulphate solution, 2×50 mL of 1M sodium hydroxide solution and 3×50 mL of brine. The organic layer was dried over anhydrous sodium sulfate and concentrated under vacuum to give 1.4 g (64%) of methyl 4-(4-(cyclohexylsulfonylmethyl)-5-methyloxazol-2-yl)benzoate as a white solid. LC-MS: (ES, m/z): 378 [M+H]$^+$, 271, 146, 105.

Step 3: Synthesis of 4-(4-(cyclohexylsulfonylmethyl)-5-methyloxazol-2-yl)benzoic acid

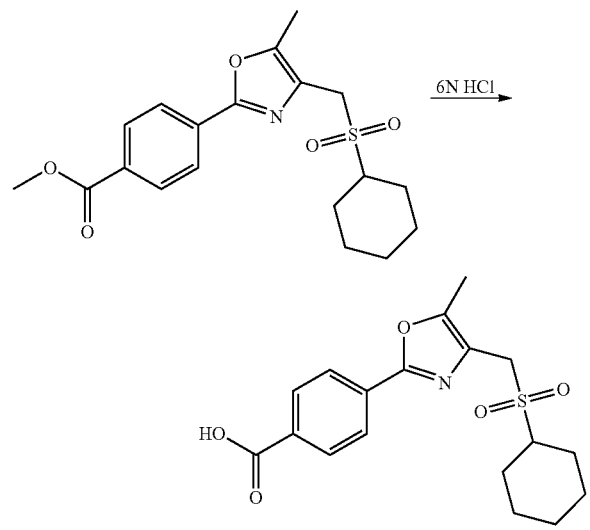

A solution of methyl 4-(4-(cyclohexylsulfonylmethyl)-5-methyloxazol-2-yl)-benzoate (1.0 g, 2.65 mmol, 1.00 equiv) in 6N hydrochloric acid (20 mL) was refluxed overnight. The reaction mixture was cooled to room temperature and 30 mL of water and ice were added. The precipitate ws collected by filtration, washed with 3×20 mL of hexane and dried in a vacuum oven to give 0.85 g (88%) of 4-(4-(cyclohexylsulfonylmethyl)-5-methyloxazol-2-yl)benzoic acid as a white solid. LC-MS: (ES, m/z): 365 [M+H]$^+$, 341, 257, 216, 189, 146, 115.

Step 4: Synthesis of 4-(4-(cyclohexylsulfonylmethyl)-5-methyloxazol-2-yl)-N-(pyridin-3-ylmethyl)benzamide

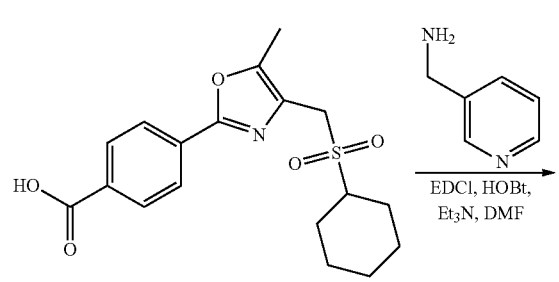

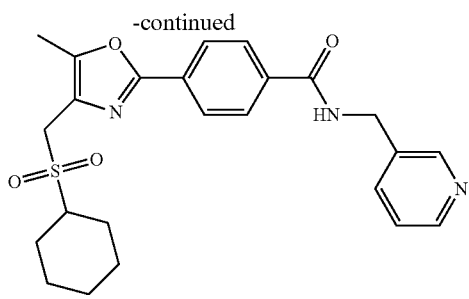

Example 29

A solution of 4-(4-(cyclohexylsulfonylmethyl)-5-methyloxazol-2-yl)benzoic acid (500 mg, 1.38 mmol, 1.00 equiv), pyridin-3-ylmethanamine (180 mg, 1.67 mmol, 1.20 equiv), EDCI (320 mg, 1.68 mmol, 1.20 equiv), HOBt (220 mg, 1.63 mmol, 1.20 equiv) and triethylamine (420 mg, 4.16 mmol, 3.00 equiv) in N,N-dimethylformamide (10 mL) was stirred overnight at room temperature. The reaction mixture was diluted with 15 mL of water and ice. The precipitate was collected by filtration, washed with water and dried in a vacuum oven to give 0.25 g (40%) of 4-(4-(cyclohexylsulfonylmethyl)-5-methyloxazol-2-yl)-N-(pyridin-3-ylmethyl) benzamide as a white solid LC-MS: (ES, m/z): 454 [M+H]$^+$, 347, 306, 238, 120 $^1$HNMR (400 MHz, CDCl$_3$, ppm) δ 8.97 (s, 1H), 8.57 (s, 2H), 8.21-8.05 (t, 4H), 7.54 (s, 2H), 4.73 (s, 2H), 4.17 (s, 2H), 3.02-2.98 (d, 2H), 2.90-2.50 (m, 6H), 2.31-2.20 (d, 2H), 1.95 (s, 2H), 1.74-1.61 (m, 3H), 1.29 (s, 3H Example 68

Synthesis of 3-(dimethylamino)phenyl 4-[[(5-methyl-2-[4-[(pyridin-3-ylmethyl)carbamoyl]phenyl]-1,3-oxazol-4-yl)methane]sulfonyl]piperidine-1-carboxylate Step 1: Synthesis of 3-(dimethylamino)phenyl carbonochloridate

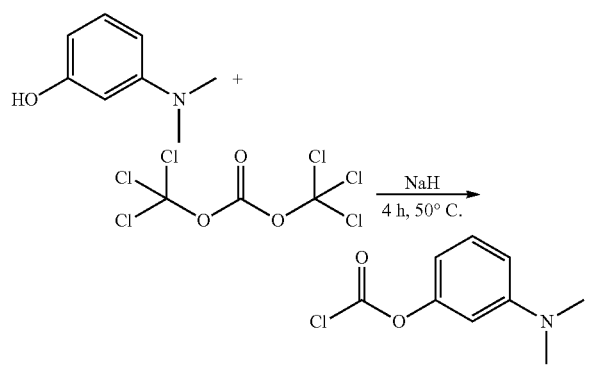

Sodium hydride (130 mg, 3.25 mmol, 1.11 equiv, 60%) was added in several batches to a solution of 3-(dimethylamino)phenol (400 mg, 2.92 mmol, 1.00 equiv) in tetrahydrofuran (15 mL). The mixture was stirred at 0° C. for 30 min then ditrichloromethyl carbonate (296.74 mg, 1.00 mmol, 0.34 equiv) was added in several batches to the mixture at 0° C. The resulting solution was stirred for 4 h at 50° C. and used in the next step without any purification Step 2: Synthesis of 3-(dimethylamino)phenyl 4-[[(5-methyl-2-[4-[(pyridin-3-ylmethyl)carbamoyl]phenyl]-1,3-oxazol-4-yl)methane]sulfonyl]piperidine-1-carboxylate

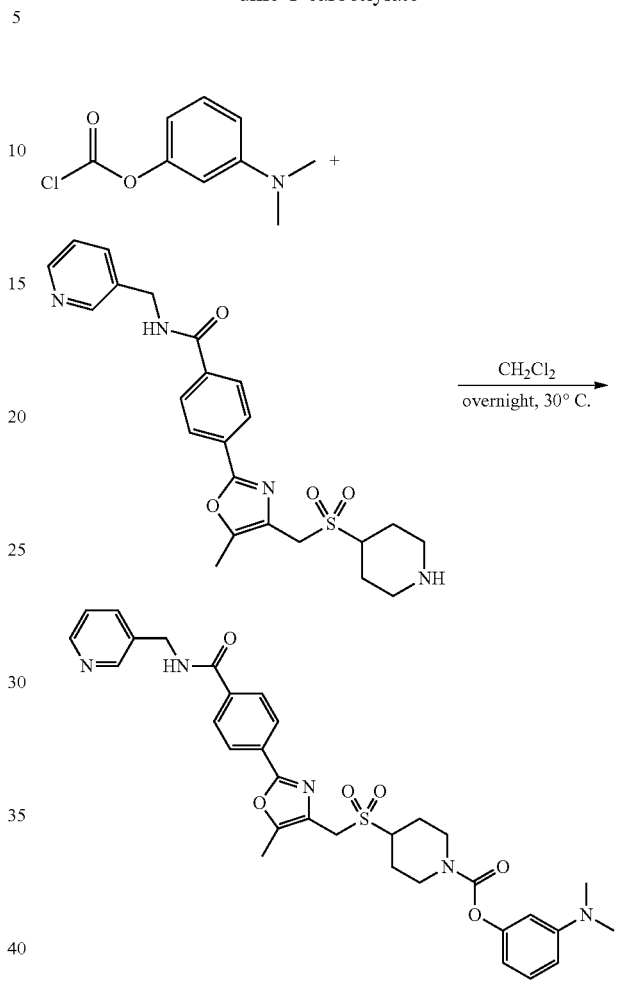

Example 30

To a solution of 4-[5-methyl-4-[(piperidine-4-sulfonyl)methyl]-1,3-oxazol-2-yl]-N-(pyridin-3-ylmethyl)benzamide (1.2 g, 2.64 mmol, 1.76 equiv) in dichloromethane (15 mL) was added the 3-(dimethylamino)phenyl chloroformate (300 mg, 1.50 mmol, 1.00 equiv) dropwise. The resulting solution was stirred overnight at 30° C. The resulting mixture was concentrated under vacuum and the residue was purified on an aluminum oxide column eluted with dichloromethane/methanol (0/100-80/20) to give 230 mg (25%) of 3-(dimethylamino)phenyl 4-[[(5-methyl-2-[4-[(pyridin-3-ylmethyl)carbamoyl]phenyl]-1,3-oxazol-4-yl)methane]sulfonyl]piperidine-1-carboxylate as a white solid. LC-MS: (ES, m/z): 618 [M+H]$^+$, 330, 310, 169, 126, 100. $^1$HNMR (400 MHz, DMSO-d6, ppm): δ 9.25 (s, 1H), 8.57 (s, 1H), 8.47 (s, 1H), 8.04 (s, 4H), 7.76 (d, 1H), 7.38 (t, 1H), 7.15 (t, 1H), 6.56 (d, 1H), 6.43 (s, 1H), 6.38 (s, 1H), 4.58-4.52 (m, 4H), 4.22 (d, 2H), 3.47 (t, 1H), 3.10 (s, 1H), 3.05 (s, 1H), 2.95 (s, 6H), 2.48 (s, 3H), 2.22 (d, 2H), 1.69 (s, 2H).

Example 69

Synthetic Lethal Targeting of Glucose Metabolism in Renal Carcinoma

Cell Culture. RCC4 parental and RCC4 with VHL-reintroduced (RCC4/VHL), SN12C and SN12C-CSCG-VHL shRNA were maintained in DMEM supplemented with 10% FCS.

Cell Viability Assays. For 2,3-bis[2-methoxy-4-nitro-5-sulfophenyl]-2H-tetrazolium-5-carboxanilide (XTT) assays, five thousand cells were plated in 96-well plates. The next day, vehicle (DMSO) or drug was added by serial dilution. Four days later, media were aspirated, XTT solution (0.3 mg/ml of XTT (Sigma), 2.65 mg/ml N-methyl dibenxopyrazine methyl sulfate (Simga) in phenol red-free media) was added, and the plates were incubated at 37° C. for 1-2 hours. Metabolism of XTT was quantified by measuring the absorbance at 450 nm $IC_{50}$s were calculated using linear interpolation. For clonogenic survival assays, three hundred cells were plated per 60 mm tissue culture dish. The cells were allowed to attach overnight and then treated with vehicle or drug for 14 days. Colonies were fixed and stained with crystal violet (0.1% crystal violet in 95% ethanol). All conditions were measured in triplicate and each experiment was done in duplicate or triplicate. To determine necrosis, cells were treated with drug for a given time point. Media and cells were collected, centrifuged, and resuspended in 0.4% trypan blue (Invitrogen). Live and dead cells were counted on a hematocytometer.

$IC_{50}$ values and selectivity ratios for certain exemplary compounds are described below. The designation A reflects an $IC_{50}$ of <1 nM; B reflects an $IC_{50}$ ranging from 1 to 20 nM; and C is an $IC_{50}$ of >20 nM. The designation "a" reflects a ratio of RCC4/RCC-VHL+ranging from 1 to ≤10; "b" reflects from 10 to ≤100; "c" reflects a ratio of >100. Compounds I-29 have an IC50 value of ≤10 μM when tested in the above assay.

TABLE 1

| SN | $IC_{50}$ RCC4 μM | Ratio |
|---|---|---|
| II-1 | B | a |
| II-2 | C | nd |
| II-3 | B | a |
| II-4 | B | a |
| II-5 | B | a |
| II-6 | C | nd |
| II-7 | C | nd |
| II-8 | C | a |

Ratio = $IC_{50}$RCC4/VHL/$IC_{50}$RCC4

TABLE 1

| Example | $IC_{50}$ RCC4 nM | Ratio (IC50 RCC4 Proficient VHL)/ IC50 RCC4 Deficient VHL) |
|---|---|---|
| Example 39 | C | b |
| Example 40 | A | b |
| Example 41 | C | b |
| Example 42 | A | b |
| Example 43 | A | b |
| Example 44 | C | b |
| Example 45 | B | b |
| Example 46 | A | b |
| Example 47 | C | b |
| Example 48 | A | b |
| Example 49 | A | b |
| Example 50 | C | b |
| Example 51 | A | b |
| Example 52 | A | a |
| Example 53 | A | a |
| Example 54 | A | b |
| Example 55 | A | a |

Ratio = $IC_{50}$RCC4/VHL/$IC_{50}$RCC4

Example 70

Clonogenic Assay. Three hundred cells are plated into 60-mm tissue culture dishes in DMEM. The next day, cells are treated with vehicle or drug and are further incubated for an additional 10 days. After 10 days, the media is removed and colonies are fixed and stained in 95% ethanol and 0.1% crystal violet for 15 minutes. The stain is removed and plates are washed in deionized water. Colonies are quantified. All conditions are measured in triplicate and all experiments are performed in triplicate.

Example 71

Glucose Uptake. One hundred thousand cells are plated into 6-well plates. The following day, the cells are treated with vehicle or drug and incubated for the indicated time. Cells are washed twice in phosphate buffered saline and low glucose media is added for 30 minutes. Cells are then incubated with 0.5 microCi of tritiated-2-deoxyglucose and incubated for an hour at 37° C. Cells are washed twice in PBS and then lysed in 0.2 N NaOH and 0.2% SDS. Lysates are transferred to scintillation tubes with scintillation fluid and quantified by scintillation counter.

Example 72

In Vivo Experiments. Five million cells are injected into the flanks of nu/nu mice (4-6 weeks old males) and allowed to grow to approximately 50 mm³. The mice are injected daily by intra-peritoneal to deliver either vehicle or drug. Tumors are measured every other day and tumor volume is calculated as 0.5 length by width squared.

While some embodiments have been shown and described, various modifications and substitutions may be made thereto without departing from the spirit and scope of the invention. For example, for claim construction purposes, it is not intended that the claims set forth herein be construed in any way narrower than the literal language thereof, and it is thus not intended that exemplary embodiments from the specification be read into the claims. Accordingly, it is to be understood that the present invention has been described by way of illustration and not limitations on the scope of the claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims

What is claimed is:
1. A compound of Formula Va:

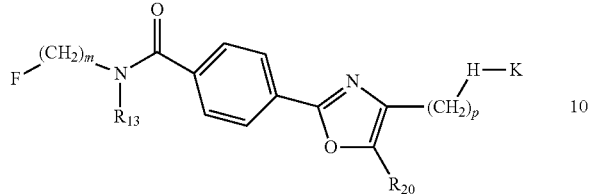

Formula Va or a pharmaceutically acceptable salt, hydrate, solvate, enantiomer, or stereoisomer thereof;
wherein:
F is a heteroaryl selected from pyridine, pyrazine, pyridazine, pyrimidine, 1,2,4-triazine or 1,3,5-triazine, optionally substituted with halogen, hydroxyl group, —CF3 group, C1-C6 alkoxy group, C1-C6 straight chain alkyl, C3-C6 branched chain alkyl or C3-C6 cycloalkyl group, wherein the number of substituents does not exceed the number of available C—H bonds of the heteroaryl; with multiple substitutions, each substituent on the heteroaryl is independent of the other substituents;
m is an integer ranging from 0 to 3;
p is an integer ranging from 1 to 5;
H is selected from —S(O)n-(CH2)q-, —O—(CH2)q-, or —C(O)—(CH2)q-;
n is an integer ranging from 0 to 2;
q is an integer ranging from 0 to 5;
K is selected from (i) C3-C7 cycloalkyl optionally substituted with two or more of R14, R15, and R16, (ii) C1-C6 straight or branched alkyl optionally substitiuted with one or more of R14, R15 and R16, and (iii)

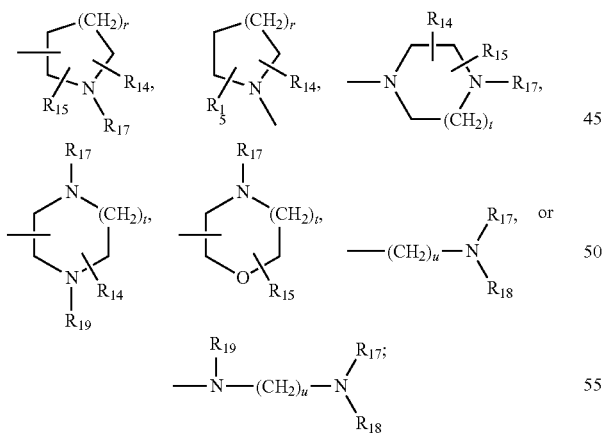

R13 is selected from H, C1-C6 straight chain alkyl, C3-C6 branched chain alkyl or C3-C6 cycloalkyl;
R20 is selected from H, —CF3, C1-C6 straight chain alkyl, C3-C6 branched chain alkyl or C3-C6 cycloalkyl;
R14, R15 and R16 can independently be H, C1-C6 straight chain alkyl, C3-C6 branched chain alkyl, C1-C6 hydroxyalkyl, C1-C6 alkoxy, alkoxyalkyl in which the alkoxy and alkyl portions each independently contain from 1 to 6 carbon atoms, alkoxyalkoxy in which the alkoxy portions each independently contain from 1 to 6 carbon atoms, halogen, —OH, —NH2, —CF3, C1-C6 monoalkylamino, C1-C6 dialkylamino, and nitrogen containing heterocycles optionally substituted with one or more of R17 and R18; or

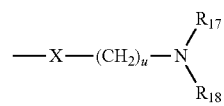

wherein X can be a bond, O, S or NR$_{19}$;
R17, R18 and R19 are independently selected from H, C1-C6 straight chain alkyl, C3-C6 branched chain alkyl, C3-C6 cycloalkyl, C1-C6 hydroxyalkyl, alkoxyalkyl in which the alkoxy and alkyl portions each independently contain from 1 to 6 carbon atoms, —CF3, or —C(O) O—, or R17 and R18 can be taken together to form a 4 to 7 membered monocycloalkyl ring or 8-14 bicycloalkyl ring, each optionally containing between 1-3 heteroatoms selected from N, O or S, or;
r is an integer ranging from 0 to 3;
t is an integer ranging from 1 to 2; and
u is an integer ranging from 1 to 6.
2. The compound according to claim 1, wherein F is selected from the group consisting 2-pyrazinyl, 2-pyrimidinyl, 2-pyridinyl, 3-pyridinyl, and 4-pyridinyl, each of which is optionally substituted.
3. The compound according to claim 2, wherein F is selected from 2-pyridinyl, 3-pyridinyl, and 4-pyridinyl.
4. The compound according to claim 1, wherein H is —SO2—.
5. The compound according to claim 1, wherein R13 is hydrogen or C1-C6 straight chain alkyl.
6. The compound according to claim 1, wherein K is

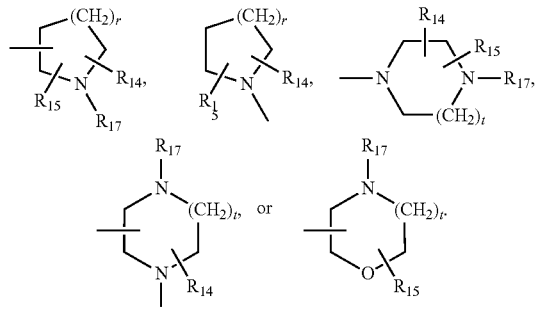

7. A pharmaceutical composition comprising a compound of claim 1, and pharmaceutically acceptable carrier.
8. The compound of claim 1, which is

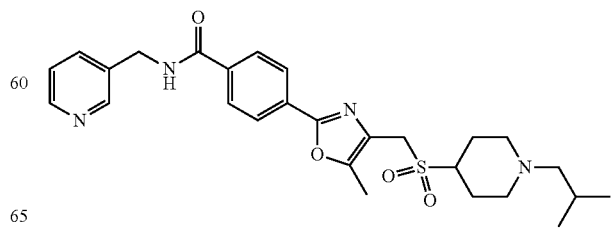

wherein, in Formula Va:
F is pyridin-3-yl;
m is 1;
p is 1;
H is—S(O)n-(CH2)q-, wherein n is 2 and q is 0;
K is,
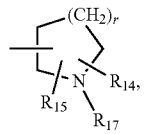
wherein r is 2, R14 and R15 are both H, and R17 is isobutyl to give 1-isobutylpiperidin-4-yl;
R13 is H; and
R20 is methyl.
9. A pharmaceutical composition comprising the compound of claim 8, and a pharmaceutically acceptable carrier.
* * * * *